US009037478B2

(12) United States Patent
Holman et al.

(10) Patent No.: US 9,037,478 B2
(45) Date of Patent: May 19, 2015

(54) SUBSTANCE ALLOCATION SYSTEM AND METHOD FOR INGESTIBLE PRODUCT PREPARATION SYSTEM AND METHOD

(75) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/317,546

(22) Filed: Oct. 19, 2011

(65) Prior Publication Data
US 2013/0053999 A1 Feb. 28, 2013

Related U.S. Application Data

(63) Continuation-in-part of application No. 13/199,361, filed on Aug. 26, 2011, and a continuation-in-part of application No. 13/199,481, filed on Aug. 30, 2011, and a continuation-in-part of application No.
(Continued)

(51) Int. Cl.
G06Q 10/10 (2012.01)
G06Q 50/22 (2012.01)
G06F 19/00 (2011.01)

(52) U.S. Cl.
CPC ............ G06Q 10/10 (2013.01); *G06F 19/3475* (2013.01); G06Q 50/22 (2013.01)

(58) Field of Classification Search
CPC ....... G06Q 10/10; G06Q 50/22; G06Q 50/24; G06F 19/3475

USPC .......................................................... 705/2–3
See application file for complete search history.

(56) References Cited

U.S. PATENT DOCUMENTS

| 1,570,405 A | 1/1926 | Salerno |
| 3,702,583 A | 11/1972 | Rullman |
| 3,859,904 A | 1/1975 | Carriazo |

(Continued)

FOREIGN PATENT DOCUMENTS

| NL | 2003661 C | 4/2011 |
| WO | WO 03/056493 A1 | 7/2003 |
| WO | WO 2006/095212 A1 | 9/2006 |

OTHER PUBLICATIONS

American Society of Hospital Pharmacists; "ASHP Technical Assistance Bulleting on Compounding Nonsterile Products in Pharmacies"; Am. J. Hosp. Pharm.; bearing a date of 1994, approved Apr. 27, 1994; pp. 73-79; vol. 51, No. 1441-8; American Society of Hospital Pharmacists, Inc.
(Continued)

*Primary Examiner* — Luke Gilligan

(57) ABSTRACT

A computationally implemented system and method that is designed to, but is not limited to: electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan. In addition to the foregoing, other method aspects are described in the claims, drawings, and text forming a part of the present disclosure.

66 Claims, 70 Drawing Sheets

Related U.S. Application Data

13/199,545, filed on Aug. 31, 2011, and a continuation-in-part of application No. 13/199,544, filed on Aug. 31, 2011, and a continuation-in-part of application No. 13/200,106, filed on Sep. 16, 2011, and a continuation-in-part of application No. 13/200,113, filed on Sep. 16, 2011, now Pat. No. 8,892,249, and a continuation-in-part of application No. 13/200,829, filed on Sep. 30, 2011, and a continuation-in-part of application No. 13/200,830, filed on Sep. 30, 2011, and a continuation-in-part of application No. 13/200,906, filed on Oct. 3, 2011, and a continuation-in-part of application No. 13/200,907, filed on Oct. 3, 2011, and a continuation of application No. 13/317,545, filed on Oct. 19, 2011.

(56) References Cited

U.S. PATENT DOCUMENTS

| | | |
|---|---|---|
| 4,076,846 A | 2/1978 | Nakatsuka et al. |
| 4,135,077 A | 1/1979 | Wills |
| 4,293,296 A | 10/1981 | Caiello et al. |
| 4,634,597 A | 1/1987 | Spiel et al. |
| 4,666,204 A | 5/1987 | Reinholtz |
| 4,681,000 A | 7/1987 | Wolters |
| 4,723,614 A | 2/1988 | Lahti |
| 4,797,818 A | 1/1989 | Cotter |
| 4,974,747 A | 12/1990 | Ahlström |
| 5,176,922 A | 1/1993 | Balsano et al. |
| 5,197,376 A | 3/1993 | Bird et al. |
| 5,261,150 A | 11/1993 | Grube et al. |
| 5,408,443 A | 4/1995 | Weinberger |
| 5,417,989 A | 5/1995 | Atwood et al. |
| 5,511,594 A | 4/1996 | Brennan et al. |
| 5,522,310 A | 6/1996 | Black, Sr. et al. |
| 5,540,943 A | 7/1996 | Naramura |
| 5,583,129 A | 12/1996 | Spona et al. |
| 5,598,947 A | 2/1997 | Smith |
| 5,697,043 A | 12/1997 | Baskaran et al. |
| 5,731,020 A | 3/1998 | Russo |
| 5,762,971 A | 6/1998 | Schirmer |
| 5,820,906 A | 10/1998 | Akesson et al. |
| 6,048,191 A | 4/2000 | Beltrami |
| 6,105,818 A | 8/2000 | Speranza |
| 6,112,182 A | 8/2000 | Akers et al. |
| 6,194,017 B1 | 2/2001 | Woodward et al. |
| 6,200,125 B1 | 3/2001 | Akutagawa |
| 6,202,923 B1 | 3/2001 | Boyer et al. |
| 6,236,974 B1 | 5/2001 | Kolawa et al. |
| 6,245,556 B1 | 6/2001 | Sako et al. |
| 6,268,004 B1 | 7/2001 | Hayashi |
| 6,280,784 B1 | 8/2001 | Yang et al. |
| 6,280,785 B1 | 8/2001 | Yang et al. |
| 6,280,786 B1 | 8/2001 | Williams et al. |
| 6,376,000 B1 | 4/2002 | Waters |
| 6,415,555 B1 | 7/2002 | Montague |
| 6,618,062 B1 | 9/2003 | Brown et al. |
| 6,622,064 B2 | 9/2003 | Bartholomew et al. |
| 6,637,432 B2 | 10/2003 | Wakefield et al. |
| 6,644,359 B1 | 11/2003 | Wertheim |
| 6,646,659 B1 | 11/2003 | Brown et al. |
| 6,660,317 B1 | 12/2003 | Akutagawa |
| 6,711,460 B1 | 3/2004 | Reese |
| 6,802,433 B2 | 10/2004 | Leykin et al. |
| 6,843,166 B1 | 1/2005 | Li |
| 6,859,215 B1 | 2/2005 | Brown et al. |
| 6,865,261 B1 | 3/2005 | Rao et al. |
| 6,998,087 B1 | 2/2006 | Hanson et al. |
| 7,006,893 B2 | 2/2006 | Hart et al. |
| 7,027,996 B2 | 4/2006 | Levinson |
| 7,054,909 B1 | 5/2006 | Ohkubo et al. |
| 7,080,597 B2 | 7/2006 | Ando |
| 7,098,794 B2 | 8/2006 | Lindsay et al. |
| 7,110,964 B2 | 9/2006 | Tengler et al. |
| 7,183,518 B2 | 2/2007 | Near et al. |
| 7,187,960 B2 | 3/2007 | Abreu |
| 7,188,082 B2 | 3/2007 | Keane et al. |
| 7,200,644 B1 | 4/2007 | Flanagan |
| 7,231,917 B2 | 6/2007 | Frederiksen |
| 7,243,789 B2 | 7/2007 | Discko, Jr. |
| 7,281,468 B2 | 10/2007 | Frem |
| 7,295,889 B2 | 11/2007 | Lähteenmäki |
| 7,299,982 B2 | 11/2007 | Kreiner et al. |
| 7,343,174 B2 | 3/2008 | Suryanarayana et al. |
| 7,364,068 B1 | 4/2008 | Strubbe et al. |
| 7,392,193 B2 | 6/2008 | Mault |
| 7,395,134 B2 | 7/2008 | Bartholomew et al. |
| 7,415,375 B2 | 8/2008 | Shakman et al. |
| 7,451,015 B2 | 11/2008 | Mazur et al. |
| 7,457,685 B2 | 11/2008 | D'Silva |
| 7,555,360 B1 | 6/2009 | Green et al. |
| 7,571,586 B1 | 8/2009 | Morales |
| 7,625,198 B2 | 12/2009 | Lipson et al. |
| 7,630,790 B2 | 12/2009 | Handfield et al. |
| 7,680,690 B1 | 3/2010 | Catalano |
| 7,747,345 B2 | 6/2010 | Ohmura et al. |
| 7,762,181 B2 | 7/2010 | Boland et al. |
| 7,783,379 B2 | 8/2010 | Beane et al. |
| 7,818,089 B2 | 10/2010 | Hanna et al. |
| 7,842,323 B1 | 11/2010 | White |
| 7,884,953 B1 | 2/2011 | Willcocks et al. |
| 7,974,873 B2 | 7/2011 | Simmons et al. |
| 8,007,847 B2 | 8/2011 | Biderman et al. |
| 8,027,748 B2 | 9/2011 | Handfield et al. |
| 8,085,135 B2 | 12/2011 | Cohen Alloro et al. |
| 8,173,186 B2 | 5/2012 | Kuwabara et al. |
| 8,190,447 B2 | 5/2012 | Hungerford et al. |
| 8,204,757 B2 | 6/2012 | Carlson et al. |
| 8,249,946 B2 | 8/2012 | Froseth et al. |
| 8,306,655 B2 | 11/2012 | Newman |
| 8,370,176 B2 | 2/2013 | Vespasiani |
| 8,412,369 B2 | 4/2013 | Ames, II et al. |
| 8,504,440 B1 | 8/2013 | Kolawa et al. |
| 8,521,326 B1 | 8/2013 | Holtje |
| 2001/0005830 A1 | 6/2001 | Kuroyanagi |
| 2001/0028308 A1 | 10/2001 | De La Huerga |
| 2001/0036495 A1 | 11/2001 | Ganan-Calvo |
| 2002/0029149 A1 | 3/2002 | Nishina |
| 2002/0049652 A1 | 4/2002 | Moore et al. |
| 2002/0081356 A1 | 6/2002 | Bebiak et al. |
| 2002/0138201 A1 | 9/2002 | Greensides |
| 2002/0192572 A1 | 12/2002 | Lau |
| 2003/0017248 A1 | 1/2003 | Gray |
| 2003/0050854 A1 | 3/2003 | Showghi et al. |
| 2003/0051606 A1 | 3/2003 | Cusenza et al. |
| 2003/0071806 A1 | 4/2003 | Annand |
| 2003/0079612 A1 | 5/2003 | Con |
| 2003/0099157 A1 | 5/2003 | Quine |
| 2003/0105555 A1 | 6/2003 | Lunak et al. |
| 2003/0121929 A1 | 7/2003 | Liff et al. |
| 2003/0125836 A1 | 7/2003 | Chirnomas |
| 2003/0125963 A1 | 7/2003 | Haken |
| 2003/0125986 A1 | 7/2003 | Collosi |
| 2003/0197005 A1 | 10/2003 | Huegerich et al. |
| 2003/0208113 A1 | 11/2003 | Mault et al. |
| 2003/0208409 A1 | 11/2003 | Mault |
| 2003/0219527 A1 | 11/2003 | Sasaki et al. |
| 2003/0236706 A1 | 12/2003 | Weiss |
| 2004/0045579 A1 | 3/2004 | Miki et al. |
| 2004/0049407 A1 | 3/2004 | Rosenberg |
| 2004/0054554 A1 | 3/2004 | Barts et al. |
| 2004/0073448 A1 | 4/2004 | Barts et al. |
| 2004/0073449 A1 | 4/2004 | Yang |
| 2004/0091843 A1 | 5/2004 | Albro et al. |
| 2004/0093265 A1 | 5/2004 | Ramchandani et al. |
| 2004/0093268 A1 | 5/2004 | Ramchandani et al. |
| 2004/0131659 A1 | 7/2004 | Gibson et al. |
| 2004/0143503 A1 | 7/2004 | Suthar |
| 2004/0151820 A1 | 8/2004 | Harris |
| 2004/0158350 A1 | 8/2004 | Ostergaard et al. |
| 2004/0158499 A1 | 8/2004 | Dev et al. |
| 2004/0193495 A1 | 9/2004 | Kim |
| 2004/0214597 A1 | 10/2004 | Suryanarayana et al. |

(56) References Cited

U.S. PATENT DOCUMENTS

| | | |
|---|---|---|
| 2004/0238555 A1 | 12/2004 | Parks |
| 2004/0246819 A1 | 12/2004 | Quine |
| 2004/0250842 A1 | 12/2004 | Adams et al. |
| 2005/0023710 A1 | 2/2005 | Brodkin et al. |
| 2005/0038719 A1 | 2/2005 | Young et al. |
| 2005/0048461 A1 | 3/2005 | Lahteenmaki |
| 2005/0059849 A1 | 3/2005 | Liu |
| 2005/0079257 A1 | 4/2005 | Neto |
| 2005/0080650 A1 | 4/2005 | Noel |
| 2005/0098169 A1 | 5/2005 | Frederiksen |
| 2005/0114149 A1 | 5/2005 | Rodriguez et al. |
| 2005/0131738 A1 | 6/2005 | Morris |
| 2005/0157148 A1 | 7/2005 | Baker et al. |
| 2005/0160052 A1 | 7/2005 | Schneider et al. |
| 2005/0171663 A1 | 8/2005 | Mittelsteadt et al. |
| 2005/0193901 A1 | 9/2005 | Buehler |
| 2005/0209915 A1 | 9/2005 | Saluccio |
| 2005/0226975 A1 | 10/2005 | Drouillard |
| 2005/0230472 A1 | 10/2005 | Chang |
| 2005/0233011 A1 | 10/2005 | Beavers |
| 2005/0241497 A1 | 11/2005 | Cantu |
| 2005/0251289 A1 | 11/2005 | Bonney et al. |
| 2005/0267811 A1 | 12/2005 | Almblad |
| 2005/0280544 A1 | 12/2005 | Mishelevich |
| 2006/0015289 A1 | 1/2006 | Shakman et al. |
| 2006/0053184 A1 | 3/2006 | Grana |
| 2006/0064037 A1 | 3/2006 | Shalon et al. |
| 2006/0081653 A1 | 4/2006 | Boland et al. |
| 2006/0108415 A1 | 5/2006 | Thomas et al. |
| 2006/0111976 A1 | 5/2006 | Pompushko |
| 2006/0161453 A1 | 7/2006 | Kost et al. |
| 2006/0191885 A1 | 8/2006 | Near et al. |
| 2006/0224419 A1 | 10/2006 | Servizio et al. |
| 2006/0237523 A1 | 10/2006 | Carlson et al. |
| 2006/0259188 A1 | 11/2006 | Berg |
| 2006/0263501 A1 | 11/2006 | Oghafua et al. |
| 2006/0277066 A1 | 12/2006 | Hungerford et al. |
| 2006/0278093 A1 | 12/2006 | Biderman et al. |
| 2006/0286218 A1 | 12/2006 | Salzman |
| 2007/0037567 A1 | 2/2007 | Ungless et al. |
| 2007/0038727 A1 | 2/2007 | Bailey et al. |
| 2007/0048407 A1 | 3/2007 | Collins et al. |
| 2007/0055550 A1 | 3/2007 | Courtney et al. |
| 2007/0055694 A1 | 3/2007 | Ruge et al. |
| 2007/0061170 A1 | 3/2007 | Lorsch |
| 2007/0062156 A1 | 3/2007 | Kim |
| 2007/0083494 A1 | 4/2007 | Carlson et al. |
| 2007/0092614 A1 | 4/2007 | Waldock |
| 2007/0150371 A1 | 6/2007 | Gangji |
| 2007/0150375 A1 | 6/2007 | Yang |
| 2007/0151984 A1 | 7/2007 | Baker et al. |
| 2007/0168205 A1 | 7/2007 | Carlson et al. |
| 2007/0185615 A1 | 8/2007 | Bossi et al. |
| 2007/0185785 A1 | 8/2007 | Carlson et al. |
| 2007/0191689 A1 | 8/2007 | Elitok |
| 2007/0192715 A1 | 8/2007 | Kataria et al. |
| 2007/0208454 A1 | 9/2007 | Forrester et al. |
| 2007/0231435 A1 | 10/2007 | Ream et al. |
| 2007/0260487 A1 | 11/2007 | Bartfeld et al. |
| 2007/0275690 A1 | 11/2007 | Hunter et al. |
| 2008/0059226 A1 | 3/2008 | Melker et al. |
| 2008/0077440 A1 | 3/2008 | Doron |
| 2008/0084450 A1 | 4/2008 | Silverbrook |
| 2008/0124433 A1 | 5/2008 | Yelden et al. |
| 2008/0125897 A1 | 5/2008 | DiGianfilippo et al. |
| 2008/0126220 A1 | 5/2008 | Baril et al. |
| 2008/0126985 A1 | 5/2008 | Baril et al. |
| 2008/0141315 A1 | 6/2008 | Ogilvie |
| 2008/0162181 A1 | 7/2008 | Ben-Haim et al. |
| 2008/0173711 A1 | 7/2008 | Handfield et al. |
| 2008/0195247 A1 | 8/2008 | Mallett et al. |
| 2008/0224823 A1 | 9/2008 | Lawson et al. |
| 2008/0249865 A1 | 10/2008 | Angell et al. |
| 2008/0260918 A1 | 10/2008 | Lai et al. |
| 2008/0272138 A1 | 11/2008 | Ross et al. |
| 2008/0288287 A1 | 11/2008 | Stanners |
| 2008/0314918 A1 | 12/2008 | Nuriely |
| 2009/0012433 A1* | 1/2009 | Fernstrom et al. ............ 600/593 |
| 2009/0029016 A1 | 1/2009 | Pfister et al. |
| 2009/0043176 A1 | 2/2009 | Nakajima et al. |
| 2009/0087819 A1 | 4/2009 | Adachi et al. |
| 2009/0099944 A1 | 4/2009 | Robinson et al. |
| 2009/0105875 A1 | 4/2009 | Wiles |
| 2009/0106313 A1 | 4/2009 | Boldyga |
| 2009/0130449 A1 | 5/2009 | El-Siblani |
| 2009/0132379 A1 | 5/2009 | Baril et al. |
| 2009/0164897 A1 | 6/2009 | Amer-Yahia et al. |
| 2009/0167553 A1 | 7/2009 | Hong et al. |
| 2009/0192898 A1 | 7/2009 | Baril |
| 2009/0198547 A1 | 8/2009 | Sudak |
| 2009/0199105 A1 | 8/2009 | Kamada et al. |
| 2009/0218363 A1 | 9/2009 | Terzini |
| 2009/0236333 A1 | 9/2009 | Ben-Shmuel et al. |
| 2009/0236334 A1 | 9/2009 | Ben-Shmuel et al. |
| 2009/0236335 A1 | 9/2009 | Ben-Shmuel et al. |
| 2009/0242620 A1 | 10/2009 | Sahuguet |
| 2009/0261175 A1 | 10/2009 | Kauppinen et al. |
| 2009/0267895 A1 | 10/2009 | Bunch |
| 2009/0294521 A1 | 12/2009 | de la Huerga |
| 2009/0295569 A1 | 12/2009 | Corwin et al. |
| 2009/0297668 A1 | 12/2009 | Cantu |
| 2009/0299645 A1 | 12/2009 | Colby et al. |
| 2009/0317519 A1 | 12/2009 | Lavie et al. |
| 2009/0326516 A1 | 12/2009 | Bangera et al. |
| 2010/0017296 A1 | 1/2010 | Spignesi, Jr. et al. |
| 2010/0038416 A1 | 2/2010 | Canora |
| 2010/0038594 A1 | 2/2010 | Bohlig et al. |
| 2010/0042427 A1 | 2/2010 | Graham et al. |
| 2010/0045705 A1 | 2/2010 | Vertegaal et al. |
| 2010/0047410 A1 | 2/2010 | Lichtenstein |
| 2010/0052900 A1 | 3/2010 | Covannon et al. |
| 2010/0055257 A1 | 3/2010 | Hervig |
| 2010/0063889 A1 | 3/2010 | Proctor, Jr. et al. |
| 2010/0087155 A1 | 4/2010 | Dubost |
| 2010/0100237 A1 | 4/2010 | Ratnakar |
| 2010/0106523 A1 | 4/2010 | Kalamas |
| 2010/0106607 A1 | 4/2010 | Riddiford et al. |
| 2010/0121722 A1 | 5/2010 | Vawter |
| 2010/0136666 A1 | 6/2010 | Kobayashi et al. |
| 2010/0139992 A1 | 6/2010 | Delia et al. |
| 2010/0145506 A1 | 6/2010 | Waugh et al. |
| 2010/0161345 A1 | 6/2010 | Cain et al. |
| 2010/0161600 A1 | 6/2010 | Higgins et al. |
| 2010/0167648 A1 | 7/2010 | Doutriaux |
| 2010/0189842 A1 | 7/2010 | Toren |
| 2010/0204676 A1 | 8/2010 | Cardullo |
| 2010/0206765 A1 | 8/2010 | Fonte |
| 2010/0235201 A1 | 9/2010 | McEvoy |
| 2010/0250384 A1 | 9/2010 | Bhargava |
| 2010/0256993 A1* | 10/2010 | Vespasiani ....................... 705/3 |
| 2010/0259719 A1 | 10/2010 | Sabeta |
| 2010/0268378 A1 | 10/2010 | Sharpley |
| 2010/0268380 A1 | 10/2010 | Waugh et al. |
| 2010/0275625 A1 | 11/2010 | Lowenstein |
| 2010/0286632 A1 | 11/2010 | Dos Santos |
| 2010/0291515 A1 | 11/2010 | Pinnisi et al. |
| 2010/0303972 A1 | 12/2010 | Srivastava |
| 2010/0305974 A1 | 12/2010 | Patch et al. |
| 2010/0310737 A1 | 12/2010 | Someya et al. |
| 2010/0312143 A1 | 12/2010 | Kim |
| 2010/0312385 A1 | 12/2010 | Deuber |
| 2010/0332140 A1 | 12/2010 | Joyce et al. |
| 2010/0332250 A1 | 12/2010 | Simpson et al. |
| 2011/0000923 A1 | 1/2011 | Morales |
| 2011/0004624 A1 | 1/2011 | Bansai et al. |
| 2011/0027432 A1 | 2/2011 | Loeser |
| 2011/0031236 A1 | 2/2011 | Ben-Shmuel et al. |
| 2011/0040660 A1 | 2/2011 | Allison et al. |
| 2011/0055044 A1 | 3/2011 | Wiedl |
| 2011/0076349 A1 | 3/2011 | Yoshihara et al. |
| 2011/0087076 A1* | 4/2011 | Brynelsen et al. ............ 600/300 |
| 2011/0124996 A1 | 5/2011 | Reinke et al. |
| 2011/0160902 A1 | 6/2011 | Postins |
| 2011/0166881 A1* | 7/2011 | Brazzo et al. ..................... 705/3 |

(56) References Cited

U.S. PATENT DOCUMENTS

| | | |
|---|---|---|
| 2011/0173062 A1 | 7/2011 | Chen et al. |
| 2011/0208617 A1 | 8/2011 | Weiland |
| 2011/0231212 A1 | 9/2011 | Hurley et al. |
| 2011/0231266 A1 | 9/2011 | Baril |
| 2011/0282712 A1 | 11/2011 | Amos et al. |
| 2011/0300270 A1 | 12/2011 | Koppens |
| 2011/0313867 A9 | 12/2011 | Silver |
| 2011/0318717 A1 | 12/2011 | Adamowicz |
| 2011/0320037 A1 | 12/2011 | Frugone |
| 2012/0004770 A1 | 1/2012 | Ooyen et al. |
| 2012/0016745 A1 | 1/2012 | Hendrickson |
| 2012/0041778 A1 | 2/2012 | Kraft |
| 2012/0088212 A1 | 4/2012 | Knaan |
| 2012/0089249 A1 | 4/2012 | Rosenblum |
| 2012/0101914 A1 | 4/2012 | Kumar et al. |
| 2012/0131619 A1 | 5/2012 | Ogilvie |
| 2012/0136731 A1 | 5/2012 | Kidron et al. |
| 2012/0137325 A1 | 5/2012 | Ogilvie |
| 2012/0152125 A1 | 6/2012 | Yoakim et al. |
| 2012/0156337 A1 | 6/2012 | Studor et al. |
| 2012/0168985 A1 | 7/2012 | Kläber |
| 2012/0173271 A1 | 7/2012 | Omidi |
| 2012/0179665 A1 | 7/2012 | Baarman et al. |
| 2012/0196011 A1 | 8/2012 | Felix |
| 2012/0214140 A1 | 8/2012 | Brynelsen et al. |
| 2012/0233002 A1 | 9/2012 | Abujbara |
| 2012/0246004 A1 | 9/2012 | Book et al. |
| 2012/0251688 A1 | 10/2012 | Zimmerman et al. |
| 2012/0251689 A1 | 10/2012 | Batchelder |
| 2012/0258216 A1 | 10/2012 | Wessels |
| 2012/0284126 A1 | 11/2012 | Giraud et al. |
| 2012/0290412 A1 | 11/2012 | Marovets |
| 2012/0323707 A1 | 12/2012 | Urban |
| 2013/0006415 A1 | 1/2013 | Paydar et al. |
| 2013/0011529 A1 | 1/2013 | Belzowski et al. |
| 2013/0018356 A1 | 1/2013 | Prince et al. |
| 2013/0034633 A1 | 2/2013 | von Hasseln |
| 2013/0089642 A1 | 4/2013 | Lipson et al. |
| 2013/0151268 A1 | 6/2013 | Fletcher |
| 2013/0158705 A1 | 6/2013 | Levy et al. |
| 2013/0171304 A1 | 7/2013 | Huntley |
| 2013/0189405 A1 | 7/2013 | Filliol et al. |
| 2013/0196035 A1 | 8/2013 | Passet et al. |
| 2013/0238118 A1 | 9/2013 | Haas |
| 2013/0273217 A1 | 10/2013 | Minvielle |
| 2013/0304529 A1 | 11/2013 | Phalake et al. |
| 2014/0013962 A1 | 1/2014 | Lipton et al. |
| 2014/0050811 A1 | 2/2014 | Lipton et al. |

OTHER PUBLICATIONS

U.S. Appl. No. 13/435,591, Holman et al.
U.S. Appl. No. 13/435,550, Holman et al.
U.S. Appl. No. 13/432,525, Holman et al.
U.S. Appl. No. 13/432,507, Holman et al.
U.S. Appl. No. 13/385,690, Holman et al.
U.S. Appl. No. 13/385,687, Holman et al.
U.S. Appl. No. 13/385,129, Holman et al.
U.S. Appl. No. 13/385,128, Holman et al.
U.S. Appl. No. 13/373,847, Holman et al.
U.S. Appl. No. 13/373,846, Holman et al.
U.S. Appl. No. 13/373,675, Holman et al.
U.S. Appl. No. 13/373,674, Holman et al.
U.S. Appl. No. 13/317,979, Holman et al.
U.S. Appl. No. 13/317,978, Holman et al.
U.S. Appl. No. 13/317,545, Holman et al.
U.S. Appl. No. 13/200,907, Holman et al.
U.S. Appl. No. 13/200,906, Holman et al.
U.S. Appl. No. 13/200,830, Holman et al.
U.S. Appl. No. 13/200,829, Holman et al.
U.S. Appl. No. 13/200,113, Holman et al.
U.S. Appl. No. 13/200,106, Holman et al.
U.S. Appl. No. 13/199,545, Holman et al.
U.S. Appl. No. 13/199,544, Holman et al.
U.S. Appl. No. 13/199,481, Holman et al.
U.S. Appl. No. 13/199,361, Holman et al.
"3D food printing"; PharmacyEscrow.com; printed on Apr. 4, 2012; 2 pages.
Blain, Loz; "Cornucopia: Digital Gastronomy—could 3D printing be the next revolution in cooking?"; Gizmag; Jan. 14, 2010; 4 pages.
Broomfield, Mark; "The Future of Food Printing"; Fab@Home; Aug. 20, 2009; 1 page.
Coelho, Marcelo; "Cornucopia"; printed on Apr. 4, 2012; 1 page; located at fluid.media.mut.edu.
Cohen et al.; "Hydrocolloid Printing: A Novel Platform for Customized Food Production"; Twentieth Annual International Solid Freeform Fabrication Symposium, Austin, Texas; bearing a date of 2009; cover page and pp. 807-818.
Fawkes, Piers; "3D Food Printing", PSFK; Jan. 17, 2008; 8 pages.
Flatley, Joseph L.; "Ikea's kitchen of the future: 3D food printing, mood lighting, virtual Gordon Ramsay"; Engadget; printed on Apr. 4, 2012; 4 pages; AOL Inc.
McKendrick, Joe; "3D food 'printing': coming to a kitchen near you"; Smartplanet; Dec. 27, 2010; 6 pages; located at www.smartplanet.com/business/blog/business-brains.
Periard et al.; "Printing Food"; Cornell University; printed on Apr. 6, 2012; 11 pages; located at www.creativemachines.cornell.edu/papers/SFF07_Periard2.pdf•.
"Printed Meats!"; Fabbaloo; Aug. 23, 2010; 5 pages; Fabbaloo.
"Prototypes and Concept Designs for a Digital Gastronomy"; Cornucopia; printed on Apr. 4, 2012; 5 pages.
Sandhana, Lakshmi; "The printed future of Christmas dinner"; BBC News Technology; Dec. 24, 2010; 4 pages; MMXI.
Seth, Radhika; "Printing My Food by the Molecule"; Yanko Design; Mar. 2, 2010; 7 pages.
Seth, Radhika; "Surreal Food Is Real and Printed"; Yanko Design; Aug. 26, 2009; 6 pages.
"The CandyFab 6000"; Evil Mad Scientist Laboratories; bearing a date of 2011; 7 pages; Evil Mad Scientist Laboratories.
"Welcome to the CandyFabProject"; CandyFab.org; Jan. 22, 2011; 3 pages; The CandyFab Project.
"Scientests create 'inhalable' food?"; bearing a date of Aug. 29, 2012; snapshot taken Apr. 12, 2009; available at http://web.archive.org/web/20090412131937/ http://chowhound.chow.com/topics/611174.
"Transdermal Nutrient Delivery Systems"; U.S. Army Soldier and Biological Chemical Command; snapshot taken Jul. 21, 2004; available at http://web.archive.org/web/20040721134210 http://archives.tproc.org/www.sbccom.army.mil/products/food/tdnds.pdf.
"Airline Tickets and Airline Reservations from American Airlines"; AA.com; 1 page; retrieved from the internet wayback machine on Oct. 27, 2011 ; located at http://web.archieve.org/web.20101027131457/http://www.aa.com.
Williams, N.T.; "Medication administration through enteral feeding tubes"; Am J Health Syst Pharm.; bearing a date of Dec. 15, 2008; 2 pages (abstract only); vol. 65, No. 24; located at http://www.ncbi.nlm.nih.gov/pubmed/19052281.
McDonald's; sample restaurant menu; Feb. 10, 2014; 1 page; located at: http://www.burgerbusiness.com/wp-content/uploads/McD_Calor . . . .
Indiana State Excise Police; "Alcohol Laws"; snapshot taken Oct. 22, 2010; pp. 1-2; located at http://web.archive.org/web/20101122202431/http://www.in.gov/atc/isep/2384.htm.
Valuevapor.com; "Starter Kits"; printed on Sep. 22, 2014; pp. 1-2; located at http://web.archive.org/web/20100610083606/http://www.valuevapor.com/VV/store/index.php?main_page=index&cPath=10.
"Easy Delft Blue Eggs"; The Sweet Adventures of Sugarbelle Blog; Mar. 25, 2012; pp. 1-7; located at: www.sweetsugarbelle.com/2012/03/simple-delft-blue-easter-egg-cookies.

* cited by examiner

Name: Jane Doe                                                                                      Code: 582215

| Day | Date | Meal | Product | Dose | Substance | Per Dose (Units) | Total Doses | Daily Total (Units) |
|---|---|---|---|---|---|---|---|---|
| 1 | Aug. 15 | 1 | Apple Sauce | 6 oz. | Hydrocodone | 7.5 | 1 | 7.5 |
| 2 | Aug. 16 | 1 | Apple Sauce | 6 oz. | Hydrocodone | 7.0 | 1 | 7.0 |
| 3 | Aug. 17 | 1 | Apple Sauce | 6 oz. | Hydrocodone | 6.5 | 1 | 6.5 |
| 4 | Aug. 18 | 1 | Apple Sauce | 6 oz. | Hydrocodone | 6.0 | 1 | 6.0 |
| 5 | Aug. 19 | 1 | Apple Sauce | 6 oz. | Hydrocodone | 5.5 | 1 | 5.5 |
| 6 | Aug. 20 | 1 | Apple Sauce | 6 oz. | Hydrocodone | 5.0 | 1 | 5.0 |
| 7 | Aug. 21 | 1 | Apple Sauce | 6 oz. | Hydrocodone | 4.5 | 1 | 4.5 |
| 1 | Aug. 15 | 2 | Protein Shake | 4 oz. | Codeine | 2.0 | 3 | 6.0 |
| 2 | Aug. 16 | 2 | Protein Shake | 4 oz. | Codeine | 2.0 | 3 | 6.0 |
| 3 | Aug. 17 | 2 | Protein Shake | 4 oz. | Codeine | 1.7 | 3 | 5.1 |
| 4 | Aug. 18 | 2 | Protein Shake | 4 oz. | Codeine | 1.7 | 3 | 5.1 |
| 5 | Aug. 19 | 2 | Protein Shake | 4 oz. | Codeine | 1.3 | 3 | 3.9 |
| 6 | Aug. 20 | 2 | Protein Shake | 4 oz. | Codeine | 1.3 | 3 | 3.9 |
| 7 | Aug. 21 | 2 | Protein Shake | 4 oz. | Codeine | 1.0 | 3 | 3.0 |
| 1 | Aug. 15 | 3 | Smoothie | 8 oz. | Aspirin | 2.5 | 2 | 5.0 |
| 2 | Aug. 16 | 3 | Smoothie | 8 oz. | Aspirin | 3.0 | 2 | 6.0 |
| 3 | Aug. 17 | 3 | Smoothie | 8 oz. | Aspirin | 3.5 | 2 | 7.0 |
| 4 | Aug. 18 | 3 | Smoothie | 8 oz. | Aspirin | 4.0 | 2 | 8.0 |
| 5 | Aug. 19 | 3 | Smoothie | 8 oz. | Aspirin | 3.75 | 2 | 7.5 |
| 6 | Aug. 20 | 3 | Smoothie | 8 oz. | Aspirin | 3.5 | 2 | 7.0 |
| 7 | Aug. 21 | 3 | Smoothie | 8 oz. | Aspirin | 3.25 | 2 | 6.5 |

Fig. 4

Name: Jane Doe    Code: 582215

| Day | Date | Meal | Product | Dose | Substance | Per Dose (Units) | Total Doses | Daily Total (Units) |
|---|---|---|---|---|---|---|---|---|
| 1 | Sept. 19 | 1 | Whole Capsule | 1 | Colestid | 8.75 | 1 | 8.75 |
| 2 | Sept. 20 | 1 | Whole Capsule | 1 | Colestid | 8.0 | 1 | 8.0 |
| 3 | Sept. 21 | 1 | Whole Capsule | 1 | Colestid | 7.25 | 1 | 7.25 |
| 4 | Sept. 22 | 1 | Whole Capsule | 1 | Colestid | 6.5 | 1 | 6.5 |
| 5 | Sept. 23 | 1 | Whole Capsule | 1 | Colestid | 5.75 | 1 | 5.75 |
| 6 | Sept. 24 | 1 | Whole Capsule | 1 | Colestid | 5.0 | 1 | 5.0 |
| 7 | Sept. 25 | 1 | Whole Capsule | 1 | Colestid | 4.25 | 1 | 4.25 |
| 1 | Sept. 19 | 2 | Whole Tablet | 1 | Lipitor | 4.25 | 2 | 8.5 |
| 2 | Sept. 20 | 2 | Whole Tablet | 1 | Lipitor | 4.0 | 2 | 8.0 |
| 3 | Sept. 21 | 2 | Whole Tablet | 1 | Lipitor | 3.75 | 2 | 7.5 |
| 4 | Sept. 22 | 2 | Whole Tablet | 1 | Lipitor | 3.5 | 2 | 7.0 |
| 5 | Sept. 23 | 2 | Whole Tablet | 1 | Lipitor | 3.25 | 2 | 6.5 |
| 6 | Sept. 24 | 2 | Whole Tablet | 1 | Lipitor | 3.0 | 2 | 6.0 |
| 7 | Sept. 25 | 2 | Whole Tablet | 1 | Lipitor | 2.75 | 2 | 5.5 |
| 1 | Sept. 19 | 3 | Egg Mix | 2 oz. | Cholesterol | 2.75 | 3 | 8.25 |
| 2 | Sept. 20 | 3 | Egg Mix | 2 oz. | Cholesterol | 2.5 | 3 | 7.5 |
| 3 | Sept. 21 | 3 | Egg Mix | 2 oz. | Cholesterol | 2.25 | 3 | 6.75 |
| 4 | Sept. 22 | 3 | Egg Mix | 2 oz. | Cholesterol | 2 | 3 | 6.0 |
| 5 | Sept. 23 | 3 | Egg Mix | 2 oz. | Cholesterol | 1.75 | 3 | 5.25 |
| 6 | Sept. 24 | 3 | Egg Mix | 2 oz. | Cholesterol | 1.5 | 3 | 4.5 |
| 7 | Sept. 25 | 3 | Egg Mix | 2 oz. | Cholesterol | 1.25 | 3 | 3.75 |

Fig. 7

Name: Jane Doe　　　　　　　　　　　　　　　　　　　　　　　　　　　　　　　　　　　　　Code: 582215

| Day | Date | Meal | Product | Dose | Substance | Per Dose (Units) | Total Doses | Daily Total (Units) |
|---|---|---|---|---|---|---|---|---|
| 1 | June. 8 | 1 | Coffee | 6 oz. | Caffeine | 7.5 | 1 | 7.5 |
| 2 | June. 9 | 1 | Coffee | 6 oz. | Caffeine | 7.0 | 1 | 7.0 |
| 3 | June. 10 | 1 | Coffee | 6 oz. | Caffeine | 6.5 | 1 | 6.5 |
| 4 | June. 11 | 1 | Coffee | 6 oz. | Caffeine | 6.0 | 1 | 6.0 |
| 5 | June. 12 | 1 | Coffee | 6 oz. | Caffeine | 5.5 | 1 | 5.5 |
| 6 | June. 13 | 1 | Coffee | 6 oz. | Caffeine | 5.0 | 1 | 5.0 |
| 7 | June. 14 | 1 | Coffee | 6 oz. | Caffeine | 4.5 | 1 | 4.5 |
| 1 | June. 8 | 2 | Black Tea | 4 oz. | Caffeine | 4.0 | 2 | 8.0 |
| 2 | June. 9 | 2 | Black Tea | 4 oz. | Caffeine | 3.5 | 2 | 7.0 |
| 3 | June. 10 | 2 | Black Tea | 4 oz. | Caffeine | 3.0 | 2 | 6.0 |
| 4 | June. 11 | 2 | Black Tea | 4 oz. | Caffeine | 2.5 | 2 | 5.0 |
| 5 | June. 12 | 2 | Black Tea | 4 oz. | Caffeine | 2.0 | 2 | 4.0 |
| 6 | June. 13 | 2 | Black Tea | 4 oz. | Caffeine | 1.5 | 2 | 3.0 |
| 7 | June. 14 | 2 | Black Tea | 4 oz. | Caffeine | 1.0 | 2 | 2.0 |
| 1 | June. 8 | 3 | Cola | 8 oz. | Caffeine | 8.5 | 1 | 8.5 |
| 2 | June. 9 | 3 | Cola | 8 oz. | Caffeine | 8.0 | 1 | 8.0 |
| 3 | June. 10 | 3 | Cola | 8 oz. | Caffeine | 7.5 | 1 | 7.5 |
| 4 | June. 11 | 3 | Cola | 8 oz. | Caffeine | 7.0 | 1 | 7.0 |
| 5 | June. 12 | 3 | Cola | 8 oz. | Caffeine | 6.5 | 1 | 6.5 |
| 6 | June. 13 | 3 | Cola | 8 oz. | Caffeine | 6.0 | 1 | 6.0 |
| 7 | June. 14 | 3 | Cola | 8 oz. | Caffeine | 5.5 | 1 | 5.5 |

*Fig. 10*

Name: Jane Doe     Code: 582215

| Day | Date | Meal | Product | Dose | Substance | Per Dose (Units) | Total Doses | Daily Total (Units) |
|---|---|---|---|---|---|---|---|---|
| 1 | May. 20 | 1 | Fruit Juice | 8 oz. | Sugar | 5.0 | 1 | 5.0 |
| 2 | May. 21 | 1 | Fruit Juice | 8 oz. | Sugar | 4.75 | 1 | 4.75 |
| 3 | May. 22 | 1 | Fruit Juice | 8 oz. | Sugar | 4.5 | 1 | 4.5 |
| 4 | May. 23 | 1 | Fruit Juice | 8 oz. | Sugar | 4.25 | 1 | 4.25 |
| 5 | May. 24 | 1 | Fruit Juice | 8 oz. | Sugar | 4.0 | 1 | 4.0 |
| 6 | May. 25 | 1 | Fruit Juice | 8 oz. | Sugar | 3.75 | 1 | 3.75 |
| 7 | May. 26 | 1 | Fruit Juice | 8 oz. | Sugar | 3.5 | 1 | 3.5 |
| 1 | May. 20 | 2 | Custard | 3 oz. | Sugar | 3.5 | 2 | 7.0 |
| 2 | May. 21 | 2 | Custard | 3 oz. | Sugar | 3.0 | 2 | 6.0 |
| 3 | May. 22 | 2 | Custard | 3 oz. | Sugar | 2.5 | 2 | 5.0 |
| 4 | May. 23 | 2 | Custard | 3 oz. | Sugar | 2.0 | 2 | 4.0 |
| 5 | May. 24 | 2 | Custard | 3 oz. | Sugar | 1.5 | 2 | 3.0 |
| 6 | May. 25 | 2 | Custard | 3 oz. | Sugar | 1.0 | 2 | 2.0 |
| 7 | May. 26 | 2 | Custard | 3 oz. | Sugar | 0.5 | 2 | 1.0 |
| 1 | May. 20 | 3 | Hard Candy | 1 | Sugar | 3.0 | 3 | 9.0 |
| 2 | May. 21 | 3 | Hard Candy | 1 | Sugar | 2.8 | 3 | 8.4 |
| 3 | May. 22 | 3 | Hard Candy | 1 | Sugar | 2.7 | 3 | 8.1 |
| 4 | May. 23 | 3 | Hard Candy | 1 | Sugar | 2.5 | 3 | 7.5 |
| 5 | May. 24 | 3 | Hard Candy | 1 | Sugar | 2.3 | 3 | 6.9 |
| 6 | May. 25 | 3 | Hard Candy | 1 | Sugar | 2.2 | 3 | 6.6 |
| 7 | May. 26 | 3 | Hard Candy | 1 | Sugar | 2.0 | 3 | 6.0 |

Fig. 13

Name: Jane Doe                                                                                       Code: 582215

| Day | Date | Meal | Product | Dose | Substance | Per Dose (Units) | Total Doses | Daily Total (Units) |
|---|---|---|---|---|---|---|---|---|
| 1 | Nov. 3 | 1 | Soup | 1 c. | Capsaicin | 1.0 | 1 | 1.0 |
| 2 | Nov. 4 | 1 | Soup | 1 c. | Capsaicin | 1.25 | 1 | 1.25 |
| 3 | Nov. 5 | 1 | Soup | 1 c. | Capsaicin | 1.5 | 1 | 1.5 |
| 4 | Nov. 6 | 1 | Soup | 1 c. | Capsaicin | 1.75 | 1 | 1.75 |
| 5 | Nov. 7 | 1 | Soup | 1 c. | Capsaicin | 2.0 | 1 | 2.0 |
| 6 | Nov. 8 | 1 | Soup | 1 c. | Capsaicin | 2.25 | 1 | 2.25 |
| 7 | Nov. 9 | 1 | Soup | 1 c. | Capsaicin | 2.5 | 1 | 2.5 |
| 1 | Nov. 3 | 2 | Meat Loaf | 3 oz. | Capsaicin | 0.17 | 3 | 0.51 |
| 2 | Nov. 4 | 2 | Meat Loaf | 3 oz. | Capsaicin | 0.33 | 3 | 0.99 |
| 3 | Nov. 5 | 2 | Meat Loaf | 3 oz. | Capsaicin | 0.5 | 3 | 1.5 |
| 4 | Nov. 6 | 2 | Meat Loaf | 3 oz. | Capsaicin | 0.75 | 3 | 2.25 |
| 5 | Nov. 7 | 2 | Meat Loaf | 3 oz. | Capsaicin | 1.1 | 3 | 3.3 |
| 6 | Nov. 8 | 2 | Meat Loaf | 3 oz. | Capsaicin | 1.25 | 3 | 3.75 |
| 7 | Nov. 9 | 2 | Meat Loaf | 3 oz. | Capsaicin | 1.4 | 3 | 4.2 |
| 1 | Nov. 3 | 3 | Chili | 4 oz. | Capsaicin | 1.0 | 2 | 2.0 |
| 2 | Nov. 4 | 3 | Chili | 4 oz. | Capsaicin | 1.25 | 2 | 2.5 |
| 3 | Nov. 5 | 3 | Chili | 4 oz. | Capsaicin | 1.8 | 2 | 3.6 |
| 4 | Nov. 6 | 3 | Chili | 4 oz. | Capsaicin | 2.5 | 2 | 5.0 |
| 5 | Nov. 7 | 3 | Chili | 4 oz. | Capsaicin | 3.4 | 2 | 6.8 |
| 6 | Nov. 8 | 3 | Chili | 4 oz. | Capsaicin | 3.5 | 2 | 7.0 |
| 7 | Nov. 9 | 3 | Chili | 4 oz. | Capsaicin | 3.6 | 2 | 7.2 |

Fig. 16

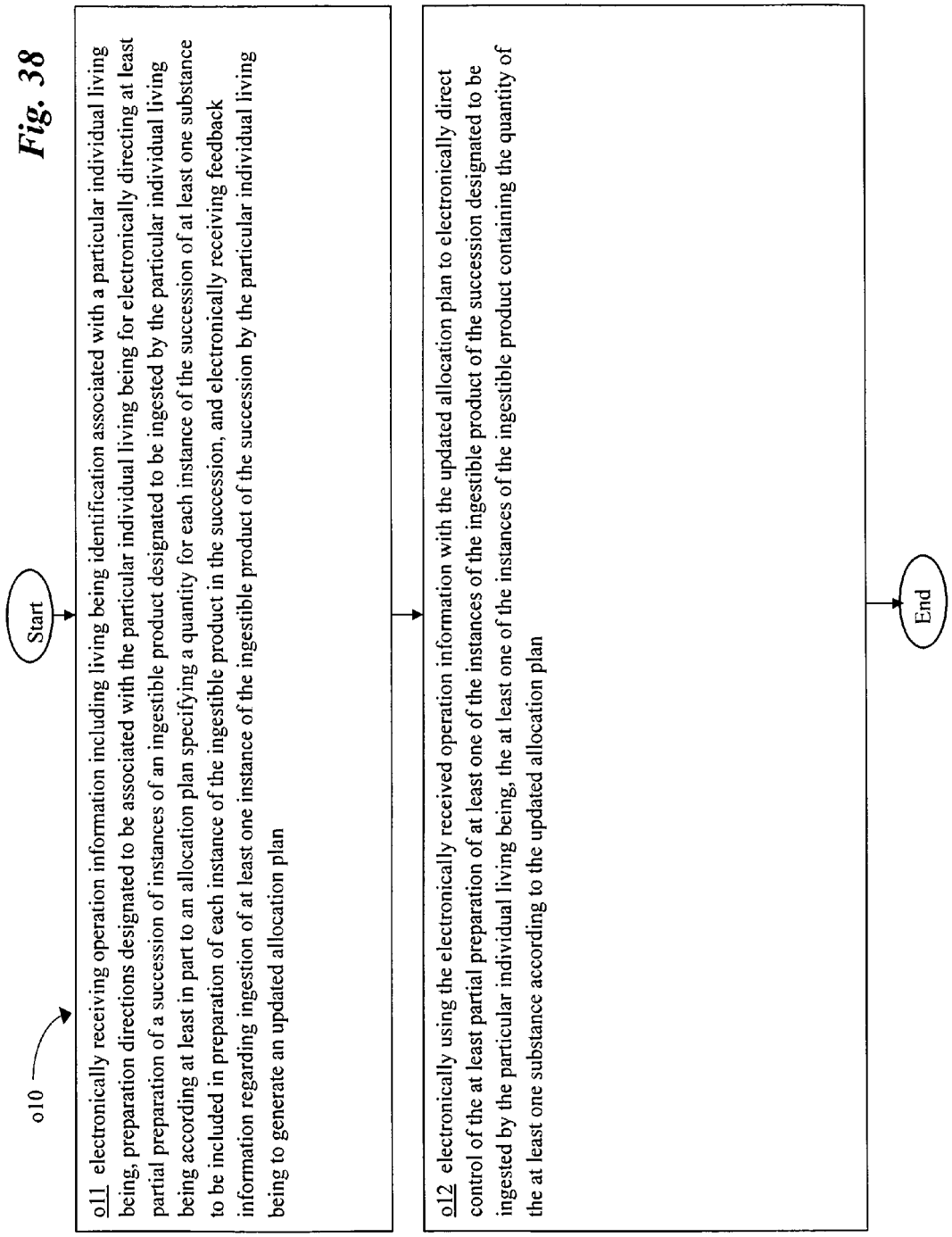

Fig. 38 o10 o11 electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan o12 electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan

*Fig. 45* o11

Start electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan o1119 electronically receiving the operation information including the allocation plan associated with an RFID tag o1120 electronically receiving the operation information including the allocation plan associated with a bar code o1121 electronically receiving the operation information including the allocation plan associated with a holographic image End

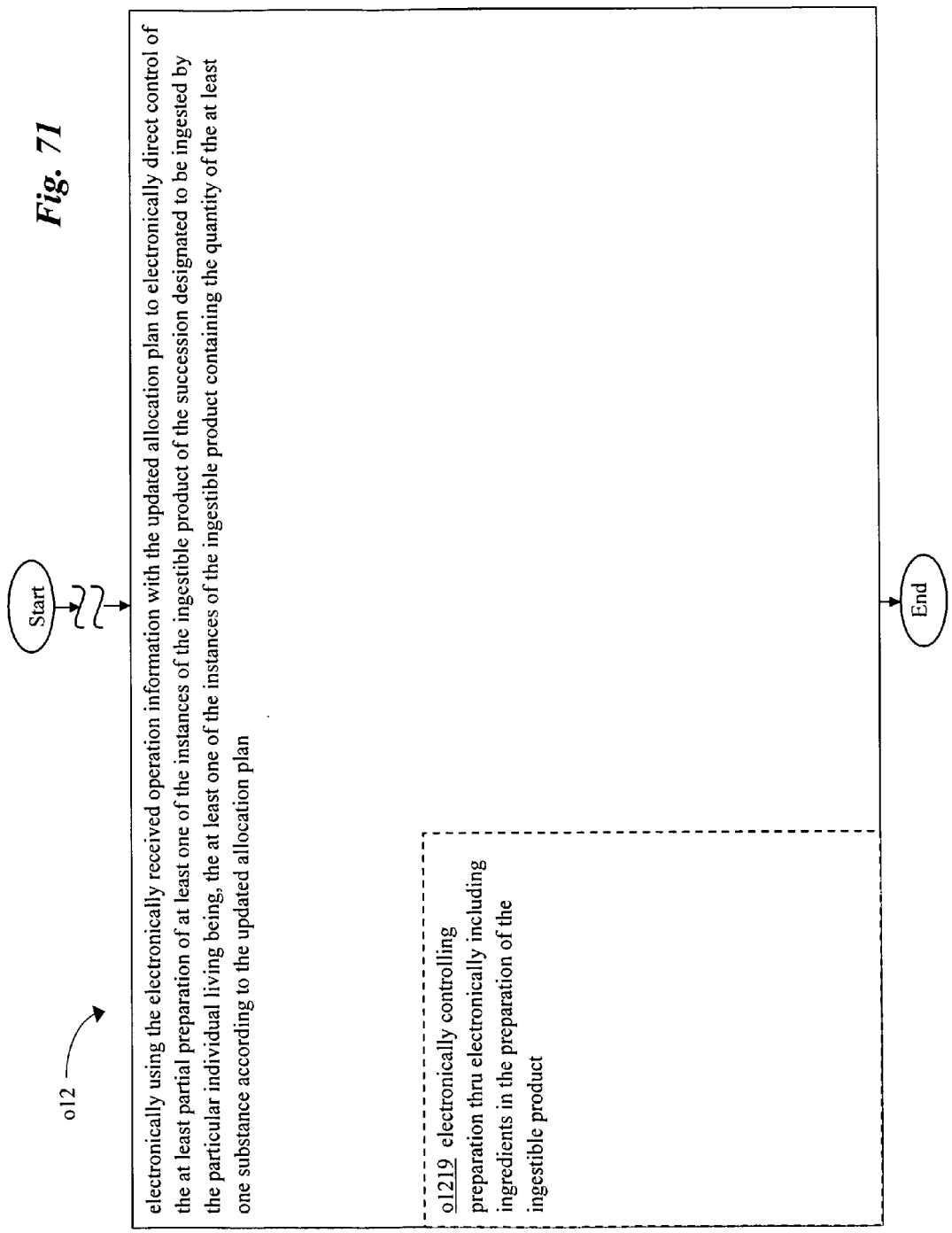

SUBSTANCE ALLOCATION SYSTEM AND METHOD FOR INGESTIBLE PRODUCT PREPARATION SYSTEM AND METHOD

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/199,361, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 26 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,481, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 30 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,545, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,544, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,106, entitled SUBSTANCE CONTROL SYSTEM AND METHOD FOR DISPENSING SYSTEMS, naming Paul Holman, Royce A. Levien, Mark A. Malamud, Neal Stephenson, and Christopher Charles Young as inventors, filed 16 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,113, entitled SUBSTANCE CONTROL SYSTEM AND METHOD FOR DISPENSING SYSTEMS, naming Paul Holman, Royce A. Levien, Mark A. Malamud, Neal Stephenson, and Christopher Charles Young as inventors, filed 16 Sep. 2011 now U.S. Pat. No. 8,892,249, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,829, entitled CLEANING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 30 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,830, entitled CLEANING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 30 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,906, entitled TREATMENT SYSTEM AND METHOD FOR INGESTIBLE PRODUCT DISPENSING SYSTEM AND METHOD, naming Paul Holman, Royce A. Levien, Mark A. Malamud, Neal Stephenson, and Christopher Charles Young as inventors, filed 3 Oct. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,907, entitled TREATMENT SYSTEM AND METHOD FOR INGESTIBLE PRODUCT DISPENSING SYSTEM AND METHOD, naming Paul Holman, Royce A. Levien, Mark A. Malamud, Neal Stephenson, and Christopher Charles Young as inventors, filed 3 Oct. 2011, which is currently co-pending or is an application of which a currently co-pending application is entitled to the benefit of the filing date.

For purposes of the USPTO extra-statutory requirements, the present application constitutes a continuation of U.S. patent application Ser. No. 13/317,545 entitled SUBSTANCE ALLOCATION SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, AND CHRISTOPHER CHARLES YOUNG as inventors, filed 19

Oct. 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A method includes, but is not limited to electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan; and electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan.

In one or more various aspects, related machines, compositions of matter, or manufactures of systems may include, but are not limited to, virtually any combination of hardware, software, and/or firmware configured to effect the herein-referenced method aspects depending upon the design choices of the system designer (limited to patentable subject matter under 35 USC 101).

A system includes, but is not limited to: means for electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan; and means for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan. In addition to the foregoing, other system aspects are described in the claims, drawings, and text forming a part of the present disclosure.

A system includes, but is not limited to a receiving information electrical circuitry arrangement for electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan; and a controlling preparation electrical circuitry arrangement for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan. In addition to the foregoing, other system aspects are described in the claims, drawings, and text forming a part of the present disclosure.

An article of manufacture including a non-transitory signal-bearing storage medium bearing one or more instructions for electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan; and one or more instructions for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4 is a schematic view of a display screen of the first exemplary implementation of the ingestible product preparation system 10 in FIG. 1 displaying a first exemplary displayed informational table.

FIG. 7 is a schematic view of a display screen of the first exemplary implementation of the ingestible product preparation system 10 in FIG. 1 displaying a first exemplary displayed informational table of the ingestible product preparation system 10 of FIG. 1.

FIG. 10 is a schematic view of a display screen of the first exemplary implementation of the ingestible product preparation system 10 in FIG. 1 displaying a first exemplary displayed informational table of the ingestible product preparation system 10 of FIG. 1.

FIG. 13 is a schematic view of a display screen of the first exemplary implementation of the ingestible product preparation system 10 in FIG. 1 displaying a first exemplary displayed informational table of the ingestible product preparation system 10 of FIG. 1.

FIG. 16 is a schematic view of a display screen of the first exemplary implementation of the ingestible product preparation system 10 in FIG. 1 displaying a first exemplary displayed informational table of the ingestible product preparation system 10 of FIG. 1.

FIG. 38 is a high-level flowchart illustrating an operational flow o10 representing exemplary operations related to electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan, and electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan at least associated with the depicted exemplary implementations of the system.

FIG. 45 is a high-level flowchart including exemplary implementations of operation O11 of FIG. 38.

FIG. 71 is a high-level flowchart including exemplary implementations of operation O12 of FIG. 38.

DETAILED DESCRIPTION

Figure 1:
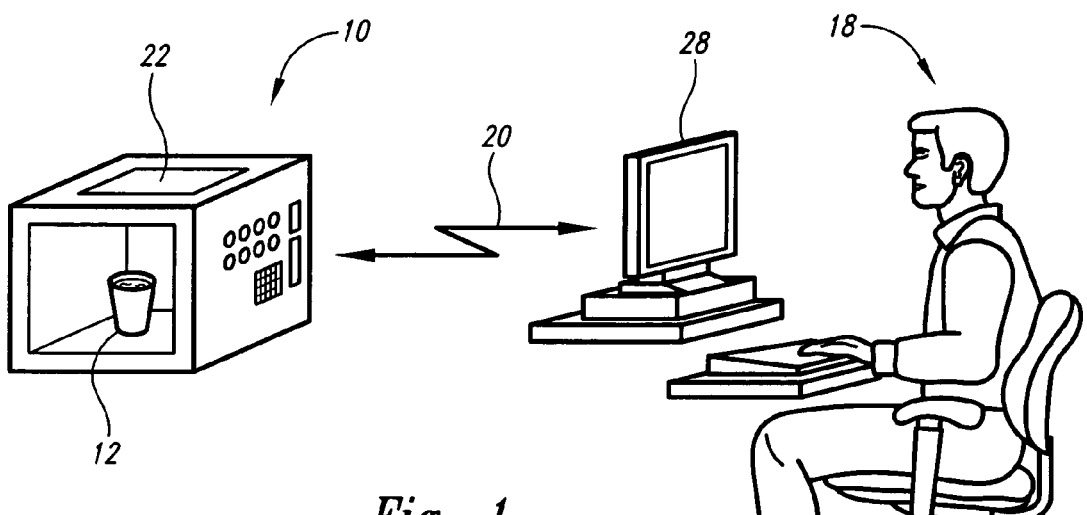
FIG. 1 is a schematic diagram depicting a first application of a first exemplary implementation of a ingestible product preparation system 10 including a substance allocation system therefor.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare and/or dispense ingestible products to be ingested by living beings such as humans, animals, plants, etc are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared and/or dispensed by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Ingestion by the living beings can occur through many pathways including, but not limited to, oral ingestion, transdermal ingestion, peg-tube ingestion, nasal ingestion, anal ingestion, injectable ingestion, tear-duct ingestion, and respiratory ingestion.

Figure 2:
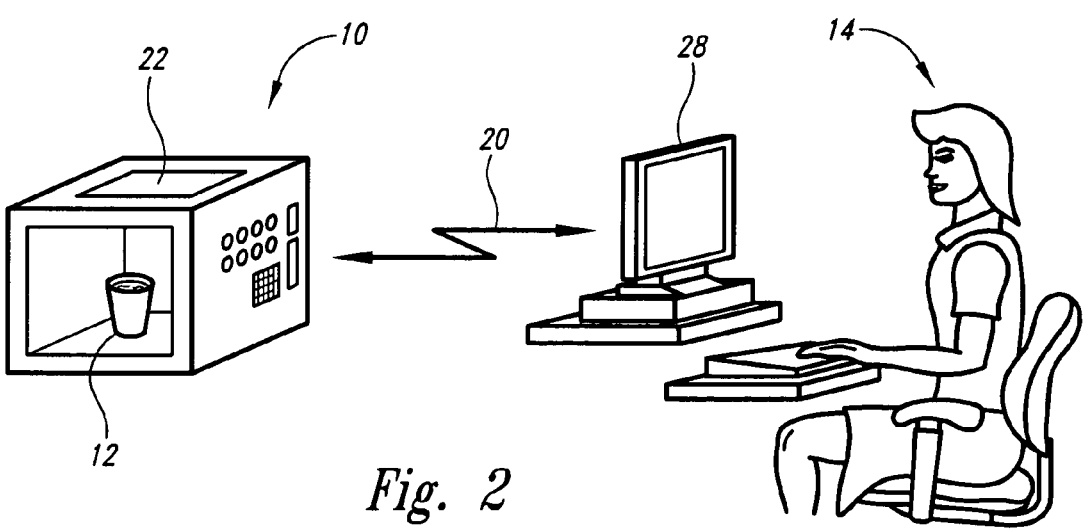
FIG. 2 is a schematic diagram depicting a second application of a first exemplary implementation of the ingestible product preparation system 10 of FIG. 1 including a substance allocation system therefor.
Figure 3:
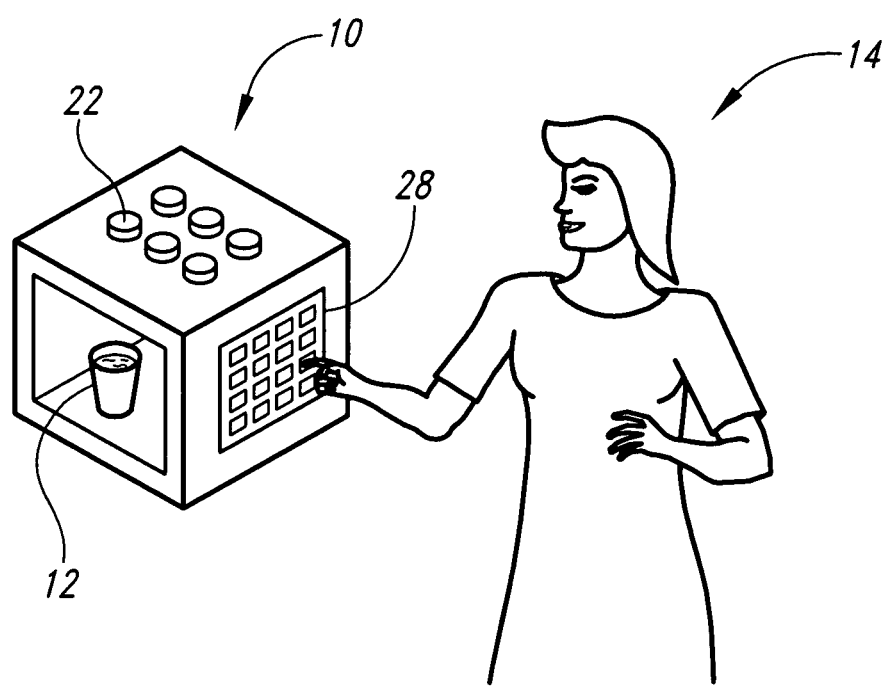
FIG. 3 is a schematic diagram depicting a second exemplary implementation of the ingestible product preparation system 10 of FIG. 1 including a substance allocation system therefor.
Figure 5:
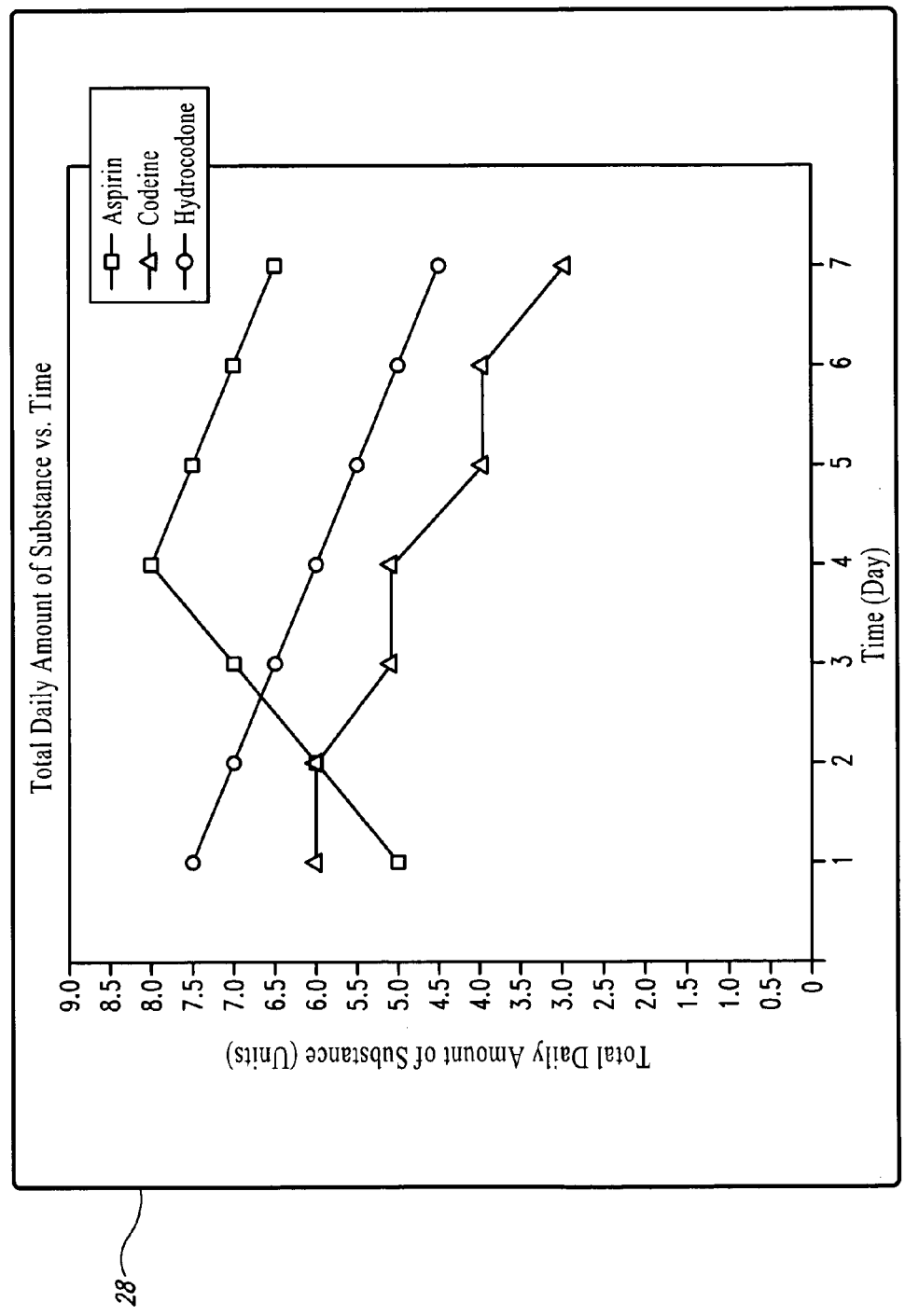
FIG. 5 is a schematic view of a display screen of the first exemplary implementation of the ingestible product preparation system 10 in FIG. 1 displaying a first exemplary displayed informational graph associated with the first exemplary displayed informational table of FIG. 4.
Figure 6:
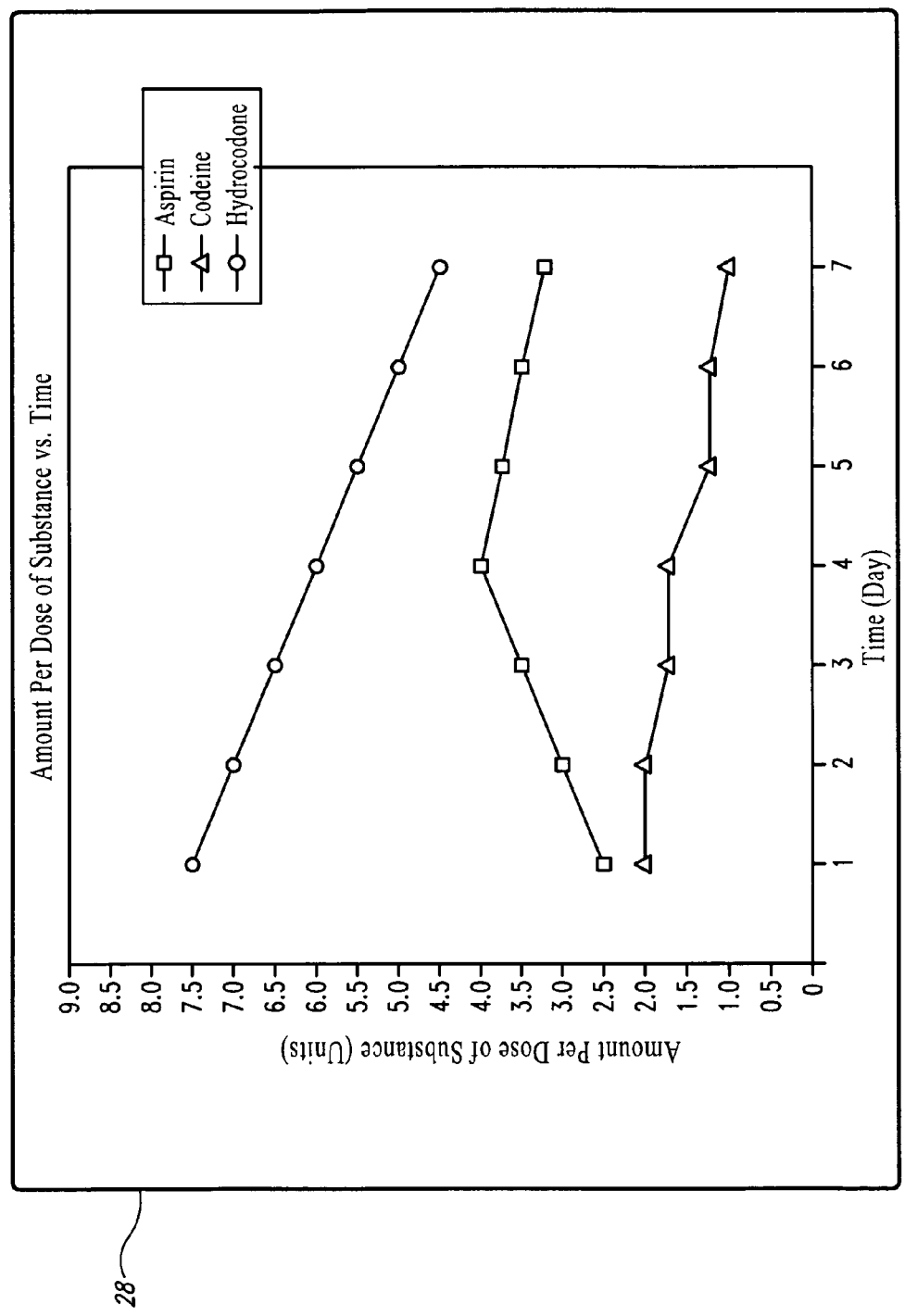
FIG. 6 is a schematic view of a display screen of the first exemplary implementation of the ingestible product preparation system 10 in FIG. 1 displaying a second exemplary displayed informational graph associated with the first exemplary displayed informational table of FIG. 4.
Figure 8:
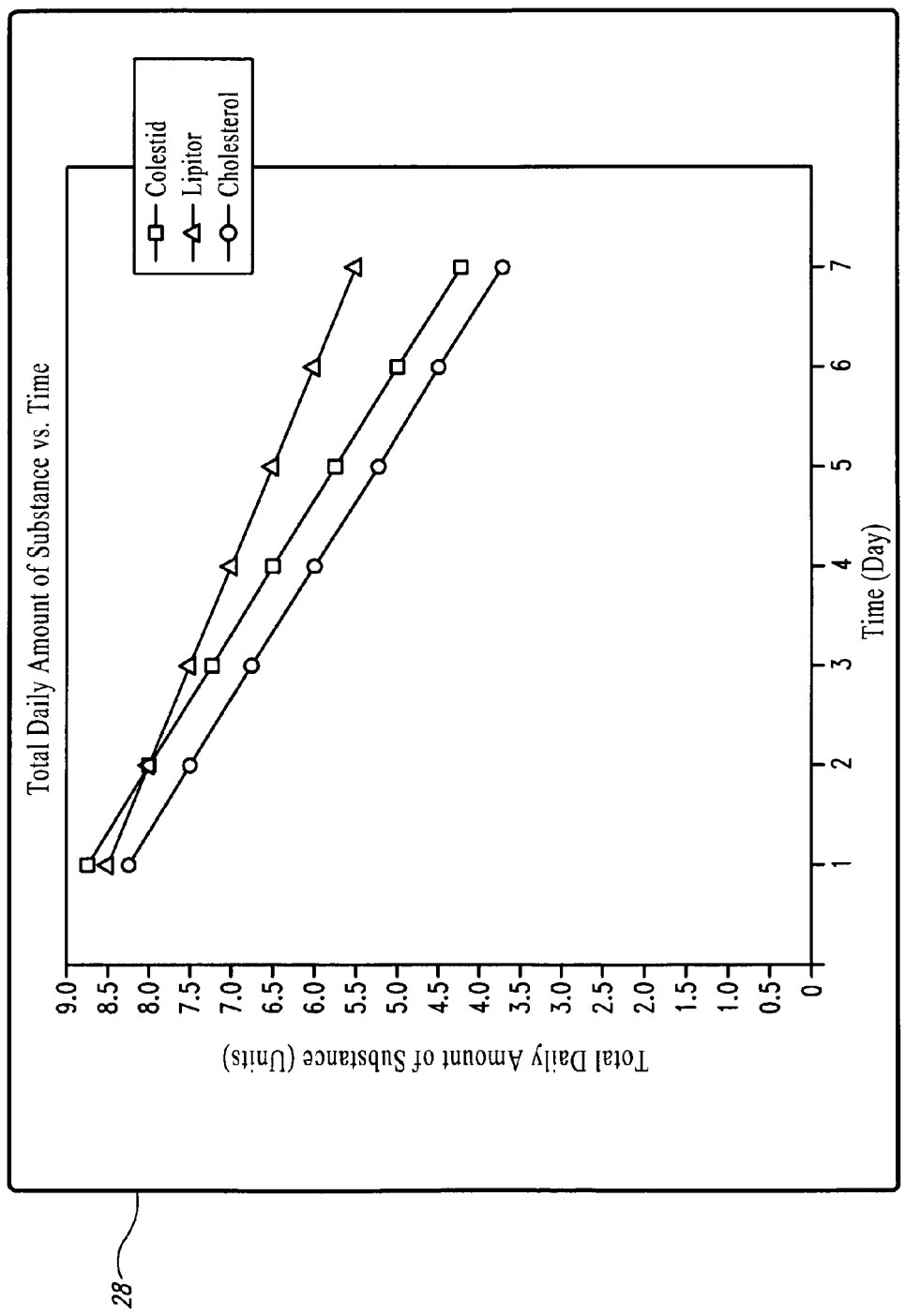
FIG. 8 is a schematic view of a display screen of the first exemplary implementation of the ingestible product preparation system 10 in FIG. 1 displaying a first exemplary displayed informational graph associated with the first exemplary displayed informational table of FIG. 7.
Figure 9:
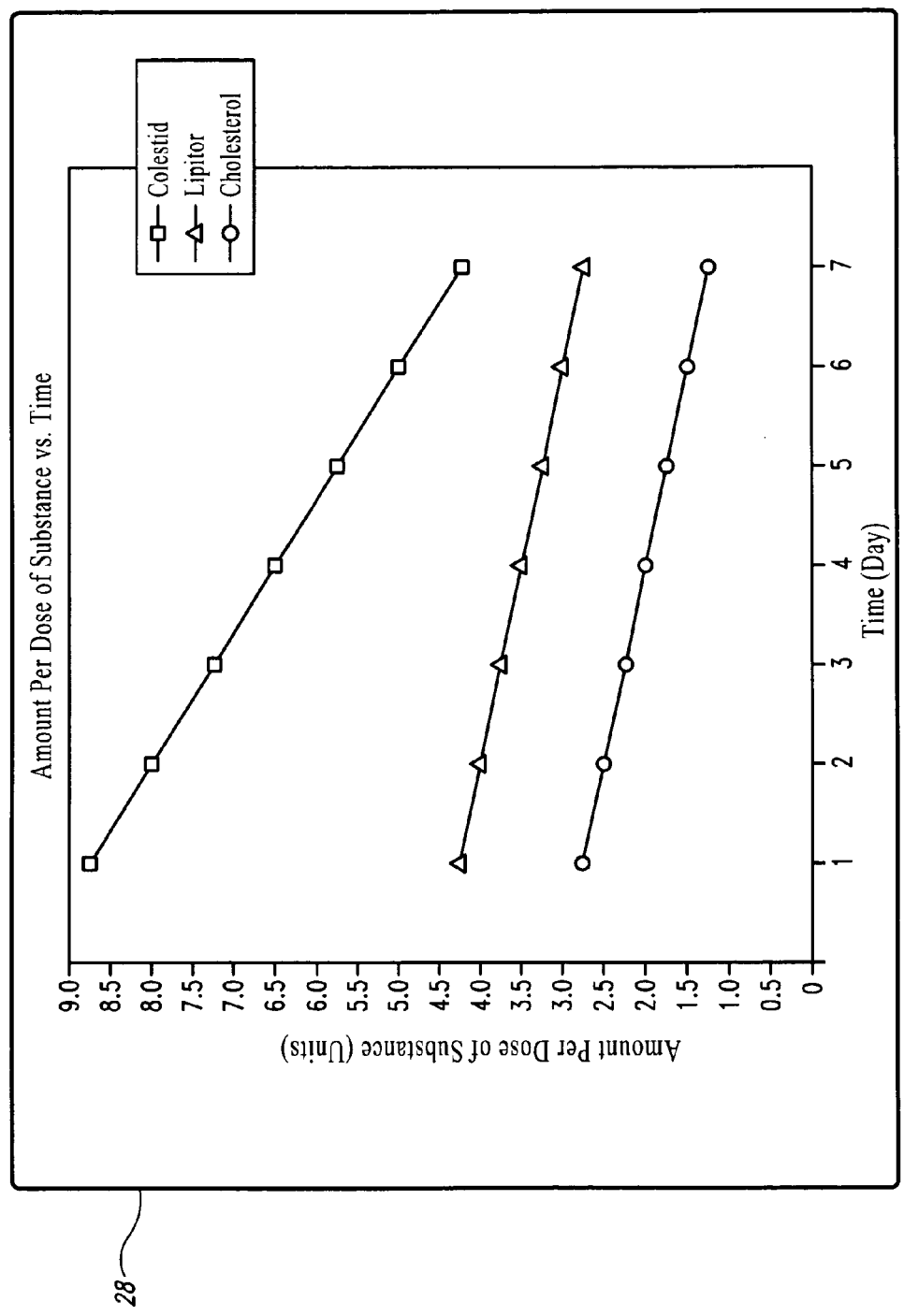
FIG. 9 is a schematic view of a display screen of the first exemplary implementation of the ingestible product preparation system 10 in FIG. 1 displaying a second exemplary displayed informational graph associated with the first exemplary displayed informational table of FIG. 7.
Figure 11:
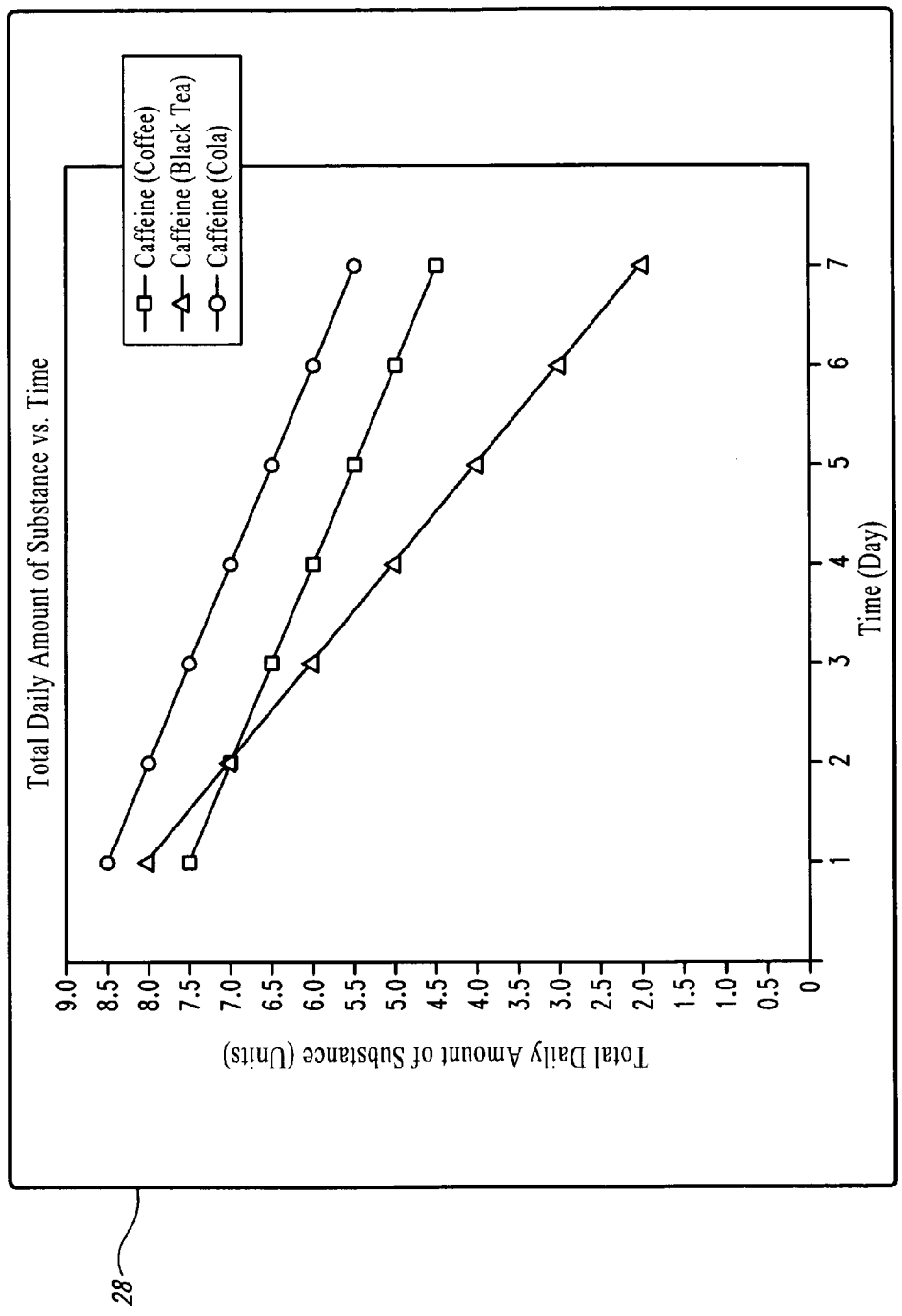
FIG. 11 is a schematic view of a display screen of the first exemplary implementation of the ingestible product preparation system 10 in FIG. 1 displaying a first exemplary displayed informational graph associated with the first exemplary displayed informational table of FIG. 10.
Figure 12:
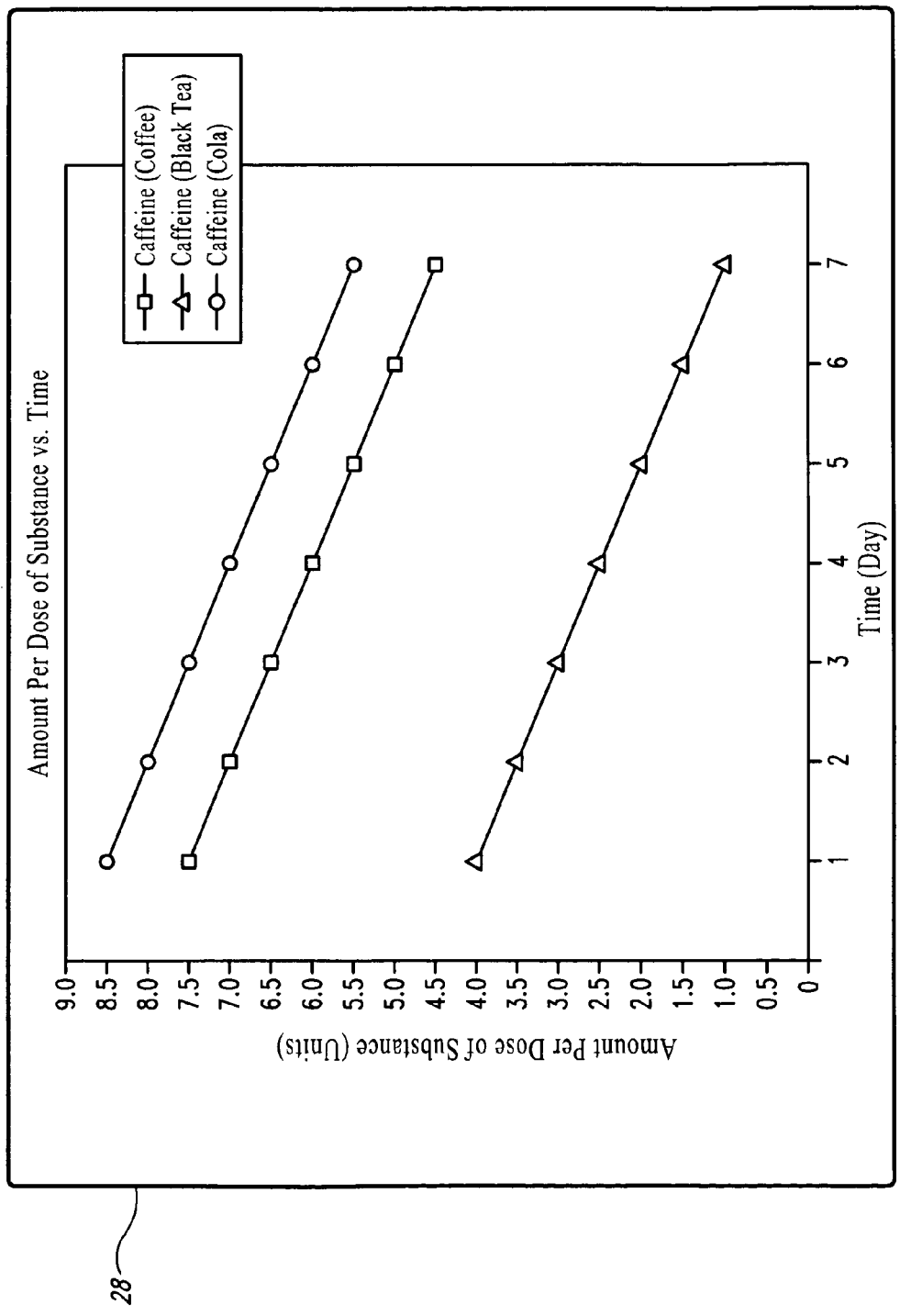
FIG. 12 is a schematic view of a display screen of the first exemplary implementation of the ingestible product preparation system 10 in FIG. 1 displaying a second exemplary displayed informational graph associated with the first exemplary displayed informational table of FIG. 10.
Figure 14:
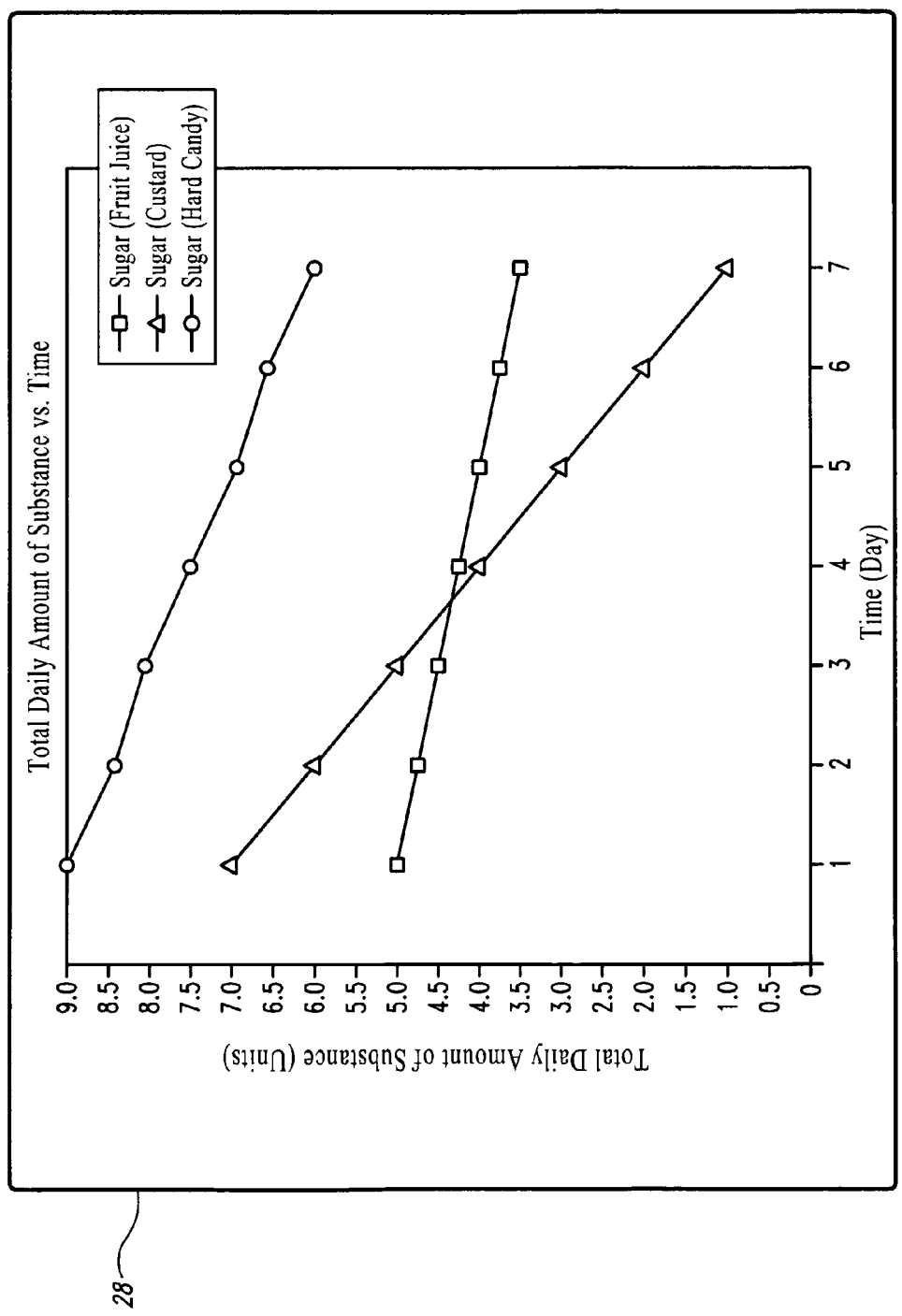
FIG. 14 is a schematic view of a display screen of the first exemplary implementation of the ingestible product preparation system 10 in FIG. 1 displaying a first exemplary displayed informational graph associated with the first exemplary displayed informational table of FIG. 13.
Figure 15:
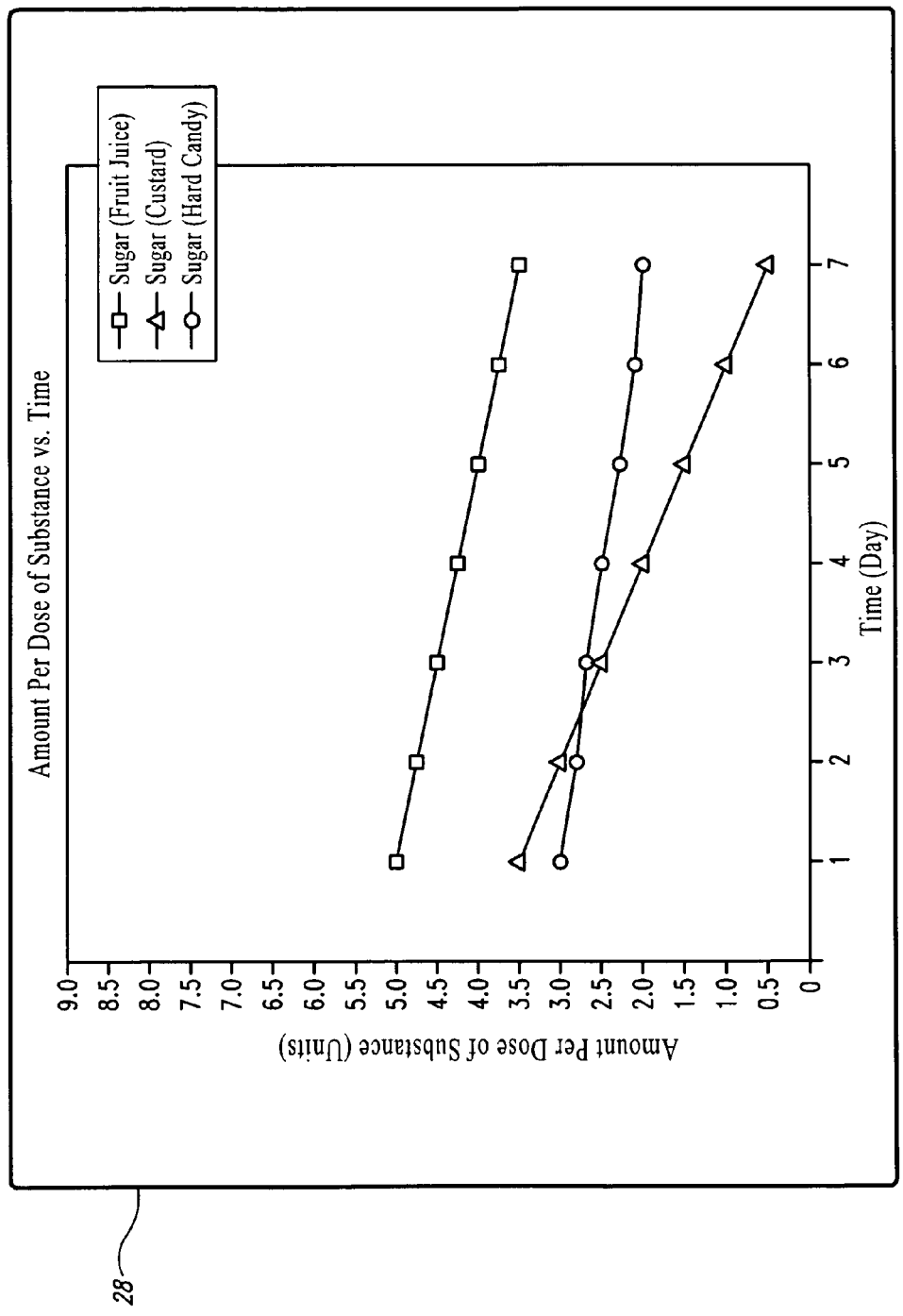
FIG. 15 is a schematic view of a display screen of the first exemplary implementation of the ingestible product preparation system 10 in FIG. 1 displaying a second exemplary displayed informational graph associated with the first exemplary displayed informational table of FIG. 13.
Figure 17:
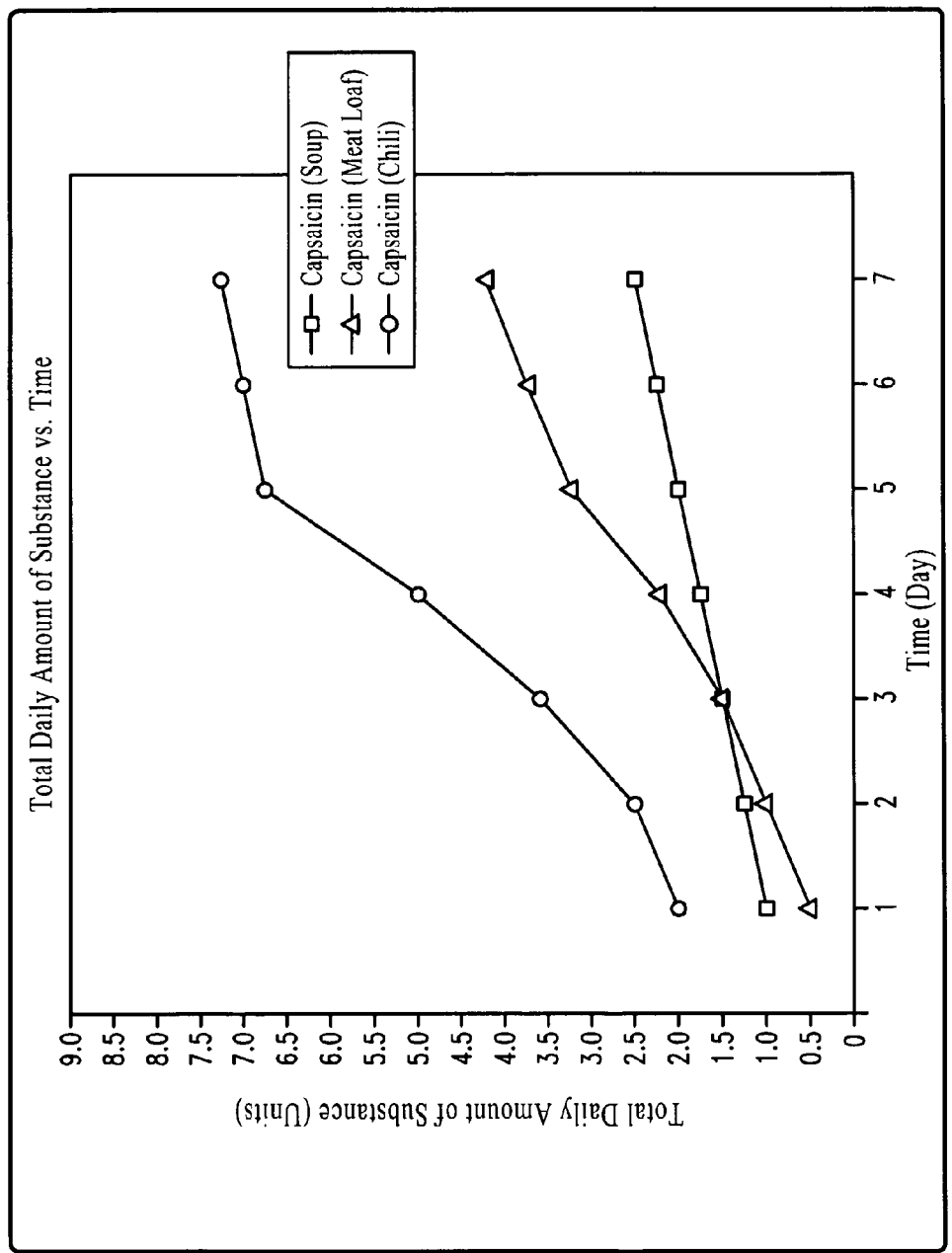
FIG. 17 is a schematic view of a display screen of the first exemplary implementation of the ingestible product preparation system 10 in FIG. 1 displaying a first exemplary displayed informational graph associated with the first exemplary displayed informational table of FIG. 16.
Figure 18:
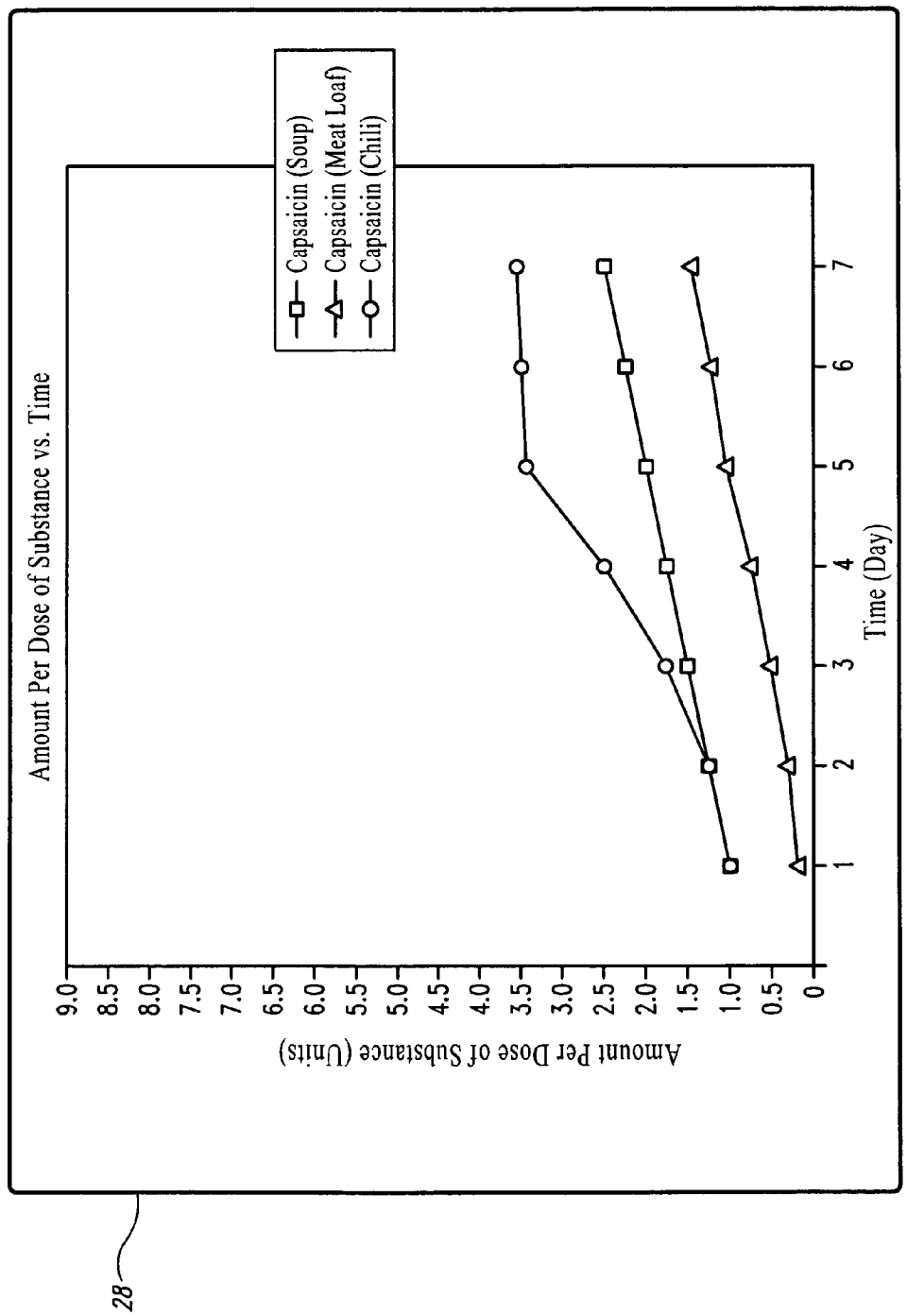
FIG. 18 is a schematic view of a display screen of the first exemplary implementation of the ingestible product preparation system 10 in FIG. 1 displaying a second exemplary displayed informational graph associated with the first exemplary displayed informational table of FIG. 16.

As depicted in FIGS. 1-3, exemplary implementations of an ingestible product preparation system 10 are shown to prepare and dispense ingestible products such as a liquid drink 12 to be consumed by a particular individual living being, such as a human being 14 (such as a user, etc.) shown. Other sorts of ingestible products can include but are not limited to sandwiches, full meals, food bars, meal replacements, snacks, plant and/or animal based products, nutraceuticals, pharmaceuticals, smoothies, etc. The ingestible product preparation system 10 is further depicted as communicating with an exemplary user 14 or an exemplary advisor 18 (e.g. physician, nurse, nutritionist, health expert, sports coach, etc.) via communication link 20 (e.g. wireless or wired network or direct electronic communication, etc.) and display screen 28. The display screen 28 can include selection indicators configured to provide information to users, such as the human being 14, what ingestible products are available to be prepared and dispensed (in some implementations prepared such as from ingredient containers 22) and to provide other sorts of information discussed herein. The display screen 28 can display textual and graphic information such as including but not limited to menu screens allowing users to select various dispensing (including in some implementations preparation) options and information requests. Other implementations can include other devices and methods for information input and output including those further discussed below.

In implementations, the ingestible product preparation system 10 includes programming capability to allow users and/or advisors to plan for modifications of content levels of one or more substances used in preparation of various ingestible products. For instance, in an exemplary application salt, sugar, or other substance could be reduced according to an allocation plan over a succession of instances of preparation of a particular ingestible product such as a hamburger or smoothie. In contrast, other substances such as a drug, vitamin, herb, etc. may be increased according to another allocation plan over a succession of preparation instances of another sort of particular ingestible product such as increasing vitamin C or capsaicin content of a bowl of chili. The ingestible product preparation system 10 further can be programmed to receive some type of feedback in order to adjust allocation plans according to the feedback. For instance, feedback may be collected through active user input (e.g. keyboard, textual, audio, graphical user interface, etc.) or passive user input (e.g. image recognition of user behavior, refuse analysis of quantity of wrappers, leftovers, audio analysis of collected unsolicited user comments, etc.). Modifying allocation plans according to feedback can help to insure user compliance or other desirable outcome.

Results, as displayed in tables and graphs, of various exemplary allocations plans are depicted in FIGS. 4-18 in which various substances (drugs (e.g. Colestid, Lipitor, etc.), food components/condiments (e.g. cholesterol, caffeine, sugar, capsaicin, etc.), etc.) are displayed by display screen 28 showing substance reduction or increase over various successions of preparation instances of various ingestible products.

The selection indicators or other display devices can also display selection information including origin, type, certification, classification, etc. of ingestible ingredients and/or products available including information related to various implementations of substance control methods, systems, and articles of manufacture disclosed herein and discussed further below. Device treatment methods and systems can be included with operation of the ingestible product preparation system 10 to allow for choice, at least to a degree, by users regarding the extent and manner that devices and components of the ingestible product preparation system 10 are to be treated prior to preparation of one or more ingestible products. The display screen 28 can also inform users of previously executed treatment procedures and/or prior digestible product preparations. Treatment procedures can include, but are not limited to, various sanitizing, de-odorizing, hygienic, energizing, sterilizing, de-gassing, quarantining, etc. Treatment procedures can also include, but are not limited to, various cleaning procedures directed to other than removing ingestible product and ingredients left behind from previous preparation operations so that the treatment procedures discussed herein address concerns other than typical cleaning procedures involved with cleaning after an ingestible product has been prepared.

Figure 19:
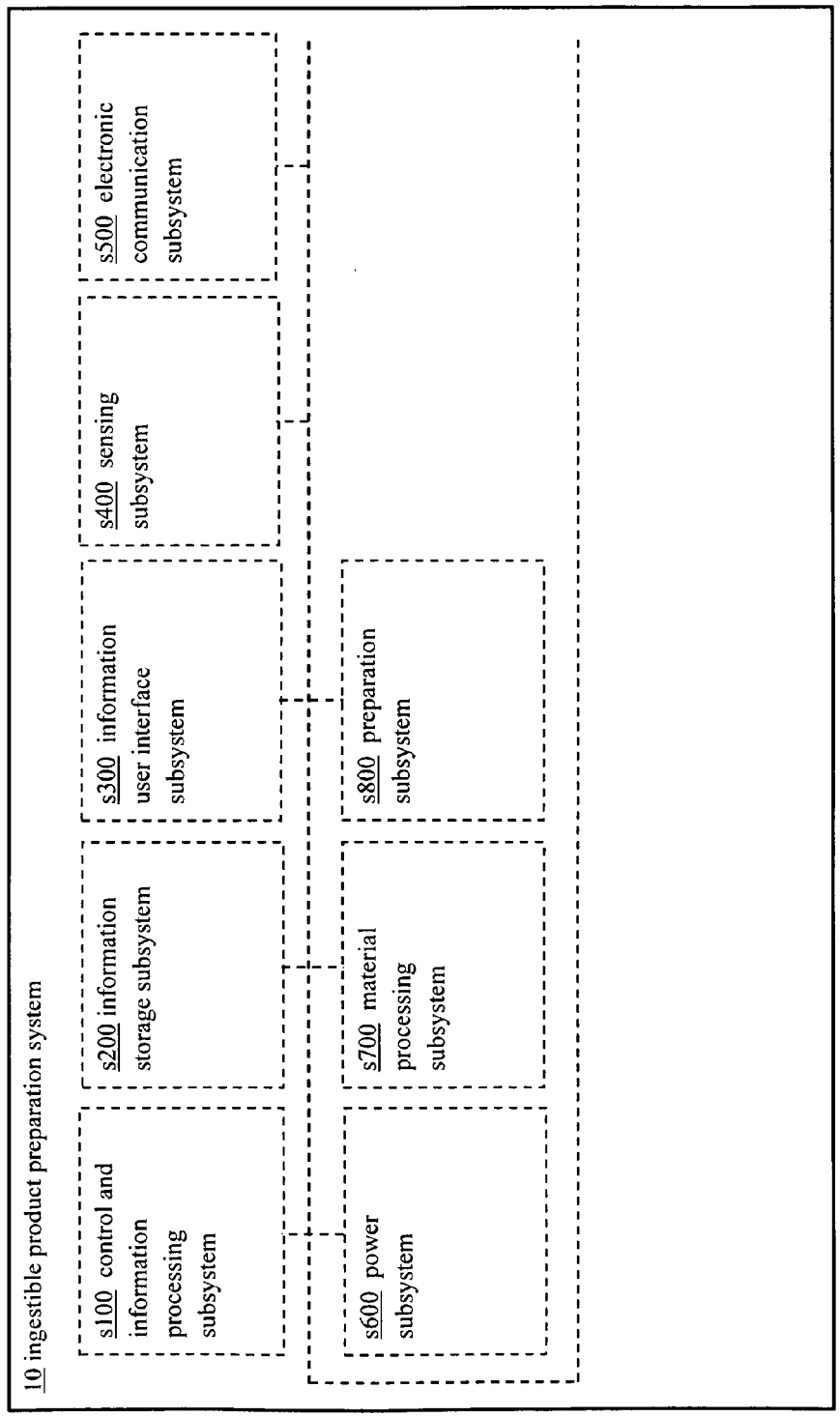
FIG. 19 is a block diagram depicting an exemplary implementation of the ingestible product preparation system 10 of FIG. 1 including exemplary subsystems.

An exemplary version of the ingestible product preparation system 10 is shown in FIG. 19 to optionally include various subsystems such as control and information processing subsystem s100, information storage subsystem s200, information user interface subsystem s300, sensing subsystem s400, electronic communication subsystem s500, power subsystem s600, material processing subsystem s700, and preparation subsystem s800.

Figure 20:
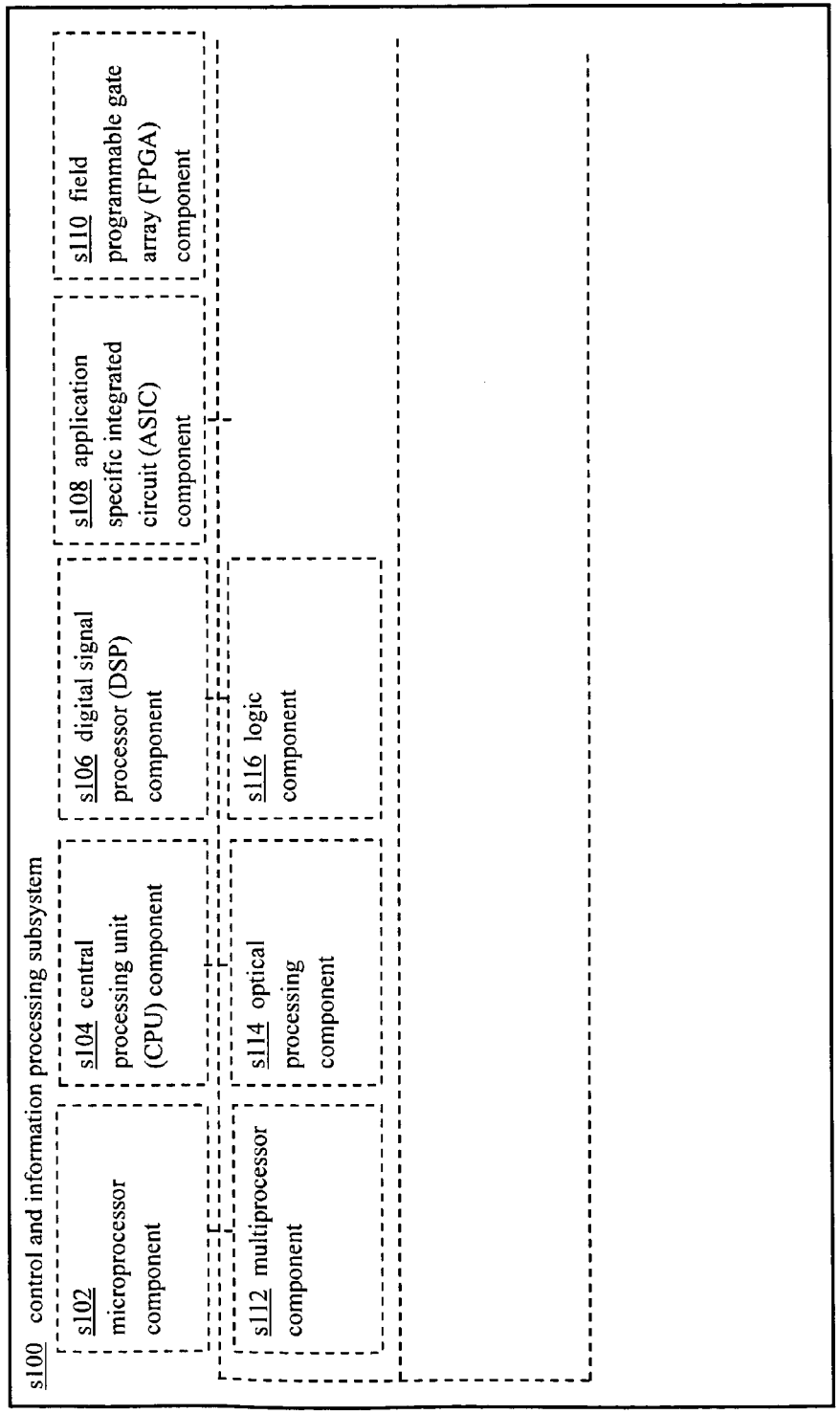
FIG. 20 is a block diagram depicting a control and information processing subsystem s100 of an exemplary implementation of the ingestible product preparation system 10 of FIG. 1.

An exemplary implementation of the control and information processing subsystem s100 is shown in FIG. 20 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, and optical processing component s114.

Figure 21:
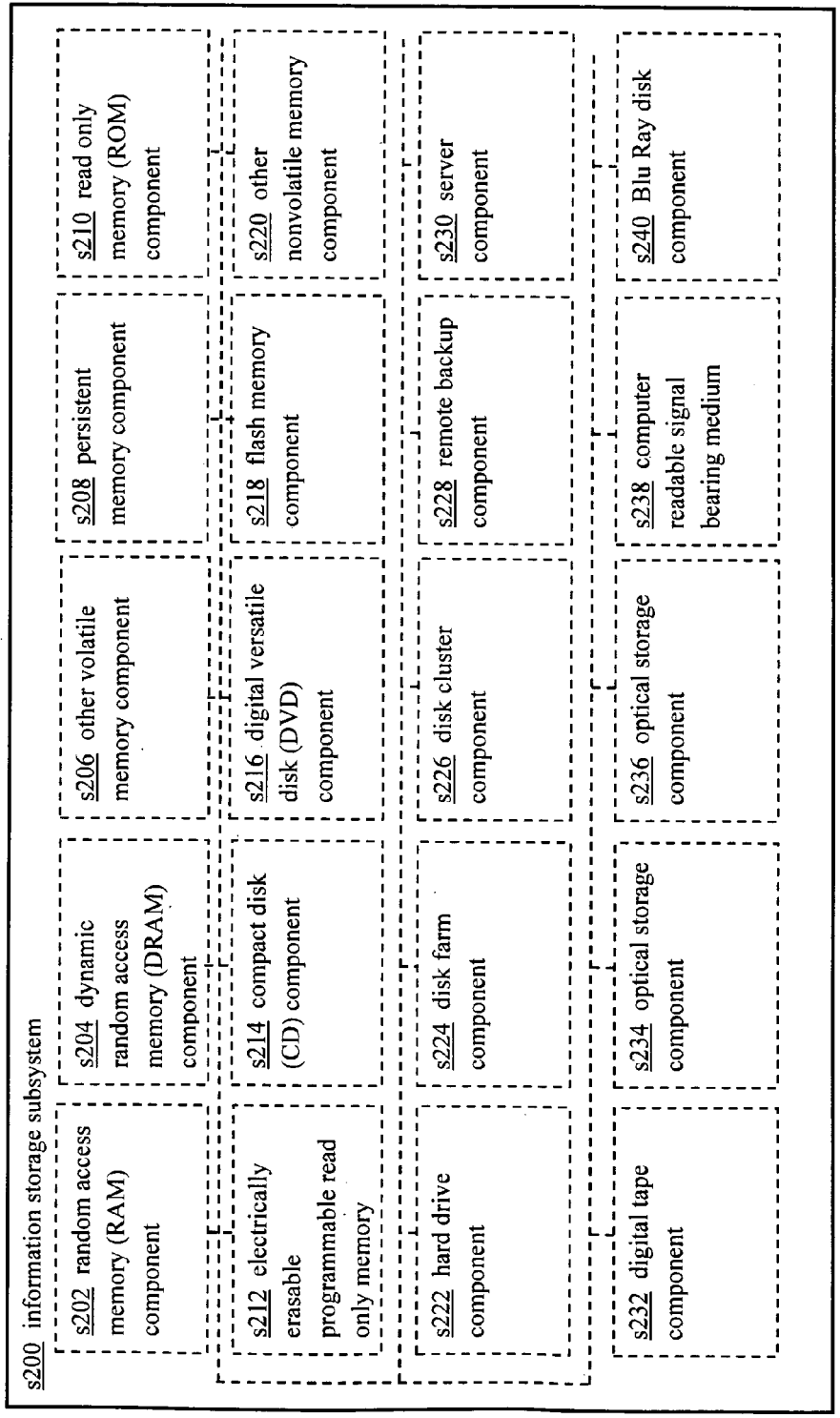
FIG. 21 is a block diagram depicting an information storage subsystem s200 of an exemplary implementation of the ingestible product preparation system 10 of FIG. 1.

An exemplary implementation of the information storage subsystem s200 is shown in FIG. 21 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, optical storage component s236, computer readable signal bearing medium s238, and Blu Ray disk component s240.

Figure 22:
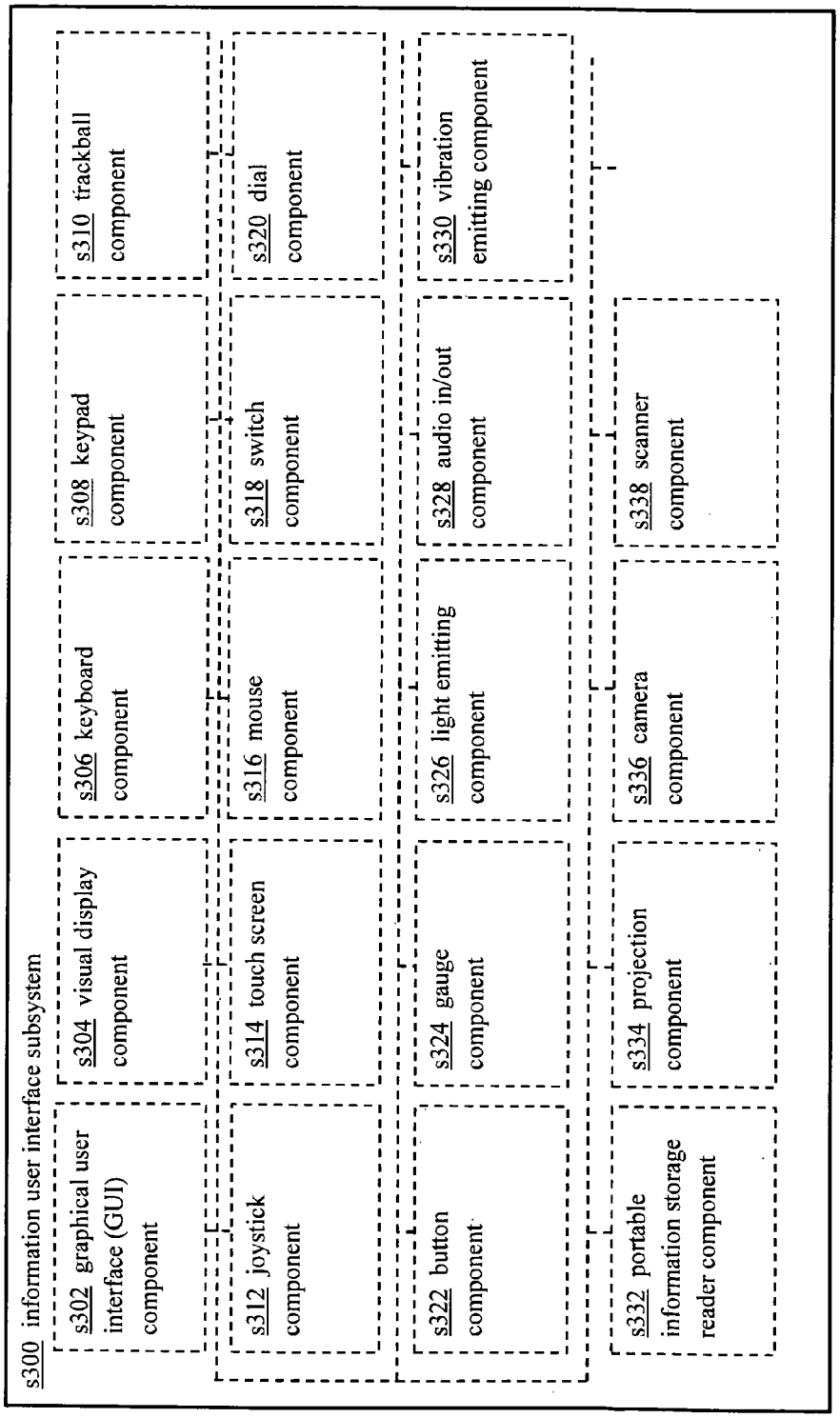
FIG. 22 is a block diagram depicting an information user interface subsystem s300 of an exemplary implementation of the ingestible product preparation system 10 of FIG. 1.

An exemplary implementation of the information user interface subsystem s300 is shown in FIG. 22 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, projection component s334, camera component s336, and scanner component s338.

Figure 23:
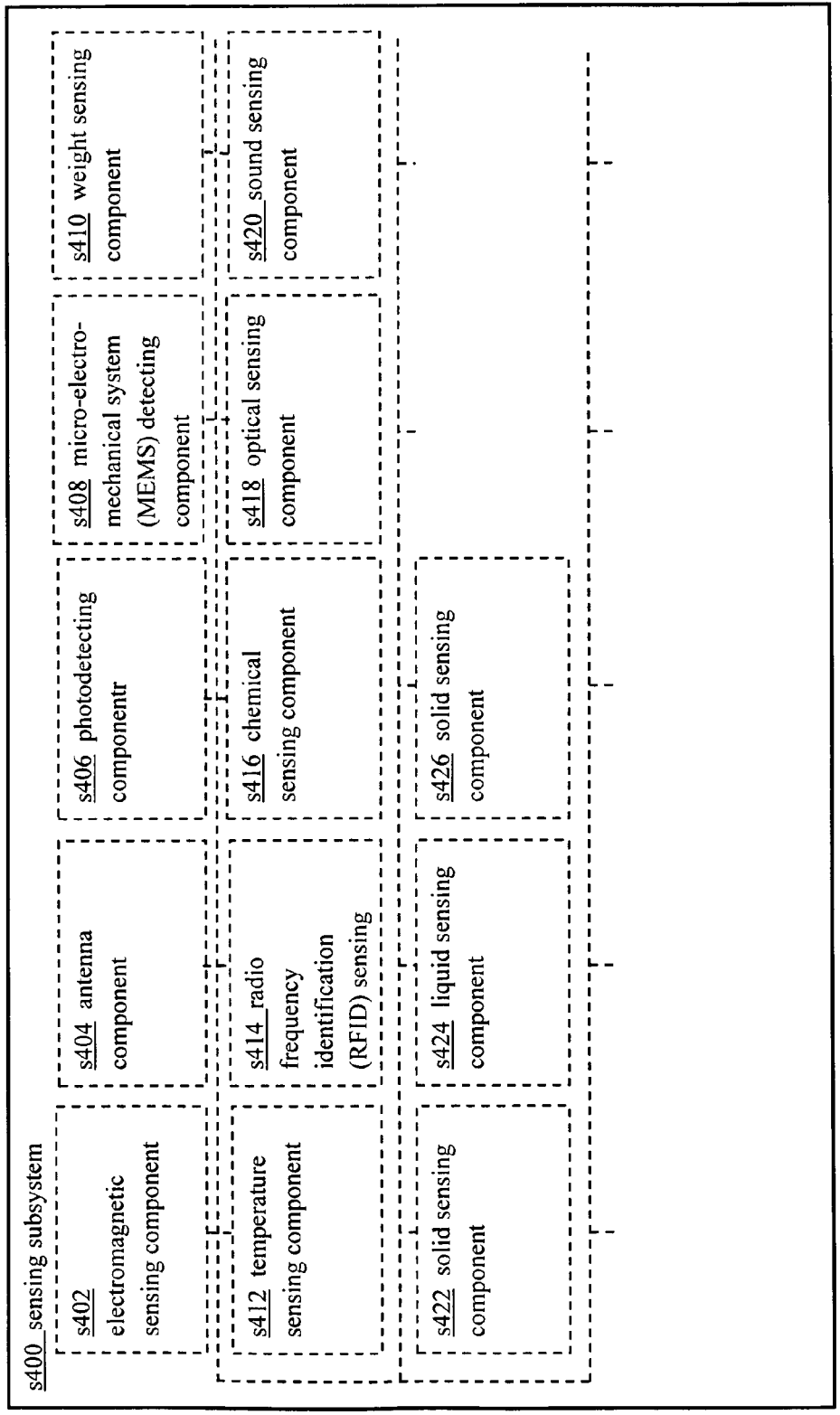
FIG. 23 is a block diagram depicting a sensing subsystem s400 of an exemplary implementation of the ingestible product preparation system 10 of FIG. 1.

An exemplary implementation of the sensing subsystem s400 is shown in FIG. 23 to optionally include various components such as electromagnetic sensing component s402, antenna component s404, photodetecting component s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 24:
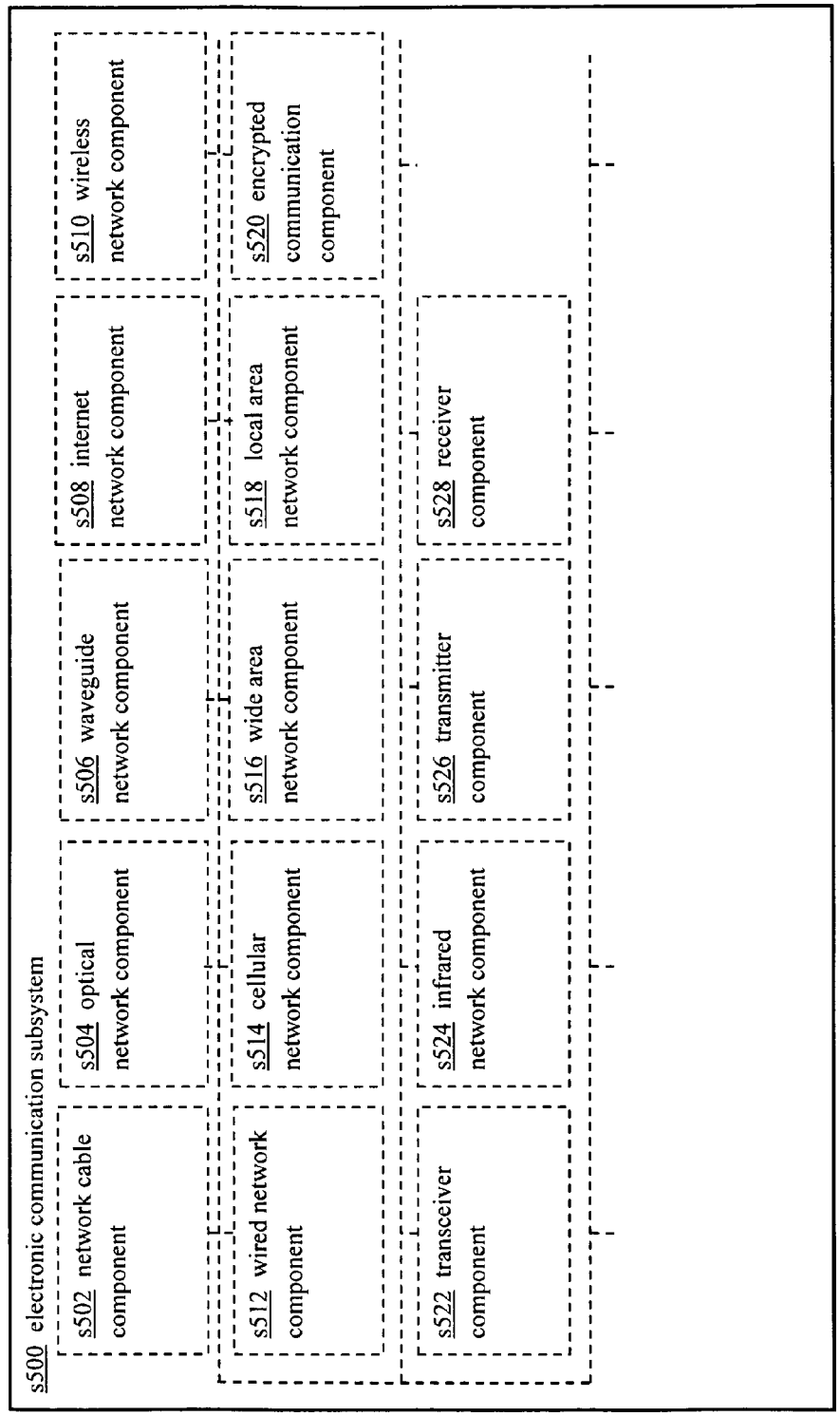
FIG. 24 is a block diagram depicting an electronic communication subsystem s500 of an exemplary implementation of the ingestible product preparation system 10 of FIG. 1.

An exemplary implementation of the electronic communication subsystem s500 is shown in FIG. 24 to optionally include various components such as network cable component s502, optical network component s504, waveguide network component s506, interne network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 25:
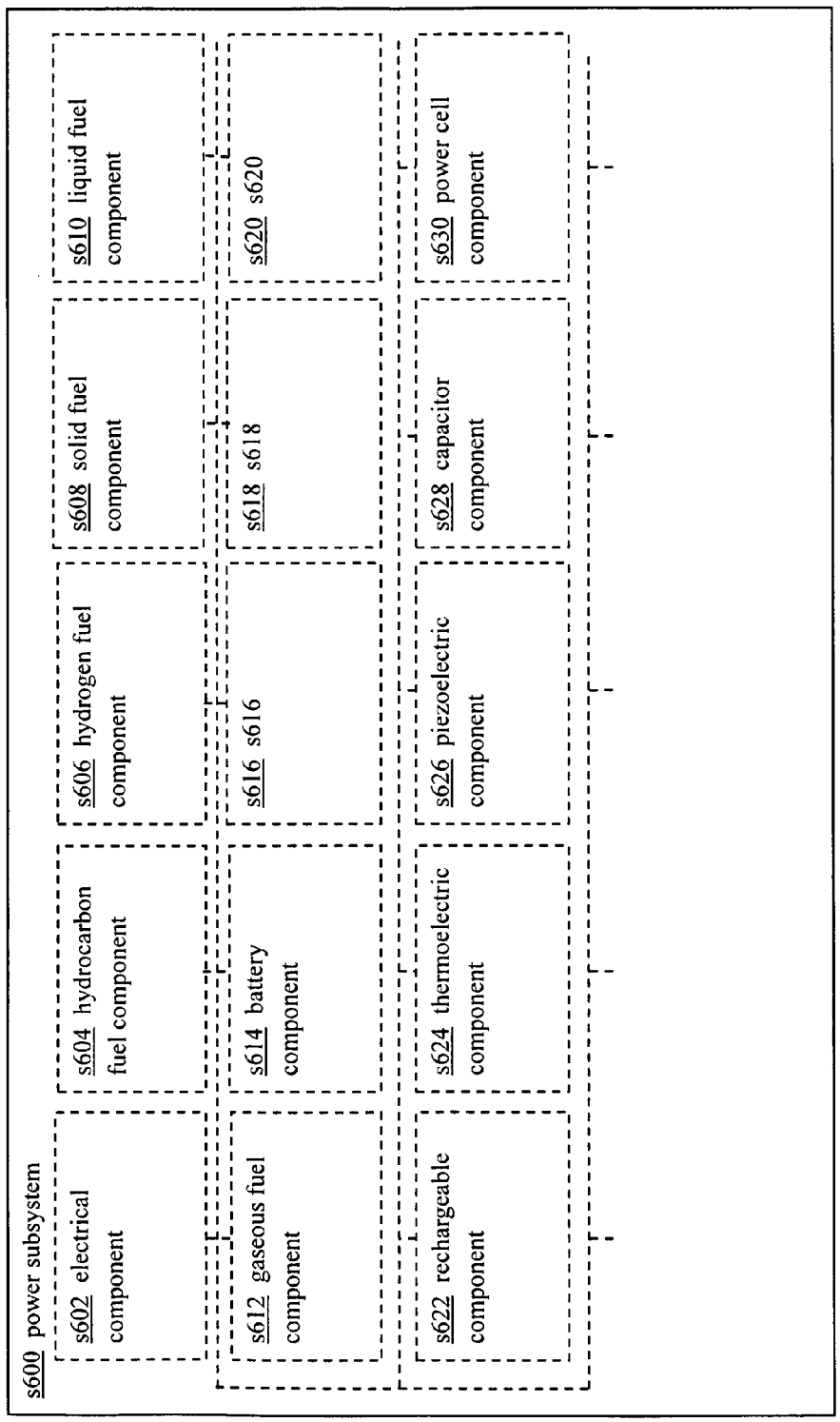
FIG. 25 is a block diagram depicting a power subsystem s600 of an exemplary implementation of the ingestible product preparation system 10 of FIG. 1.

An exemplary implementation of the power subsystem s600 is shown in FIG. 25 to optionally include various components such as electrical component s602, hydrocarbon fuel component s604, hydrogen fuel component s606, solid fuel component s608, liquid fuel component s610, gaseous fuel component s612, and battery component s614.

Figure 26:
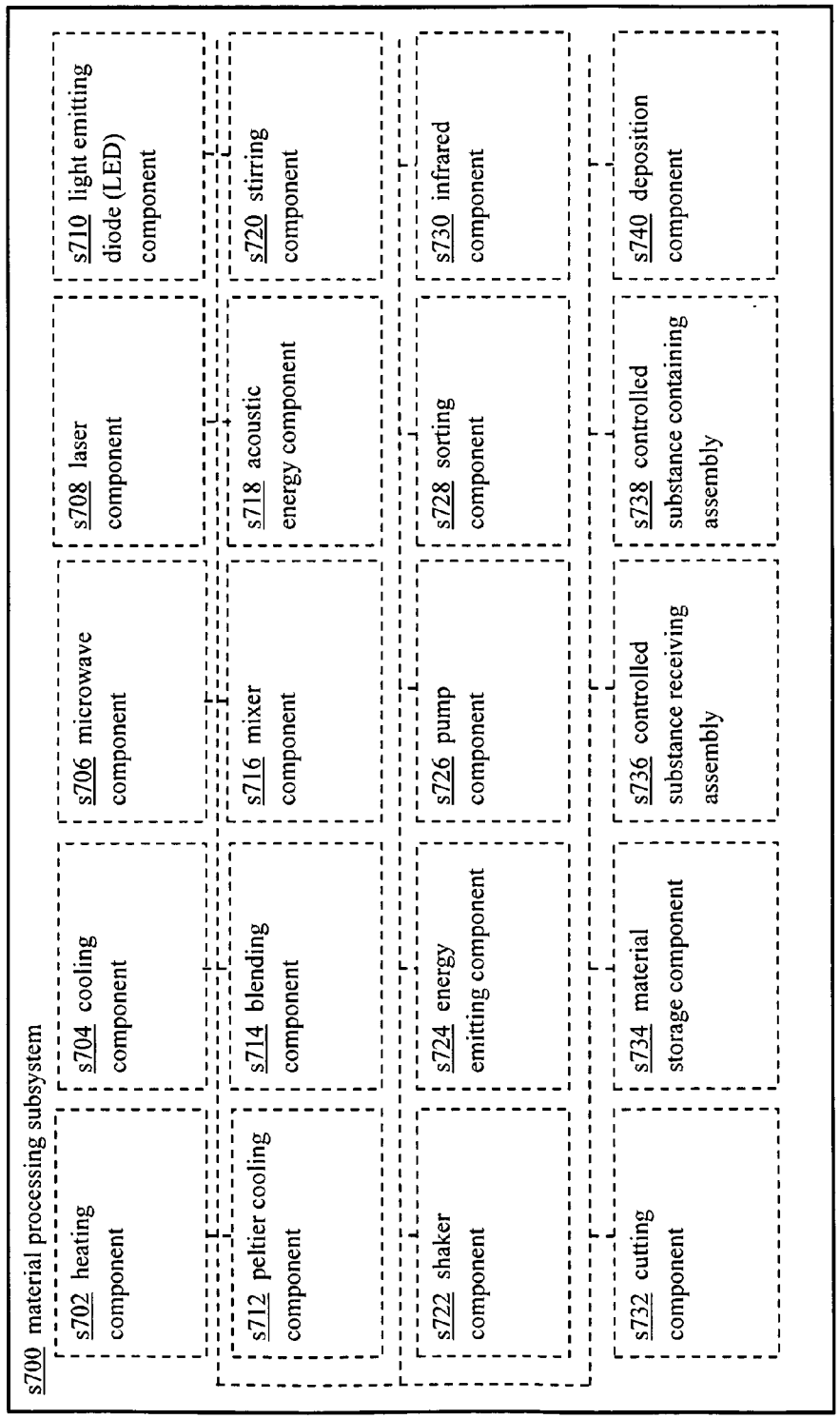
FIG. 26 is a block diagram depicting a material processing subsystem s700 of an exemplary implementation of the ingestible product preparation system 10 of FIG. 1.

An exemplary implementation of the material processing subsystem s700 is shown in FIG. 26 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, material storage component s734, controlled substance receiving assembly s736, and controlled substance containing assembly s738.

Figure 27:
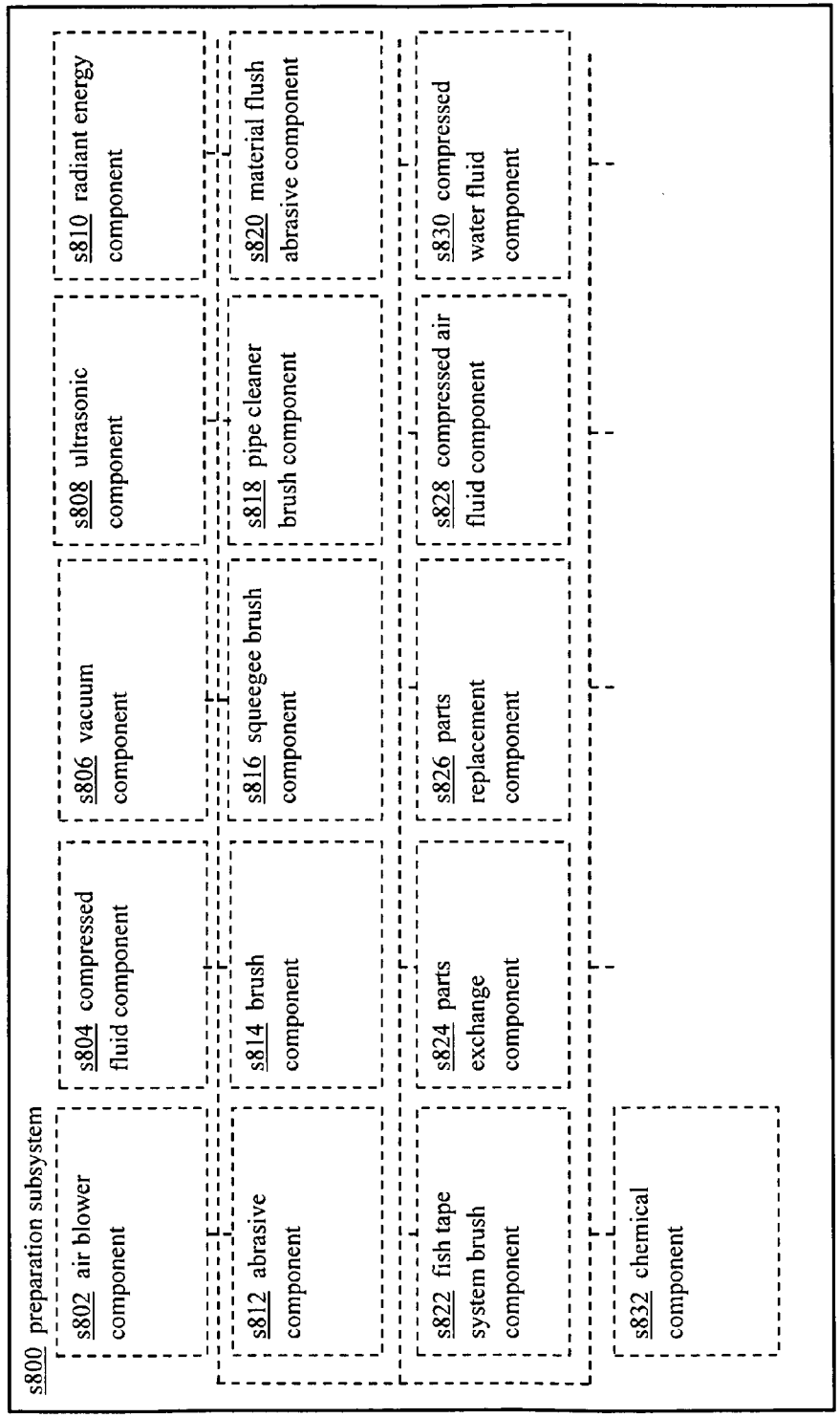
FIG. 27 is a block diagram depicting a preparation subsystem s800 of an exemplary implementation of the ingestible product preparation system 10 of FIG. 1.

An exemplary implementation of the preparation subsystem s800 is shown in FIG. 27 to optionally include various components such as air blower component s802, compressed fluid component s804, vacuum component s806, ultrasonic component s808, radiant energy component s810, abrasive component s812, brush component s814, squeegee brush component s816, pipe cleaner brush component s818, material flush abrasive component s820, fish tape system brush component s822, parts exchange component s824, parts replacement component s826, compressed air fluid component s828, compressed water fluid component s830, and chemical component s832.

Figure 28:
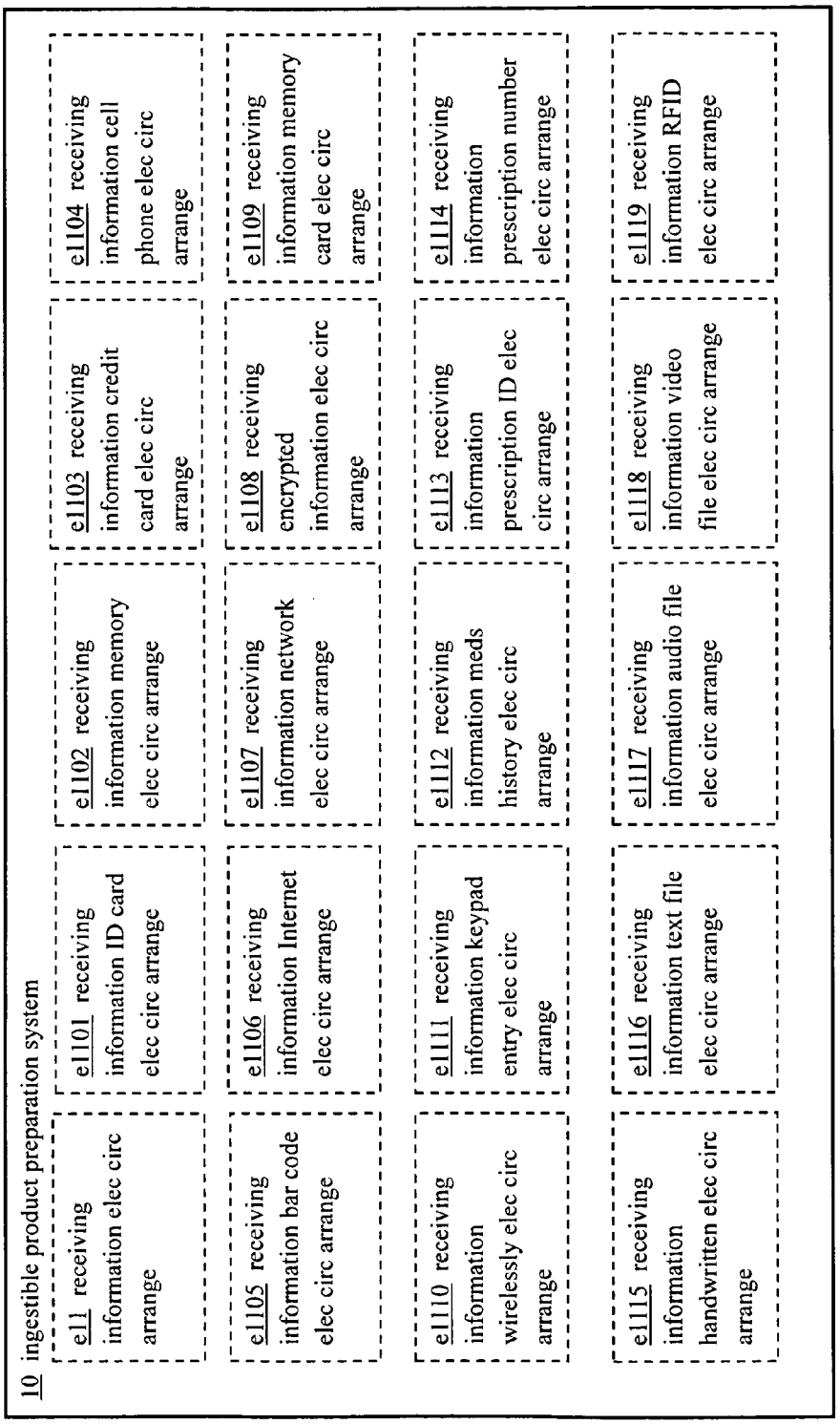
FIG. 28 is a block diagram depicting one or more exemplary electrical circuitry arrangements of the ingestible product preparation system 10 of FIG. 1.

Implementations involve different combinations (otherwise known as "electrical circuitry arrangements") of components from the subsystems of the ingestible product preparation system 10. Exemplary depictions of some of these electrical circuitry arrangements are shown in FIG. 28 to include receiving information electrical circuitry arrangement e11, receiving information ID card electrical circuitry arrangement e1101, receiving information memory electrical circuitry arrangement e1102, receiving information credit card electrical circuitry arrangement e1103, receiving information cell phone electrical circuitry arrangement e1104, receiving information bar code electrical circuitry arrangement e1105, receiving information Internet electrical circuitry arrangement e1106, receiving information network electrical circuitry arrangement e1107, receiving encrypted information electrical circuitry arrangement e1108, receiving information memory card electrical circuitry arrangement e1109, receiving information wirelessly electrical circuitry arrangement e1110, receiving information keypad entry electrical circuitry arrangement e1111, receiving information meds history electrical circuitry arrangement e1112, receiving information prescription ID electrical circuitry arrangement e1113, receiving information prescription number electrical circuitry arrangement e1114, receiving information handwritten electrical circuitry arrangement e1115, receiving information text file electrical circuitry arrangement e1116, receiving information audio file electrical circuitry arrangement e1117, receiving information video file electrical circuitry arrangement e1118, and receiving information RFID electrical circuitry arrangement e1119.

Figure 29:
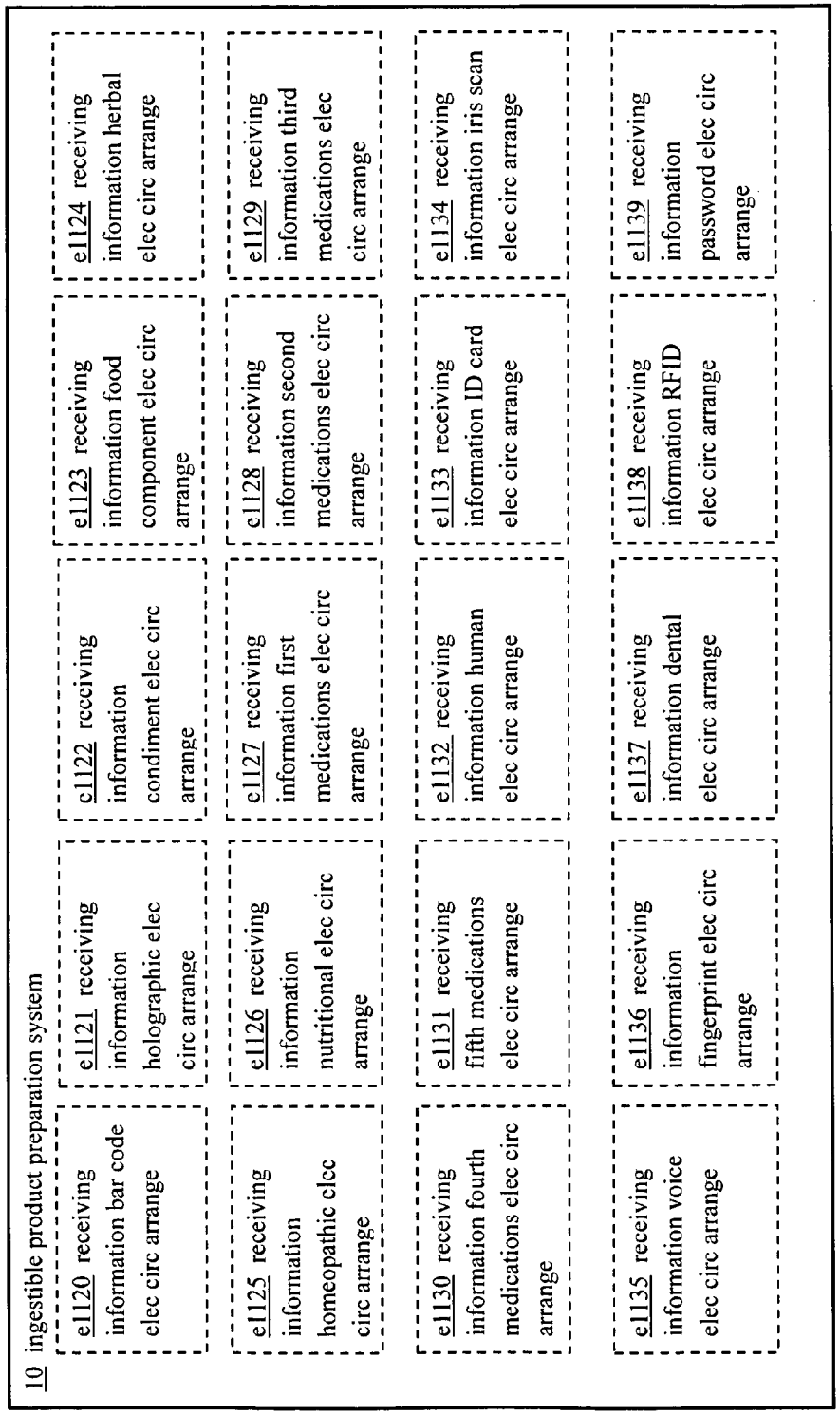
FIG. 29 is a block diagram depicting one or more exemplary electrical circuitry arrangements of the ingestible product preparation system 10 of FIG. 1.

Some of these electrical circuitry arrangements are depicted in FIG. 29 to include receiving information bar code electrical circuitry arrangement e1120, receiving information holographic electrical circuitry arrangement e1121, receiving information condiment electrical circuitry arrangement e1122, receiving information food component electrical circuitry arrangement e1123, receiving information herbal electrical circuitry arrangement e1124, receiving information homeopathic electrical circuitry arrangement e1125, receiving information nutritional electrical circuitry arrangement e1126, receiving information first medications electrical circuitry arrangement e1127, receiving information second medications electrical circuitry arrangement e1128, receiving information third medications electrical circuitry arrangement e1129, receiving information fourth medications electrical circuitry arrangement e1130, receiving fifth medications electrical circuitry arrangement e113, receiving information human electrical circuitry arrangement e1132, receiving information ID card electrical circuitry arrangement e1133, receiving information iris scan electrical circuitry arrangement e1134, receiving information voice electrical circuitry arrangement e1135, receiving information fingerprint electrical circuitry arrangement e1136, receiving information dental electrical circuitry arrangement e1137, receiving information RFID electrical circuitry arrangement e1138, and receiving information password electrical circuitry arrangement e1139.

Figure 30:
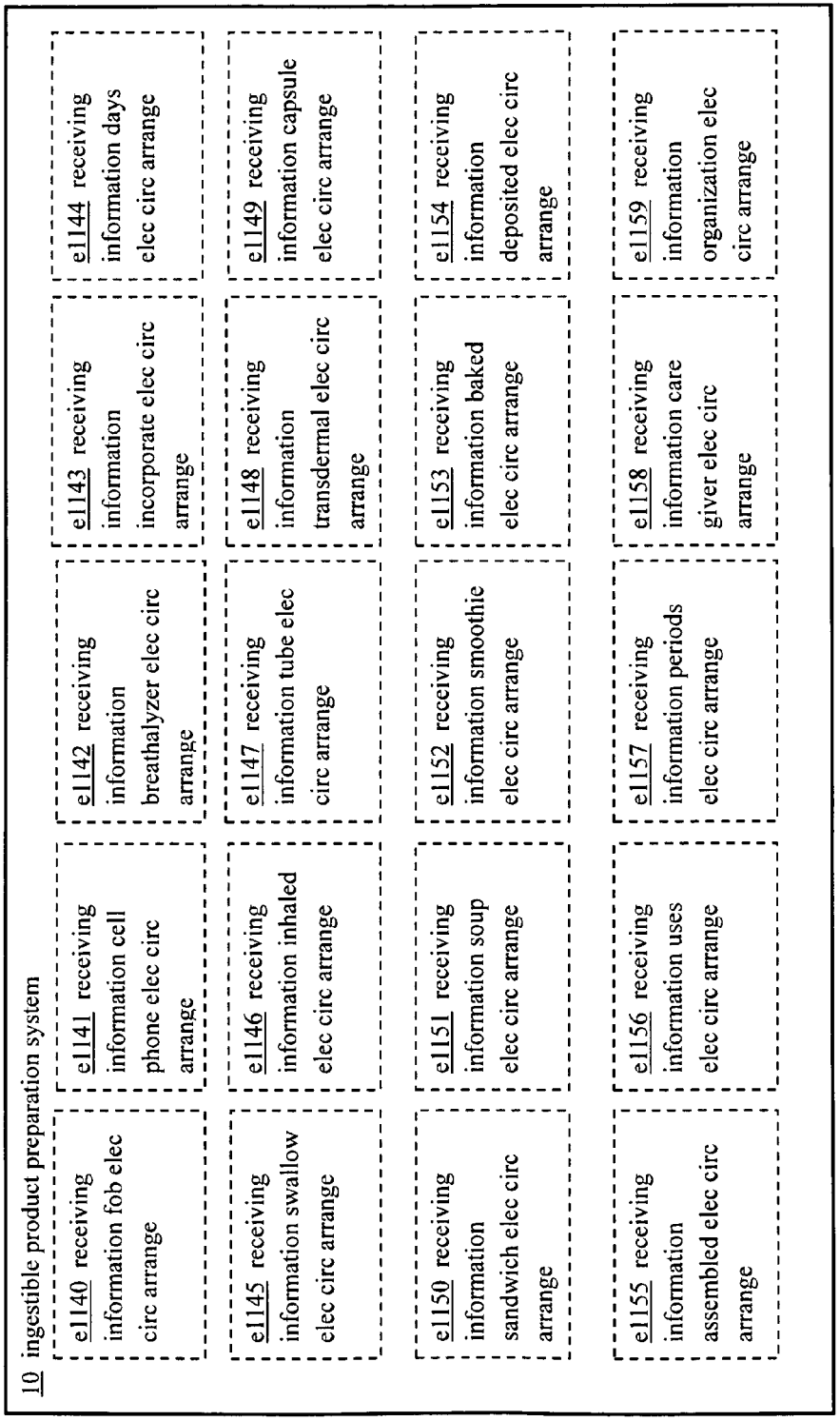
FIG. 30 is a block diagram depicting one or more exemplary electrical circuitry arrangements of the ingestible product preparation system 10 of FIG. 1.

Some of these electrical circuitry arrangements are depicted in FIG. 30 to include receiving information fob electrical circuitry arrangement e1140, receiving information cell phone electrical circuitry arrangement e1141, receiving information breathalyzer electrical circuitry arrangement e1142, receiving information incorporate electrical circuitry arrangement e1143, receiving information days electrical circuitry arrangement e1144, receiving information swallow electrical circuitry arrangement e1145, receiving information inhaled electrical circuitry arrangement e1146, receiving information tube electrical circuitry arrangement e1147, receiving information transdermal electrical circuitry arrangement e1148, receiving information capsule electrical circuitry arrangement e1149, receiving information sandwich electrical circuitry arrangement e1150, receiving information soup electrical circuitry arrangement e1151, receiving information smoothie electrical circuitry arrangement e1152, receiving information baked electrical circuitry arrangement e1153, receiving information deposited electrical circuitry arrangement e1154, receiving information assembled electrical circuitry arrangement e1155, receiving information uses electrical circuitry arrangement e1156, receiving information periods electrical circuitry arrangement e1157, receiving information care giver electrical circuitry arrangement e1158, and receiving information organization electrical circuitry arrangement e1159.

Figure 31:
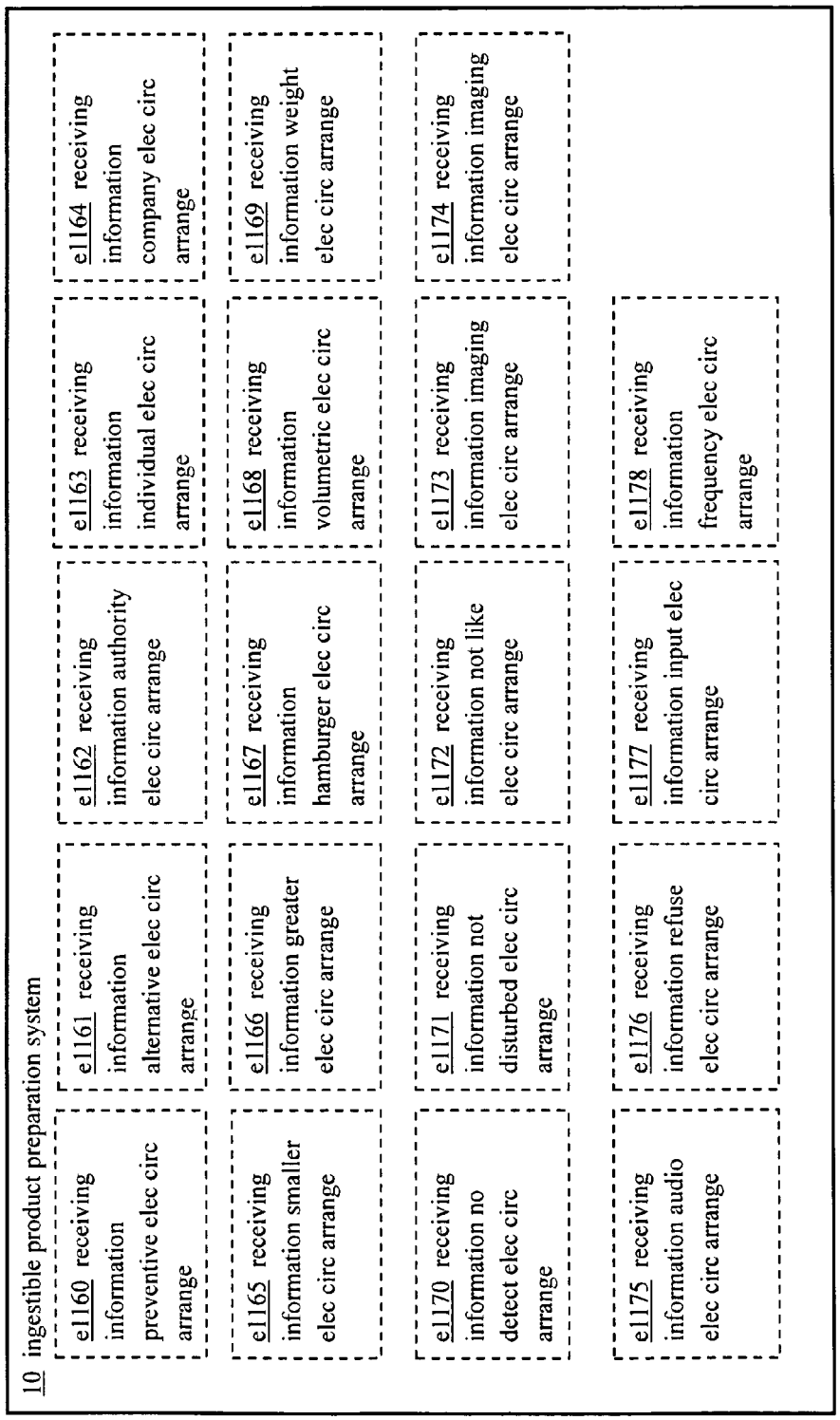
FIG. 31 is a block diagram depicting one or more exemplary electrical circuitry arrangements of the ingestible product preparation system 10 of FIG. 1.

Some of these electrical circuitry arrangements are depicted in FIG. 31 to include receiving information preventive electrical circuitry arrangement e1160, receiving information alternative electrical circuitry arrangement e1161, receiving information authority electrical circuitry arrangement e1162, receiving information individual electrical circuitry arrangement e1163, receiving information company electrical circuitry arrangement e1164, receiving information smaller electrical circuitry arrangement e1165, and receiving information greater electrical circuitry arrangement e1166, receiving information tube electrical circuitry arrangement e1167, receiving information transdermal electrical circuitry arrangement e1168, receiving information capsule electrical circuitry arrangement e1169, receiving information sandwich electrical circuitry arrangement e1170, receiving information soup electrical circuitry arrangement e1171, receiving information smoothie electrical circuitry arrangement e1172, receiving information baked electrical circuitry arrangement e1173, receiving information deposited electrical circuitry arrangement e1174, receiving information assembled electrical circuitry arrangement e1175, receiving information uses electrical circuitry arrangement e1176, receiving information periods electrical circuitry arrangement e1177, and receiving information care giver electrical circuitry arrangement e1178.

Figure 32:
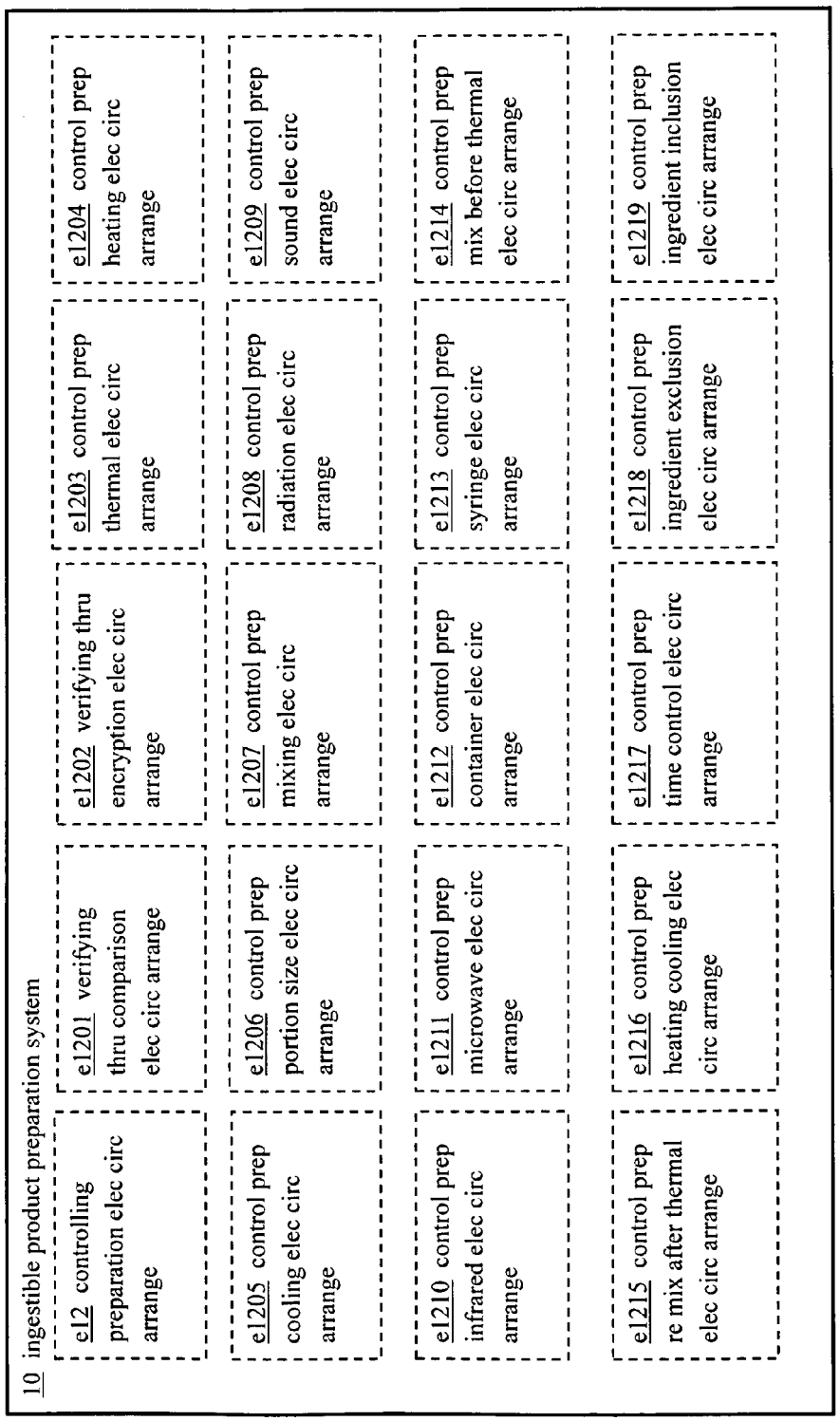
FIG. 32 is a block diagram depicting one or more exemplary electrical circuitry arrangements of the ingestible product preparation system 10 of FIG. 1.

Some of these electrical circuitry arrangements are depicted in FIG. 32 to include controlling preparation electrical circuitry arrangement e12, verifying thru comparison electrical circuitry arrangement e1201, verifying thru encryption electrical circuitry arrangement e1202, control prep thermal electrical circuitry arrangement e1203, control prep heating electrical circuitry arrangement e1204, control prep cooling electrical circuitry arrangement e1205, control prep portion size electrical circuitry arrangement e1206, control prep mixing electrical circuitry arrangement e1207, control prep radiation electrical circuitry arrangement e1208, control prep sound electrical circuitry arrangement e1209, control prep infrared electrical circuitry arrangement e1210, control prep microwave electrical circuitry arrangement e1211, and control prep container electrical circuitry arrangement e1212, control prep syringe electrical circuitry arrangement e1213, control prep mix before thermal electrical circuitry arrangement e1214, control prep re mix after thermal electrical circuitry arrangement e1215, control prep heating cooling electrical circuitry arrangement e1216, control prep time control electrical circuitry arrangement e1217, control prep ingredient exclusion electrical circuitry arrangement e1218, and control prep ingredient inclusion electrical circuitry arrangement e1219.

Figure 33:
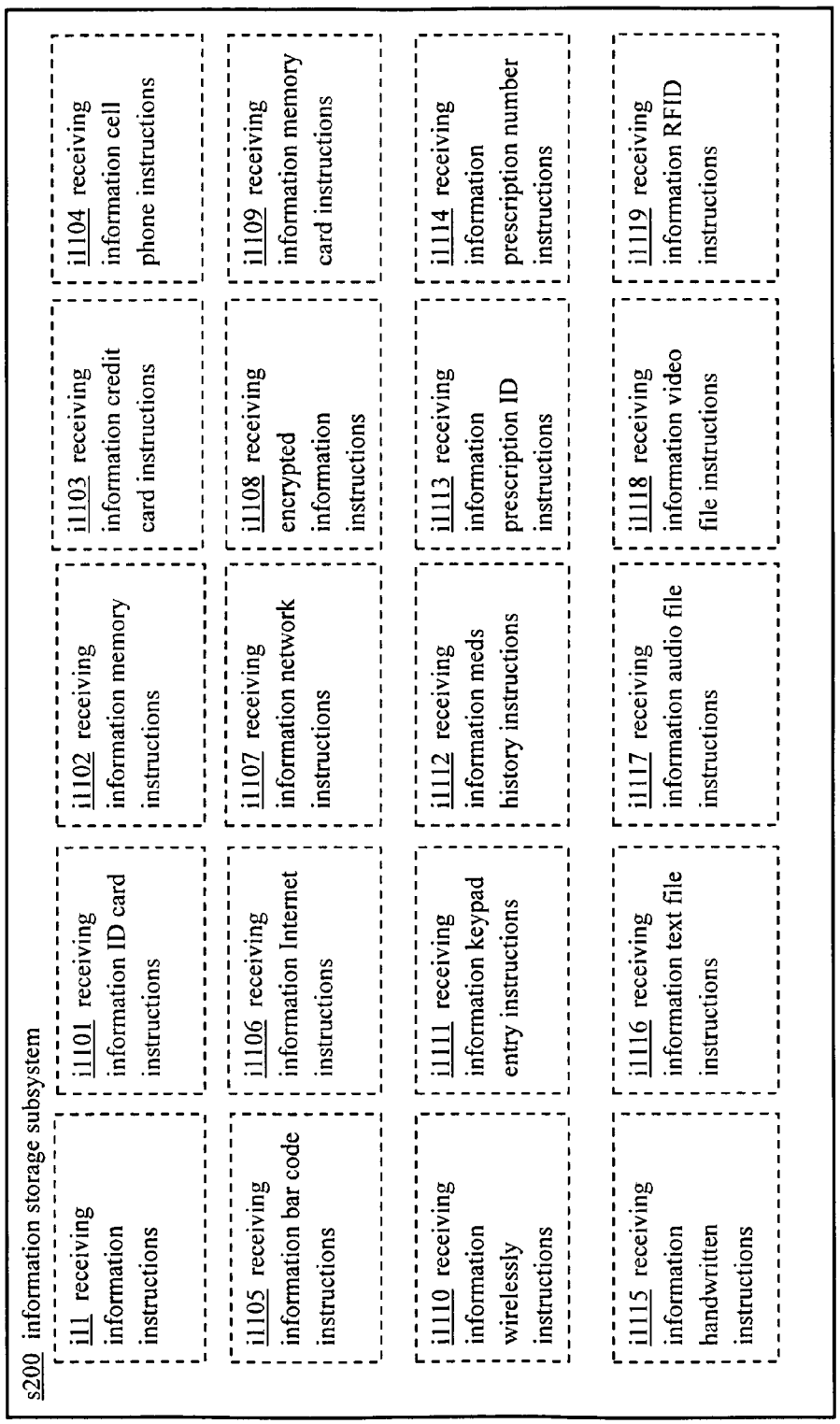
FIG. 33 is a block diagram depicting one or more exemplary instructions of the information storage subsystem s200 of the ingestible product preparation system 10 of FIG. 1.

In implementations one or more instructions are stored and/or otherwise borne in various subsystems, components, and/or accessories of the ingestible product preparation system 10 such as being borne in a non-transitory signal bearing medium of information storage subsystem s200. One or more exemplary instructions depicted in FIG. 33 as being borne in an exemplary version of a non-transitory signal bearing medium of information storage subsystem s200 include one or more receiving information instructions i11, one or more receiving information ID card instructions i1101, one or more receiving information memory instructions i1102, one or more receiving information credit card instructions i1103, one or more receiving information cell phone instructions i1104, one or more receiving information bar code instructions i1105, one or more receiving information Internet instructions i1106, one or more receiving information network instructions i1107, one or more receiving encrypted information instructions i1108, one or more receiving information memory card instructions i1109, one or more receiving information wirelessly instructions i1110, one or more receiving information keypad entry instructions i1111, one or more receiving information meds history instructions i1112, one or more receiving information prescription ID instructions i1113, one or more receiving information prescription number instructions i1114, one or more receiving information handwritten instructions i1115, one or more receiving information text file instructions i1116, one or more receiving information audio file instructions i1117, one or more receiving information video file instructions i1118, and one or more receiving information RFID instructions i1119.

Figure 34:
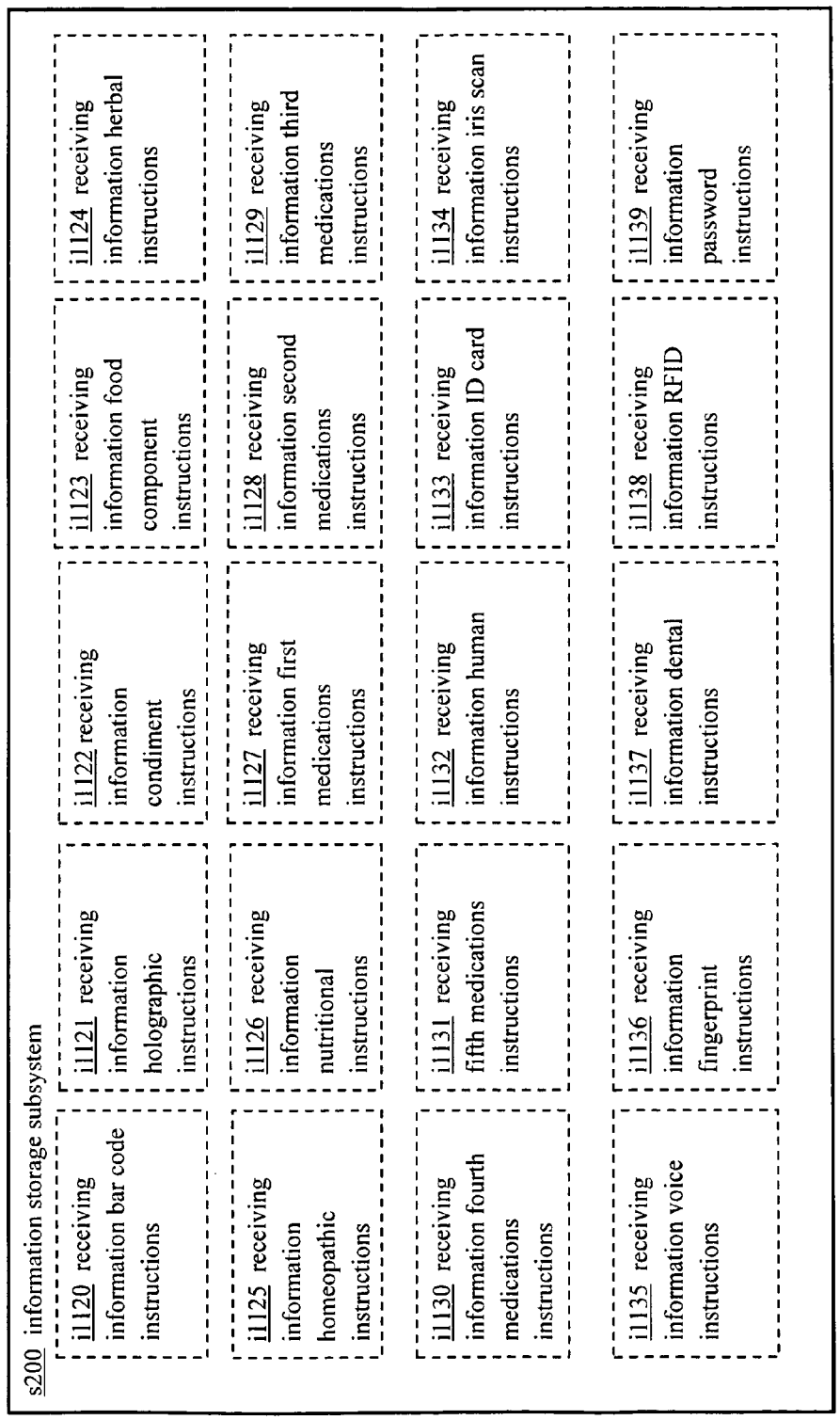
FIG. 34 is a block diagram depicting one or more exemplary instructions of the information storage subsystem s200 of the ingestible product preparation system 10 of FIG. 1.

One or more exemplary instructions depicted in FIG. 34 as being borne in an exemplary version of a non-transitory signal bearing medium of information storage subsystem s200 include one or more receiving information bar code instructions i1120, one or more receiving information holographic instructions i1121, one or more receiving information condiment instructions i1122, one or more receiving information food component instructions i1123, one or more receiving information herbal instructions i1124, one or more receiving information homeopathic instructions i1125, one or more receiving information nutritional instructions i1126, one or more receiving information first medications instructions i1127, one or more receiving information second medications instructions i1128, one or more receiving information third medications instructions i1129, one or more receiving information fourth medications instructions i1130, one or more receiving fifth medications instructions i1131, one or more receiving information human instructions i1132, one or more receiving information ID card instructions i1133, one or more receiving information iris scan instructions i1134, one or more receiving information voice instructions i1135, one or more receiving information fingerprint instructions i1136, one or more receiving information dental instructions i1137, one or more receiving information RFID instructions i1138, and one or more receiving information password instructions i1139.

Figure 35:
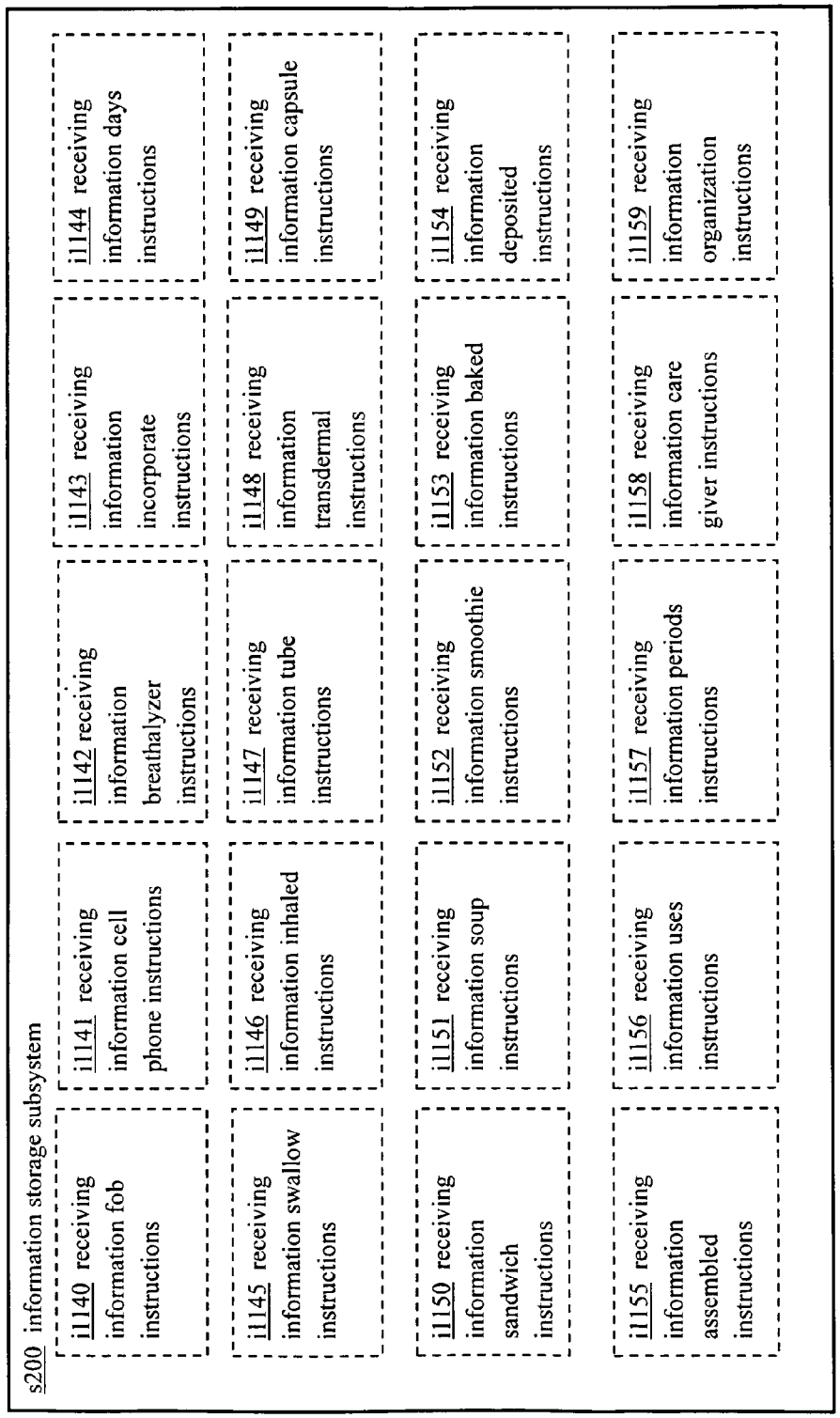
FIG. 35 is a block diagram depicting one or more exemplary instructions of the information storage subsystem s200 of the ingestible product preparation system 10 of FIG. 1.
Figure 36:
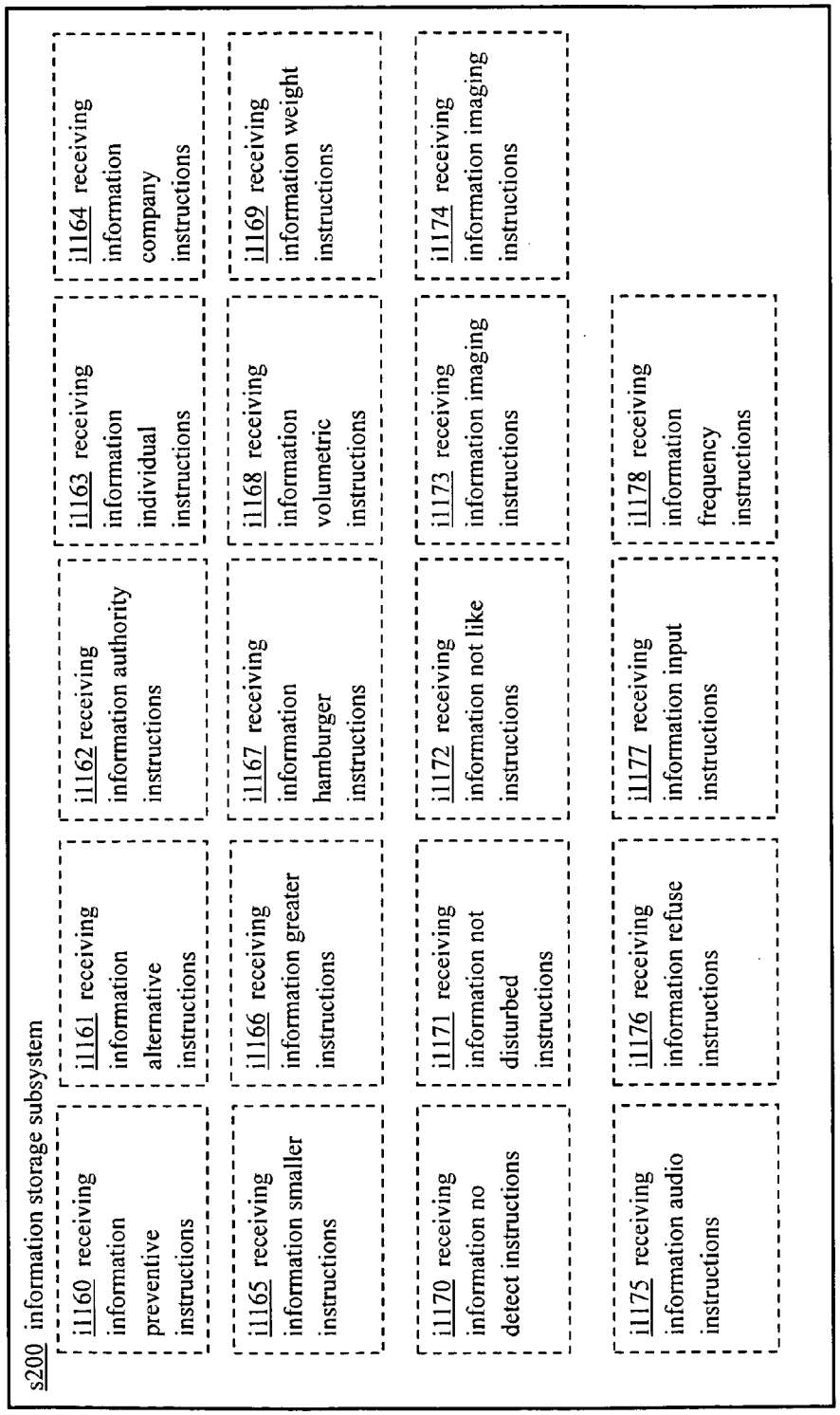
FIG. 36 is a block diagram depicting one or more exemplary instructions of the information storage subsystem s200 of the ingestible product preparation system 10 of FIG. 1.
Figure 37:
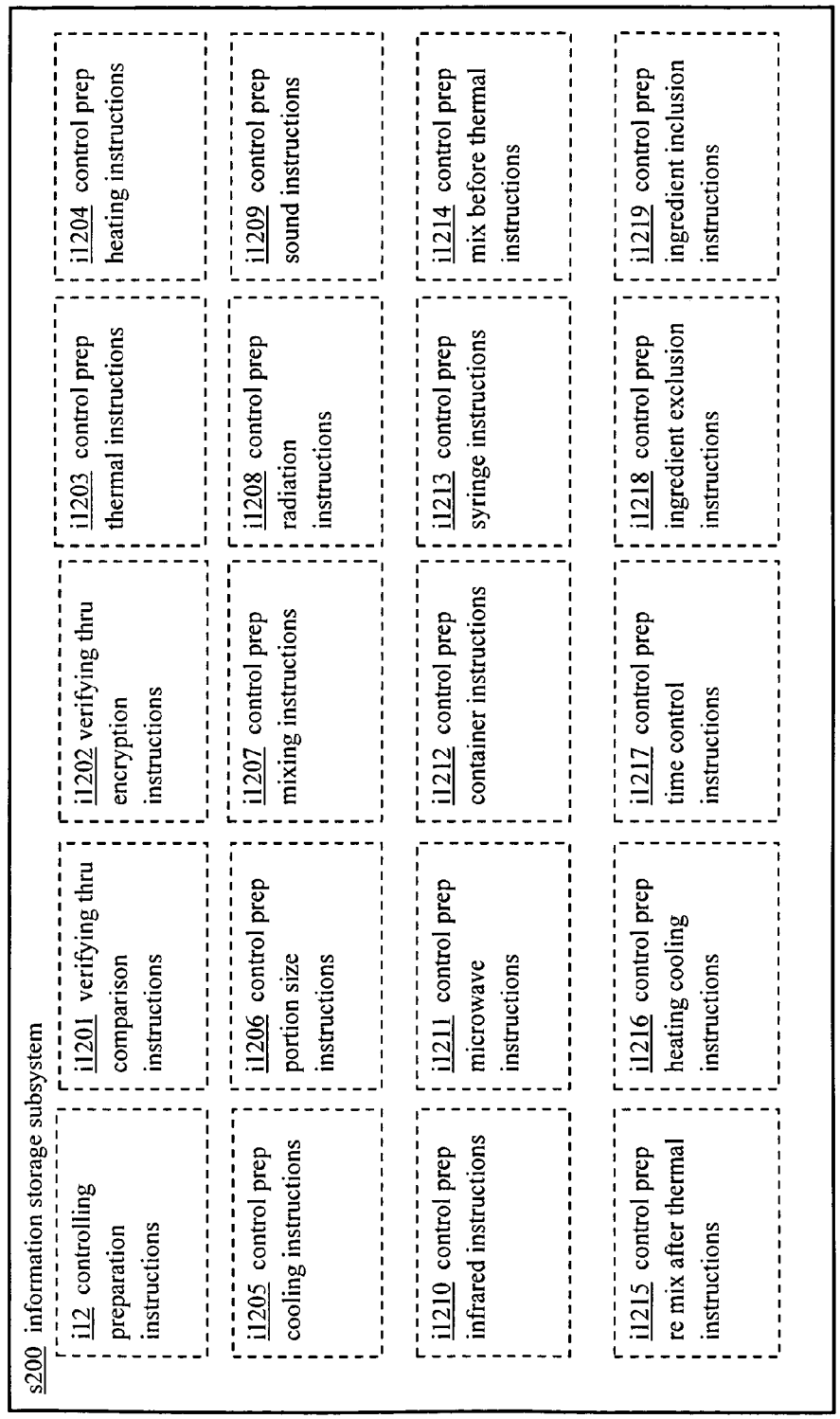
FIG. 37 is a block diagram depicting one or more exemplary instructions of the information storage subsystem s200 of the ingestible product preparation system 10 of FIG. 1.

One or more exemplary instructions depicted in FIG. 35 as being borne in an exemplary version of a non-transitory signal bearing medium of information storage subsystem s200 include one or more receiving information fob instructions i1140, one or more receiving information cell phone instructions i1141, one or more receiving information breathalyzer instructions i1142, one or more receiving information incorporate instructions i1143, one or more receiving information days instructions i1144, one or more receiving information swallow instructions i1145, one or more receiving information inhaled instructions i1146, one or more receiving information tube instructions i1147, one or more receiving information transdermal instructions i1148, one or more receiving information capsule instructions i1149, one or more receiving information sandwich instructions i1150, one or more receiving information soup instructions i1151, one or more receiving information smoothie instructions i1152, one or more receiving information baked instructions i1153, one or more receiving information deposited instructions i1154, one or more receiving information assembled instructions i1155, one or more receiving information uses instructions i1156, one or more receiving information periods instructions i1157, one or more receiving information care giver instructions i1158, and one or more receiving information organization instructions i1159.

One or more exemplary instructions depicted in FIG. 36 as being borne in an exemplary version of a non-transitory signal bearing medium of information storage subsystem s200 include one or more receiving information preventive instructions i1160, one or more receiving information alternative instructions i1161, one or more receiving information authority instructions i1162, one or more receiving information individual instructions i1163, one or more receiving information company instructions i1164, one or more receiving information smaller instructions i1165, and one or more receiving information greater instructions i1166, one or more receiving information hamburger instructions i1167, one or more receiving information volumetric instructions i1168, one or more receiving information weight instructions i1169, one or more receiving information no detect instructions i1170, one or more receiving information not disturbed instructions i1171, one or more receiving information not like instructions i1172, one or more receiving information imaging instructions i1173, one or more receiving information imaging instructions i1174, one or more receiving information audio instructions i1175, one or more receiving information refuse instructions i1176, one or more receiving information input instructions i1177, and one or more receiving information frequency instructions i1178.

One or more exemplary instructions depicted in FIG. 37 as being borne in an exemplary version of a non-transitory signal bearing medium of information storage subsystem s200 include one or more controlling preparation instructions i12, one or more verifying thru comparison instructions i1201, one or more verifying thru encryption instructions i1202, one or more control prep thermal instructions i1203, one or more control prep heating instructions i1204, one or more control prep cooling instructions i1205, one or more control prep portion size instructions i1206, one or more control prep mixing instructions i1207, one or more control prep radiation instructions i1208, one or more control prep sound instructions i1209, one or more control prep infrared instructions i1210, one or more control prep microwave instructions i1211, one or more control prep container instructions i1212, one or more control prep syringe instructions i1213, one or more control prep mix before thermal instructions i1214, one or more control prep re mix after thermal instructions i1215, one or more control prep heating cooling instructions i1216, one or more control prep time control instructions i1217, one or more control prep ingredient exclusion instructions i1218, and one or more control prep ingredient inclusion instructions i1219.

An operational flow o10 as shown in FIG. 38 represents example operations related to electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan and electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan.

FIG. 38 and those figures that follow may have various examples of operational flows, and explanation may be provided with respect to the above-described examples of FIGS. 1-7 and/or with respect to other examples and contexts. Nonetheless, it should be understood that the operational flows may be executed in a number of other environments and contexts, and/or in modified versions of FIGS. 1-7. Furthermore, although the various operational flows are presented in the sequence(s) illustrated, it should be understood that the various operations may be performed in other orders than those which are illustrated, or may be performed concurrently.

In FIG. 38 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 38, the operational flow o10 proceeds to operation o11 for electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan. An exemplary version of a non-transitory signal bearing medium of information storage subsystem s200 is depicted as bearing one or more receiving information instructions i11 that when executed will direct performance of the operation o11. In an implementation, the one or more receiving information instructions i11 when executed direct electronically receiving (e.g. the network cable component s502 carries information to the transceiver component s522, etc.) operation information including living being identification associated with a particular individual living being (e.g. a particular human being, animal, plant, etc.), and preparation directions designated to be associated with the particular individual living being for electronically directing at least partial preparation of a succession of instances of an ingestible product designated to be ingested by the particular individual living being (e.g. such as partial preparation of a smoothie to be ingested by a human child, etc.) according at least in part to an allocation plan specifying a quantity for each instance of the succession of at least one substance to be included in preparation of each instance of the ingestible product in the succession (e.g. such as including a pharmaceutical medication in a smoothie for a young child, etc.), and electronically receiving feedback information regarding ingestion of at least one instance of the ingestible product of the succession by the particular individual living being to generate an updated allocation plan (e.g. a young child has noticed that a smoothie has become less satisfying over a succession of prepared smoothies with progressively less sugar content and more stevia content so that his mother has conveyed this information through a touch pad of a graphical user interface whereupon an allocation plan to reduce sugar and increase stevia over a course of successive smoothies is adjusted to lessen rates of decrease of sugar and increase of stevia for further smoothies to be subsequently produced, etc.). Furthermore, the receiving information electrical circuitry arrangement ("elec circ arrange") e11 when activated will perform the operation o11. In an implementation, the receiving information electrical circuitry arrangement e11, when activated performs electronically receiving (e.g. the network cable component s502 carries information to the transceiver component s522, etc.) operation information including living being identification associated with a particular individual living being (e.g. a particular human being, animal, plant, etc.), and preparation directions designated to be associated with the particular individual living being for electronically directing at least partial preparation of a succession of instances of an ingestible product designated to be ingested by the particular individual living being (e.g. such as partial preparation of a smoothie to be ingested by a human child, etc.) according at least in part to an allocation plan specifying a quantity for each instance of the succession of at least one substance to be included in preparation of each instance of the ingestible product in the succession (e.g. such as including a pharmaceutical medication in a smoothie for a young child, etc.), and electronically receiving feedback information regarding ingestion of at least one instance of the ingestible product of the succession by the particular individual living being to generate an updated allocation plan (e.g. a young child has noticed that a smoothie has become less satisfying over a succession of prepared smoothies with progressively less sugar content and more stevia content so that his mother has conveyed this information through a touch pad of a graphical user interface whereupon an allocation plan to reduce sugar and increase stevia over a course of successive smoothies is adjusted to lessen rates of decrease of sugar and increase of stevia for further smoothies to be subsequently produced, etc.). In an implementation, the electronically receiving operation information including living being identification associated with a particular individual living being, preparation directions designated to be associated with the particular individual living being for electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, and electronically receiving feedback information regarding ingestion of at least one instance of the ingestible product of the succession by the particular individual living being to generate an updated allocation plan is carried out by electronically receiving (e.g. the network cable component s502 carries information to the transceiver component s522, etc.) operation information including living being identification associated with a particular individual living being (e.g. a particular human being, animal, plant, etc.), and preparation directions designated to be associated with the particular individual living being for electronically directing at least partial preparation of a succession of instances of an ingestible product designated to be ingested by the particular individual living being (e.g. such as partial preparation of a smoothie to be ingested by a human child, etc.) according at least in part to an allocation plan specifying a quantity for each instance of the succession of at least one substance to be included in preparation of each instance of the ingestible product in the succession (e.g. such as including a pharmaceutical medication in a smoothie for a young child, etc.), and electronically receiving feedback information regarding ingestion of at least one instance of the ingestible product of the succession by the particular individual living being to generate an updated allocation plan (e.g. a young child has noticed that a smoothie has become less satisfying over a succession of prepared smoothies with progressively less sugar content and more stevia content so that his mother has conveyed this information through a touch pad of a graphical user interface whereupon an allocation plan to reduce sugar and increase stevia over a course of successive smoothies is adjusted to lessen rates of decrease of sugar and increase of stevia for further smoothies to be subsequently produced, etc.).

Figure 39:
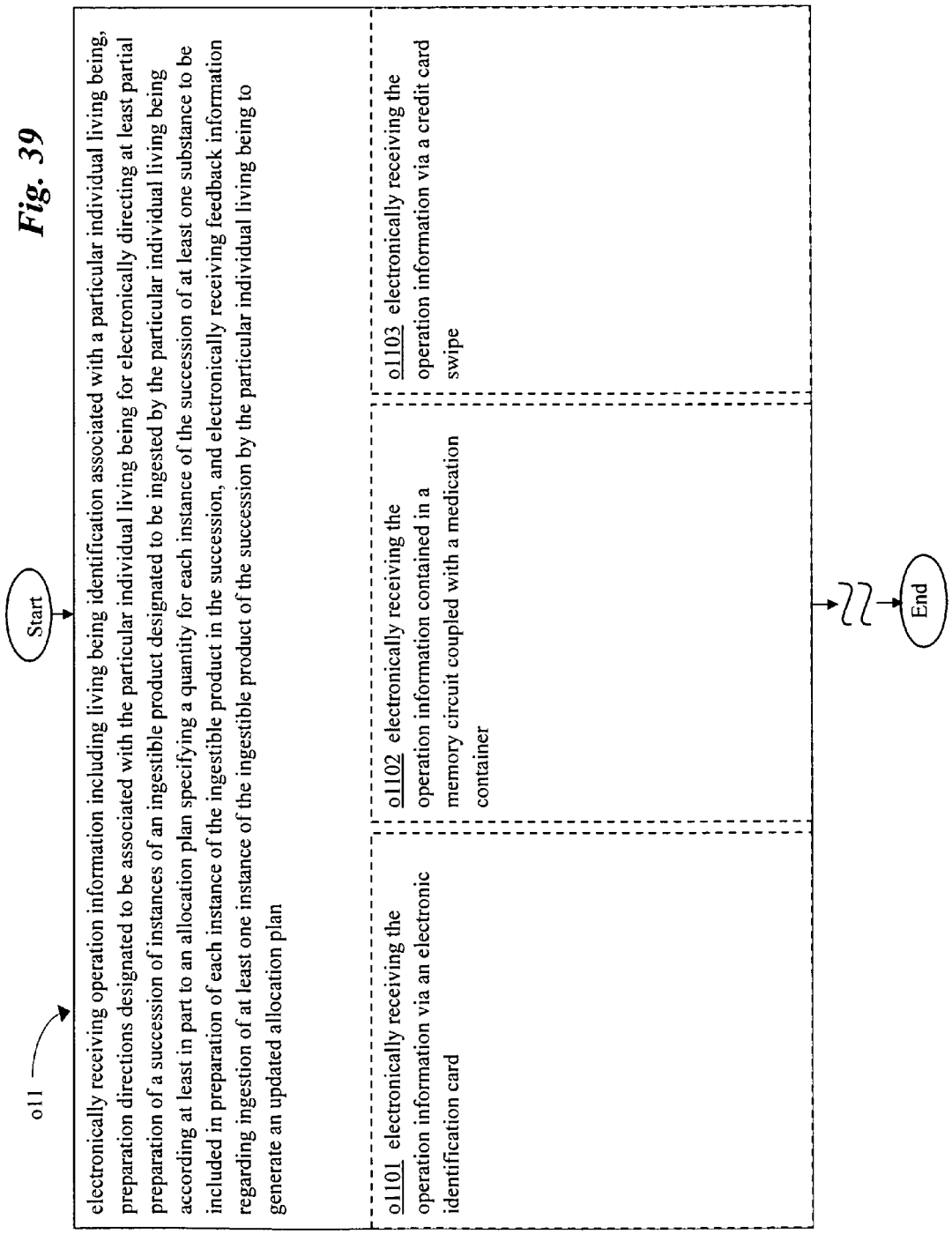
FIG. 39 is a high-level flowchart including exemplary implementations of operation O11 of FIG. 38.

In one or more implementations, as shown in FIG. 39, operation o11 includes an operation o1101 for electronically receiving the operation information via an electronic identification card. An exemplary version of a non-transitory signal bearing medium of information storage subsystem s200 is depicted as bearing one or more receiving information ID card instructions i1101 that when executed will direct performance of the operation o1101. In an implementation, the one, or more receiving information ID card instructions i1101 when executed direct electronically receiving the operation information via an electronic identification card (e.g. an implementation of the receiver component s528 is configured to electronically engage with a card having memory storage holding the direction information, etc.). Furthermore, the receiving information ID card electrical circuitry arrangement ("elec circ arrange") e1101 when activated will perform the operation o1101. In an implementation, the receiving information ID card electrical circuitry arrangement e1101, when activated performs electronically receiving the operation information via an electronic identification card (e.g. an implementation of the receiver component s528 is configured to electronically engage with a card having memory storage holding the direction information, etc.). In an implementation, the electronically receiving the operation information via an electronic identification card is carried out by electronically receiving the operation information via an electronic identification card (e.g. an implementation of the receiver component s528 is configured to electronically engage with a card having memory storage holding the direction information, etc.).

In one or more implementations, operation o11 includes an operation o1102 for electronically receiving the operation information contained in a memory circuit coupled with a medication container. An exemplary version of a non-transitory signal bearing medium of information storage subsystem s200 is depicted as bearing one or more receiving information memory instructions i1102 that when executed will direct performance of the operation o1102. In an implementation, the one or more receiving information memory instructions i1102 when executed direct electronically receiving the operation information contained in a memory circuit coupled with a medication container (e.g. an implementation of the receiver component s528 is configured to electronically engage with a memory storage coupled with a medication container to receive the operation information in electronic form, etc.). Furthermore, the receiving information memory electrical circuitry arrangement e1102 when activated will perform the operation o1102. In an implementation, the receiving information memory electrical circuitry arrangement e1102, when activated performs electronically receiving the operation information contained in a memory circuit coupled with a medication container (e.g. an implementation of the receiver component s528 is configured to electronically engage with a memory storage coupled with a medication container to receive the operation information in electronic form, etc.). In an implementation, the electronically receiving the operation information contained in a memory circuit coupled with a medication container is carried out by electronically receiving the operation information contained in a memory circuit coupled with a medication container (e.g. an implementation of the receiver component s528 is configured to electronically engage with a memory storage coupled with a medication container to receive the operation information in electronic form, etc.).

In one or more implementations, operation o11 includes an operation o1103 for electronically receiving the operation information via a credit card swipe. An exemplary version of a non-transitory signal bearing medium of information storage subsystem s200 is depicted as bearing one or more receiving information credit card instructions i1103 that when executed will direct performance of the operation o1103. In an implementation, the one or more receiving information credit card instructions i1103 when executed direct electronically receiving the operation information via a credit card swipe (e.g. an implementation of the receiver component s528 is configured to electronically engage with an electronic memory stripe integrated into a credit card to receive the operation information, etc.). Furthermore, the receiving information credit card electrical circuitry arrangement e1103 when activated will perform the operation o1103. In an implementation, the receiving information credit card electrical circuitry arrangement e1103, when activated performs electronically receiving the operation information via a credit card swipe (e.g. an implementation of the receiver component s528 is configured to electronically engage with an electronic memory stripe integrated into a credit card to receive the operation information, etc.). In an implementation, the is electronically receiving the operation information via a credit card swipe carried out by electronically receiving the operation information via a credit card swipe (e.g. an implementation of the receiver component s528 is configured to electronically engage with an electronic memory stripe integrated into a credit card to receive the operation information, etc.).

Figure 40:
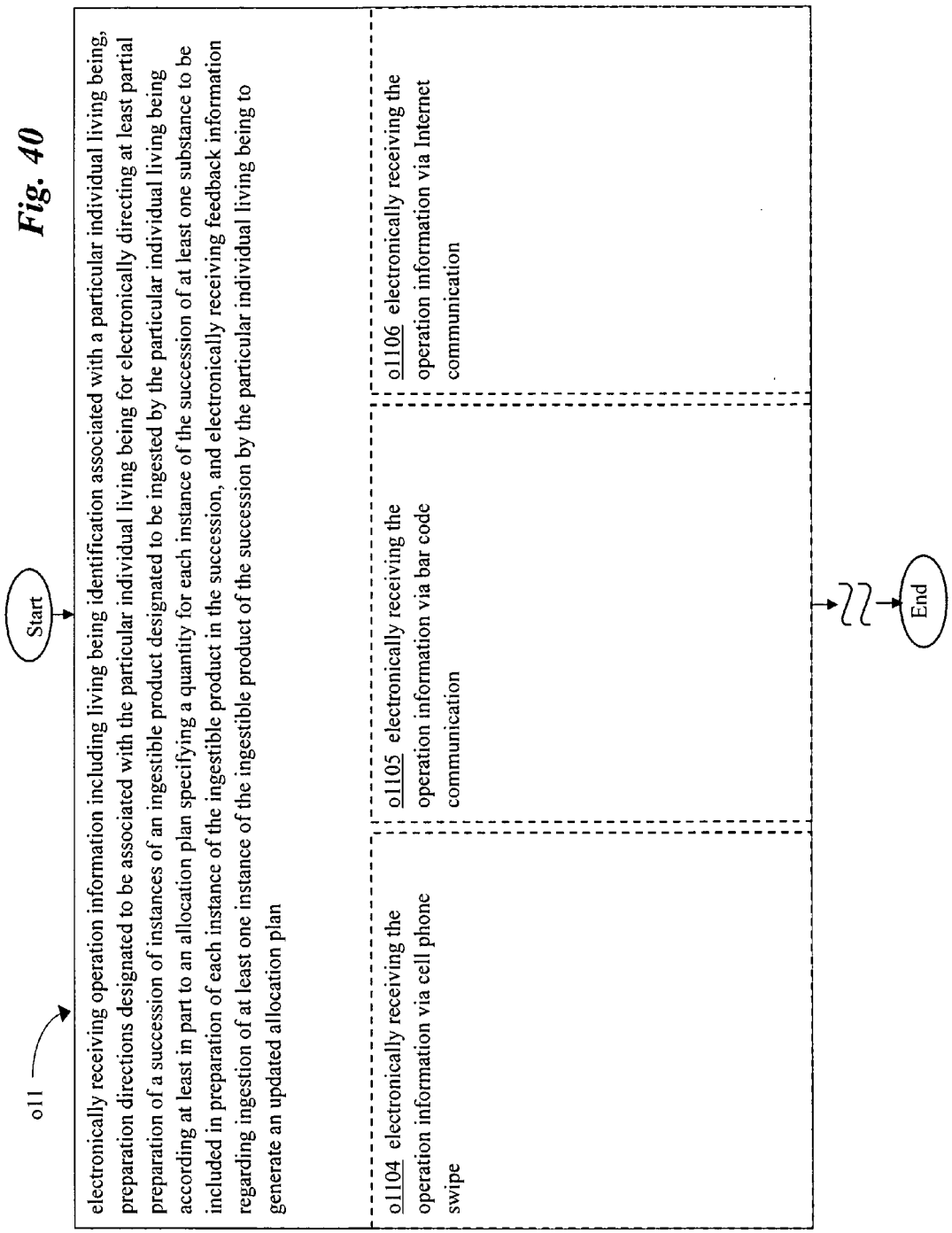
FIG. 40 is a high-level flowchart including exemplary implementations of operation O11 of FIG. 38.

In one or more implementations, as shown in FIG. 40, operation o11 includes an operation o1104 for electronically receiving the operation information via cell phone swipe. An exemplary version of a non-transitory signal bearing medium of information storage subsystem s200 is depicted as bearing one or more receiving information cell phone instructions i1104 that when executed will direct performance of the operation o1104. In an implementation, the one or more receiving information cell phone instructions i1104 when executed direct electronically receiving the operation information via cell phone swipe (e.g. an implementation of the receiver component s528 is configured to electronically engage with an electronic memory component integrated into a cell phone to receive the operation information, etc.). Furthermore, the receiving information cell phone electrical circuitry arrangement e1104 when activated will perform the operation o1104. In an implementation, the receiving information cell phone electrical circuitry arrangement e1104, when activated performs electronically receiving the operation information via cell phone swipe (e.g. an implementation of the receiver component s528 is configured to electronically engage with an electronic memory component integrated into a cell phone to receive the operation information, etc.). In an implementation, the is electronically receiving the operation information via cell phone swipe carried out by electronically receiving the operation information via cell phone swipe (e.g. an implementation of the receiver component s528 is configured to electronically engage with an electronic memory component integrated into a cell phone to receive the operation information, etc.).

In one or more implementations, operation o11 includes an operation o1105 for electronically receiving the operation information via bar code communication. An exemplary version of a non-transitory signal bearing medium of information storage subsystem s200 is depicted as bearing one or more receiving information bar code instructions i1105 that when executed will direct performance of the operation o1105. In an implementation, the one or more receiving information bar code instructions i1105 when executed direct electronically receiving the operation information via bar code communication (e.g. an implementation of the receiver component s528 is configured to electronically read a bar code label to receive the operation information, etc.). Furthermore, the receiving information bar code electrical circuitry arrangement e1105 when activated will perform the operation o1105. In an implementation, the receiving information bar code electrical circuitry arrangement e1105, when activated performs electronically receiving the operation information via bar code communication (e.g. an implementation of the receiver component s528 is configured to electronically read a bar code label to receive the operation information, etc.). In an implementation, the electronically receiving the operation information via bar code communication is carried out by electronically receiving the operation information via bar code communication (e.g. an implementation of the receiver component s528 is configured to electronically read a bar code label to receive the operation information, etc.).

In one or more implementations, operation o11 includes an operation o1106 for electronically receiving the operation information via Internet communication. An exemplary version of a non-transitory signal bearing medium of information storage subsystem s200 is depicted as bearing one or more receiving information Internet instructions i1106 that when executed will direct performance of the operation o1106. In an implementation, the one or more receiving information Internet instructions i1106 when executed direct electronically receiving the operation information via Internet communication (e.g. an implementation of the receiver component s528 is configured to electronically receive through the internet network component s508 the operation information, etc.). Furthermore, the receiving information Internet electrical circuitry arrangement e1106 when activated will perform the operation o1106. In an implementation, the receiving information Internet electrical circuitry arrangement e1106, when activated performs electronically receiving the operation information via Internet communication (e.g. an implementation of the receiver component s528 is configured to electronically receive through the internet network component s508 the operation information, etc.). In an implementation, the electronically receiving the operation information via Internet communication is carried out by electronically receiving the operation information via Internet communication (e.g. an implementation of the receiver component s528 is configured to electronically receive through the internet network component s508 the operation information, etc.).

Figure 41:
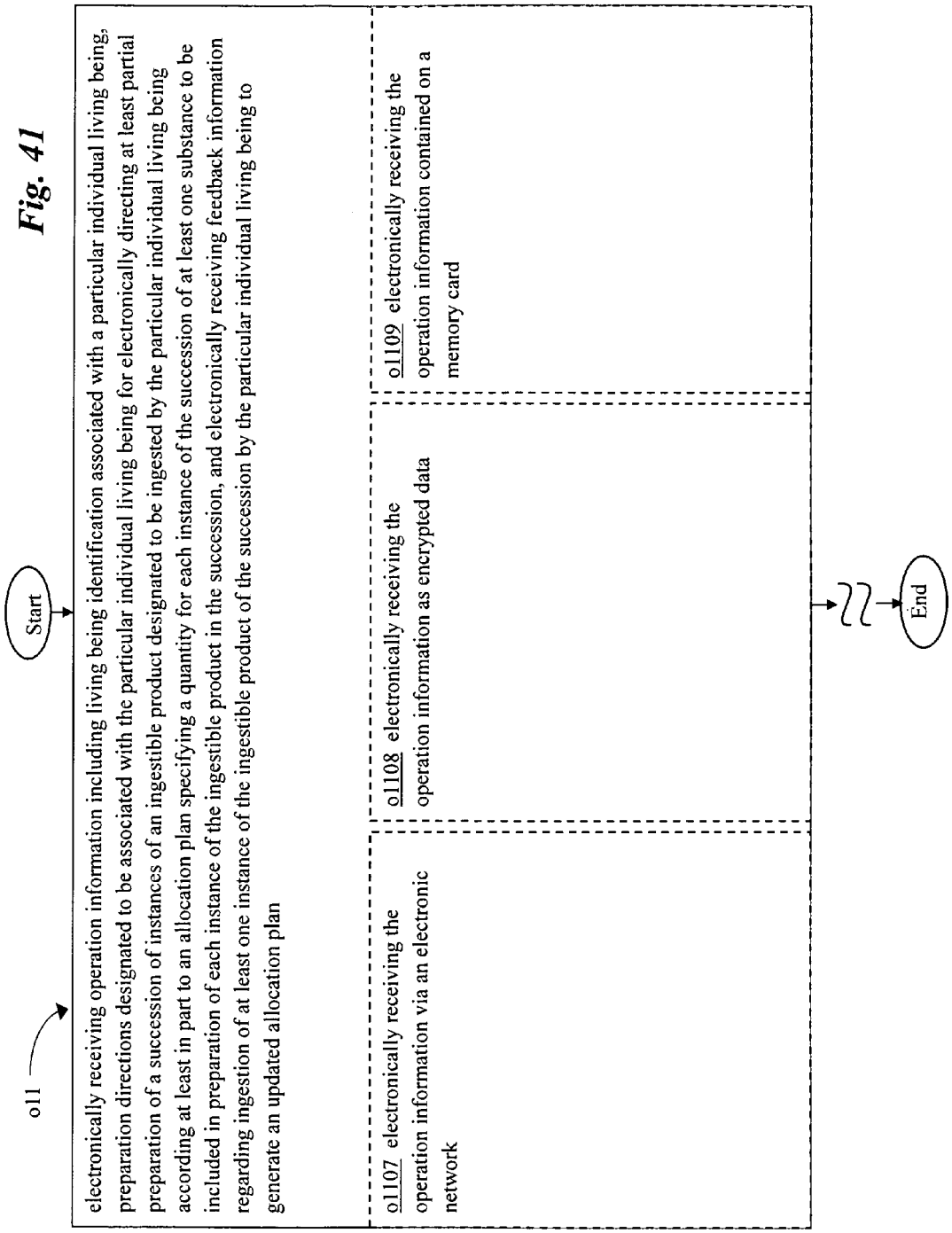
FIG. 41 is a high-level flowchart including exemplary implementations of operation O11 of FIG. 38.

In one or more implementations, as shown in FIG. 41, operation o11 includes an operation o1107 for electronically receiving the operation information via an electronic network. An exemplary version of a non-transitory signal bearing medium of information storage subsystem s200 is depicted as bearing one or more receiving information network instructions i1107 that when executed will direct performance of the operation o1107. In an implementation, the one or more receiving information network instructions i1107 when executed direct electronically receiving the operation information via an electronic network (e.g. an implementation of the receiver component s528 is configured to electronically engage with the network cable component s502 to receive the operation information, etc.). Furthermore, the receiving information network electrical circuitry arrangement e1107 when activated will perform the operation o1107. In an implementation, the receiving information network electrical circuitry arrangement e1107, when activated performs electronically receiving the operation information via an electronic network (e.g. an implementation of the receiver component s528 is configured to electronically engage with the network cable component s502 to receive the operation information, etc.). In an implementation, the electronically receiving the operation information via an electronic network is carried out by electronically receiving the operation information via an electronic network (e.g. an implementation of the receiver component s528 is configured to electronically engage with the network cable component s502 to receive the operation information, etc.).

In one or more implementations, operation o11 includes an operation o1108 for electronically receiving the operation information as encrypted data. An exemplary version of a non-transitory signal bearing medium of information storage subsystem s200 is depicted as bearing one or more receiving encrypted information instructions i1108 that when executed will direct performance of the operation o1108. In an implementation, the one or more receiving encrypted information instructions i1108 when executed direct electronically receiving the operation information as encrypted data (e.g. an implementation of the receiver component s528 is configured to electronically receive through the encrypted communication component s520 the operation information, etc.). Furthermore, the receiving encrypted information electrical circuitry arrangement e1108 when activated will perform the operation o1108. In an implementation, the receiving encrypted information electrical circuitry arrangement e1108, when activated performs electronically receiving the operation information as encrypted data (e.g. an implementation of the receiver component s528 is configured to electronically receive through the encrypted communication component s520 the operation information, etc.). In an implementation, the electronically receiving the operation information as encrypted data is carried out by electronically receiving the operation information as encrypted data (e.g. an implementation of the receiver component s528 is configured to electronically receive through the encrypted communication component s520 the operation information, etc.).

In one or more implementations, operation o11 includes an operation o1109 for electronically receiving the operation information contained on a memory card. An exemplary version of a non-transitory signal bearing medium of information storage subsystem s200 is depicted as bearing one or more receiving information memory card instructions i1109 that when executed will direct performance of the operation o1109. In an implementation, the one or more receiving information memory card instructions i1109 when executed direct electronically receiving the operation information contained on a memory card (e.g. an implementation of the receiver component s528 is configured to electronically engage with an electronic memory card to receive the operation information, etc.). Furthermore, the receiving information memory card electrical circuitry arrangement e1109 when activated will perform the operation o1109. In an implementation, the receiving information memory card electrical circuitry arrangement e1109, when activated performs electronically receiving the operation information contained on a memory card (e.g. an implementation of the receiver component s528 is configured to electronically engage with an electronic memory card to receive the operation information, etc.). In an implementation, the electronically receiving the operation information contained on a memory card is carried out by electronically receiving the operation information contained on a memory card (e.g. an implementation of the receiver component s528 is configured to electronically engage with an electronic memory card to receive the operation information, etc.).

Figure 42:
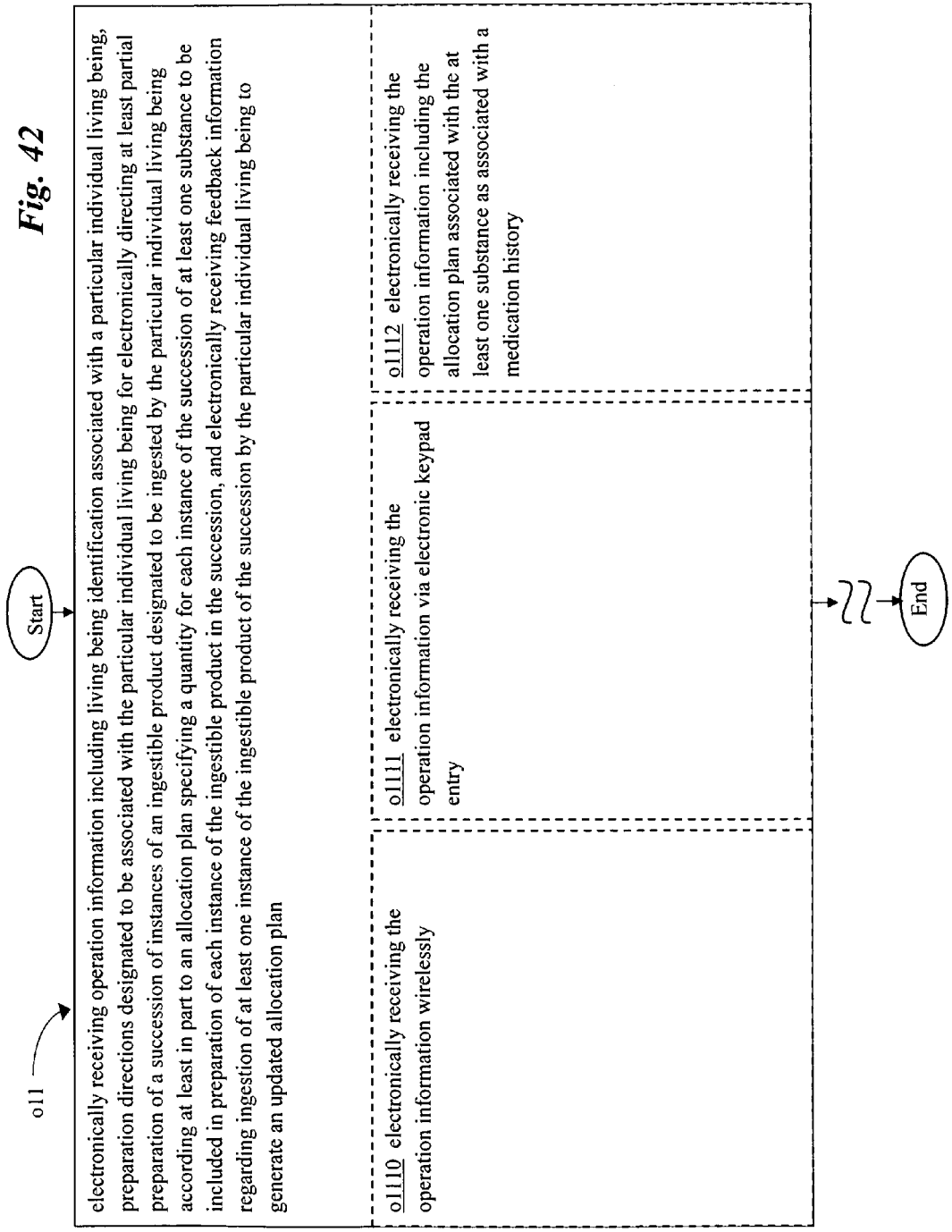
FIG. 42 is a high-level flowchart including exemplary implementations of operation O11 of FIG. 38.

In one or more implementations, as shown in FIG. 42, operation o11 includes an operation o1110 for electronically receiving the operation information wirelessly. An exemplary version of a non-transitory signal bearing medium of information storage subsystem s200 is depicted as bearing one or more receiving information wirelessly instructions i1110 that when executed will direct performance of the operation o1110. In an implementation, the one or more receiving information wirelessly instructions i1110 when executed direct electronically receiving the operation information wirelessly (e.g. an implementation of the receiver component s528 is configured to electronically receive through the wireless network component s512 the operation information, etc.). Furthermore, the receiving information wirelessly electrical circuitry arrangement e1110 when activated will perform the operation o1110. In an implementation, the receiving information wirelessly electrical circuitry arrangement e1110, when activated performs electronically receiving the operation information wirelessly (e.g. an implementation of the receiver component s528 is configured to electronically receive through the wireless network component s512 the operation information, etc.). In an implementation, the electronically receiving the operation information wirelessly is carried out by electronically receiving the operation information wirelessly (e.g. an implementation of the receiver component s528 is configured to electronically receive through the wireless network component s512 the operation information, etc.).

In one or more implementations, operation o11 includes an operation o1111 for electronically receiving the operation information via electronic keypad entry. An exemplary version of a non-transitory signal bearing medium of information storage subsystem s200 is depicted as bearing one or more receiving information keypad entry instructions i1111 that when executed will direct performance of the operation o1111. In an implementation, the one or more receiving information keypad entry instructions i1111 when executed direct electronically receiving the operation information via electronic keypad entry (e.g. an implementation of the receiver component s528 is configured to electronically engage with the keypad component s308 to receive the operation information as inputted by a user, etc.). Furthermore, the receiving information keypad entry electrical circuitry arrangement e1111 when activated will perform the operation o1111. In an implementation, the receiving information keypad entry electrical circuitry arrangement e1111, when activated performs electronically receiving the operation information via electronic keypad entry (e.g. an implementation of the receiver component s528 is configured to electronically engage with the keypad component s308 to receive the operation information as inputted by a user, etc.). In an implementation, the electronically receiving the operation information via electronic keypad entry is carried out by electronically receiving the operation information via electronic keypad entry (e.g. an implementation of the receiver component s528 is configured to electronically engage with the keypad component s308 to receive the operation information as inputted by a user, etc.).

In one or more implementations, operation o11 includes an operation o1112 for electronically receiving the operation information including the allocation plan associated with the at least one substance as associated with a medication history. An exemplary version of a non-transitory signal bearing medium of information storage subsystem s200 is depicted as bearing one or more receiving information meds history instructions i1112 that when executed will direct performance of the operation o1112. In an implementation, the one or more receiving information meds history instructions i1112 when executed direct electronically receiving the operation information including the allocation plan associated with the at least one substance as associated with a medication history (e.g. an implementation of the receiver component s528 is configured to electronically engage with the processor component s102 to receive the operation information including the allocation plan as determined by the processor component to identify name and control number of the at least one substance and the name and control number of the medication history of the particular individual living being, etc.). Furthermore, the receiving information meds history electrical circuitry arrangement e1112 when activated will perform the operation o1112. In an implementation, the receiving information meds history electrical circuitry arrangement e1112, when activated performs electronically receiving the operation information including the allocation plan associated with the at least one substance as associated with a medication history (e.g. an implementation of the receiver component s528 is configured to electronically engage with the processor component s102 to receive the operation information including the allocation plan as determined by the processor component to identify name and control number of the at least one substance and the name and control number of the medication history of the particular individual living being, etc.). In an implementation, the electronically receiving the operation information including the allocation plan associated with the at least one substance as associated with a medication history is carried out by electronically receiving the operation information including the allocation plan associated with the at least one substance as associated with a medication history (e.g. an implementation of the receiver component s528 is configured to electronically engage with the processor component s102 to receive the operation information including the allocation plan as determined by the processor component to identify name and control number of the at least one substance and the name and control number of the medication history of the particular individual living being, etc.).

Figure 43:
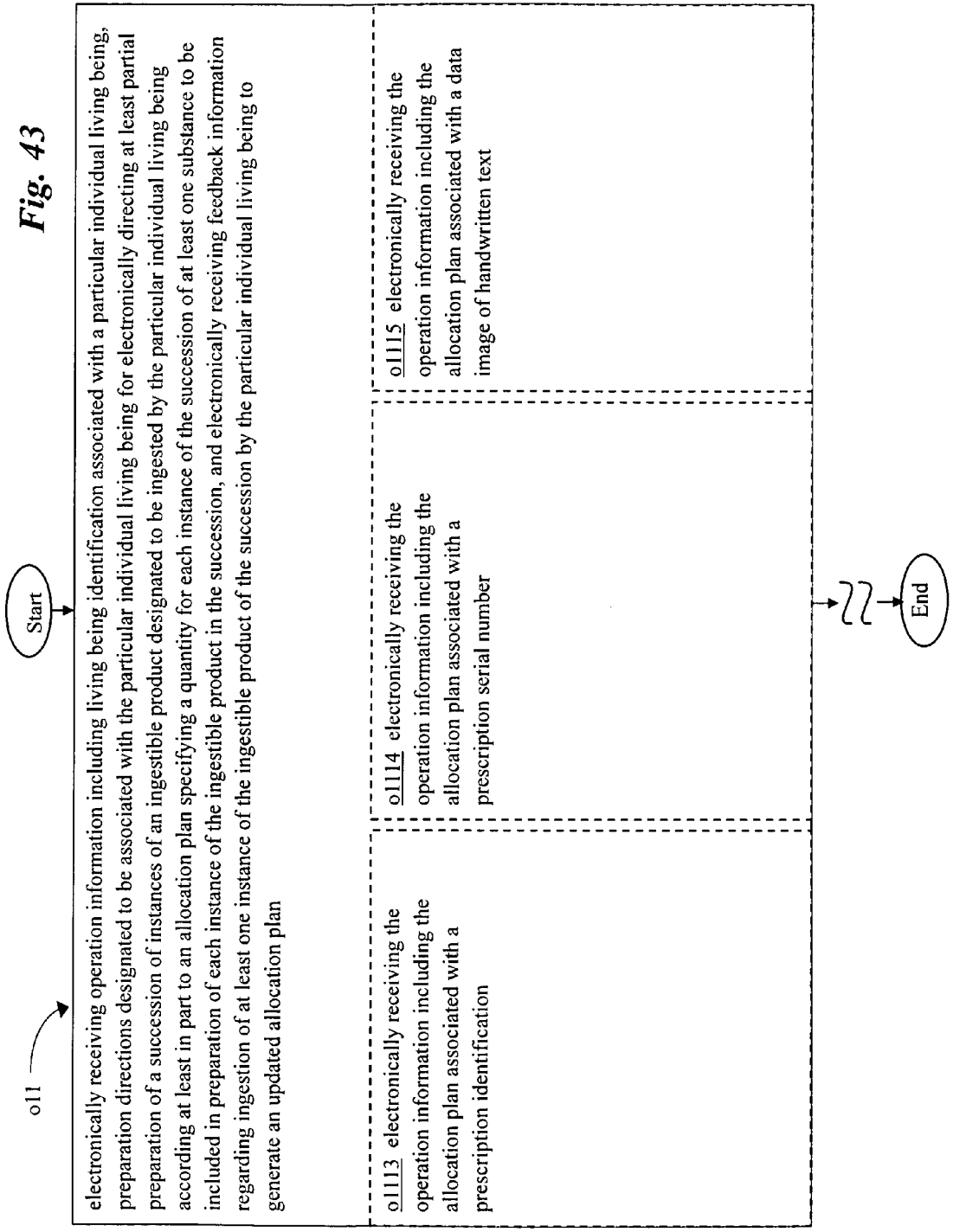
FIG. 43 is a high-level flowchart including exemplary implementations of operation O11 of FIG. 38.

In one or more implementations, as shown in FIG. 43, operation o11 includes an operation o1113 for electronically receiving the operation information including the allocation plan associated with a prescription identification. An exemplary version of a non-transitory signal bearing medium of information storage subsystem s200 is depicted as bearing one or more receiving information prescription ID instructions i1113 that when executed will direct performance of the operation o1113. In an implementation, the one or more receiving information prescription ID instructions i1113 when executed direct electronically receiving the operation information including the allocation plan associated with a prescription identification (e.g. an implementation of the receiver component s528 is configured to electronically engage with the processor component s102 to receive the operation information including the allocation plan as determined by the processor component to include a name of an issuing physician, etc.). Furthermore, the receiving information prescription ID electrical circuitry arrangement e1113 when activated will perform the operation o1113. In an implementation, the receiving information prescription ID electrical circuitry arrangement e1113, when activated performs electronically receiving the operation information including the allocation plan associated with a prescription identification (e.g. an implementation of the receiver component s528 is configured to electronically engage with the processor component s102 to receive the operation information including the allocation plan as determined by the processor component to include a name of an issuing physician, etc.). In an implementation, the electronically receiving the operation information including the allocation plan associated with a prescription identification is carried out by electronically receiving the operation information including the allocation plan associated with a prescription identification (e.g. an implementation of the receiver component s528 is configured to electronically engage with the processor component s102 to receive the operation information including the allocation plan as determined by the processor component to include a name of an issuing physician, etc.).

In one or more implementations, operation o11 includes an operation o1114 for electronically receiving the operation information including the allocation plan associated with a prescription serial number. An exemplary version of a non-transitory signal bearing medium of information storage subsystem s200 is depicted as bearing one or more receiving information prescription number instructions i1114 that when executed will direct performance of the operation o1114. In an implementation, the one or more receiving information prescription number instructions i1114 when executed direct electronically receiving the operation information including the allocation plan associated with a prescription serial number (e.g. an implementation of the receiver component s528 is configured to electronically engage with the processor component s102 to receive the operation information including the allocation plan as determined by the processor component to include a prescription serial number for the substance, etc.). Furthermore, the receiving information prescription number electrical circuitry arrangement e1114 when activated will perform the operation o1114. In an implementation, the receiving information prescription number electrical circuitry arrangement e1114, when activated performs electronically receiving the operation information including the allocation plan associated with a prescription serial number (e.g. an implementation of the receiver component s528 is configured to electronically engage with the processor component s102 to receive the operation information including the allocation plan as determined by the processor component to include a prescription serial number for the substance, etc.). In an implementation, the electronically receiving the operation information including the allocation plan associated with a prescription serial number is carried out by electronically receiving the operation information including the allocation plan associated with a prescription serial number (e.g. an implementation of the receiver component s528 is configured to electronically engage with the processor component s102 to receive the operation information including the allocation plan as determined by the processor component to include a prescription serial number for the substance, etc.).

In one or more implementations, operation o11 includes an operation o1115 for electronically receiving the operation information including the allocation plan associated with a data image of handwritten text. An exemplary version of a non-transitory signal bearing medium of information storage subsystem s200 is depicted as bearing one or more receiving information handwritten instructions i1115 that when executed will direct performance of the operation o1115. In an implementation, the one or more receiving information handwritten instructions i1115 when executed direct electronically receiving the operation information including the allocation plan associated with a data image of handwritten text (e.g. an implementation of the receiver component s528 is configured to electronically engage with the processor component s102 to receive the operation information including a name of the substance as determined by the processor component through electronic handwriting analysis of the data image of the handwritten text, etc.). Furthermore, the receiving information handwritten electrical circuitry arrangement e1115 when activated will perform the operation o1115. In an implementation, the receiving information handwritten electrical circuitry arrangement e1115, when activated performs electronically receiving the operation information including the allocation plan associated with a data image of handwritten text (e.g. an implementation of the receiver component s528 is configured to electronically engage with the processor component s102 to receive the operation information including a name of the substance as determined by the processor component through electronic handwriting analysis of the data image of the handwritten text, etc.). In an implementation, the electronically receiving the operation information including the allocation plan associated with a data image of handwritten text is carried out by electronically receiving the operation information including the allocation plan associated with a data image of handwritten text (e.g. an implementation of the receiver component s528 is configured to electronically engage with the processor component s102 to receive the operation information including a name of the substance as determined by the processor component through electronic handwriting analysis of the data image of the handwritten text, etc.).

Figure 44:
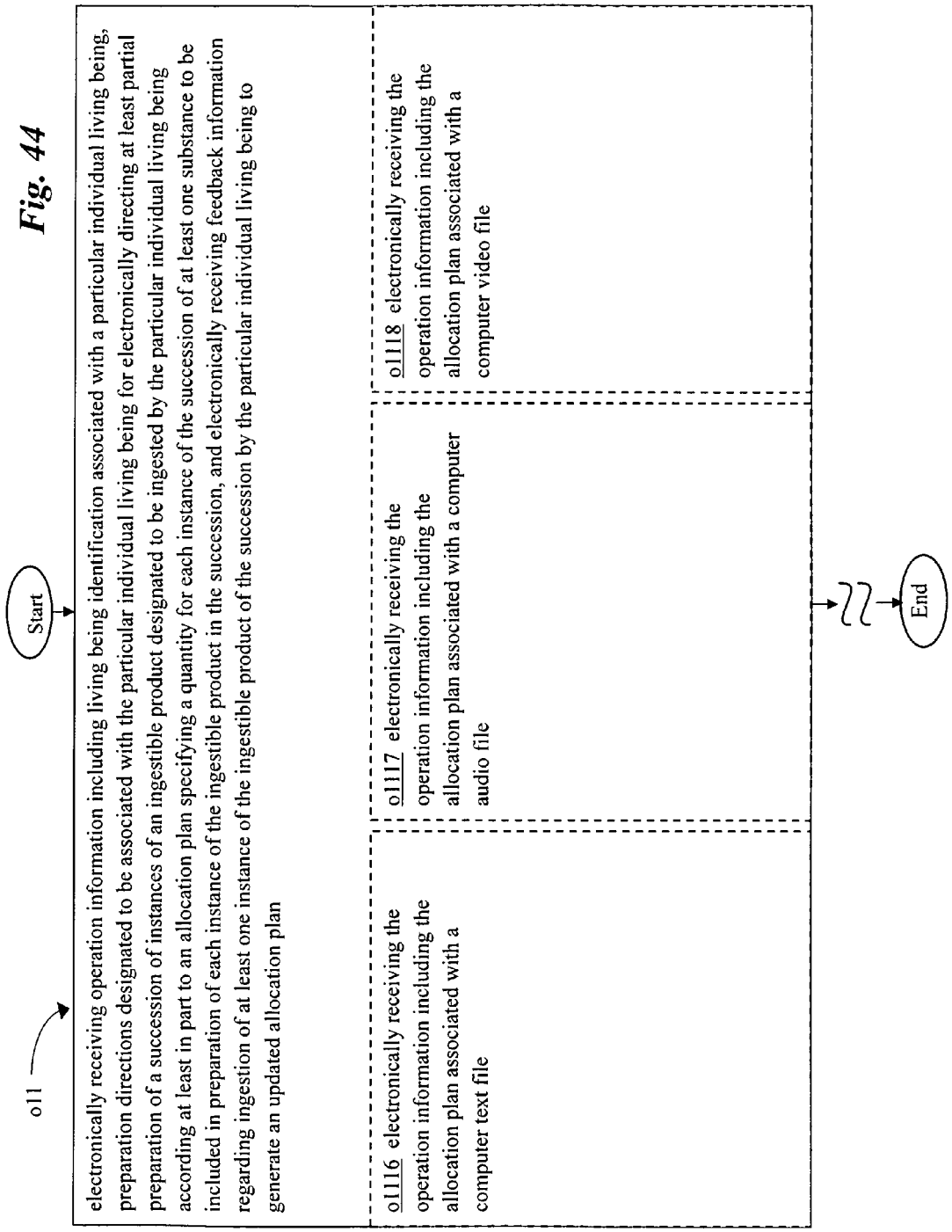
FIG. 44 is a high-level flowchart including exemplary implementations of operation O11 of FIG. 38.

In one or more implementations, as shown in FIG. 44, operation o11 includes an operation o1116 for electronically receiving the operation information including the allocation plan associated with a computer text file. An exemplary version of a non-transitory signal bearing medium of information storage subsystem s200 is depicted as bearing one or more receiving information text file instructions i1116 that when executed will direct performance of the operation o1116. In an implementation, the one or more receiving information text file instructions i1116 when executed direct electronically receiving the operation information including the allocation plan associated with a computer text file (e.g. an implementation of the receiver component s528 is configured to electronically engage with the processor component s102 to receive the operation information including the allocation plan as determined by the processor component through electronic reading of the computer text file, etc.). Furthermore, the receiving information text file electrical circuitry arrangement e1116 when activated will perform the operation o1116. In an implementation, the receiving information text file electrical circuitry arrangement e1116, when activated performs electronically receiving the operation information including the allocation plan associated with a computer text file (e.g. an implementation of the receiver component s528 is configured to electronically engage with the processor component s102 to receive the operation information including the allocation plan as determined by the processor component through electronic reading of the computer text file, etc.). In an implementation, the electronically receiving the operation information including the allocation plan associated with a computer text file is carried out by electronically receiving the operation information including the allocation plan associated with a computer text file (e.g. an implementation of the receiver component s528 is configured to electronically engage with the processor component s102 to receive the operation information including the allocation plan as determined by the processor component through electronic reading of the computer text file, etc.).

In one or more implementations, operation o11 includes an operation o1117 for electronically receiving the operation information including the allocation plan associated with a computer audio file. An exemplary version of a non-transitory signal bearing medium of information storage subsystem s200 is depicted as bearing one or more receiving information audio file instructions i1117 that when executed will direct performance of the operation o1117. In an implementation, the one or more receiving information audio file instructions i1117 when executed direct electronically receiving the operation information including the allocation plan associated with a computer audio file (e.g. an implementation of the receiver component s528 is configured to electronically engage with the processor component s102 to receive the operation information including the allocation plan as determined by the processor component through electronic reading of the computer audio file, etc.). Furthermore, the receiving information audio file electrical circuitry arrangement e1117 when activated will perform the operation o1117. In an implementation, the receiving information audio file electrical circuitry arrangement e1117, when activated performs electronically receiving the operation information including the allocation plan associated with a computer audio file (e.g. an implementation of the receiver component s528 is configured to electronically engage with the processor component s102 to receive the operation information including the allocation plan as determined by the processor component through electronic reading of the computer audio file, etc.). In an implementation, the electronically receiving the operation information including the allocation plan associated with a computer audio file is carried out by electronically receiving the operation information including the allocation plan associated with a computer audio file (e.g. an implementation of the receiver component s528 is configured to electronically engage with the processor component s102 to receive the operation information including the allocation plan as determined by the processor component through electronic reading of the computer audio file, etc.).

In one or more implementations, operation o11 includes an operation o1118 for electronically receiving the operation information including the allocation plan associated with a computer video file. An exemplary version of a non-transitory signal bearing medium of information storage subsystem s200 is depicted as bearing one or more receiving information video file instructions i1118 that when executed will direct performance of the operation o1118. In an implementation, the one or more receiving information video file instructions i1118 when executed direct electronically receiving the operation information including the allocation plan associated with a computer video file (e.g. an implementation of the receiver component s528 is configured to electronically engage with the processor component s102 to receive the operation information including the allocation plan as determined by the processor component through electronic reading of the computer video file, etc.). Furthermore, the receiving information video file electrical circuitry arrangement e1118 when activated will perform the operation o1118. In an implementation, the receiving information video file electrical circuitry arrangement e1118, when activated performs electronically receiving the operation information including the allocation plan associated with a computer video file (e.g. an implementation of the receiver component s528 is configured to electronically engage with the processor component s102 to receive the operation information including the allocation plan as determined by the processor component through electronic reading of the computer video file, etc.). In an implementation, the electronically receiving the operation information including the allocation plan associated with a computer video file is carried out by electronically receiving the operation information including the allocation plan associated with a computer video file (e.g. an implementation of the receiver component s528 is configured to electronically engage with the processor component s102 to receive the operation information including the allocation plan as determined by the processor component through electronic reading of the computer video file, etc.).

In one or more implementations, as shown in FIG. 45, operation o11 includes an operation o1119 for electronically receiving the operation information including the allocation plan associated with an RFID tag. An exemplary version of a non-transitory signal bearing medium of information storage subsystem s200 is depicted as bearing one or more receiving information RFID instructions i1119 that when executed will direct performance of the operation o1119. In an implementation, the one or more receiving information RFID instructions i1119 when executed direct electronically receiving the operation information including the allocation plan associated with an RFID tag (e.g. an implementation of the receiver component s528 is configured to electronically engage with the processor component s102 to receive the operation information including the allocation plan as determined by the processor component through electronic reading be the radio frequency identification (RFID) sensing component s414 of the RFID tag, etc.). Furthermore, the receiving information RFID electrical circuitry arrangement e1119 when activated will perform the operation o1119. In an implementation, the receiving information RFID electrical circuitry arrangement e1119, when activated performs electronically receiving the operation information including the allocation plan associated with an RFID tag (e.g. an implementation of the receiver component s528 is configured to electronically engage with the processor component s102 to receive the operation information including the allocation plan as determined by the processor component through electronic reading be the radio frequency identification (RFID) sensing component s414 of the RFID tag, etc.). In an implementation, the electronically receiving the operation information including the allocation plan associated with an RFID tag is carried out by electronically receiving the operation information including the allocation plan associated with an RFID tag (e.g. an implementation of the receiver component s528 is configured to electronically engage with the processor component s102 to receive the operation information including the allocation plan as determined by the processor component through electronic reading be the radio frequency identification (RFID) sensing component s414 of the RFID tag, etc.).

In one or more implementations, operation o11 includes an operation o1120 for electronically receiving the operation information including the allocation plan associated with a bar code. An exemplary version of a non-transitory signal bearing medium of information storage subsystem s200 is depicted as bearing one or more receiving information bar code instructions i1120 that when executed will direct performance of the operation o1120. In an implementation, the one or more receiving information bar code instructions i1120 when executed direct electronically receiving the operation information including the allocation plan associated with a bar code (e.g. an implementation of the receiver component s528 is configured to electronically engage with the processor component s102 to receive the operation information including the allocation plan as determined by the processor component through electronic reading of the bar code, etc.). Furthermore, the receiving information bar code electrical circuitry arrangement e1120 when activated will perform the operation electronically receiving the operation information including the allocation plan associated with a bar code. In an implementation, the receiving information bar code electrical circuitry arrangement e1120, when activated performs electronically receiving the operation information including the allocation plan associated with a bar code (e.g. an implementation of the receiver component s528 is configured to electronically engage with the processor component s102 to receive the operation information including the allocation plan as determined by the processor component through electronic reading of the bar code, etc.). In an implementation, the electronically receiving the operation information including the allocation plan associated with a bar code is carried out by electronically receiving the operation information including the allocation plan associated with a bar code (e.g. an implementation of the receiver component s528 is configured to electronically engage with the processor component s102 to receive the operation information including the allocation plan as determined by the processor component through electronic reading of the bar code, etc.).

In one or more implementations, operation o11 includes an operation o1121 for electronically receiving the operation information including the allocation plan associated with a holographic image. An exemplary version of a non-transitory signal bearing medium of information storage subsystem s200 is depicted as bearing one or more receiving information holographic instructions i1121 that when executed will direct performance of the operation o1121. In an implementation, the one or more receiving information holographic instructions i1121 when executed direct electronically receiving the operation information including the allocation plan associated with a holographic image (e.g. an implementation of the receiver component s528 is configured to electronically engage with the processor component s102 to receive the operation information including the allocation plan as determined by the processor component through electronic reading of the holographic image, etc.). Furthermore, the receiving information holographic electrical circuitry arrangement e1121 when activated will perform the operation o1121. In an implementation, the receiving information holographic electrical circuitry arrangement e1121, when activated performs electronically receiving the operation information including the allocation plan associated with a holographic image (e.g. an implementation of the receiver component s528 is configured to electronically engage with the processor component s102 to receive the operation information including the allocation plan as determined by the processor component through electronic reading of the holographic image, etc.). In an implementation, the electronically receiving the operation information including the allocation plan associated with a holographic image is carried out by electronically receiving the operation information including the allocation plan associated with a holographic image (e.g. an implementation of the receiver component s528 is configured to electronically engage with the processor component s102 to receive the operation information including the allocation plan as determined by the processor component through electronic reading of the holographic image, etc.).

Figure 46:
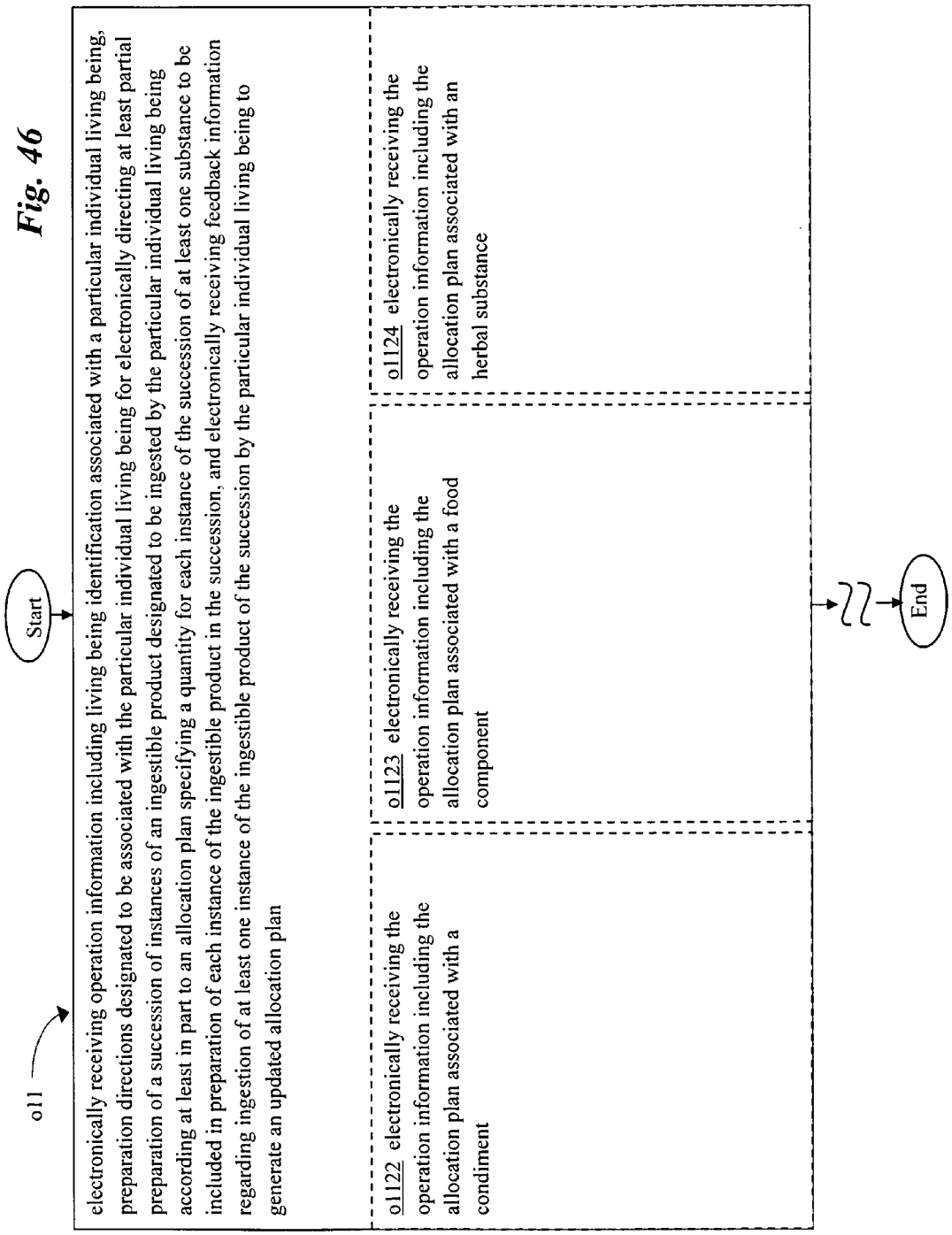
FIG. 46 is a high-level flowchart including exemplary implementations of operation O11 of FIG. 38.

In one or more implementations, as shown in FIG. 46, operation o11 includes an operation o1122 for electronically receiving the operation information including the allocation plan associated with a condiment. An exemplary version of a non-transitory signal bearing medium of information storage subsystem s200 is depicted as bearing one or more receiving information condiment instructions i1122 that when executed will direct performance of the operation o1122. In an implementation, the one or more receiving information condiment instructions i1122 when executed direct electronically receiving the operation information including the allocation plan associated with a condiment (e.g. an implementation of the receiver component s528 is configured to electronically engage with the processor component s102 to receive the operation information including the allocation plan as determined by the processor component to be associated with a condiment such as salt, sugar, cayenne, etc.). Furthermore, the receiving information condiment electrical circuitry arrangement e1122 when activated will perform the operation o1122. In an implementation, the receiving information condiment electrical circuitry arrangement e1122, when activated performs electronically receiving the operation information including the allocation plan associated with a condiment (e.g. an implementation of the receiver component s528 is configured to electronically engage with the processor component s102 to receive the operation information including the allocation plan as determined by the processor component to be associated with a condiment such as salt, sugar, cayenne, etc.). In an implementation, the electronically receiving the operation information including the allocation plan associated with a condiment is carried out by electronically receiving the operation information including the allocation plan associated with a condiment (e.g. an implementation of the receiver component s528 is configured to electronically engage with the processor component s102 to receive the operation information including the allocation plan as determined by the processor component to be associated with a condiment such as salt, sugar, cayenne, etc.).

In one or more implementations, operation o11 includes an operation o1123 for electronically receiving the operation information including the allocation plan associated with a food component. An exemplary version of a non-transitory signal bearing medium of information storage subsystem s200 is depicted as bearing one or more receiving information food component instructions i1123 that when executed will direct performance of the operation o1123. In an implementation, the one or more receiving information food component instructions i1123 when executed direct electronically receiving the operation information including the allocation plan associated with a food component (e.g. an implementation of the receiver component s528 is configured to electronically engage with the processor component s102 to receive the operation information including the allocation plan as determined by the processor component to be associated with a food component such as cholesterol, saturated fat, unsaturated fat, monounsaturated fat, refined carbohydrates, fiber, one or more essential fatty acids, vitamin B complex, etc.). Furthermore, the receiving information food component electrical circuitry arrangement e1123 when activated will perform the operation o1123. In an implementation, the receiving information food component electrical circuitry arrangement e1123, when activated performs electronically receiving the operation information including the allocation plan associated with a food component (e.g. an implementation of the receiver component s528 is configured to electronically engage with the processor component s102 to receive the operation information including the allocation plan as determined by the processor component to be associated with a food component such as cholesterol, saturated fat, unsaturated fat, monounsaturated fat, refined carbohydrates, fiber, one or more essential fatty acids, vitamin B complex, etc.). In an implementation, the electronically receiving the operation information including the allocation plan associated with a food component is carried out by electronically receiving the operation information including the allocation plan associated with a food component (e.g. an implementation of the receiver component s528 is configured to electronically engage with the processor component s102 to receive the operation information including the allocation plan as determined by the processor component to be associated with a food component such as cholesterol, saturated fat, unsaturated fat, monounsaturated fat, refined carbohydrates, fiber, one or more essential fatty acids, vitamin B complex, etc.).

In one or more implementations, operation o11 includes an operation o1124 for electronically receiving the operation information including the allocation plan associated with an herbal substance. An exemplary version of a non-transitory signal bearing medium of information storage subsystem s200 is depicted as bearing one or more receiving information herbal instructions i1124 that when executed will direct performance of the operation o1124. In an implementation, the one or more receiving information herbal instructions i1124 when executed direct electronically receiving the operation information including the allocation plan associated with an herbal substance (e.g. an implementation of the receiver component s528 is configured to electronically engage with the processor component s102 to receive the operation information including the allocation plan as determined by the processor component to be identifying an herbal substance, etc.). Furthermore, the receiving information herbal electrical circuitry arrangement e1124 when activated will perform the operation o1124. In an implementation, the receiving information herbal electrical circuitry arrangement e1124, when activated performs electronically receiving the operation information including the allocation plan associated with an herbal substance (e.g. an implementation of the receiver component s528 is configured to electronically engage with the processor component s102 to receive the operation information including the allocation plan as determined by the processor component to be identifying an herbal substance, etc.). In an implementation, the electronically receiving the operation information including the allocation plan associated with an herbal substance is carried out by electronically receiving the operation information including the allocation plan associated with an herbal substance (e.g. an implementation of the receiver component s528 is configured to electronically engage with the processor component s102 to receive the operation information including the allocation plan as determined by the processor component to be identifying an herbal substance, etc.).

Figure 47:
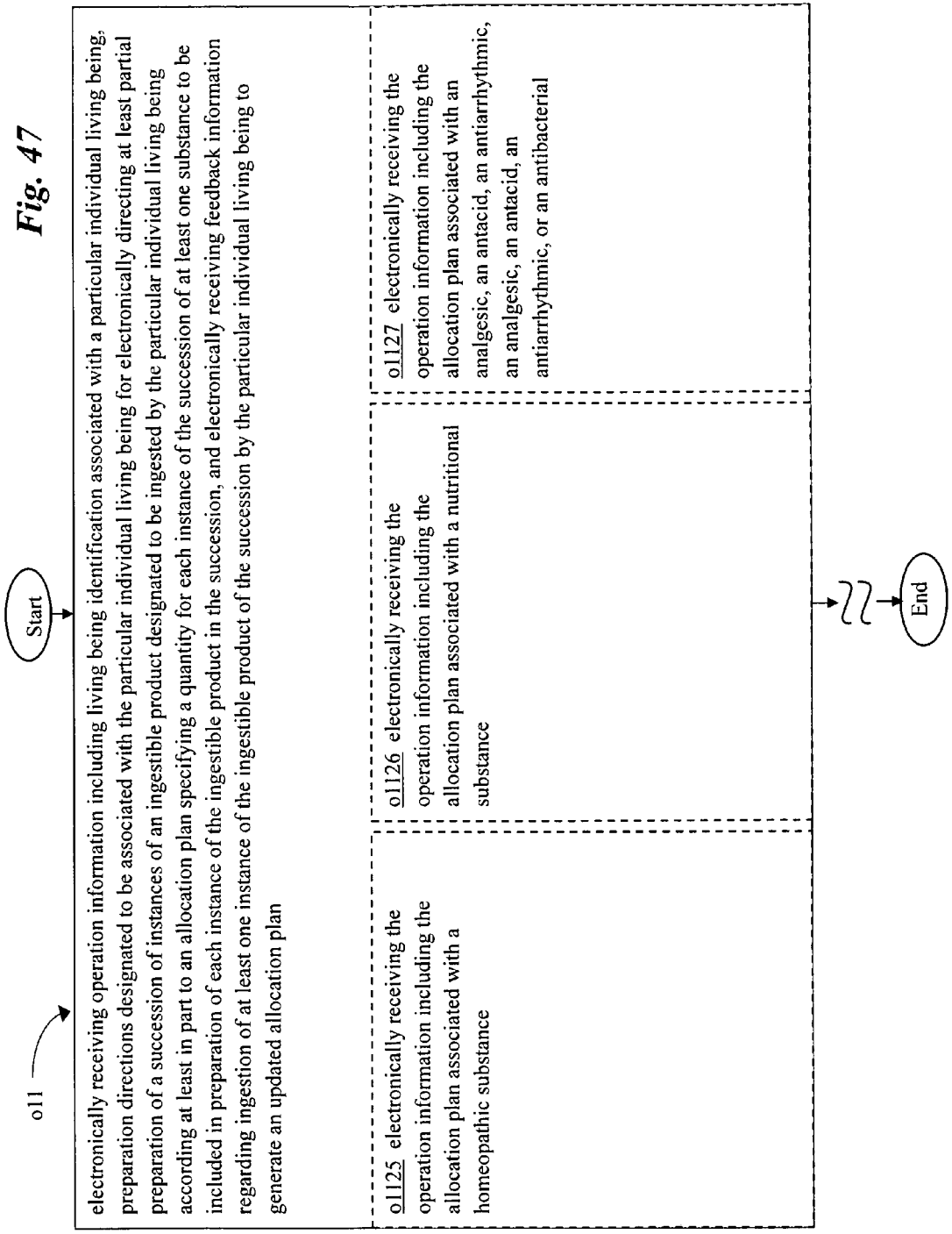
FIG. 47 is a high-level flowchart including exemplary implementations of operation O11 of FIG. 38.

In one or more implementations, as shown in FIG. 47, operation o11 includes an operation o1125 for electronically receiving the operation information including the allocation plan associated with a homeopathic substance. An exemplary version of a non-transitory signal bearing medium of information storage subsystem s200 is depicted as bearing one or more receiving information homeopathic instructions i1125 that when executed will direct performance of the operation o1125. In an implementation, the one or more receiving information homeopathic instructions i1125 when executed direct electronically receiving the operation information including the allocation plan associated with a homeopathic substance (e.g. an implementation of the receiver component s528 is configured to electronically engage with the processor component s102 to receive the operation information including the allocation plan as determined by the processor component to be identifying a homeopathic substance, etc.). Furthermore, the receiving information homeopathic electrical circuitry arrangement e1125 when activated will perform the operation o1125. In an implementation, the receiving information homeopathic electrical circuitry arrangement e1125, when activated performs electronically receiving the operation information including the allocation plan associated with a homeopathic substance (e.g. an implementation of the receiver component s528 is configured to electronically engage with the processor component s102 to receive the operation information including the allocation plan as determined by the processor component to be identifying a homeopathic substance, etc.). In an implementation, the electronically receiving the operation information including the allocation plan associated with a homeopathic substance is carried out by electronically receiving the operation information including the allocation plan associated with a homeopathic substance (e.g. an implementation of the receiver component s528 is configured to electronically engage with the processor component s102 to receive the operation information including the allocation plan as determined by the processor component to be identifying a homeopathic substance, etc.).

In one or more implementations, operation o11 includes an operation o1126 for electronically receiving the operation information including the allocation plan associated with a nutritional substance. An exemplary version of a non-transitory signal bearing medium of information storage subsystem s200 is depicted as bearing one or more receiving information nutritional instructions i1126 that when executed will direct performance of the operation o1126. In an implementation, the one or more receiving information nutritional instructions i1126 when executed direct electronically receiving the operation information including the allocation plan associated with a nutritional substance (e.g. an implementation of the receiver component s528 is configured to electronically engage with the processor component s102 to receive the operation information including the allocation plan as determined by the processor component to be identifying a nutritional substance, etc.). Furthermore, the receiving information nutritional electrical circuitry arrangement e1126 when activated will perform the operation o1126. In an implementation, the receiving information nutritional electrical circuitry arrangement e1126, when activated performs electronically receiving the operation information including the allocation plan associated with a nutritional substance (e.g. an implementation of the receiver component s528 is configured to electronically engage with the processor component s102 to receive the operation information including the allocation plan as determined by the processor component to be identifying a nutritional substance, etc.). In an implementation, the electronically receiving the operation information including the allocation plan associated with a nutritional substance is carried out by electronically receiving the operation information including the allocation plan associated with a nutritional substance (e.g. an implementation of the receiver component s528 is configured to electronically engage with the processor component s102 to receive the operation information including the allocation plan as determined by the processor component to be identifying a nutritional substance, etc.).

In one or more implementations, operation o11 includes an operation o1127 for electronically receiving the operation information including the allocation plan associated with an analgesic, an antacid, an antiarrhythmic, an analgesic, an antacid, an antiarrhythmic, or an antibacterial. An exemplary version of a non-transitory signal bearing medium of information storage subsystem s200 is depicted as bearing one or more receiving information first medications instructions i1127 that when executed will direct performance of the operation o1127. In an implementation, the one or more receiving information first medications instructions i1127 when executed direct electronically receiving the operation information including the allocation plan associated with an analgesic, an antacid, an antiarrhythmic, an analgesic, an antacid, an antiarrhythmic, or an antibacteria (e.g. an implementation of the receiver component s528 is configured to electronically engage with the processor component s102 to receive the operation information including the allocation plan as determined by the processor component to be identifying an analgesic, an antacid, an antiarrhythmic, an analgesic, an antacid, an antiarrhythmic, or an antibacteria, etc.)1. Furthermore, the receiving information first medications electrical circuitry arrangement e1127 when activated will perform the operation o1127. In an implementation, the receiving information first medications electrical circuitry arrangement e1127, when activated performs electronically receiving the operation information including the allocation plan associated with an analgesic, an antacid, an antiarrhythmic, an analgesic, an antacid, an antiarrhythmic, or an antibacteria (e.g. an implementation of the receiver component s528 is configured to electronically engage with the processor component s102 to receive the operation information including the allocation plan as determined by the processor component to be identifying an analgesic, an antacid, an antiarrhythmic, an analgesic, an antacid, an antiarrhythmic, or an antibacteria, etc.)1. In an implementation, the electronically receiving the operation information including the allocation plan associated with an analgesic, an antacid, an antiarrhythmic, an analgesic, an antacid, an antiarrhythmic, or an antibacterial is carried out by electronically receiving the operation information including the allocation plan associated with an analgesic, an antacid, an antiarrhythmic, an analgesic, an antacid, an antiarrhythmic, or an antibacteria (e.g. an implementation of the receiver component s528 is configured to electronically engage with the processor component s102 to receive the operation information including the allocation plan as determined by the processor component to be identifying an analgesic, an antacid, an antiarrhythmic, an analgesic, an antacid, an antiarrhythmic, or an antibacteria, etc.)1.

Figure 48:
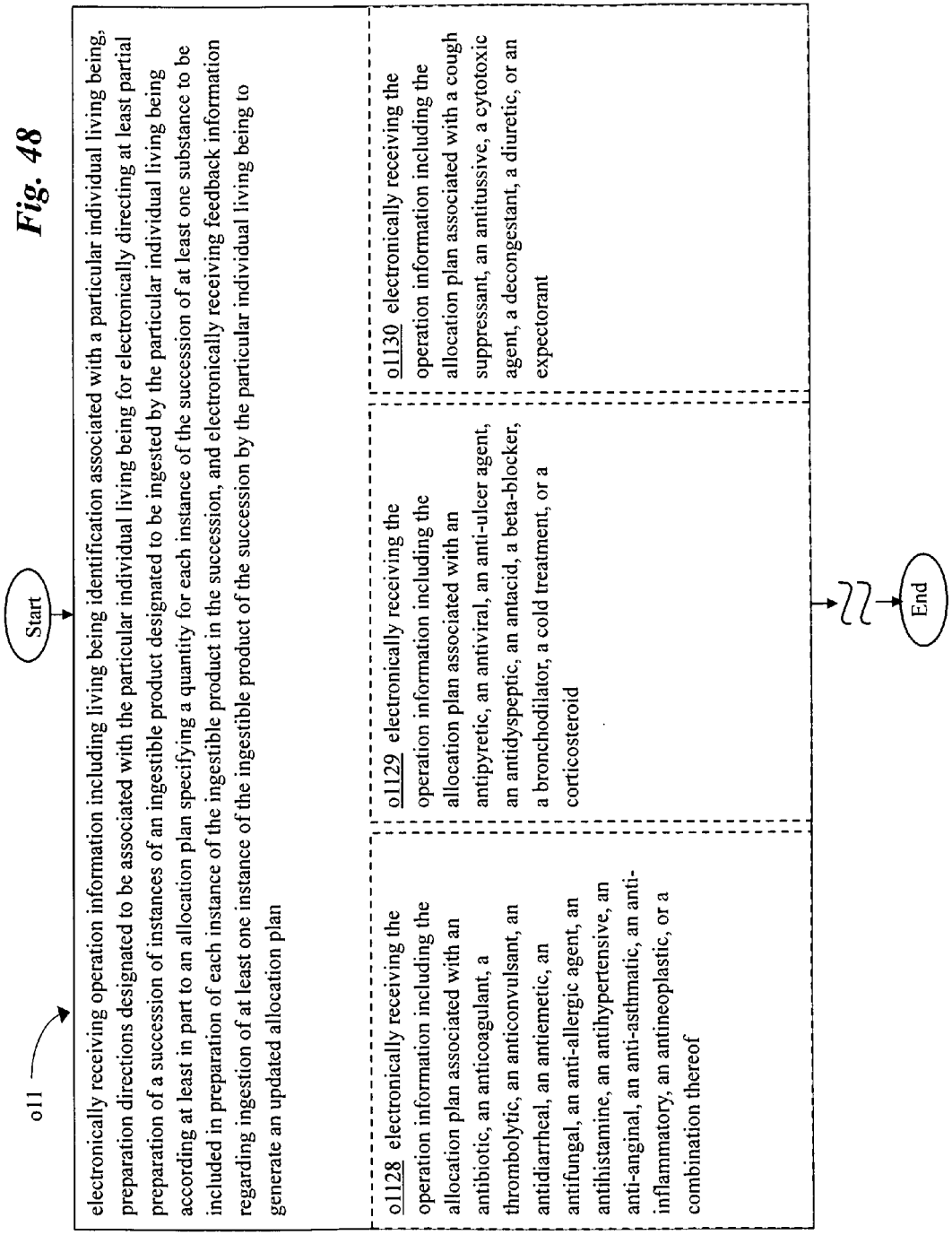
FIG. 48 is a high-level flowchart including exemplary implementations of operation O11 of FIG. 38.

In one or more implementations, as shown in FIG. 48, operation o11 includes an operation o1128 for electronically receiving the operation information including the allocation plan associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof. An exemplary version of a non-transitory signal bearing medium of information storage subsystem s200 is depicted as bearing one or more receiving information second medications instructions i1128 that when executed will direct performance of the operation o1128. In an implementation, the one or more receiving information second medications instructions i1128 when executed direct electronically receiving the operation information including the allocation plan associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the operation information including the allocation plan as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). Furthermore, the receiving information second medications electrical circuitry arrangement e1128 when activated will perform the operation o1128. In an implementation, the receiving information second medications electrical circuitry arrangement e1128, when activated performs electronically receiving the operation information including the allocation plan associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the operation information including the allocation plan as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). In an implementation, the electronically receiving the operation information including the allocation plan associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof is carried out by electronically receiving the operation information including the allocation plan associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the operation information including the allocation plan as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.).

In one or more implementations, operation o11 includes an operation o1129 for electronically receiving the operation information including the allocation plan associated with an antipyretic, an antiviral, an anti-ulcer agent, an antidyspeptic, an antacid, a beta-blocker, a bronchodilator, a cold treatment, or a corticosteroid. An exemplary version of a non-transitory signal bearing medium of information storage subsystem s200 is depicted as bearing one or more receiving information third medications instructions i1129 that when executed will direct performance of the operation o1129. In an implementation, the one or more receiving information third medications instructions i1129 when executed direct electronically receiving the operation information including the allocation plan associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the operation information including the allocation plan as determined by the processor component to be identifying an antipyretic, an antiviral, an anti-ulcer agent, an antidyspeptic, an antacid, a beta-blocker, a bronchodilator, a cold treatment, or a corticosteroid, etc.). Furthermore, the receiving information third medications electrical circuitry arrangement e1129 when activated will perform the operation o1129. In an implementation, the receiving information third medications electrical circuitry arrangement e1129, when activated performs electronically receiving the operation information including the allocation plan associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the operation information including the allocation plan as determined by the processor component to be identifying an antipyretic, an antiviral, an anti-ulcer agent, an antidyspeptic, an antacid, a beta-blocker, a bronchodilator, a cold treatment, or a corticosteroid, etc.). In an implementation, the electronically receiving the operation information including the allocation plan associated with an antipyretic, an antiviral, an anti-ulcer agent, an antidyspeptic, an antacid, a beta-blocker, a bronchodilator, a cold treatment, or a corticosteroid is carried out by electronically receiving the operation information including the allocation plan associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the operation information including the allocation plan as determined by the processor component to be identifying an antipyretic, an antiviral, an anti-ulcer agent, an antidyspeptic, an antacid, a beta-blocker, a bronchodilator, a cold treatment, or a corticosteroid, etc.).

In one or more implementations, operation o11 includes an operation o1130 for electronically receiving the operation information including the allocation plan associated with a cough suppressant, an antitussive, a cytotoxic agent, a decongestant, a diuretic, or an expectorant. An exemplary version of a non-transitory signal bearing medium of information storage subsystem s200 is depicted as bearing one or more receiving information fourth medications instructions i1130 that when executed will direct performance of the operation o1130. In an implementation, the one or more receiving information fourth medications instructions i1130 when executed direct electronically receiving the operation information including the allocation plan associated with a cough suppressant, an antitussive, a cytotoxic agent, a decongestant, a diuretic, or an expectorant (e.g. an implementation of the receiver component s528 is configured to electronically engage with the processor component s102 to receive the operation information including the allocation plan as determined by the processor component to be identifying a cough suppressant, an antitussive, a cytotoxic agent, a decongestant, a diuretic, or an expectorant, etc.). Furthermore, the receiving information fourth medications electrical circuitry arrangement e1130 when activated will perform the operation o1130. In an implementation, the receiving information fourth medications electrical circuitry arrangement e1130, when activated performs electronically receiving the operation information including the allocation plan associated with a cough suppressant, an antitussive, a cytotoxic agent, a decongestant, a diuretic, or an expectorant (e.g. an implementation of the receiver component s528 is configured to electronically engage with the processor component s102 to receive the operation information including the allocation plan as determined by the processor component to be identifying a cough suppressant, an antitussive, a cytotoxic agent, a decongestant, a diuretic, or an expectorant, etc.). In an implementation, the electronically receiving the operation information including the allocation plan associated with a cough suppressant, an antitussive, a cytotoxic agent, a decongestant, a diuretic, or an expectorant is carried out by electronically receiving the operation information including the allocation plan associated with a cough suppressant, an antitussive, a cytotoxic agent, a decongestant, a diuretic, or an expectorant (e.g. an implementation of the receiver component s528 is configured to electronically engage with the processor component s102 to receive the operation information including the allocation plan as determined by the processor component to be identifying a cough suppressant, an antitussive, a cytotoxic agent, a decongestant, a diuretic, or an expectorant, etc.).

Figure 49:
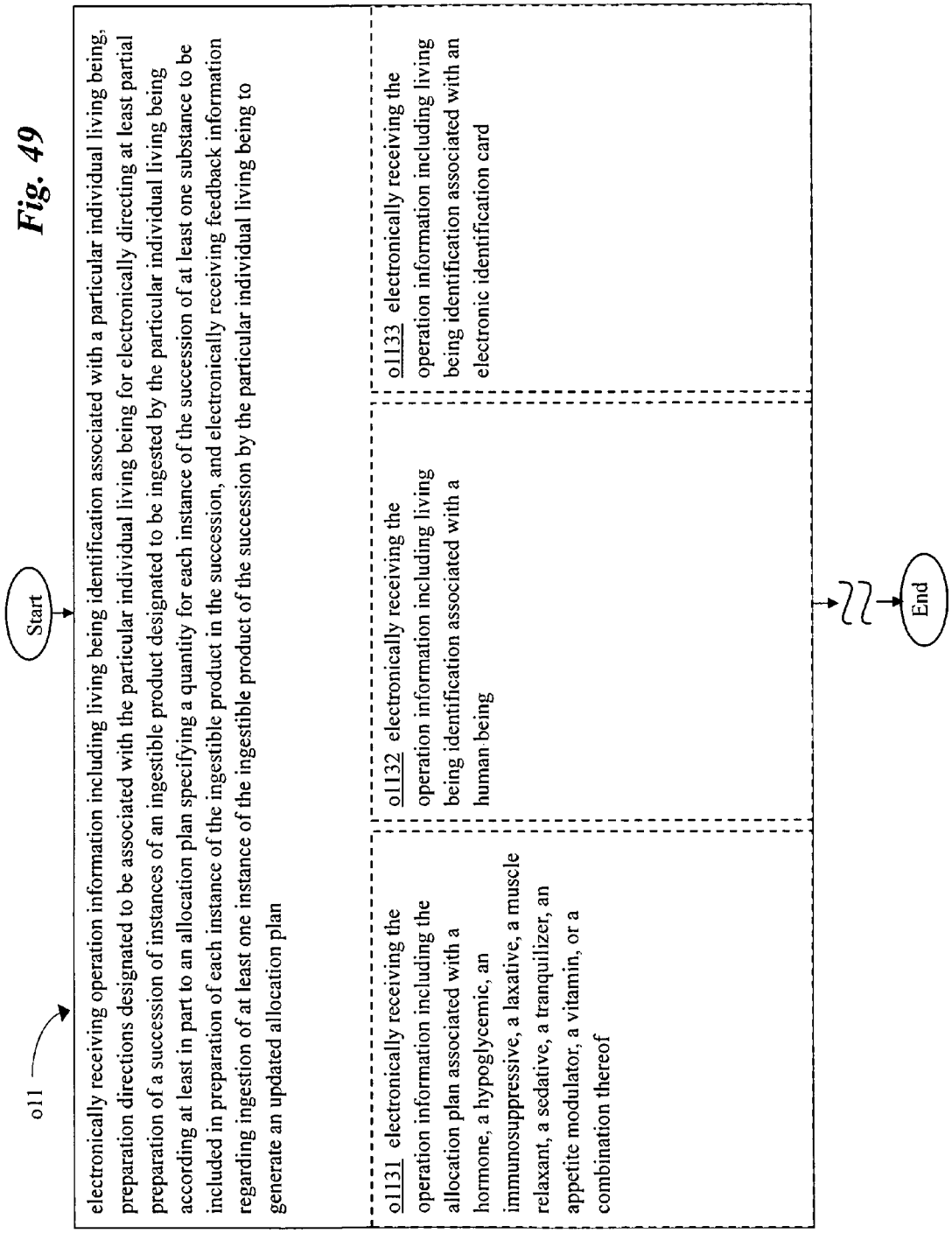
FIG. 49 is a high-level flowchart including exemplary implementations of operation O11 of FIG. 38.

In one or more implementations, as shown in FIG. 49, operation o11 includes an operation o1131 for electronically receiving the operation information including the allocation plan associated with a hormone, a hypoglycemic, an immunosuppressive, a laxative, a muscle relaxant, a sedative, a tranquilizer, an appetite modulator, a vitamin, or a combination thereof. An exemplary version of a non-transitory signal bearing medium of information storage subsystem s200 is depicted as bearing one or more receiving fifth medications instructions i1131 that when executed will direct performance of the operation o1131. In an implementation, the one or more receiving fifth medications instructions i1131 when executed direct electronically receiving the operation information including the allocation plan associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the operation information including the allocation plan as determined by the processor component to be identifying a hormone, a hypoglycemic, an immunosuppressive, a laxative, a muscle relaxant, a sedative, a tranquilizer, an appetite modulator, a vitamin, or a combination thereof, etc.). Furthermore, the receiving fifth medications electrical circuitry arrangement e1131 when activated will perform the operation o1131. In an implementation, the receiving fifth medications electrical circuitry arrangement e1131, when activated performs electronically receiving the operation information including the allocation plan associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the operation information including the allocation plan as determined by the processor component to be identifying a hormone, a hypoglycemic, an immunosuppressive, a laxative, a muscle relaxant, a sedative, a tranquilizer, an appetite modulator, a vitamin, or a combination thereof, etc.). In an implementation, the electronically receiving the operation information including the allocation plan associated with a hormone, a hypoglycemic, an immunosuppressive, a laxative, a muscle relaxant, a sedative, a tranquilizer, an appetite modulator, a vitamin, or a combination thereof is carried out by electronically receiving the operation information including the allocation plan associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the operation information including the allocation plan as determined by the processor component to be identifying a hormone, a hypoglycemic, an immunosuppressive, a laxative, a muscle relaxant, a sedative, a tranquilizer, an appetite modulator, a vitamin, or a combination thereof, etc.).

In one or more implementations, operation o11 includes an operation o1132 for electronically receiving the operation information including living being identification associated with a human being. An exemplary version of a non-transitory signal bearing medium of information storage subsystem s200 is depicted as bearing one or more receiving information human instructions i1132 that when executed will direct performance of the operation o1132. In an implementation, the one or more receiving information human instructions i1132 when executed direct electronically receiving the operation information including living being identification associated with a human being (e.g. an implementation of the receiver component s528 is configured to electronically engage with the processor component s102 to receive the operation information including living being identification as determined by the processor component to be identifying a human being, etc.). Furthermore, the receiving information human electrical circuitry arrangement e1132 when activated will perform the operation o1132. In an implementation, the receiving information human electrical circuitry arrangement e1132, when activated performs electronically receiving the operation information including living being identification associated with a human being (e.g. an implementation of the receiver component s528 is configured to electronically engage with the processor component s102 to receive the operation information including living being identification as determined by the processor component to be identifying a human being, etc.). In an implementation, the electronically receiving the operation information including living being identification associated with a human being is carried out by electronically receiving the operation information including living being identification associated with a human being (e.g. an implementation of the receiver component s528 is configured to electronically engage with the processor component s102 to receive the operation information including living being identification as determined by the processor component to be identifying a human being, etc.).

In one or more implementations, operation o11 includes an operation o1133 for electronically receiving the operation information including living being identification associated with an electronic identification card. An exemplary version of a non-transitory signal bearing medium of information storage subsystem s200 is depicted as bearing one or more receiving information ID card instructions i1133 that when executed will direct performance of the operation o1133. In an implementation, the one or more receiving information ID card instructions i1133 when executed direct electronically receiving the operation information including living being identification associated with an electronic identification card (e.g. an implementation of the receiver component s528 is configured to electronically engage with the processor component s102 to receive the operation information including living being identification as determined by the processor component to be identifying a living being through the electronic identification card, etc.). Furthermore, the receiving information ID card electrical circuitry arrangement e1133 when activated will perform the operation o1133. In an implementation, the receiving information ID card electrical circuitry arrangement e1133, when activated performs electronically receiving the operation information including living being identification associated with an electronic identification card (e.g. an implementation of the receiver component s528 is configured to electronically engage with the processor component s102 to receive the operation information including living being identification as determined by the processor component to be identifying a living being through the electronic identification card, etc.). In an implementation, the electronically receiving the operation information including living being identification associated with an electronic identification card is carried out by electronically receiving the operation information including living being identification associated with an electronic identification card (e.g. an implementation of the receiver component s528 is configured to electronically engage with the processor component s102 to receive the operation information including living being identification as determined by the processor component to be identifying a living being through the electronic identification card, etc.).

Figure 50:
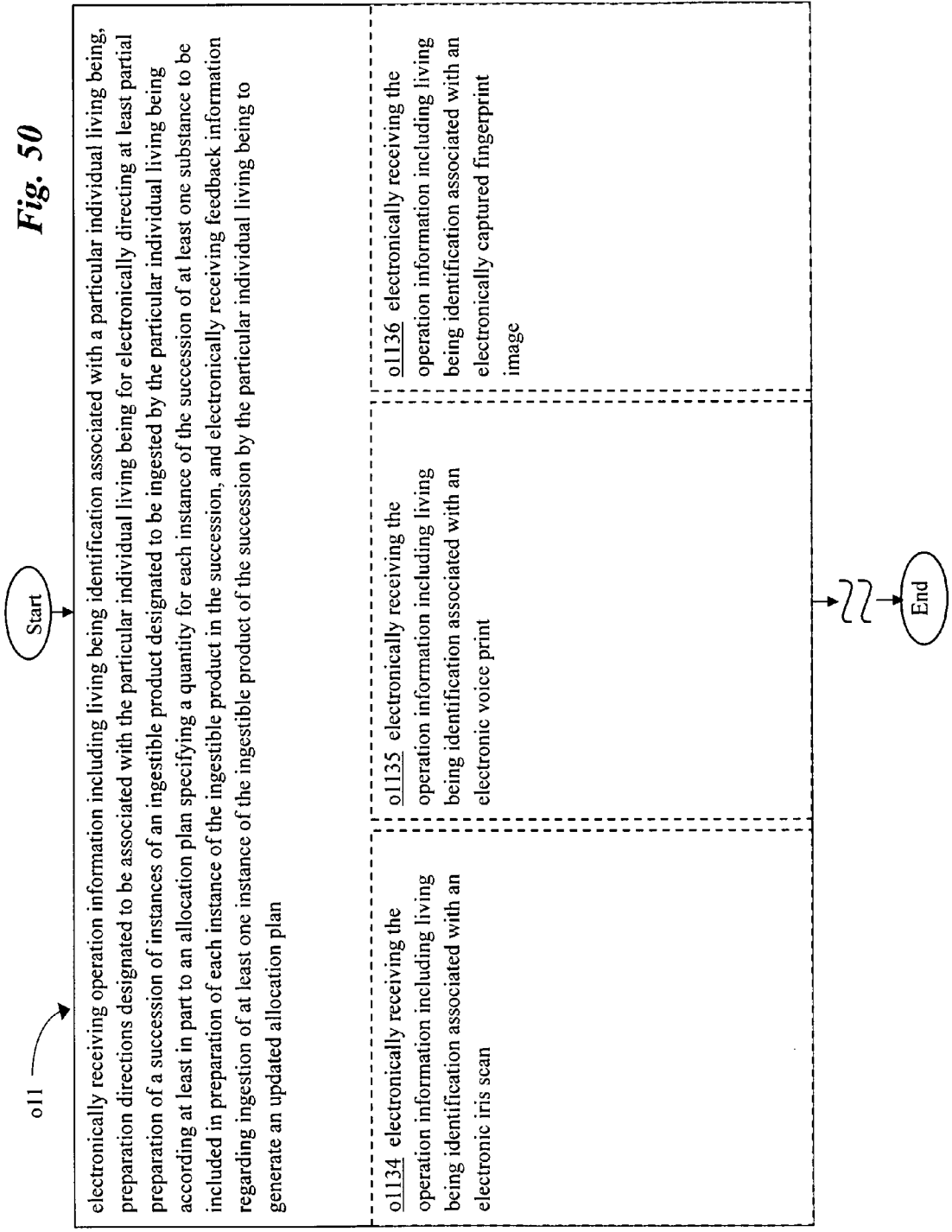
FIG. 50 is a high-level flowchart including exemplary implementations of operation O11 of FIG. 38.

In one or more implementations, as shown in FIG. 50, operation o11 includes an operation o1134 for electronically receiving the operation information including living being identification associated with an electronic iris scan. An exemplary version of a non-transitory signal bearing medium of information storage subsystem s200 is depicted as bearing one or more receiving information iris scan instructions i1134 that when executed will direct performance of the operation o1134. In an implementation, the one or more receiving information iris scan instructions i1134 when executed direct electronically receiving the operation information including living being identification associated with an electronic iris scan (e.g. an implementation of the receiver component s528 is configured to electronically engage with the processor component s102 to receive the operation information including living being identification as determined by the processor component to be identifying the living being through the electronic iris scan, etc.). Furthermore, the receiving information iris scan electrical circuitry arrangement e1134 when activated will perform the operation o1134. In an implementation, the receiving information iris scan electrical circuitry arrangement e1134, when activated performs electronically receiving the operation information including living being identification associated with an electronic iris scan (e.g. an implementation of the receiver component s528 is configured to electronically engage with the processor component s102 to receive the operation information including living being identification as determined by the processor component to be identifying the living being through the electronic iris scan, etc.). In an implementation, the electronically receiving the operation information including living being identification associated with an electronic iris scan is carried out by electronically receiving the operation information including living being identification associated with an electronic iris scan (e.g. an implementation of the receiver component s528 is configured to electronically engage with the processor component s102 to receive the operation information including living being identification as determined by the processor component to be identifying the living being through the electronic iris scan, etc.).

In one or more implementations, operation o11 includes an operation o1135 for electronically receiving the operation information including living being identification associated with an electronic voice print. An exemplary version of a non-transitory signal bearing medium of information storage subsystem s200 is depicted as bearing one or more receiving information voice instructions i1135 that when executed will direct performance of the operation o1135. In an implementation, the one or more receiving information voice instructions i1135 when executed direct electronically receiving the operation information including living being identification associated with an electronic voice print (e.g. an implementation of the receiver component s528 is configured to electronically engage with the processor component s102 to receive the operation information including living being identification as determined by the processor component to be identifying the living being through the electronic voice print, etc.). Furthermore, the receiving information voice electrical circuitry arrangement e1135 when activated will perform the operation o1135. In an implementation, the receiving information voice electrical circuitry arrangement e1135, when activated performs electronically receiving the operation information including living being identification associated with an electronic voice print (e.g. an implementation of the receiver component s528 is configured to electronically engage with the processor component s102 to receive the operation information including living being identification as determined by the processor component to be identifying the living being through the electronic voice print, etc.). In an implementation, the electronically receiving the operation information including living being identification associated with an electronic voice print is carried out by electronically receiving the operation information including living being identification associated with an electronic voice print (e.g. an implementation of the receiver component s528 is configured to electronically engage with the processor component s102 to receive the operation information including living being identification as determined by the processor component to be identifying the living being through the electronic voice print, etc.).

In one or more implementations, operation o11 includes an operation o1136 for electronically receiving the operation information including living being identification associated with an electronically captured fingerprint image. An exemplary version of a non-transitory signal bearing medium of information storage subsystem s200 is depicted as bearing one or more receiving information fingerprint instructions i1136 that when executed will direct performance of the operation o1136. In an implementation, the one or more receiving information fingerprint instructions i1136 when executed direct electronically receiving the operation information including living being identification associated with an electronically captured fingerprint image (e.g. an implementation of the receiver component s528 is configured to electronically engage with the processor component s102 to receive the operation information including living being identification as determined by the processor component to be identifying the living being through the electronically captured fingerprint image, etc.). Furthermore, the receiving information fingerprint electrical circuitry arrangement e1136 when activated will perform the operation o1136. In an implementation, the receiving information fingerprint electrical circuitry arrangement e1136, when activated performs electronically receiving the operation information including living being identification associated with an electronically captured fingerprint image (e.g. an implementation of the receiver component s528 is configured to electronically engage with the processor component s102 to receive the operation information including living being identification as determined by the processor component to be identifying the living being through the electronically captured fingerprint image, etc.). In an implementation, the electronically receiving the operation information including living being identification associated with an electronically captured fingerprint image is carried out by electronically receiving the operation information including living being identification associated with an electronically captured fingerprint image (e.g. an implementation of the receiver component s528 is configured to electronically engage with the processor component s102 to receive the operation information including living being identification as determined by the processor component to be identifying the living being through the electronically captured fingerprint image, etc.).

Figure 51:
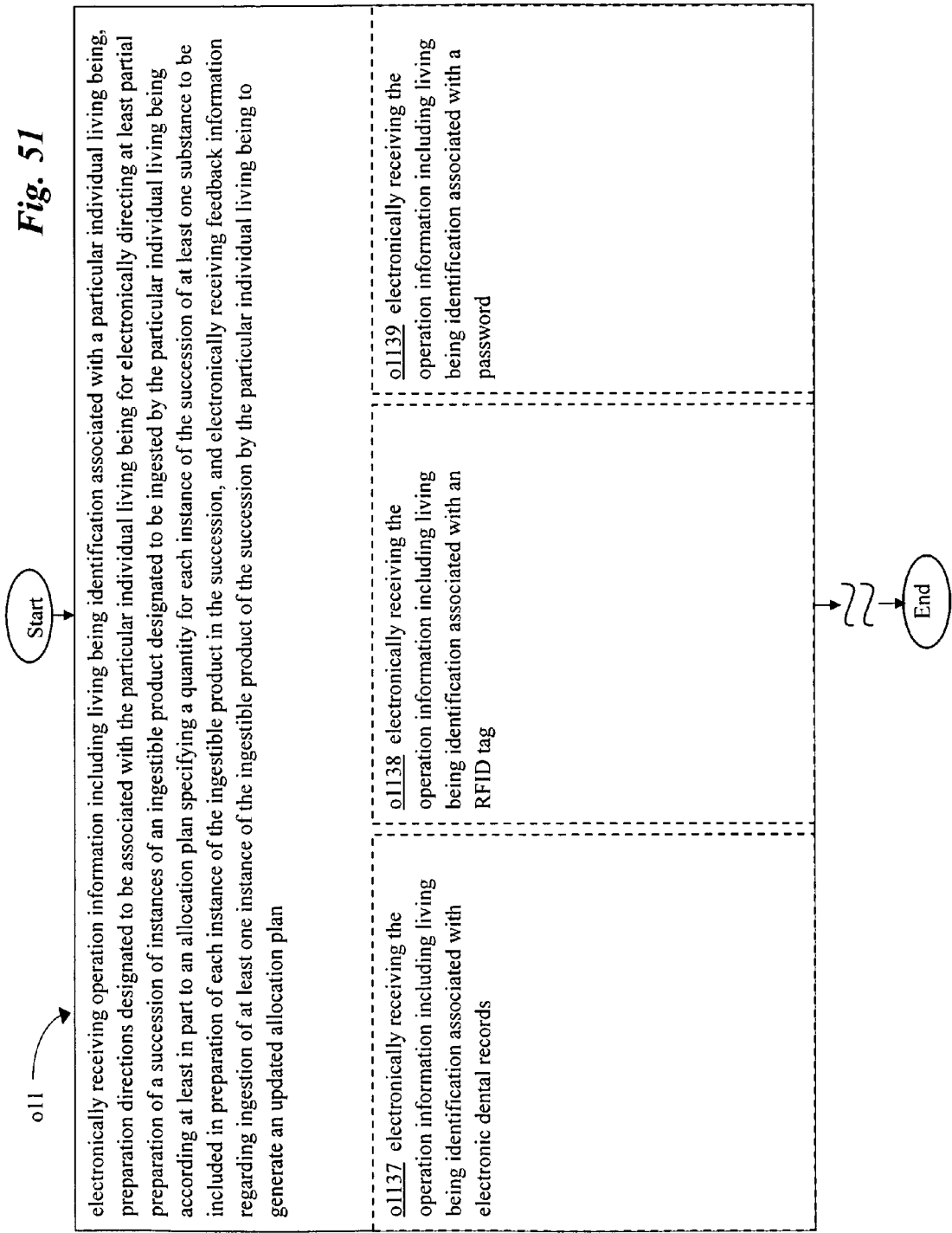
FIG. 51 is a high-level flowchart including exemplary implementations of operation O11 of FIG. 38.

In one or more implementations, as shown in FIG. 51, operation o11 includes an operation o1137 for electronically receiving the operation information including living being identification associated with electronic dental records. An exemplary version of a non-transitory signal bearing medium of information storage subsystem s200 is depicted as bearing one or more receiving information dental instructions i1137 that when executed will direct performance of the operation o1137. In an implementation, the one or more receiving information dental instructions i1137 when executed direct electronically receiving the operation information including living being identification associated with electronic dental records (e.g. an implementation of the receiver component s528 is configured to electronically engage with the processor component s102 to receive the operation information including living being identification as determined by the processor component to be identifying the living being through the electronic dental records, etc.). Furthermore, the receiving information dental electrical circuitry arrangement e1137 when activated will perform the operation o1137. In an implementation, the receiving information dental electrical circuitry arrangement e1137, when activated performs electronically receiving the operation information including living being identification associated with electronic dental records (e.g. an implementation of the receiver component s528 is configured to electronically engage with the processor component s102 to receive the operation information including living being identification as determined by the processor component to be identifying the living being through the electronic dental records, etc.). In an implementation, the electronically receiving the operation information including living being identification associated with electronic dental records is carried out by electronically receiving the operation information including living being identification associated with electronic dental records (e.g. an implementation of the receiver component s528 is configured to electronically engage with the processor component s102 to receive the operation information including living being identification as determined by the processor component to be identifying the living being through the electronic dental records, etc.).

In one or more implementations, operation o11 includes an operation o1138 for electronically receiving the operation information including living being identification associated with an RFID tag. An exemplary version of a non-transitory signal bearing medium of information storage subsystem s200 is depicted as bearing one or more receiving information RFID instructions i1138 that when executed will direct performance of the operation o1138. In an implementation, the one or more receiving information RFID instructions i1138 when executed direct electronically receiving the operation information including living being identification associated with an RFID tag (e.g. an implementation of the receiver component s528 is configured to electronically engage with the processor component s102 to receive the operation information including living being identification as determined by the processor component to be identifying the living being through the RFID tag, etc.). Furthermore, the receiving information RFID electrical circuitry arrangement e1138 when activated will perform the operation o1138. In an implementation, the receiving information RFID electrical circuitry arrangement e1138, when activated performs electronically receiving the operation information including living being identification associated with an RFID tag (e.g. an implementation of the receiver component s528 is configured to electronically engage with the processor component s102 to receive the operation information including living being identification as determined by the processor component to be identifying the living being through the RFID tag, etc.). In an implementation, the electronically receiving the operation information including living being identification associated with an RFID tag is carried out by electronically receiving the operation information including living being identification associated with an RFID tag (e.g. an implementation of the receiver component s528 is configured to electronically engage with the processor component s102 to receive the operation information including living being identification as determined by the processor component to be identifying the living being through the RFID tag, etc.).

In one or more implementations, operation o11 includes an operation o1139 for electronically receiving the operation information including living being identification associated with a password. An exemplary version of a non-transitory signal bearing medium of information storage subsystem s200 is depicted as bearing one or more receiving information password instructions i1139 that when executed will direct performance of the operation o1139. In an implementation, the one or more receiving information password instructions i1139 when executed direct electronically receiving the operation information including living being identification associated with a password (e.g. an implementation of the receiver component s528 is configured to electronically engage with the processor component s102 to receive the operation information including living being identification as determined by the processor component to be identifying the living being through the password, etc.). Furthermore, the receiving information password electrical circuitry arrangement e1139 when activated will perform the operation o1139. In an implementation, the receiving information password electrical circuitry arrangement e1139, when activated performs electronically receiving the operation information including living being identification associated with a password (e.g. an implementation of the receiver component s528 is configured to electronically engage with the processor component s102 to receive the operation information including living being identification as determined by the processor component to be identifying the living being through the password, etc.). In an implementation, the electronically receiving the operation information including living being identification associated with a password is carried out by electronically receiving the operation information including living being identification associated with a password (e.g. an implementation of the receiver component s528 is configured to electronically engage with the processor component s102 to receive the operation information including living being identification as determined by the processor component to be identifying the living being through the password, etc.).

Figure 52:
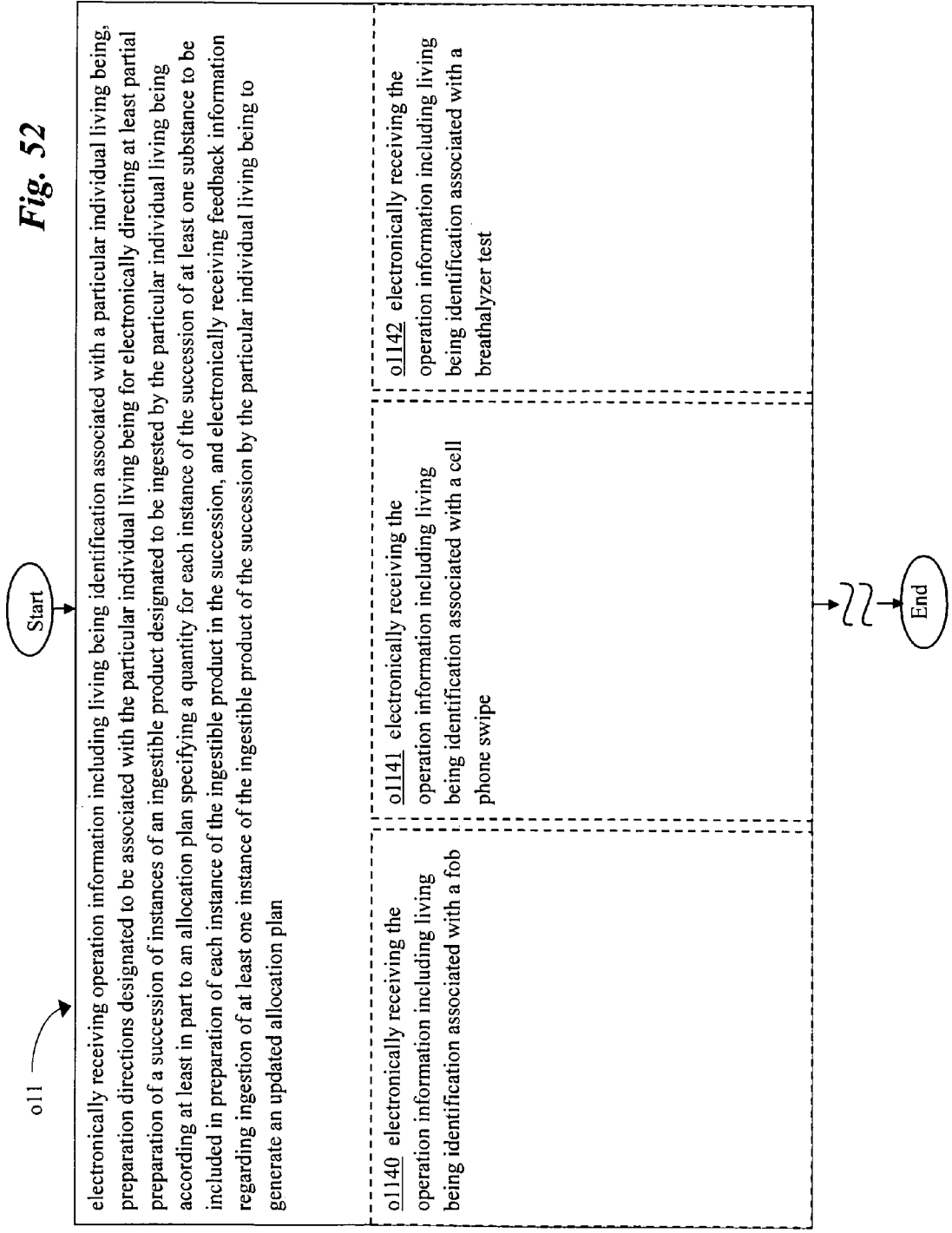
FIG. 52 is a high-level flowchart including exemplary implementations of operation O11 of FIG. 38.

In one or more implementations, as shown in FIG. 52, operation o11 includes an operation o1140 for electronically receiving the operation information including living being identification associated with a fob. An exemplary version of a non-transitory signal bearing medium of information storage subsystem s200 is depicted as bearing one or more receiving information fob instructions i1140 that when executed will direct performance of the operation o1140. In an implementation, the one or more receiving information fob instructions i1140 when executed direct electronically receiving the operation information including living being identification associated with a fob (e.g. an implementation of the receiver component s528 is configured to electronically engage with the processor component s102 to receive the operation information including living being identification as determined by the processor component to be identifying the living being through electronic data contained on the fob, etc.). Furthermore, the receiving information fob electrical circuitry arrangement e1140 when activated will perform the operation o1140. In an implementation, the receiving information fob electrical circuitry arrangement e1140, when activated performs electronically receiving the operation information including living being identification associated with a fob (e.g. an implementation of the receiver component s528 is configured to electronically engage with the processor component s102 to receive the operation information including living being identification as determined by the processor component to be identifying the living being through electronic data contained on the fob, etc.). In an implementation, the electronically receiving the operation information including living being identification associated with a fob is carried out by electronically receiving the operation information including living being identification associated with a fob (e.g. an implementation of the receiver component s528 is configured to electronically engage with the processor component s102 to receive the operation information including living being identification as determined by the processor component to be identifying the living being through electronic data contained on the fob, etc.).

In one or more implementations, operation o11 includes an operation o1141 for electronically receiving the operation information including living being identification associated with a cell phone swipe. An exemplary version of a non-transitory signal bearing medium of information storage subsystem s200 is depicted as bearing one or more receiving information cell phone instructions i1141 that when executed will direct performance of the operation o1141. In an implementation, the one or more receiving information cell phone instructions i1141 when executed direct electronically receiving the operation information including living being identification associated with a cell phone swipe (e.g. an implementation of the receiver component s528 is configured to electronically engage with the processor component s102 to receive the operation information including living being identification as determined by the processor component to be identifying the living being through passing the cell phone in close proximity to the cell phone, etc.). Furthermore, the receiving information cell phone electrical circuitry arrangement e1141 when activated will perform the operation o1141. In an implementation, the receiving information cell phone electrical circuitry arrangement e1141, when activated performs electronically receiving the operation information including living being identification associated with a cell phone swipe (e.g. an implementation of the receiver component s528 is configured to electronically engage with the processor component s102 to receive the operation information including living being identification as determined by the processor component to be identifying the living being through passing the cell phone in close proximity to the cell phone, etc.). In an implementation, the electronically receiving the operation information including living being identification associated with a cell phone swipe is carried out by electronically receiving the operation information including living being identification associated with a cell phone swipe (e.g. an implementation of the receiver component s528 is configured to electronically engage with the processor component s102 to receive the operation information including living being identification as determined by the processor component to be identifying the living being through passing the cell phone in close proximity to the cell phone, etc.).

In one or more implementations, operation o11 includes an operation o1142 for electronically receiving the operation information including living being identification associated with a breathalyzer test. An exemplary version of a non-transitory signal bearing medium of information storage subsystem s200 is depicted as bearing one or more receiving information breathalyzer instructions i1142 that when executed will direct performance of the operation o1142. In an implementation, the one or more receiving information breathalyzer instructions i1142 when executed direct electronically receiving the operation information including living being identification associated with a breathalyzer test (e.g. an implementation of the receiver component s528 is configured to electronically engage with the processor component s102 to receive the operation information including living being identification as determined by the processor component to be identifying the living being through the breathalyzer test of the living being, etc.). Furthermore, the receiving information breathalyzer electrical circuitry arrangement e1142 when activated will perform the operation o1142. In an implementation, the receiving information breathalyzer electrical circuitry arrangement e1142, when activated performs electronically receiving the operation information including living being identification associated with a breathalyzer test (e.g. an implementation of the receiver component s528 is configured to electronically engage with the processor component s102 to receive the operation information including living being identification as determined by the processor component to be identifying the living being through the breathalyzer test of the living being, etc.). In an implementation, the electronically receiving the operation information including living being identification associated with a breathalyzer test is carried out by electronically receiving the operation information including living being identification associated with a breathalyzer test (e.g. an implementation of the receiver component s528 is configured to electronically engage with the processor component s102 to receive the operation information including living being identification as determined by the processor component to be identifying the living being through the breathalyzer test of the living being, etc.).

Figure 53:
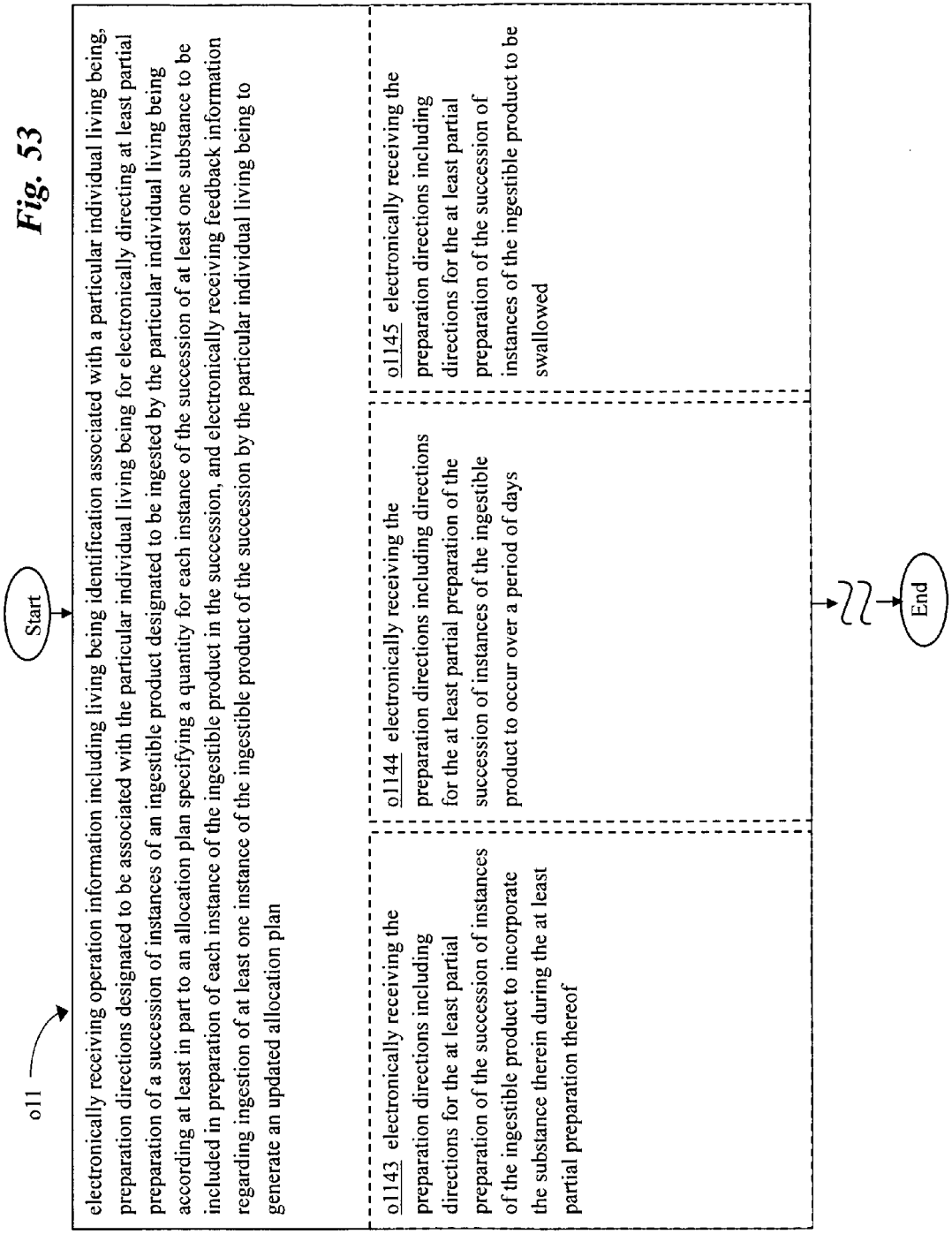
FIG. 53 is a high-level flowchart including exemplary implementations of operation O11 of FIG. 38.

In one or more implementations, as shown in FIG. 53, operation o11 includes an operation o1143 for electronically receiving the preparation directions including directions for the at least partial preparation of the succession of instances of the ingestible product to incorporate the substance therein during the at least partial preparation thereof. An exemplary version of a non-transitory signal bearing medium of information storage subsystem s200 is depicted as bearing one or more receiving information incorporate instructions i1143 that when executed will direct performance of the operation o1143. In an implementation, the one or more receiving information incorporate instructions i1143 when executed direct electronically receiving the preparation directions including directions for the at least partial preparation of the succession of instances of the ingestible product to incorporate the substance therein during the at least partial preparation thereof (e.g. an implementation of the receiver component s528 is configured to electronically receive the preparation directions and engage with the processor component s102 to direct the material processing subsystem s700 to at least partially prepare the succession of instances of the ingestible product such as a sandwich to include the substance as an amino acid incorporated into the sandwich, etc.). Furthermore, the receiving information incorporate electrical circuitry arrangement e1143 when activated will perform the operation o1143. In an implementation, the receiving information incorporate electrical circuitry arrangement e1143, when activated performs electronically receiving the preparation directions including directions for the at least partial preparation of the succession of instances of the ingestible product to incorporate the substance therein during the at least partial preparation thereof (e.g. an implementation of the receiver component s528 is configured to electronically receive the preparation directions and engage with the processor component s102 to direct the material processing subsystem s700 to at least partially prepare the succession of instances of the ingestible product such as a sandwich to include the substance as an amino acid incorporated into the sandwich, etc.). In an implementation, the electronically receiving the preparation directions including directions for the at least partial preparation of the succession of instances of the ingestible product to incorporate the substance therein during the at least partial preparation thereof is carried out by electronically receiving the preparation directions including directions for the at least partial preparation of the succession of instances of the ingestible product to incorporate the substance therein during the at least partial preparation thereof (e.g. an implementation of the receiver component s528 is configured to electronically receive the preparation directions and engage with the processor component s102 to direct the material processing subsystem s700 to at least partially prepare the succession of instances of the ingestible product such as a sandwich to include the substance as an amino acid incorporated into the sandwich, etc.).

In one or more implementations, operation o11 includes an operation o1144 for electronically receiving the preparation directions including directions for the at least partial preparation of the succession of instances of the ingestible product to occur over a period of days. An exemplary version of a non-transitory signal bearing medium of information storage subsystem s200 is depicted as bearing one or more receiving information days instructions i1144 that when executed will direct performance of the operation o1144. In an implementation, the one or more receiving information days instructions i1144 when executed direct electronically receiving the preparation directions including directions for at least partial preparation of the succession of instances of the ingestible product to occur over a period of days (e.g. an implementation of the receiver component s528 is configured to electronically receive the preparation directions and engage with the processor component s102 to direct the material processing subsystem s700 to at least partially prepare the succession of instances of the ingestible product such as a smoothie to contain an activator that is designed to interact with a substance, such as a pharmaceutical agent that is encapsulated in pill form to be ingested by a living being, such as a boy, at the same time that the smoothie is being ingested by the boy, etc.). Furthermore, the receiving information days electrical circuitry arrangement e1144 when activated will perform the operation o1144. In an implementation, the receiving information days electrical circuitry arrangement e1144, when activated performs electronically receiving the preparation directions including directions for at least partial preparation of the succession of instances of the ingestible product to occur over a period of days (e.g. an implementation of the receiver component s528 is configured to electronically receive the preparation directions and engage with the processor component s102 to direct the material processing subsystem s700 to at least partially prepare the succession of instances of the ingestible product such as a smoothie to contain an activator that is designed to interact with a substance, such as a pharmaceutical agent that is encapsulated in pill form to be ingested by a living being, such as a boy, at the same time that the smoothie is being ingested by the boy, etc.). In an implementation, the electronically receiving the preparation directions including directions for the at least partial preparation of the succession of instances of the ingestible product to occur over a period of days is carried out by electronically receiving the preparation directions including directions for at least partial preparation of the succession of instances of the ingestible product to occur over a period of days (e.g. an implementation of the receiver component s528 is configured to electronically receive the preparation directions and engage with the processor component s102 to direct the material processing subsystem s700 to at least partially prepare the succession of instances of the ingestible product such as a smoothie to contain an activator that is designed to interact with a substance, such as a pharmaceutical agent that is encapsulated in pill form to be ingested by a living being, such as a boy, at the same time that the smoothie is being ingested by the boy, etc.).

In one or more implementations, operation o11 includes an operation o1145 for electronically receiving the preparation directions including directions for the at least partial preparation of the succession of instances of the ingestible product to be swallowed. An exemplary version of a non-transitory signal bearing medium of information storage subsystem s200 is depicted as bearing one or more receiving information swallow instructions i1145 that when executed will direct performance of the operation o1145. In an implementation, the one or more receiving information swallow instructions i1145 when executed direct electronically receiving the preparation directions including directions for the at least partial preparation of the succession of instances of the ingestible product to be swallowed (e.g., an implementation of the receiver component s528 is configured to electronically receive the preparation directions and engage with the processor component s102 to direct the material processing subsystem s700 to at least partially prepare the succession of instances of the ingestible product to be swallowed such as a snack bar, etc.). Furthermore, the receiving information swallow electrical circuitry arrangement e1145 when activated will perform the operation o1145. In an implementation, the receiving information swallow electrical circuitry arrangement e1145, when activated performs electronically receiving the preparation directions including directions for the at least partial preparation of the succession of instances of the ingestible product to be swallowed (e.g., an implementation of the receiver component s528 is configured to electronically receive the preparation directions and engage with the processor component s102 to direct the material processing subsystem s700 to at least partially prepare the succession of instances of the ingestible product to be swallowed such as a snack bar, etc.). In an implementation, the electronically receiving the preparation directions including directions for the at least partial preparation of the succession of instances of the ingestible product to be swallowed is carried out by electronically receiving the preparation directions including directions for the at least partial preparation of the succession of instances of the ingestible product to be swallowed (e.g., an implementation of the receiver component s528 is configured to electronically receive the preparation directions and engage with the processor component s102 to direct the material processing subsystem s700 to at least partially prepare the succession of instances of the ingestible product to be swallowed such as a snack bar, etc.).

Figure 54:
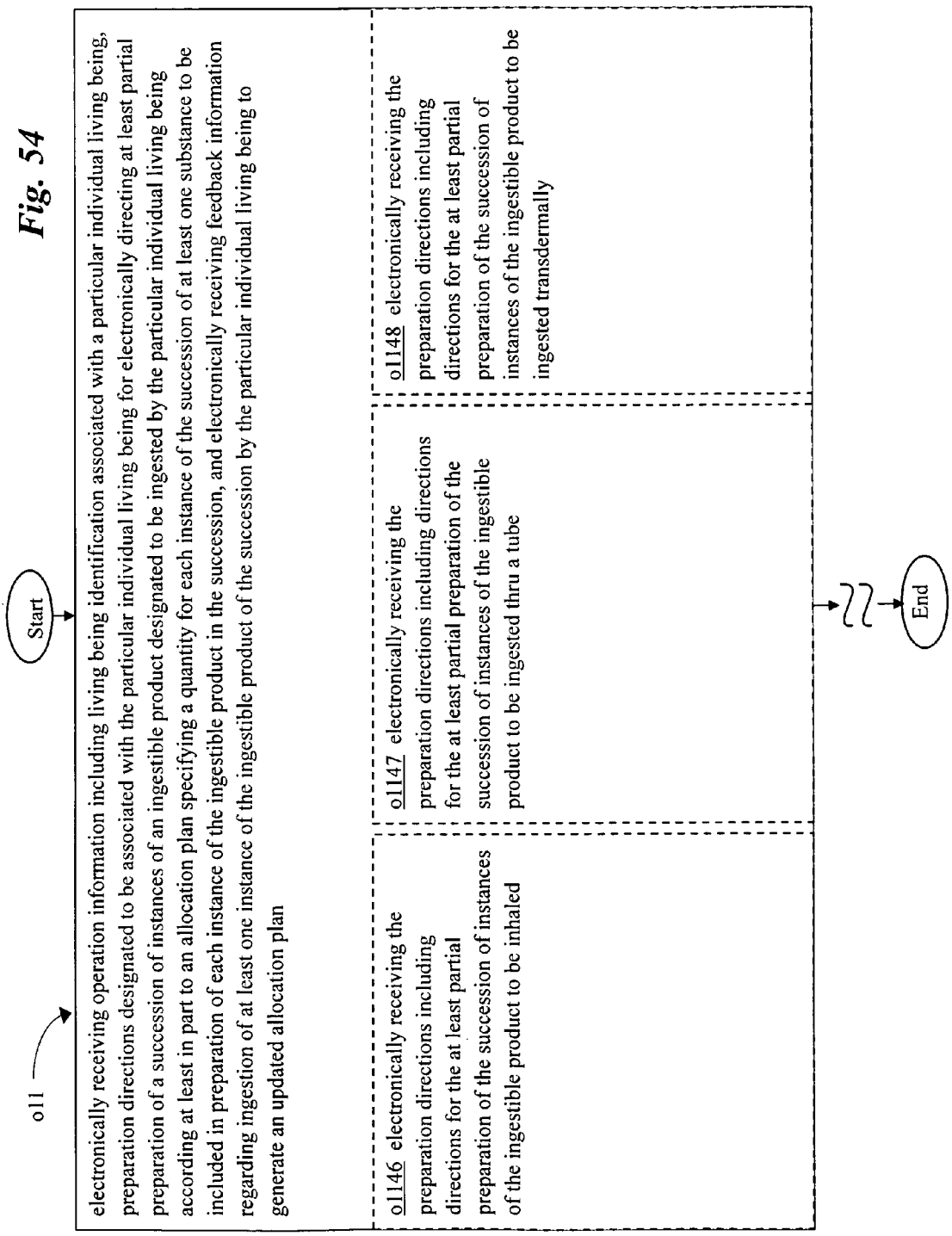
FIG. 54 is a high-level flowchart including exemplary implementations of operation O11 of FIG. 38.

In one or more implementations, as shown in FIG. 54, operation o11 includes an operation o1146 for electronically receiving the preparation directions including directions for the at least partial preparation of the succession of instances of the ingestible product to be inhaled. An exemplary version of a non-transitory signal bearing medium of information storage subsystem s200 is depicted as bearing one or more receiving information inhaled instructions i1146 that when executed will direct performance of the operation o1146. In an implementation, the one or more receiving information inhaled instructions i1146 when executed direct electronically receiving the preparation directions including directions for the at least partial preparation of the succession of instances of the ingestible product to be inhaled (e.g. an implementation of the receiver component s528 is configured to electronically receive the preparation directions and engage with the processor component s102 to direct the material processing subsystem s700 to at least partially prepare the succession of instances of the ingestible product to be inhaled such as a medicament dispensed through a nebulizer, etc.). Furthermore, the receiving information inhaled electrical circuitry arrangement e1146 when activated will perform the operation o1146. In an implementation, the receiving information inhaled electrical circuitry arrangement e1146, when activated performs electronically receiving the preparation directions including directions for the at least partial preparation of the succession of instances of the ingestible product to be inhaled (e.g. an implementation of the receiver component s528 is configured to electronically receive the preparation directions and engage with the processor component s102 to direct the material processing subsystem s700 to at least partially prepare the succession of instances of the ingestible product to be inhaled such as a medicament dispensed through a nebulizer, etc.). In an implementation, the electronically receiving the preparation directions including directions for the at least partial preparation of the succession of instances of the ingestible product to be inhaled is carried out by electronically receiving the preparation directions including directions for the at least partial preparation of the succession of instances of the ingestible product to be inhaled (e.g. an implementation of the receiver component s528 is configured to electronically receive the preparation directions and engage with the processor component s102 to direct the material processing subsystem s700 to at least partially prepare the succession of instances of the ingestible product to be inhaled such as a medicament dispensed through a nebulizer, etc.).

In one or more implementations, operation o11 includes an operation o1147 for electronically receiving the preparation directions including directions for the at least partial preparation of the succession of instances of the ingestible product to be ingested thru a tube. An exemplary version of a non-transitory signal bearing medium of information storage subsystem s200 is depicted as bearing one or more receiving information tube instructions i1147 that when executed will direct performance of the operation o1147. In an implementation, the one or more receiving information tube instructions i1147 when executed direct electronically receiving the preparation directions including directions for the at least partial preparation of the succession of instances of the ingestible product to be ingested thru a tube (e.g., an implementation of the receiver component s528 is configured to electronically receive the preparation directions and engage with the processor component s102 to direct the material processing subsystem s700 to at least partially prepare the succession of instances of the ingestible product to be ingested through a tube such as a liquid meal replacement, etc.). Furthermore, the receiving information tube electrical circuitry arrangement e1147 when activated will perform the operation o1147. In an implementation, the receiving information tube electrical circuitry arrangement e1147, when activated performs electronically receiving the preparation directions including directions for the at least partial preparation of the succession of instances of the ingestible product to be ingested thru a tube (e.g., an implementation of the receiver component s528 is configured to electronically receive the preparation directions and engage with the processor component s102 to direct the material processing subsystem s700 to at least partially prepare the succession of instances of the ingestible product to be ingested through a tube such as a liquid meal replacement, etc.). In an implementation, the electronically receiving the preparation directions including directions for the at least partial preparation of the succession of instances of the ingestible product to be ingested thru a tube is carried out by electronically receiving the preparation directions including directions for the at least partial preparation of the succession of instances of the ingestible product to be ingested thru a tube (e.g., an implementation of the receiver component s528 is configured to electronically receive the preparation directions and engage with the processor component s102 to direct the material processing subsystem s700 to at least partially prepare the succession of instances of the ingestible product to be ingested through a tube such as a liquid meal replacement, etc.).

In one or more implementations, operation o11 includes an operation o1148 for electronically receiving the preparation directions including directions for the at least partial preparation of the succession of instances of the ingestible product to be ingested transdermally. An exemplary version of a non-transitory signal bearing medium of information storage subsystem s200 is depicted as bearing one or more receiving information transdermal instructions i1148 that when executed will direct performance of the operation o1148. In an implementation, the one or more receiving information transdermal instructions i1148 when executed direct electronically receiving the preparation directions including directions for at least partial preparation of at least the succession of instances of the ingestible product to be ingested transdermally (e.g. an implementation of the receiver component s528 is configured to electronically receive the preparation directions and engage with the processor component s102 to direct the material processing subsystem s700 to at least partially prepare the succession of instances of the ingestible product to be ingested transdermally such as a cream, etc.). Furthermore, the receiving information transdermal electrical circuitry arrangement e1148 when activated will perform the operation o1148. In an implementation, the receiving information transdermal electrical circuitry arrangement e1148, when activated performs electronically receiving the preparation directions including directions for at least partial preparation of at least the succession of instances of the ingestible product to be ingested transdermally (e.g. an implementation of the receiver component s528 is configured to electronically receive the preparation directions and engage with the processor component s102 to direct the material processing subsystem s700 to at least partially prepare the succession of instances of the ingestible product to be ingested transdermally such as a cream, etc.). In an implementation, the electronically receiving the preparation directions including directions for the at least partial preparation of the succession of instances of the ingestible product to be ingested transdermally is carried out by electronically receiving the preparation directions including directions for at least partial preparation of at least the succession of instances of the ingestible product to be ingested transdermally (e.g. an implementation of the receiver component s528 is configured to electronically receive the preparation directions and engage with the processor component s102 to direct the material processing subsystem s700 to at least partially prepare the succession of instances of the ingestible product to be ingested transdermally such as a cream, etc.).

Figure 55:
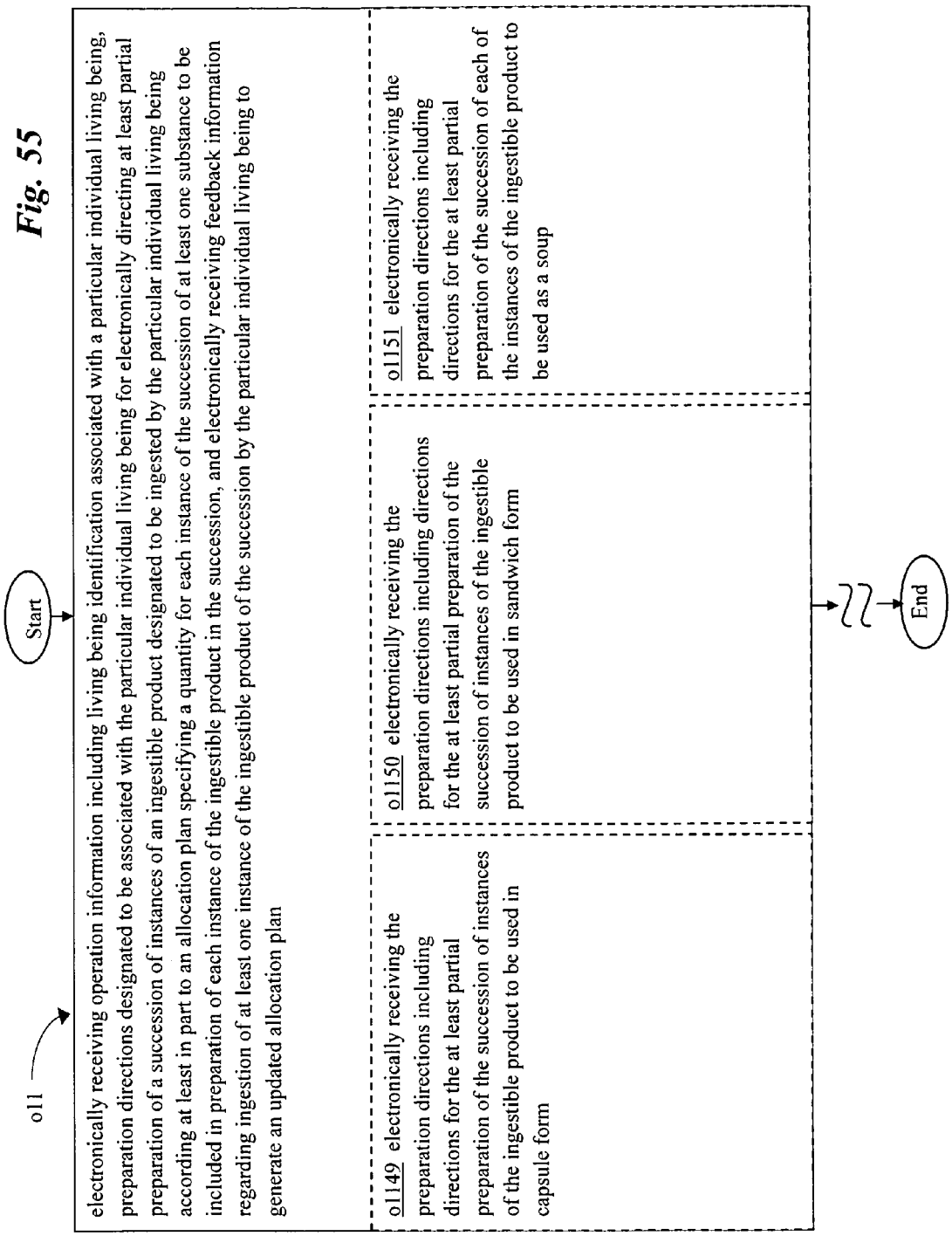
FIG. 55 is a high-level flowchart including exemplary implementations of operation O11 of FIG. 38.

In one or more implementations, as shown in FIG. 55, operation o11 includes an operation o1149 for electronically receiving the preparation directions including directions for the at least partial preparation of the succession of instances of the ingestible product to be used in capsule form. An exemplary version of a non-transitory signal bearing medium of information storage subsystem s200 is depicted as bearing one or more receiving information capsule instructions i1149 that when executed will direct performance of the operation o1149. In an implementation, the one or more receiving information capsule instructions i1149 when executed direct electronically receiving the preparation directions including directions for at least partial preparation of at least the succession of instances of the ingestible product to be used in a capsule form (e.g. an implementation of the receiver component s528 is configured to electronically receive the preparation directions and engage with the processor component s102 to direct the material processing subsystem s700 to at least partially prepare, such as through encapsulation, the succession of instances of the ingestible product such as capsules, etc.). Furthermore, the receiving information capsule electrical circuitry arrangement e1149 when activated will perform the operation o1149. In an implementation, the receiving information capsule electrical circuitry arrangement e1149, when activated performs electronically receiving the preparation directions including directions for at least partial preparation of at least the succession of instances of the ingestible product to be used in a capsule form (e.g. an implementation of the receiver component s528 is configured to electronically receive the preparation directions and engage with the processor component s102 to direct the material processing subsystem s700 to at least partially prepare, such as through encapsulation, the succession of instances of the ingestible product such as capsules, etc.). In an implementation, the electronically receiving the preparation directions including directions for the at least partial preparation of the succession of instances of the ingestible product to be used in capsule form is carried out by electronically receiving the preparation directions including directions for at least partial preparation of at least the succession of instances of the ingestible product to be used in a capsule form (e.g. an implementation of the receiver component s528 is configured to electronically receive the preparation directions and engage with the processor component s102 to direct the material processing subsystem s700 to at least partially prepare, such as through encapsulation, the succession of instances of the ingestible product such as capsules, etc.).

In one or more implementations, operation o11 includes an operation o1150 for electronically receiving the preparation directions including directions for the at least partial preparation of the succession of instances of the ingestible product to be used in sandwich form. An exemplary version of a non-transitory signal bearing medium of information storage subsystem s200 is depicted as bearing one or more receiving information sandwich instructions i1150 that when executed will direct performance of the operation o1150. In an implementation, the one or more receiving information sandwich instructions i1150 when executed direct electronically receiving the preparation directions including directions for at least partial preparation of at least the succession of instances of the ingestible product to be used in sandwich form (e.g. an implementation of the receiver component s528 is configured to electronically receive the preparation directions and engage with the processor component s102 to direct the material processing subsystem s700 to at least partially prepare the succession of instances of the ingestible product such as a sandwich, etc.). Furthermore, the receiving information sandwich electrical circuitry arrangement e1150 when activated will perform the operation o1150. In an implementation, the receiving information sandwich electrical circuitry arrangement e1150, when activated performs electronically receiving the preparation directions including directions for at least partial preparation of at least the succession of instances of the ingestible product to be used in sandwich form (e.g. an implementation of the receiver component s528 is configured to electronically receive the preparation directions and engage with the processor component s102 to direct the material processing subsystem s700 to at least partially prepare the succession of instances of the ingestible product such as a sandwich, etc.). In an implementation, the electronically receiving the preparation directions including directions for the at least partial preparation of the succession of instances of the ingestible product to be used in sandwich form is carried out by electronically receiving the preparation directions including directions for at least partial preparation of at least the succession of instances of the ingestible product to be used in sandwich form (e.g. an implementation of the receiver component s528 is configured to electronically receive the preparation directions and engage with the processor component s102 to direct the material processing subsystem s700 to at least partially prepare the succession of instances of the ingestible product such as a sandwich, etc.).

In one or more implementations, operation o11 includes an operation o1151 for electronically receiving the preparation directions including directions for the at least partial preparation of the succession of each of the instances of the ingestible product to be used as a soup. An exemplary version of a non-transitory signal bearing medium of information storage subsystem s200 is depicted as bearing one or more receiving information soup instructions i1151 that when executed will direct performance of the operation o1151. In an implementation, the one or more receiving information soup instructions i1151 when executed direct electronically receiving the preparation directions including directions for at least partial preparation of at least the succession of instances of the ingestible product to be used as a soup (e.g. an implementation of the receiver component s528 is configured to electronically receive the preparation directions and engage with the processor component s102 to direct the material processing subsystem s700 to at least partially prepare the succession of instances of the ingestible product such as a soup, etc.). Furthermore, the receiving information soup electrical circuitry arrangement e1151 when activated will perform the operation o1151. In an implementation, the receiving information soup electrical circuitry arrangement e1151, when activated performs electronically receiving the preparation directions including directions for at least partial preparation of at least the succession of instances of the ingestible product to be used as a soup (e.g. an implementation of the receiver component s528 is configured to electronically receive the preparation directions and engage with the processor component s102 to direct the material processing subsystem s700 to at least partially prepare the succession of instances of the ingestible product such as a soup, etc.). In an implementation, the electronically receiving the preparation directions including directions for the at least partial preparation of the succession of each of the instances of the ingestible product to be used as a soup is carried out by electronically receiving the preparation directions including directions for at least partial preparation of at least the succession of instances of the ingestible product to be used as a soup (e.g. an implementation of the receiver component s528 is configured to electronically receive the preparation directions and engage with the processor component s102 to direct the material processing subsystem s700 to at least partially prepare the succession of instances of the ingestible product such as a soup, etc.).

Figure 56:
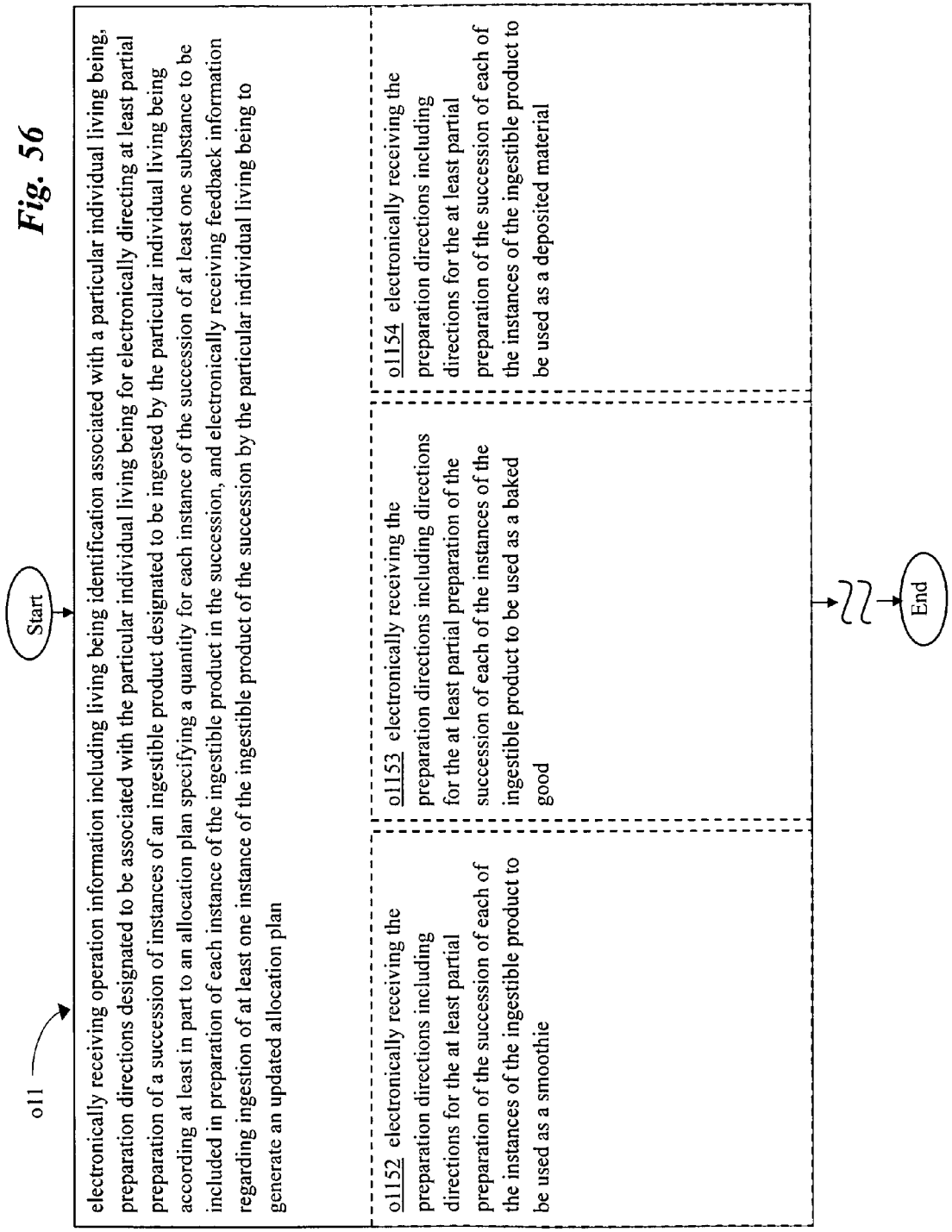
FIG. 56 is a high-level flowchart including exemplary implementations of operation O11 of FIG. 38.

In one or more implementations, as shown in FIG. 56, operation o11 includes an operation o1152 for electronically receiving the preparation directions including directions for the at least partial preparation of the succession of each of the instances of the ingestible product to be used as a smoothie. An exemplary version of a non-transitory signal bearing medium of information storage subsystem s200 is depicted as bearing one or more receiving information smoothie instructions i1152 that when executed will direct performance of the operation o1152. In an implementation, the one or more receiving information smoothie instructions i1152 when executed direct electronically receiving the preparation directions including directions for at least partial preparation of at least the succession of instances of the ingestible product to be used as a smoothie (e.g. an implementation of the receiver component s528 is configured to electronically receive the preparation directions and engage with the processor component s102 to direct the material processing subsystem s700 to at least partially prepare the succession of instances of the ingestible product such as a smoothie, etc.). Furthermore, the receiving information smoothie electrical circuitry arrangement e1152 when activated will perform the operation o1152. In an implementation, the receiving information smoothie electrical circuitry arrangement e1152, when activated performs electronically receiving the preparation directions including directions for at least partial preparation of at least the succession of instances of the ingestible product to be used as a smoothie (e.g. an implementation of the receiver component s528 is configured to electronically receive the preparation directions and engage with the processor component s102 to direct the material processing subsystem s700 to at least partially prepare the succession of instances of the ingestible product such as a smoothie, etc.). In an implementation, the electronically receiving the preparation directions including directions for the at least partial preparation of the succession of each of the instances of the ingestible product to be used as a smoothie is carried out by electronically receiving the preparation directions including directions for at least partial preparation of at least the succession of instances of the ingestible product to be used as a smoothie (e.g. an implementation of the receiver component s528 is configured to electronically receive the preparation directions and engage with the processor component s102 to direct the material processing subsystem s700 to at least partially prepare the succession of instances of the ingestible product such as a smoothie, etc.).

In one or more implementations, operation o11 includes an operation o1153 for electronically receiving the preparation directions including directions for the at least partial preparation of the succession of each of the instances of the ingestible product to be used as a baked good. An exemplary version of a non-transitory signal bearing medium of information storage subsystem s200 is depicted as bearing one or more receiving information baked instructions i1153 that when executed will direct performance of the operation o1153. In an implementation, the one or more receiving information baked instructions i1153 when executed direct electronically receiving the preparation directions including directions for at least partial preparation of at least the succession of instances of the ingestible product to be used as a baked good (e.g. an implementation of the receiver component s528 is configured to electronically receive the preparation directions and engage with the processor component s102 to direct the material processing subsystem s700 to at least partially prepare the succession of instances of the ingestible product such as a baked good, etc.). Furthermore, the receiving information baked electrical circuitry arrangement e1153 when activated will perform the operation o1153. In an implementation, the receiving information baked electrical circuitry arrangement e1153, when activated performs electronically receiving the preparation directions including directions for at least partial preparation of at least the succession of instances of the ingestible product to be used as a baked good (e.g. an implementation of the receiver component s528 is configured to electronically receive the preparation directions and engage with the processor component s102 to direct the material processing subsystem s700 to at least partially prepare the succession of instances of the ingestible product such as a baked good, etc.). In an implementation, the electronically receiving the preparation directions including directions for the at least partial preparation of the succession of each of the instances of the ingestible product to be used as a baked good is carried out by electronically receiving the preparation directions including directions for at least partial preparation of at least the succession of instances of the ingestible product to be used as a baked good (e.g. an implementation of the receiver component s528 is configured to electronically receive the preparation directions and engage with the processor component s102 to direct the material processing subsystem s700 to at least partially prepare the succession of instances of the ingestible product such as a baked good, etc.).

In one or more implementations, operation o11 includes an operation o1154 for electronically receiving the preparation directions including directions for the at least partial preparation of the succession of each of the instances of the ingestible product to be used as a deposited material. An exemplary version of a non-transitory signal bearing medium of information storage subsystem s200 is depicted as bearing one or more receiving information deposited instructions i1154 that when executed will direct performance of the operation o1154. In an implementation, the one or more receiving information deposited instructions i1154 when executed direct electronically receiving the preparation directions including directions for at least partial preparation of at least the succession of instances of the ingestible product to be used as a deposited material (e.g. an implementation of the receiver component s528 is configured to electronically receive the preparation directions and engage with the processor component s102 to direct the material processing subsystem s700 to at least partially prepare the succession of instances of the ingestible product as having deposited material such as a multi-layered cake, etc.). Furthermore, the receiving information deposited electrical circuitry arrangement e1154 when activated will perform the operation o1154. In an implementation, the receiving information deposited electrical circuitry arrangement e1154, when activated performs electronically receiving the preparation directions including directions for at least partial preparation of at least the succession of instances of the ingestible product to be used as a deposited material (e.g. an implementation of the receiver component s528 is configured to electronically receive the preparation directions and engage with the processor component s102 to direct the material processing subsystem s700 to at least partially prepare the succession of instances of the ingestible product as having deposited material such as a multi-layered cake, etc.). In an implementation, the electronically receiving the preparation directions including directions for the at least partial preparation of the succession of each of the instances of the ingestible product to be used as a deposited material is carried out by electronically receiving the preparation directions including directions for at least partial preparation of at least the succession of instances of the ingestible product to be used as a deposited material (e.g. an implementation of the receiver component s528 is configured to electronically receive the preparation directions and engage with the processor component s102 to direct the material processing subsystem s700 to at least partially prepare the succession of instances of the ingestible product as having deposited material such as a multi-layered cake, etc.).

Figure 57:
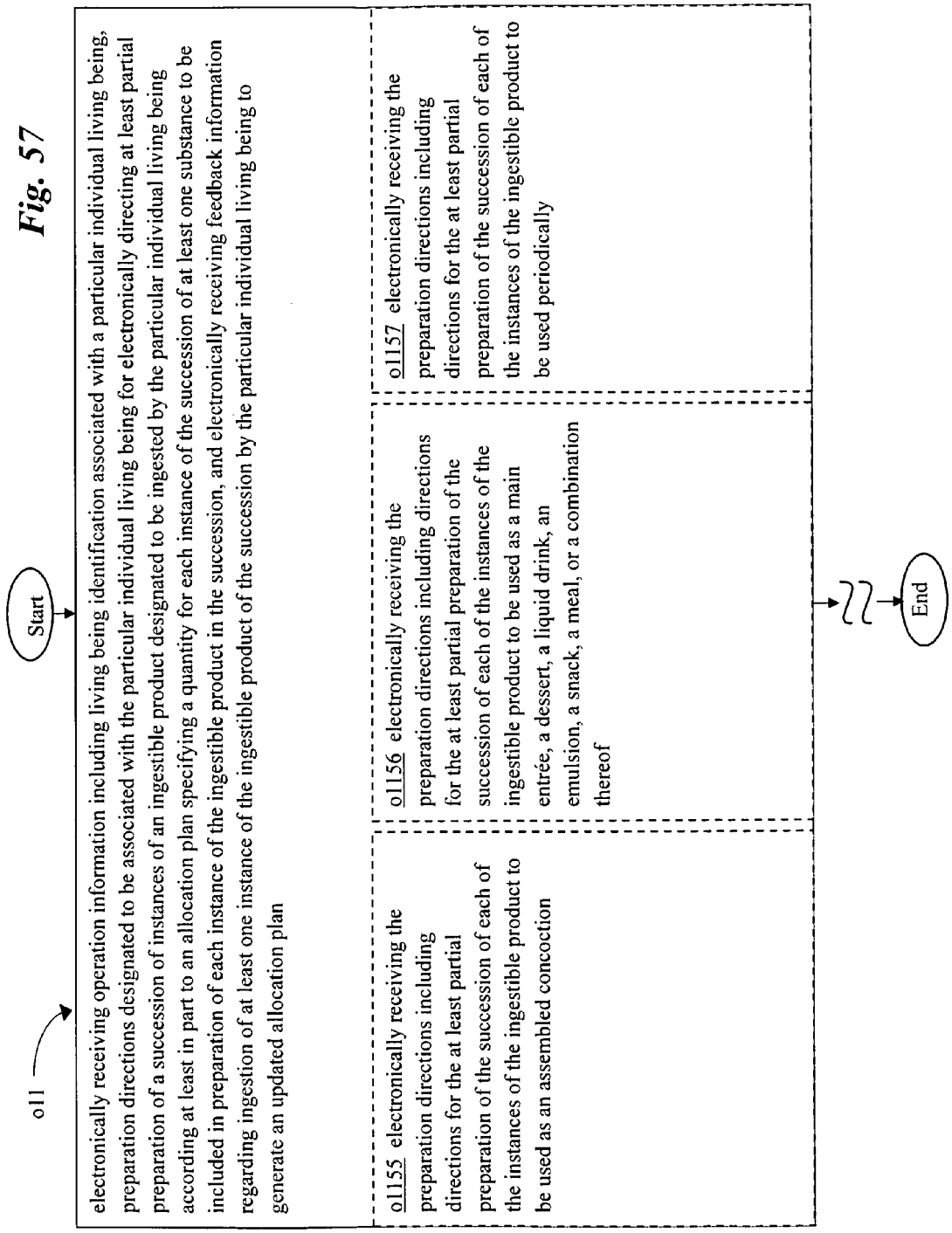
FIG. 57 is a high-level flowchart including exemplary implementations of operation O11 of FIG. 38.

In one or more implementations, as shown in FIG. 57, operation o11 includes an operation o1155 for electronically receiving the preparation directions including directions for the at least partial preparation of the succession of each of the instances of the ingestible product to be used as an assembled concoction. An exemplary version of a non-transitory signal bearing medium of information storage subsystem s200 is depicted as bearing one or more receiving information assembled instructions i1155 that when executed will direct performance of the operation o1155. In an implementation, the one or more receiving information assembled instructions i1155 when executed direct electronically receiving the preparation directions including directions for at least partial preparation of at least the succession of instances of the ingestible product to be used as an assembled concoction (e.g. an implementation of the receiver component s528 is configured to electronically receive the preparation directions and engage with the processor component s102 to direct the material processing subsystem s700 to at least partially prepare the succession of instances of the ingestible product as an assembled concoction such as a decorated confection, etc.). Furthermore, the receiving information assembled electrical circuitry arrangement e1155 when activated will perform the operation o1155. In an implementation, the receiving information assembled electrical circuitry arrangement e1155, when activated performs electronically receiving the preparation directions including directions for at least partial preparation of at least the succession of instances of the ingestible product to be used as an assembled concoction (e.g. an implementation of the receiver component s528 is configured to electronically receive the preparation directions and engage with the processor component s102 to direct the material processing subsystem s700 to at least partially prepare the succession of instances of the ingestible product as an assembled concoction such as a decorated confection, etc.). In an implementation, the electronically receiving the preparation directions including directions for the at least partial preparation of the succession of each of the instances of the ingestible product to be used as an assembled concoction is carried out by electronically receiving the preparation directions including directions for at least partial preparation of at least the succession of instances of the ingestible product to be used as an assembled concoction (e.g. an implementation of the receiver component s528 is configured to electronically receive the preparation directions and engage with the processor component s102 to direct the material processing subsystem s700 to at least partially prepare the succession of instances of the ingestible product as an assembled concoction such as a decorated confection, etc.).

In one or more implementations, operation o11 includes an operation o1156 for electronically receiving the preparation directions including directions for the at least partial preparation of the succession of each of the instances of the ingestible product to be used as a main entrée, a dessert, a liquid drink, an emulsion, a snack, a meal, or a combination thereof. An exemplary version of a non-transitory signal bearing medium of information storage subsystem s200 is depicted as bearing one or more receiving information uses instructions i1156 that when executed will direct performance of the operation o1156. In an implementation, the one or more receiving information uses instructions i1156 when executed direct electronically receiving the preparation directions including directions for at least partial preparation of at least the succession of instances of the ingestible product to be used as a main entrée, a dessert, a liquid drink, an emulsion, a snack, a meal, or a combination thereof (e.g. an implementation of the receiver component s528 is configured to electronically receive the preparation directions and engage with the processor component s102 to direct the material processing subsystem s700 to at least partially prepare the succession of instances of the ingestible product such as a steak, etc.). Furthermore, the receiving information uses electrical circuitry arrangement e1156 when activated will perform the operation o1156. In an implementation, the receiving information uses electrical circuitry arrangement e1156, when activated performs electronically receiving the preparation directions including directions for at least partial preparation of at least the succession of instances of the ingestible product to be used as a main entrée, a dessert, a liquid drink, an emulsion, a snack, a meal, or a combination thereof (e.g. an implementation of the receiver component s528 is configured to electronically receive the preparation directions and engage with the processor component s102 to direct the material processing subsystem s700 to at least partially prepare the succession of instances of the ingestible product such as a steak, etc.). In an implementation, the electronically receiving the preparation directions including directions for the at least partial preparation of the succession of each of the instances of the ingestible product to be used as a main entrée, a dessert, a liquid drink, an emulsion, a snack, a meal, or a combination thereof is carried out by electronically receiving the preparation directions including directions for at least partial preparation of at least the succession of instances of the ingestible product to be used as a main entrée, a dessert, a liquid drink, an emulsion, a snack, a meal, or a combination thereof (e.g. an implementation of the receiver component s528 is configured to electronically receive the preparation directions and engage with the processor component s102 to direct the material processing subsystem s700 to at least partially prepare the succession of instances of the ingestible product such as a steak, etc.).

In one or more implementations, operation o11 includes an operation o1157 for electronically receiving the preparation directions including directions for the at least partial preparation of the succession of each of the instances of the ingestible product to be used periodically. An exemplary version of a non-transitory signal bearing medium of information storage subsystem s200 is depicted as bearing one or more receiving information periods instructions i1157 that when executed will direct performance of the operation o1157. In an implementation, the one or more receiving information periods instructions i1157 when executed direct electronically receiving the preparation directions including directions for the at least partial preparation of the succession of each of the instances of the ingestible product to be used periodically (e.g. an implementation of the receiver component s528 is configured to electronically receive the preparation directions and engage with the processor component s102 to direct the material processing subsystem s700 to at least partially prepare the succession of instances of the ingestible product such as once a week, etc.). Furthermore, the receiving information periods electrical circuitry arrangement e1157 when activated will perform the operation o1157. In an implementation, the receiving information periods electrical circuitry arrangement e1157, when activated performs electronically receiving the preparation directions including directions for the at least partial preparation of the succession of each of the instances of the ingestible product to be used periodically (e.g. an implementation of the receiver component s528 is configured to electronically receive the preparation directions and engage with the processor component s102 to direct the material processing subsystem s700 to at least partially prepare the succession of instances of the ingestible product such as once a week, etc.). In an implementation, the electronically receiving the preparation directions including directions for the at least partial preparation of the succession of each of the instances of the ingestible product to be used periodically is carried out by electronically receiving the preparation directions including directions for the at least partial preparation of the succession of each of the instances of the ingestible product to be used periodically (e.g. an implementation of the receiver component s528 is configured to electronically receive the preparation directions and engage with the processor component s102 to direct the material processing subsystem s700 to at least partially prepare the succession of instances of the ingestible product such as once a week, etc.).

Figure 58:
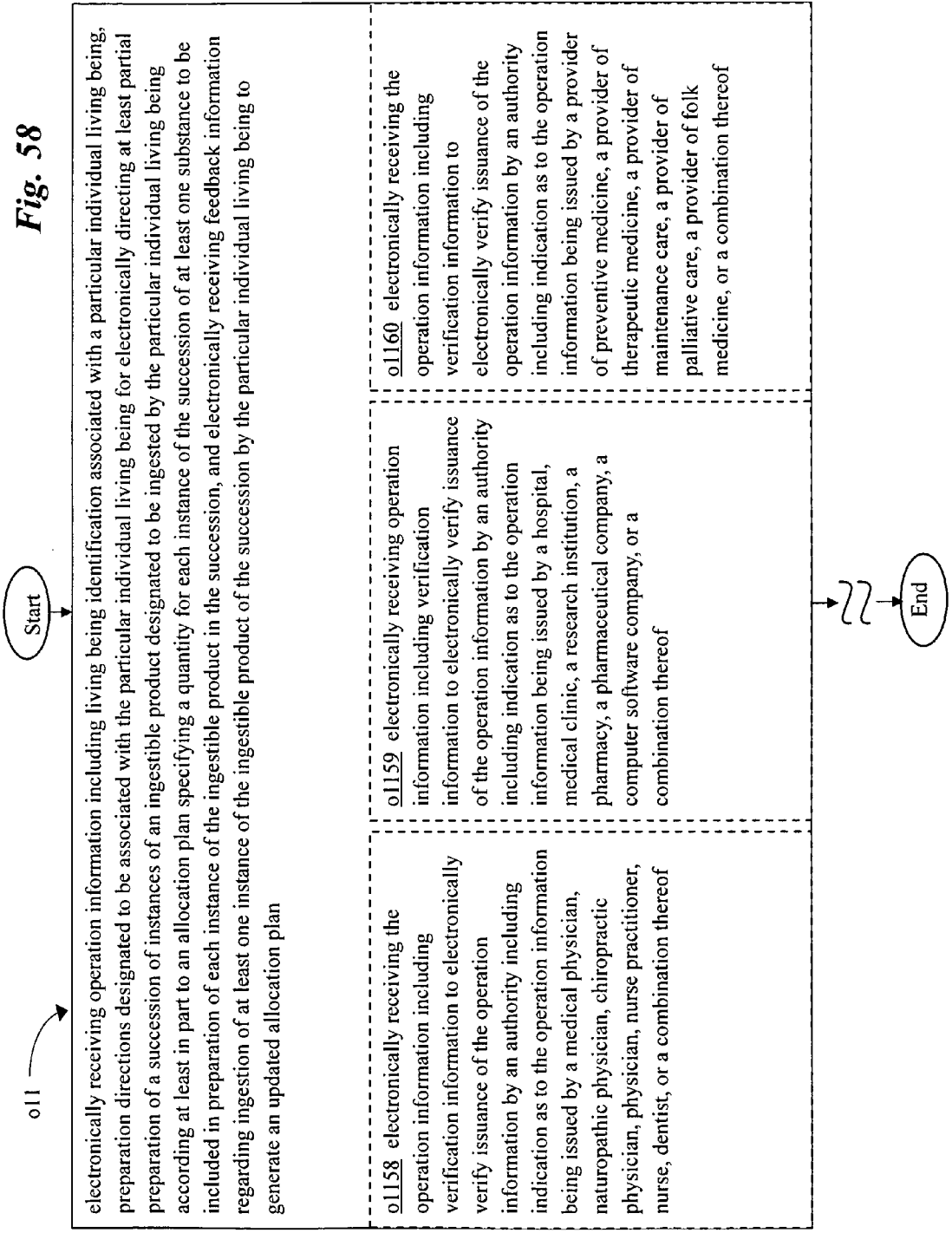
FIG. 58 is a high-level flowchart including exemplary implementations of operation O11 of FIG. 38.

In one or more implementations, as shown in FIG. 58, operation o11 includes an operation o1158 for electronically receiving the operation information including verification information to electronically verify issuance of the operation information by an authority including indication as to the operation information being issued by a medical physician, naturopathic physician, chiropractic physician, physician, nurse practitioner, nurse, dentist, or a combination thereof. An exemplary version of a non-transitory signal bearing medium of information storage subsystem s200 is depicted as bearing one or more receiving information care giver instructions i1158 that when executed will direct performance of the operation o1158. In an implementation, the one or more receiving information care giver instructions i1158 when executed direct electronically receiving the operation information including verification information to electronically verify issuance of the operation information by an authority including indication as to the operation information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the operation information as a health care provider such as a medical physician, etc.). Furthermore, the receiving information care giver electrical circuitry arrangement e1158 when activated will perform the operation o1158. In an implementation, the receiving information care giver electrical circuitry arrangement e1158, when activated performs electronically receiving the operation information including verification information to electronically verify issuance of the operation information by an authority including indication as to the operation information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the operation information as a health care provider such as a medical physician, etc.). In an implementation, the electronically receiving the operation information including verification information to electronically verify issuance of the operation information by an authority including indication as to the operation information being issued by a medical physician, naturopathic physician, chiropractic physician, physician, nurse practitioner, nurse, dentist, or a combination thereof is carried out by electronically receiving the operation information including verification information to electronically verify issuance of the operation information by an authority including indication as to the operation information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the operation information as a health care provider such as a medical physician, etc.).

In one or more implementations, operation o11 includes an operation o1159 for electronically receiving operation information including verification information to electronically verify issuance of the operation information by an authority including indication as to the operation information being issued by a hospital, medical clinic, a research institution, a pharmacy, a pharmaceutical company, a computer software company, or a combination thereof. An exemplary version of a non-transitory signal bearing medium of information storage subsystem s200 is depicted as bearing one or more receiving information organization instructions i1159 that when executed will direct performance of the operation o1159. In an implementation, the one or more receiving information organization instructions i1159 when executed direct electronically receiving the operation information including verification information to electronically verify issuance of the operation information by an authority including indication as to the operation information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the operation information as an institution such as a medical clinic, etc.). Furthermore, the receiving information organization electrical circuitry arrangement e1159 when activated will perform the operation o1159. In an implementation, the receiving information organization electrical circuitry arrangement e1159, when activated performs electronically receiving the operation information including verification information to electronically verify issuance of the operation information by an authority including indication as to the operation information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the operation information as an institution such as a medical clinic, etc.). In an implementation, the electronically receiving operation information including verification information to electronically verify issuance of the operation information by an authority including indication as to the operation information being issued by a hospital, medical clinic, a research institution, a pharmacy, a pharmaceutical company, a computer software company, or a combination thereof is carried out by electronically receiving the operation information including verification information to electronically verify issuance of the operation information by an authority including indication as to the operation information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the operation information as an institution such as a medical clinic, etc.).

In one or more implementations, operation o11 includes an operation o1160 for electronically receiving the operation information including verification information to electronically verify issuance of the operation information by an authority including indication as to the operation information being issued by a provider of preventive medicine, a provider of therapeutic medicine, a provider of maintenance care, a provider of palliative care, a provider of folk medicine, or a combination thereof. An exemplary version of a non-transitory signal bearing medium of information storage subsystem s200 is depicted as bearing one or more receiving information preventive instructions i1160 that when executed will direct performance of the operation o1160. In an implementation, the one or more receiving information preventive instructions i1160 when executed direct electronically receiving the operation information including verification information to electronically verify issuance of the operation information by an authority including indication as to the operation information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the operation information as a provider such as a provider of preventive medicine, etc.). Furthermore, the receiving information preventive electrical circuitry arrangement e1160 when activated will perform the operation o1160. In an implementation, the receiving information preventive electrical circuitry arrangement e1160, when activated performs electronically receiving the operation information including verification information to electronically verify issuance of the operation information by an authority including indication as to the operation information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the operation information as a provider such as a provider of preventive medicine, etc.). In an implementation, the electronically receiving the operation information including verification information to electronically verify issuance of the operation information by an authority including indication as to the operation information being issued by a provider of preventive medicine, a provider of therapeutic medicine, a provider of maintenance care, a provider of palliative care, a provider of folk medicine, or a combination thereof is carried out by electronically receiving the operation information including verification information to electronically verify issuance of the operation information by an authority including indication as to the operation information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the operation information as a provider such as a provider of preventive medicine, etc.).

Figure 59:
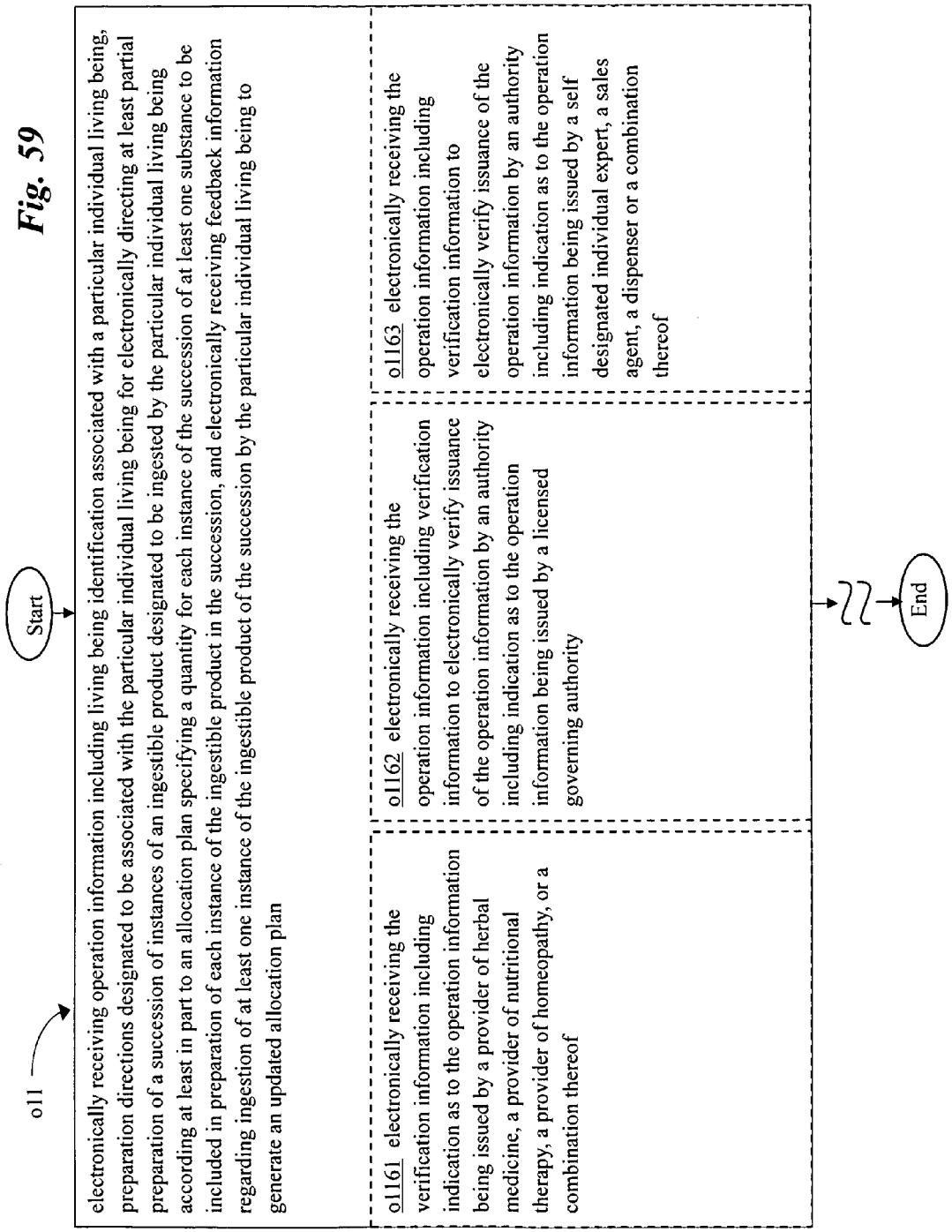
FIG. 59 is a high-level flowchart including exemplary implementations of operation O11 of FIG. 38.

In one or more implementations, as shown in FIG. 59, operation o11 includes an operation o1161 for electronically receiving the verification information including indication as to the operation information being issued by a provider of herbal medicine, a provider of nutritional therapy, a provider of homeopathy, or a combination thereof. An exemplary version of a non-transitory signal bearing medium of information storage subsystem s200 is depicted as bearing one or more receiving information alternative instructions i1161 that when executed will direct performance of the operation o1161. In an implementation, the one or more receiving information alternative instructions i1161 when executed direct electronically receiving the operation information including verification information to electronically verify issuance of the operation information by an authority including indication as to the operation information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the operation information as a provider such as a provider of homeopathy, etc.). Furthermore, the receiving information alternative electrical circuitry arrangement e1161 when activated will perform the operation o1161. In an implementation, the receiving information alternative electrical circuitry arrangement e1161, when activated performs electronically receiving the operation information including verification information to electronically verify issuance of the operation information by an authority including indication as to the operation information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the operation information as a provider such as a provider of homeopathy, etc.). In an implementation, the electronically receiving the verification information including indication as to the operation information being issued by a provider of herbal medicine, a provider of nutritional therapy, a provider of homeopathy, or a combination thereof is carried out by electronically receiving the operation information including verification information to electronically verify issuance of the operation information by an authority including indication as to the operation information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the operation information as a provider such as a provider of homeopathy, etc.).

In one or more implementations, operation o11 includes an operation o1162 for electronically receiving the operation information including verification information to electronically verify issuance of the operation information by an authority including indication as to the operation information being issued by a licensed governing authority. An exemplary version of a non-transitory signal bearing medium of information storage subsystem s200 is depicted as bearing one or more receiving information authority instructions i1162 that when executed will direct performance of the operation o1162. In an implementation, the one or more receiving information authority instructions i1162 when executed direct electronically receiving the operation information including verification information to electronically verify issuance of the operation information by an authority including indication as to the operation information being issued by a licensed governing authority (e.g. an implementation of the receiver component s528 is configured to electronically receive the verification information in a format for the processor component s102 to identify the issuer of the operation information as a licensed governing authority such as a veterans administration hospital, etc.). Furthermore, the receiving information authority electrical circuitry arrangement e1162 when activated will perform the operation o1162. In an implementation, the receiving information authority electrical circuitry arrangement e1162, when activated performs electronically receiving the operation information including verification information to electronically verify issuance of the operation information by an authority including indication as to the operation information being issued by a licensed governing authority (e.g. an implementation of the receiver component s528 is configured to electronically receive the verification information in a format for the processor component s102 to identify the issuer of the operation information as a licensed governing authority such as a veterans administration hospital, etc.). In an implementation, the electronically receiving the operation information including verification information to electronically verify issuance of the operation information by an authority including indication as to the operation information being issued by a licensed governing authority is carried out by electronically receiving the operation information including verification information to electronically verify issuance of the operation information by an authority including indication as to the operation information being issued by a licensed governing authority (e.g. an implementation of the receiver component s528 is configured to electronically receive the verification information in a format for the processor component s102 to identify the issuer of the operation information as a licensed governing authority such as a veterans administration hospital, etc.).

In one or more implementations, operation o11 includes an operation o1163 for electronically receiving the operation information including verification information to electronically verify issuance of the operation information by an authority including indication as to the operation information being issued by a self designated individual expert, a sales agent, a dispenser or a combination thereof. An exemplary version of a non-transitory signal bearing medium of information storage subsystem s200 is depicted as bearing one or more receiving information individual instructions i1163 that when executed will direct performance of the operation o1163. In an implementation, the one or more receiving information individual instructions i1163 when executed direct electronically receiving the operation information including verification information to electronically verify issuance of the operation information by an authority including indication as to the operation information being issued by a self designated individual expert, a sales agent, a dispenser or a combination thereof (e.g. an implementation of the receiver component s528 is configured to electronically receive the verification information in a format for the processor component s102 to identify the issuer of the operation information as an individual such as a self designated individual expert, etc.). Furthermore, the receiving information individual electrical circuitry arrangement e1163 when activated will perform the operation o1163. In an implementation, the receiving information individual electrical circuitry arrangement e1163, when activated performs electronically receiving the operation information including verification information to electronically verify issuance of the operation information by an authority including indication as to the operation information being issued by a self designated individual expert, a sales agent, a dispenser or a combination thereof (e.g. an implementation of the receiver component s528 is configured to electronically receive the verification information in a format for the processor component s102 to identify the issuer of the operation information as an individual such as a self designated individual expert, etc.). In an implementation, the electronically receiving the operation information including verification information to electronically verify issuance of the operation information by an authority including indication as to the operation information being issued by a self designated individual expert, a sales agent, a dispenser or a combination thereof is carried out by electronically receiving the operation information including verification information to electronically verify issuance of the operation information by an authority including indication as to the operation information being issued by a self designated individual expert, a sales agent, a dispenser or a combination thereof (e.g. an implementation of the receiver component s528 is configured to electronically receive the verification information in a format for the processor component s102 to identify the issuer of the operation information as an individual such as a self designated individual expert, etc.).

Figure 60:
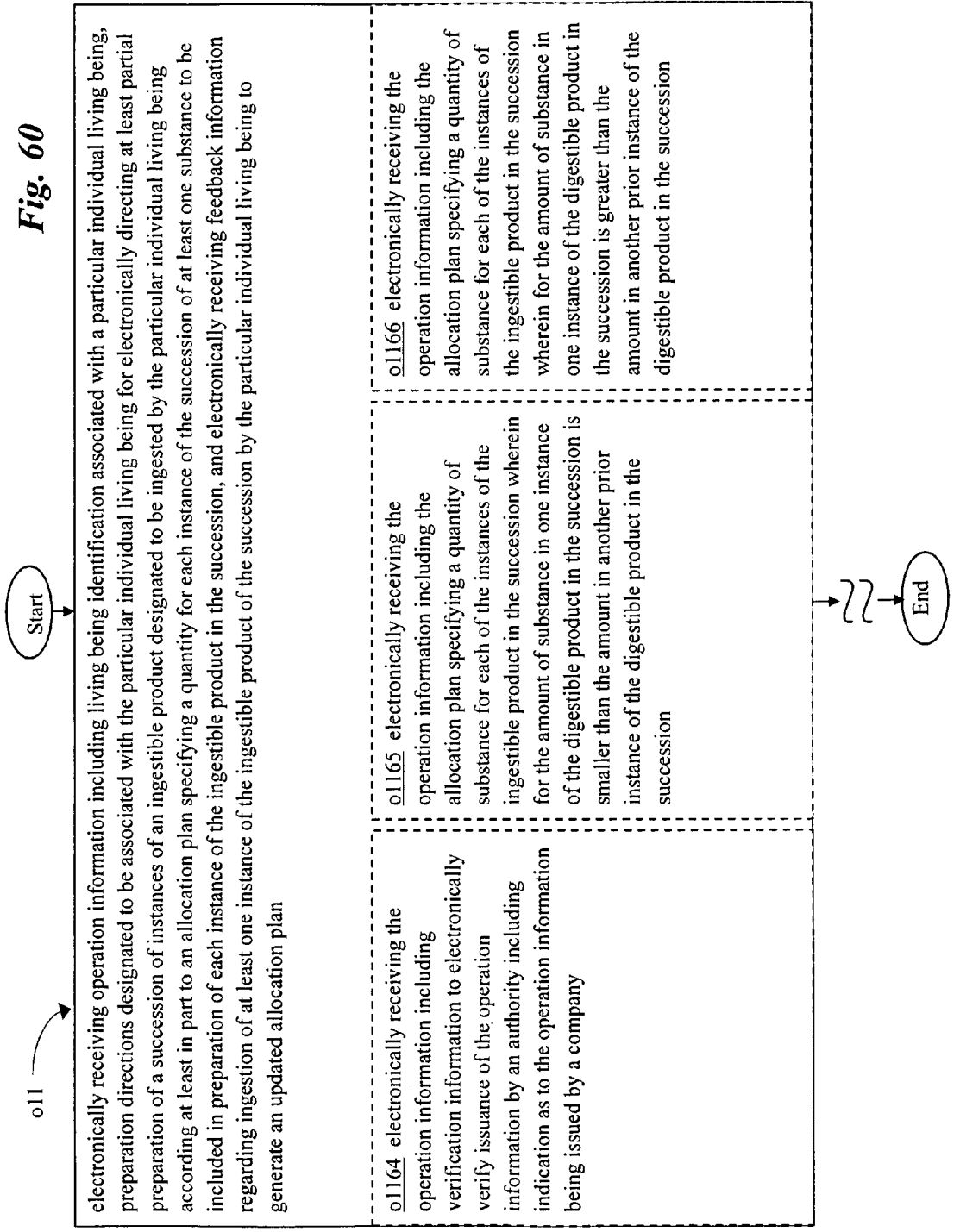
FIG. 60 is a high-level flowchart including exemplary implementations of operation O11 of FIG. 38.

In one or more implementations, as shown in FIG. 60, operation o11 includes an operation o1164 for electronically receiving the operation information including verification information to electronically verify issuance of the operation information by an authority including indication as to the operation information being issued by a company. An exemplary version of a non-transitory signal bearing medium of information storage subsystem s200 is depicted as bearing one or more receiving information company instructions i1164 that when executed will direct performance of the operation o1164. In an implementation, the one or more receiving information company instructions i1164 when executed direct electronically receiving the operation information including verification information to electronically verify issuance of the operation information by an authority including indication as to the operation information being issued by a company (e.g. an implementation of the receiver component s528 is configured to electronically receive the verification information in a format for the processor component s102 to identify the issuer of the operation information as a company such as a pharmaceutical company, etc.). Furthermore, the receiving information company electrical circuitry arrangement e1164 when activated will perform the operation o1164. In an implementation, the receiving information company electrical circuitry arrangement e1164, when activated performs electronically receiving the operation information including verification information to electronically verify issuance of the operation information by an authority including indication as to the operation information being issued by a company (e.g. an implementation of the receiver component s528 is configured to electronically receive the verification information in a format for the processor component s102 to identify the issuer of the operation information as a company such as a pharmaceutical company, etc.). In an implementation, the electronically receiving the operation information including verification information to electronically verify issuance of the operation information by an authority including indication as to the operation information being issued by a company is carried out by electronically receiving the operation information including verification information to electronically verify issuance of the operation information by an authority including indication as to the operation information being issued by a company (e.g. an implementation of the receiver component s528 is configured to electronically receive the verification information in a format for the processor component s102 to identify the issuer of the operation information as a company such as a pharmaceutical company, etc.).

In one or more implementations, operation o11 includes an operation o1165 for electronically receiving the operation information including the allocation plan specifying a quantity of substance for each of the instances of the ingestible product in the succession wherein for the amount of substance in one instance of the digestible product in the succession is smaller than the amount in another prior instance of the digestible product in the succession. A non-transitory signal bearing medium includes one or more receiving information smaller instructions i1165 that when executed will direct performance of the operation o1165. In an implementation, the one or more receiving information smaller instructions i1165 when executed direct electronically receiving the operation information including the allocation plan specifying a quantity of substance for each of the instances of the ingestible product in the succession wherein for the amount of substance in one instance of the digestible product in the succession is smaller than the amount in another prior instance of the digestible product in the succession (e.g. an implementation of the receiver component s528 is configured to electronically receive the operation information in a format for the processor component s102 to identify the amount of sugar used in an earlier prepared smoothie is more than the amount of sugar used in a subsequently prepared smoothie, etc.). Furthermore, the receiving information smaller electrical circuitry arrangement e1165 when activated will perform the operation o1165. In an implementation, the receiving information smaller electrical circuitry arrangement e1165, when activated performs electronically receiving the operation information including the allocation plan specifying a quantity of substance for each of the instances of the ingestible product in the succession wherein for the amount of substance in one instance of the digestible product in the succession is smaller than the amount in another prior instance of the digestible product in the succession (e.g. an implementation of the receiver component s528 is configured to electronically receive the operation information in a format for the processor component s102 to identify the amount of sugar used in an earlier prepared smoothie is more than the amount of sugar used in a subsequently prepared smoothie, etc.). In an implementation, the electronically receiving the operation information including the allocation plan specifying a quantity of substance for each of the instances of the ingestible product in the succession wherein for the amount of substance in one instance of the digestible product in the succession is smaller than the amount in another prior instance of the digestible product in the succession is carried out by electronically receiving the operation information including the allocation plan specifying a quantity of substance for each of the instances of the ingestible product in the succession wherein for the amount of substance in one instance of the digestible product in the succession is smaller than the amount in another prior instance of the digestible product in the succession (e.g. an implementation of the receiver component s528 is configured to electronically receive the operation information in a format for the processor component s102 to identify the amount of sugar used in an earlier prepared smoothie is more than the amount of sugar used in a subsequently prepared smoothie, etc.).

In one or more implementations, operation o11 includes an operation o1166 for electronically receiving the operation information including the allocation plan specifying a quantity of substance for each of the instances of the ingestible product in the succession wherein for the amount of substance in one instance of the digestible product in the succession is greater than the amount in another prior instance of the digestible product in the succession. A non-transitory signal bearing medium includes one or more receiving information greater instructions i1166 that when executed will direct performance of the operation o1166. In an implementation, the one or more receiving information greater instructions i1166 when executed direct electronically receiving the operation information including the allocation plan specifying a quantity of substance for each of the instances of the ingestible product in the succession wherein for the amount of substance in one instance of the digestible product in the succession is greater than the amount in another prior instance of the digestible product in the succession (e.g. an implementation of the receiver component s528 is configured to electronically receive the operation information in a format for the processor component s102 to identify the amount of cayenne used in an earlier prepared bowl of chili is more than the amount of cayenne used in a subsequently prepared bowl of chili, etc.). Furthermore, the receiving information greater electrical circuitry arrangement e1166 when activated will perform the operation o1166. In an implementation, the receiving information greater electrical circuitry arrangement e1166, when activated performs electronically receiving the operation information including the allocation plan specifying a quantity of substance for each of the instances of the ingestible product in the succession wherein for the amount of substance in one instance of the digestible product in the succession is greater than the amount in another prior instance of the digestible product in the succession (e.g. an implementation of the receiver component s528 is configured to electronically receive the operation information in a format for the processor component s102 to identify the amount of cayenne used in an earlier prepared bowl of chili is more than the amount of cayenne used in a subsequently prepared bowl of chili, etc.). In an implementation, the electronically receiving the operation information including the allocation plan specifying a quantity of substance for each of the instances of the ingestible product in the succession wherein for the amount of substance in one instance of the digestible product in the succession is greater than the amount in another prior instance of the digestible product in the succession is carried out by electronically receiving the operation information including the allocation plan specifying a quantity of substance for each of the instances of the ingestible product in the succession wherein for the amount of substance in one instance of the digestible product in the succession is greater than the amount in another prior instance of the digestible product in the succession (e.g. an implementation of the receiver component s528 is configured to electronically receive the operation information in a format for the processor component s102 to identify the amount of cayenne used in an earlier prepared bowl of chili is more than the amount of cayenne used in a subsequently prepared bowl of chili, etc.).

Figure 61:
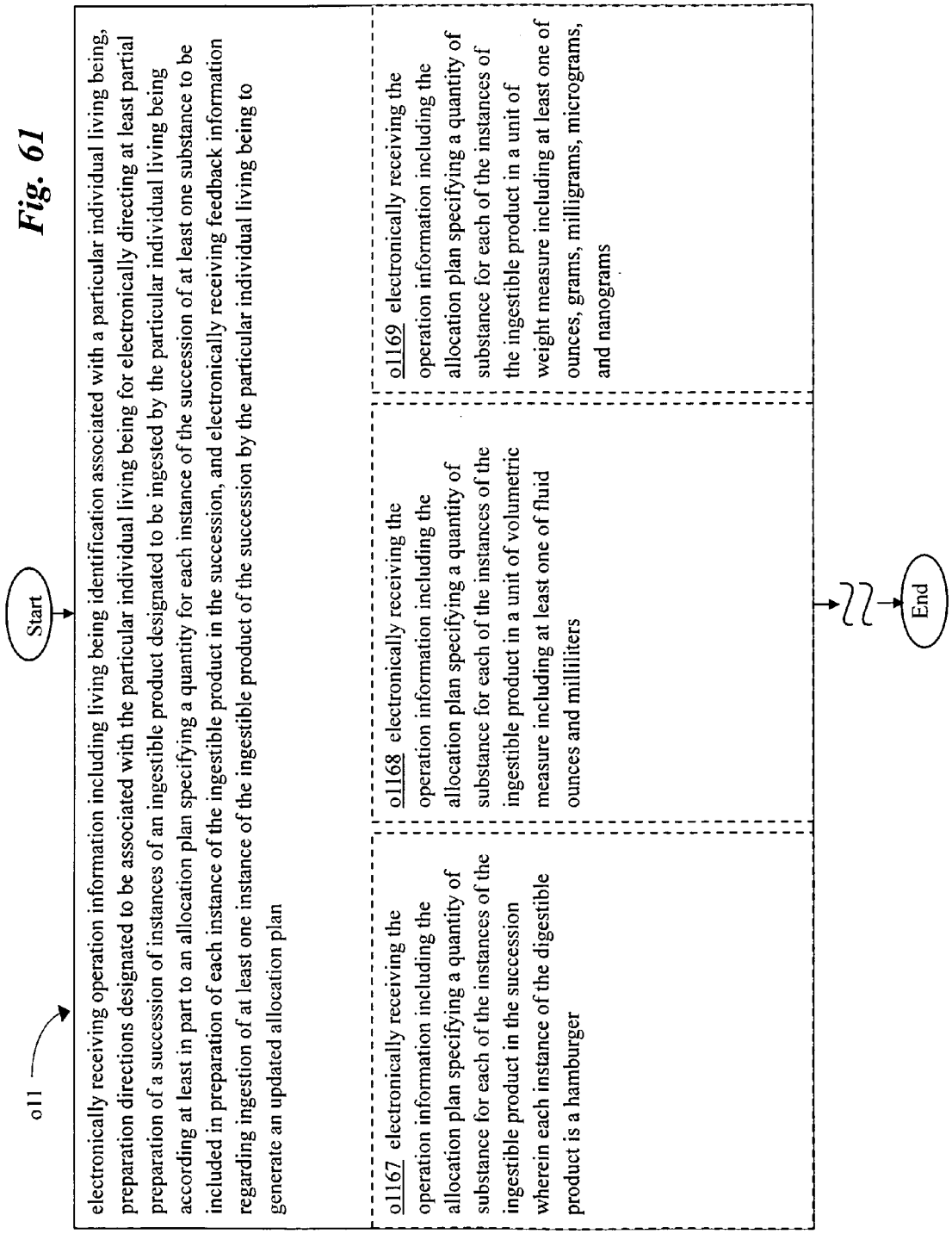
FIG. 61 is a high-level flowchart including exemplary implementations of operation O11 of FIG. 38.

In one or more implementations, as shown in FIG. 61, operation o11 includes an operation o1167 for electronically receiving the operation information including the allocation plan specifying a quantity of substance for each of the instances of the ingestible product in the succession wherein each instance of the digestible product is a hamburger. An exemplary version of a non-transitory signal bearing medium of information storage subsystem s200 is depicted as bearing one or more receiving information hamburger instructions i1167 that when executed will direct performance of the operation o1167. In an implementation, the one or more receiving information hamburger instructions i1167 when executed direct electronically receiving the operation information including the allocation plan specifying a quantity of substance for each of the instances of the ingestible product in the succession wherein each instance of the digestible product is a hamburger (e.g. an implementation of the receiver component s528 is configured to electronically receive the operation information in a format for the processor component s102 to identify the amount of salt to be used for each of a succession of hamburgers to be prepared for an older adult being introduced to a salt restrictive diet, etc.). Furthermore, the receiving information hamburger electrical circuitry arrangement e1167 when activated will perform the operation o1167. In an implementation, the receiving information hamburger electrical circuitry arrangement e1167, when activated performs electronically receiving the operation information including the allocation plan specifying a quantity of substance for each of the instances of the ingestible product in the succession wherein each instance of the digestible product is a hamburger (e.g. an implementation of the receiver component s528 is configured to electronically receive the operation information in a format for the processor component s102 to identify the amount of salt to be used for each of a succession of hamburgers to be prepared for an older adult being introduced to a salt restrictive diet, etc.). In an implementation, the electronically receiving the operation information including the allocation plan specifying a quantity of substance for each of the instances of the ingestible product in the succession wherein each instance of the digestible product is a hamburger is carried out by electronically receiving the operation information including the allocation plan specifying a quantity of substance for each of the instances of the ingestible product in the succession wherein each instance of the digestible product is a hamburger (e.g. an implementation of the receiver component s528 is configured to electronically receive the operation information in a format for the processor component s102 to identify the amount of salt to be used for each of a succession of hamburgers to be prepared for an older adult being introduced to a salt restrictive diet, etc.).

In one or more implementations, operation o11 includes an operation o1168 for electronically receiving the operation information including the allocation plan specifying a quantity of substance for each of the instances of the ingestible product in a unit of volumetric measure including at least one of fluid ounces and milliliters. A non-transitory signal bearing medium includes one or more receiving information volumetric instructions i1168 that when executed will direct performance of the operation o1168. In an implementation, the one or more receiving information volumetric instructions i1168 when executed direct electronically receiving the operation information including the allocation plan specifying a quantity of substance for each of the instances of the ingestible product in a unit of volumetric measure including at least one of fluid ounces and milliliters (e.g. an implementation of the receiver component s528 is configured to electronically receive the operation information in a format for the processor component s102 to identify the amount in milliliters of emulsified fat to be used in each of a succession of servings of stew to be prepared for an teenager on a modified fat diet, etc.). Furthermore, the receiving information volumetric electrical circuitry arrangement e1168 when activated will perform the operation o1168. In an implementation, the receiving information volumetric electrical circuitry arrangement e1168, when activated performs electronically receiving the operation information including the allocation plan specifying a quantity of substance for each of the instances of the ingestible product in a unit of volumetric measure including at least one of fluid ounces and milliliters (e.g. an implementation of the receiver component s528 is configured to electronically receive the operation information in a format for the processor component s102 to identify the amount in milliliters of emulsified fat to be used in each of a succession of servings of stew to be prepared for an teenager on a modified fat diet, etc.). In an implementation, the electronically receiving the operation information including the allocation plan specifying a quantity of substance for each of the instances of the ingestible product in a unit of volumetric measure including at least one of fluid ounces and milliliters is carried out by electronically receiving the operation information including the allocation plan specifying a quantity of substance for each of the instances of the ingestible product in a unit of volumetric measure including at least one of fluid ounces and milliliters (e.g. an implementation of the receiver component s528 is configured to electronically receive the operation information in a format for the processor component s102 to identify the amount in milliliters of emulsified fat to be used in each of a succession of servings of stew to be prepared for an teenager on a modified fat diet, etc.).

In one or more implementations, operation o11 includes an operation o1169 for electronically receiving the operation information including the allocation plan specifying a quantity of substance for each of the instances of the ingestible product in a unit of weight measure including at least one of ounces, grams, milligrams, micrograms, and nanograms. A non-transitory signal bearing medium includes one or more receiving information weight instructions i1169 that when executed will direct performance of the operation o1169. In an implementation, the one or more receiving information weight instructions i1169 when executed direct electronically receiving the operation information including the allocation plan specifying a quantity of substance for each of the instances of the ingestible product in a unit of weight measure including at least one of ounces, grams, milligrams, micrograms, and nanograms (e.g. an implementation of the receiver component s528 is configured to electronically receive the operation information in a format for the processor component s102 to identify the amount in milligrams of vitamin C to be used in each of a succession of servings of tropical fruit punch to be prepared for an elderly individual with a weaken immune system, etc.). Furthermore, the receiving information weight electrical circuitry arrangement e1169 when activated will perform the operation o1169. In an implementation, the receiving information weight electrical circuitry arrangement e1169, when activated performs electronically receiving the operation information including the allocation plan specifying a quantity of substance for each of the instances of the ingestible product in a unit of weight measure including at least one of ounces, grams, milligrams, micrograms, and nanograms (e.g. an implementation of the receiver component s528 is configured to electronically receive the operation information in a format for the processor component s102 to identify the amount in milligrams of vitamin C to be used in each of a succession of servings of tropical fruit punch to be prepared for an elderly individual with a weaken immune system, etc.). In an implementation, the electronically receiving the operation information including the allocation plan specifying a quantity of substance for each of the instances of the ingestible product in a unit of weight measure including at least one of ounces, grams, milligrams, micrograms, and nanograms is carried out by electronically receiving the operation information including the allocation plan specifying a quantity of substance for each of the instances of the ingestible product in a unit of weight measure including at least one of ounces, grams, milligrams, micrograms, and nanograms (e.g. an implementation of the receiver component s528 is configured to electronically receive the operation information in a format for the processor component s102 to identify the amount in milligrams of vitamin C to be used in each of a succession of servings of tropical fruit punch to be prepared for an elderly individual with a weaken immune system, etc.).

Figure 62:
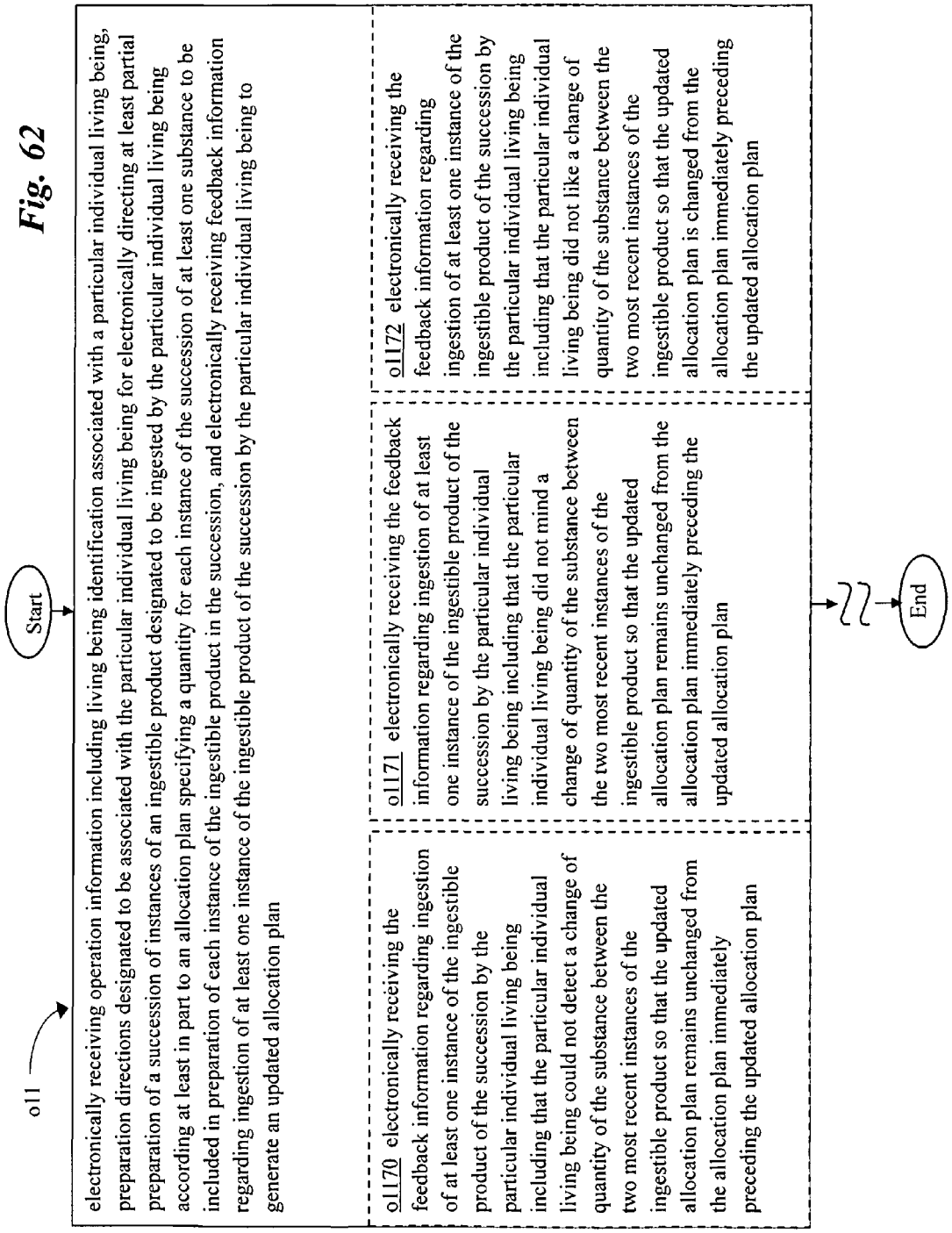
FIG. 62 is a high-level flowchart including exemplary implementations of operation O11 of FIG. 38.

In one or more implementations, as shown in FIG. 62, operation o11 includes an operation o1170 for electronically receiving the feedback information regarding ingestion of at least one instance of the ingestible product of the succession by the particular individual living being including that the particular individual living being could not detect a change of quantity of the substance between the two most recent instances of the ingestible product so that the updated allocation plan remains unchanged from the allocation plan immediately preceding the updated allocation plan. An exemplary version of a non-transitory signal bearing medium of information storage subsystem s200 is depicted as bearing one or more receiving information no detect instructions i1170 that when executed will direct performance of the operation o1170. In an implementation, the one or more receiving information no detect instructions i1170 when executed direct electronically receiving the feedback information regarding ingestion of at least one instance of the ingestible product of the succession by the particular individual living being including that the particular individual living being could not detect a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information from an individual inputting through a graphical user interface in a format for the processor component s102 to determine that subsequent chicken breasts can be prepared according to an existing allocation plan to reduce the amount of salt by 5 milligrams for each of a succession of servings over a 30 day period for the individual who is being introduce to a salt restrictive diet, etc.). Furthermore, the receiving information no detect electrical circuitry arrangement e1170 when activated will perform the operation o1170. In an implementation, the receiving information no detect electrical circuitry arrangement e1170, when activated performs electronically receiving the feedback information regarding ingestion of at least one instance of the ingestible product of the succession by the particular individual living being including that the particular individual living being could not detect a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information from an individual inputting through a graphical user interface in a format for the processor component s102 to determine that subsequent chicken breasts can be prepared according to an existing allocation plan to reduce the amount of salt by 5 milligrams for each of a succession of servings over a 30 day period for the individual who is being introduce to a salt restrictive diet, etc.). In an implementation, the electronically receiving the feedback information regarding ingestion of at least one instance of the ingestible product of the succession by the particular individual living being including that the particular individual living being could not detect a change of quantity of the substance between the two most recent instances of the ingestible product so that the updated allocation plan remains unchanged from the allocation plan immediately preceding the updated allocation plan is carried out by electronically receiving the feedback information regarding ingestion of at least one instance of the ingestible product of the succession by the particular individual living being including that the particular individual living being could not detect a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information from an individual inputting through a graphical user interface in a format for the processor component s102 to determine that subsequent chicken breasts can be prepared according to an existing allocation plan to reduce the amount of salt by 5 milligrams for each of a succession of servings over a 30 day period for the individual who is being introduce to a salt restrictive diet, etc.).

In one or more implementations, operation o11 includes an operation o1171 for electronically receiving the feedback information regarding ingestion of at least one instance of the ingestible product of the succession by the particular individual living being including that the particular individual living being did not mind a change of quantity of the substance between the two most recent instances of the ingestible product so that the updated allocation plan remains unchanged from the allocation plan immediately preceding the updated allocation plan. A non-transitory signal bearing medium includes one or more receiving information not disturbed instructions i1171 that when executed will direct performance of the operation o1171. In an implementation, the one or more receiving information not disturbed instructions i1171 when executed direct electronically receiving the feedback information regarding ingestion of at least one instance of the ingestible product of the succession by the particular individual living being including that the particular individual living being did not mind a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information through image recognition of an individual while consuming one of a succession of pizzas in a format for the processor component s102 to determine that subsequent pizzas can be prepared according to an existing allocation plan to increase the amount of cayenne by 3 milligrams for each of a succession of servings over a 120 day period for an individual that is being introduce to a capsaicin enhanced diet, etc.). Furthermore, the receiving information not disturbed electrical circuitry arrangement e1171 when activated will perform the operation o1171. In an implementation, the receiving information not disturbed electrical circuitry arrangement e1171, when activated performs electronically receiving the feedback information regarding ingestion of at least one instance of the ingestible product of the succession by the particular individual living being including that the particular individual living being did not mind a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information through image recognition of an individual while consuming one of a succession of pizzas in a format for the processor component s102 to determine that subsequent pizzas can be prepared according to an existing allocation plan to increase the amount of cayenne by 3 milligrams for each of a succession of servings over a 120 day period for an individual that is being introduce to a capsaicin enhanced diet, etc.). In an implementation, the electronically receiving the feedback information regarding ingestion of at least one instance of the ingestible product of the succession by the particular individual living being including that the particular individual living being did not mind a change of quantity of the substance between the two most recent instances of the ingestible product so that the updated allocation plan remains unchanged from the allocation plan immediately preceding the updated allocation plan is carried out by electronically receiving the feedback information regarding ingestion of at least one instance of the ingestible product of the succession by the particular individual living being including that the particular individual living being did not mind a change of quantity of the substance between the two most recent instances of the ingestible product so that the updated allocation plan remains unchanged from the allocation plan immediately preceding the updated allocation plan (e.g. an implementation of the receiver component s528 is configured to electronically receive the feedback information through image recognition of an individual while consuming one of a succession of pizzas in a format for the processor component s102 to determine that subsequent pizzas can be prepared according to an existing allocation plan to increase the amount of cayenne by 3 milligrams for each of a succession of servings over a 120 day period for an individual that is being introduce to a capsaicin enhanced diet, etc.).

In one or more implementations, operation o11 includes an operation o1172 for electronically receiving the feedback information regarding ingestion of at least one instance of the ingestible product of the succession by the particular individual living being including that the particular individual living being did not like a change of quantity of the substance between the two most recent instances of the ingestible product so that the updated allocation plan is changed from the allocation plan immediately preceding the updated allocation plan. A non-transitory signal bearing medium includes one or more receiving information not like instructions i1172 that when executed will direct performance of the operation o1172. In an implementation, the one or more receiving information not like instructions i1172 when executed direct electronically receiving the feedback information regarding ingestion of at least one instance of the ingestible product of the succession by the particular individual living being including that the particular individual living being did not like a change of quantity of the substance between the two most recent instances of the ingestible product so that the updated allocation plan is changed from the allocation plan immediately preceding the updated allocation plan (e.g. an implementation of the receiver component s528 is configured to electronically receive the feedback information through image recognition of an individual while consuming one of a succession of ice cream servings in a format for the processor component s102 to determine that subsequent ice cream servings need to be sweeter by 75 milligrams of sucrose each of the subsequent successive servings involved with the allocation plan over a 90 day period so that the allocation plan is to be modified by the processor component accordingly, etc.). Furthermore, the receiving information not like electrical circuitry arrangement e1172 when activated will perform the operation o1172. In an implementation, the receiving information not like electrical circuitry arrangement e1172, when activated performs electronically receiving the feedback information regarding ingestion of at least one instance of the ingestible product of the succession by the particular individual living being including that the particular individual living being did not like a change of quantity of the substance between the two most recent instances of the ingestible product so that the updated allocation plan is changed from the allocation plan immediately preceding the updated allocation plan (e.g. an implementation of the receiver component s528 is configured to electronically receive the feedback information through image recognition of an individual while consuming one of a succession of ice cream servings in a format for the processor component s102 to determine that subsequent ice cream servings need to be sweeter by 75 milligrams of sucrose each of the subsequent successive servings involved with the allocation plan over a 90 day period so that the allocation plan is to be modified by the processor component accordingly, etc.). In an implementation, the electronically receiving the feedback information regarding ingestion of at least one instance of the ingestible product of the succession by the particular individual living being including that the particular individual living being did not like a change of quantity of the substance between the two most recent instances of the ingestible product so that the updated allocation plan is changed from the allocation plan immediately preceding the updated allocation plan is carried out by electronically receiving the feedback information regarding ingestion of at least one instance of the ingestible product of the succession by the particular individual living being including that the particular individual living being did not like a change of quantity of the substance between the two most recent instances of the ingestible product so that the updated allocation plan is changed from the allocation plan immediately preceding the updated allocation plan (e.g. an implementation of the receiver component s528 is configured to electronically receive the feedback information through image recognition of an individual while consuming one of a succession of ice cream servings in a format for the processor component s102 to determine that subsequent ice cream servings need to be sweeter by 75 milligrams of sucrose each of the subsequent successive servings involved with the allocation plan over a 90 day period so that the allocation plan is to be modified by the processor component accordingly, etc.).

Figure 63:
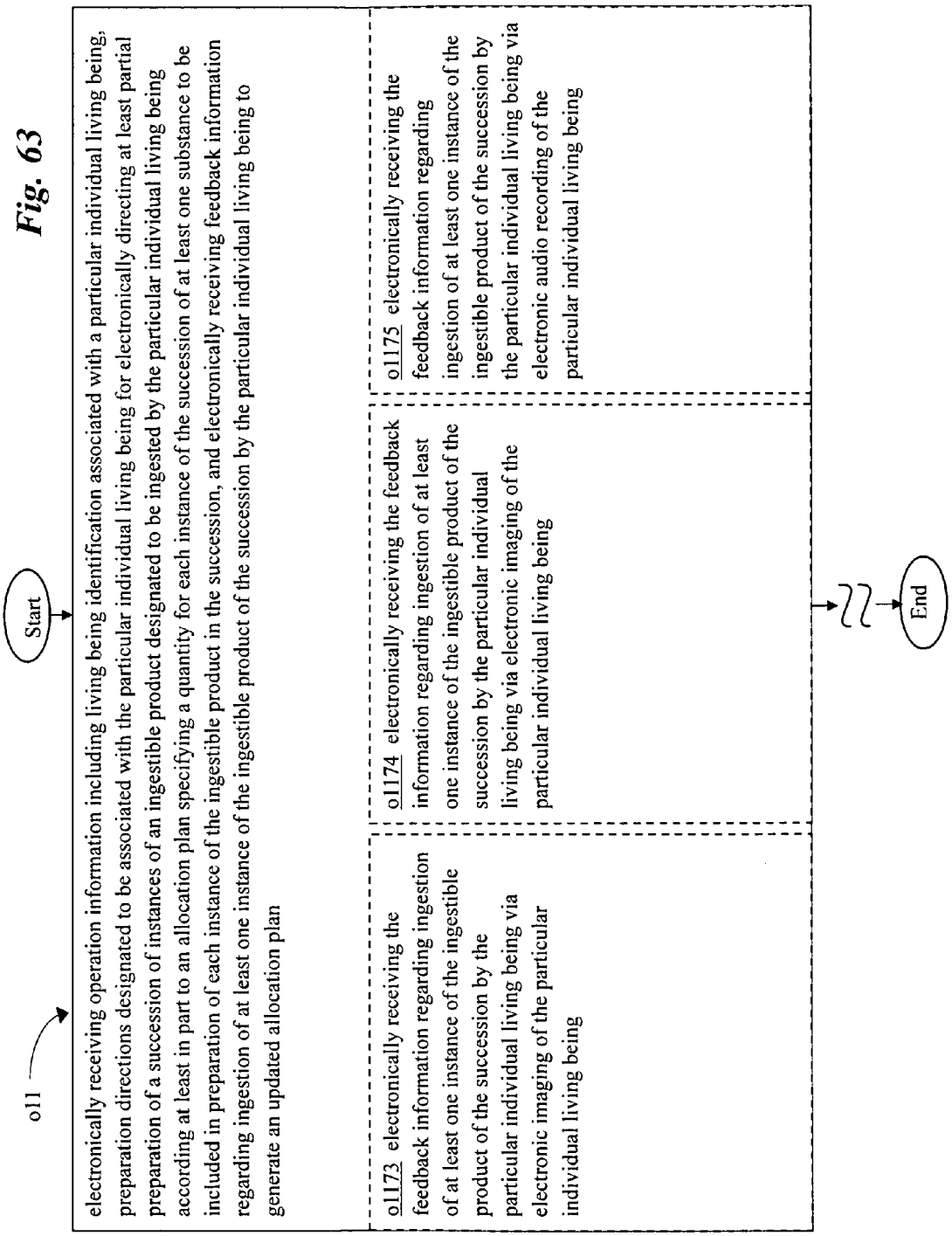
FIG. 63 is a high-level flowchart including exemplary implementations of operation O11 of FIG. 38.

In one or more implementations, as shown in FIG. 63, operation o11 includes an operation o1173 for electronically receiving the feedback information regarding ingestion of at least one instance of the ingestible product of the succession by the particular individual living being via electronic imaging of the particular individual living being. An exemplary version of a non-transitory signal bearing medium of information storage subsystem s200 is depicted as bearing one or more receiving information imaging instructions i1173 that when executed will direct performance of the operation o1173. In an implementation, the one or more receiving information imaging instructions i1173 when executed direct electronically receiving the feedback information regarding ingestion of at least one instance of the ingestible product of the succession by the particular individual living being via electronic imaging of the particular individual living being (e.g. image recognition is used during consumption of servings by a user to determine that over successive servings of banana bread the user is eating less banana bread as the amount of sugar is decreased according to the allocation plan, etc.). Furthermore, the receiving information imaging electrical circuitry arrangement e1173 when activated will perform the operation o1173. In an implementation, the receiving information imaging electrical circuitry arrangement e1173, when activated performs electronically receiving the feedback information regarding ingestion of at least one instance of the ingestible product of the succession by the particular individual living being via electronic imaging of the particular individual living being (e.g. image recognition is used during consumption of servings by a user to determine that over successive servings of banana bread the user is eating less banana bread as the amount of sugar is decreased according to the allocation plan, etc.). In an implementation, the electronically receiving the feedback information regarding ingestion of at least one instance of the ingestible product of the succession by the particular individual living being via electronic imaging of the particular individual living being is carried out by electronically receiving the feedback information regarding ingestion of at least one instance of the ingestible product of the succession by the particular individual living being via electronic imaging of the particular individual living being (e.g. image recognition is used during consumption of servings by a user to determine that over successive servings of banana bread the user is eating less banana bread as the amount of sugar is decreased according to the allocation plan, etc.).

In one or more implementations, operation o11 includes an operation o1174 for electronically receiving the feedback information regarding ingestion of at least one instance of the ingestible product of the succession by the particular individual living being via electronic imaging of the particular individual living being. A non-transitory signal bearing medium includes one or more receiving information imaging instructions i1174 that when executed will direct performance of the operation o1174. In an implementation, the one or more receiving information imaging instructions 1174 when executed direct electronically receiving the feedback information regarding ingestion of at least one instance of the ingestible product of the succession by the particular individual living being via electronic imaging of the particular individual living being (e.g. video imaging is used to capture acts of disposing of refuse after consuming the digestible product as apple dumplings over successive servings that the amount of digestible product consumed has not changed even though the amount of shortening used to make each successive serving has been considerably reduced, etc.). Furthermore, the receiving information imaging electrical circuitry arrangement e1174 when activated will perform the operation o1174. In an implementation, the receiving information imaging electrical circuitry arrangement e1174, when activated performs electronically receiving the feedback information regarding ingestion of at least one instance of the ingestible product of the succession by the particular individual living being via electronic imaging of the particular individual living being (e.g. video imaging is used to capture acts of disposing of refuse after consuming the digestible product as apple dumplings over successive servings that the amount of digestible product consumed has not changed even though the amount of shortening used to make each successive serving has been considerably reduced, etc.). In an implementation, the electronically receiving the feedback information regarding ingestion of at least one instance of the ingestible product of the succession by the particular individual living being via electronic imaging of the particular individual living being is carried out by electronically receiving the feedback information regarding ingestion of at least one instance of the ingestible product of the succession by the particular individual living being via electronic imaging of the particular individual living being (e.g. video imaging is used to capture acts of disposing of refuse after consuming the digestible product as apple dumplings over successive servings that the amount of digestible product consumed has not changed even though the amount of shortening used to make each successive serving has been considerably reduced, etc.).

In one or more implementations, operation o11 includes an operation o1175 for electronically receiving the feedback information regarding ingestion of at least one instance of the ingestible product of the succession by the particular individual living being via electronic audio recording of the particular individual living being. A non-transitory signal bearing medium includes one or more receiving information audio instructions i1175 that when executed will direct performance of the operation o1175. In an implementation, the one or more receiving information audio instructions 1175 when executed direct electronically receiving the feedback information regarding ingestion of at least one instance of the ingestible product of the succession by the particular individual living being via electronic audio recording of the particular individual living being (e.g. audio recording of user verbal comments during and after consumption of each serving in the succession is used to determine user satisfaction with modification to each serving in accordance with the allocation plan, etc.). Furthermore, the receiving information audio electrical circuitry arrangement e1175 when activated will perform the operation o1175. In an implementation, the receiving information audio electrical circuitry arrangement e1175, when activated performs electronically receiving the feedback information regarding ingestion of at least one instance of the ingestible product of the succession by the particular individual living being via electronic audio recording of the particular individual living being (e.g. audio recording of user verbal comments during and after consumption of each serving in the succession is used to determine user satisfaction with modification to each serving in accordance with the allocation plan, etc.). In an implementation, the electronically receiving the feedback information regarding ingestion of at least one instance of the ingestible product of the succession by the particular individual living being via electronic audio recording of the particular individual living being is carried out by electronically receiving the feedback information regarding ingestion of at least one instance of the ingestible product of the succession by the particular individual living being via electronic audio recording of the particular individual living being (e.g. audio recording of user verbal comments during and after consumption of each serving in the succession is used to determine user satisfaction with modification to each serving in accordance with the allocation plan, etc.).

Figure 64:
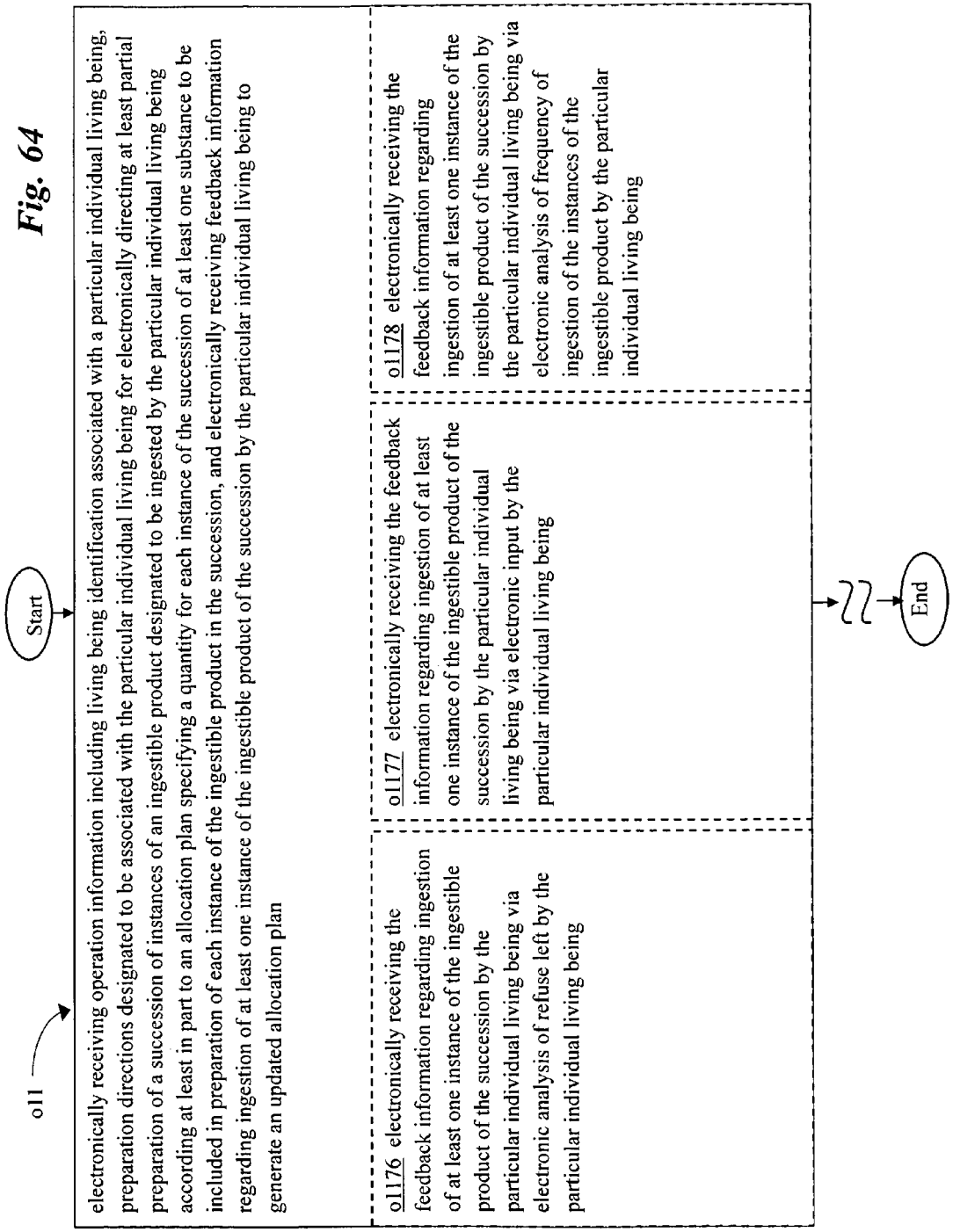
FIG. 64 is a high-level flowchart including exemplary implementations of operation O11 of FIG. 38.

In one or more implementations, as shown in FIG. 64, operation o11 includes an operation o1176 for electronically receiving the feedback information regarding ingestion of at least one instance of the ingestible product of the succession by the particular individual living being via electronic analysis of refuse left by the particular individual living being. An exemplary version of a non-transitory signal bearing medium of information storage subsystem s200 is depicted as bearing one or more receiving information refuse instructions i1176 that when executed will direct performance of the operation o1176. In an implementation, the one or more receiving information refuse instructions i1176 when executed direct electronically receiving the feedback information regarding ingestion of at least one instance of the ingestible product of the succession by the particular individual living being via electronic analysis of refuse left by the particular individual living being (e.g. electronic analysis of the weight of refuse left by the particular individual being after consumption of each serving in the succession is used to determine user satisfaction with modification to each serving in accordance with the allocation plan, etc.). Furthermore, the receiving information refuse electrical circuitry arrangement e1176 when activated will perform the operation o1176. In an implementation, the receiving information refuse electrical circuitry arrangement e1176, when activated performs electronically receiving the feedback information regarding ingestion of at least one instance of the ingestible product of the succession by the particular individual living being via electronic analysis of refuse left by the particular individual living being (e.g. electronic analysis of the weight of refuse left by the particular individual being after consumption of each serving in the succession is used to determine user satisfaction with modification to each serving in accordance with the allocation plan, etc.). In an implementation, the electronically receiving the feedback information regarding ingestion of at least one instance of the ingestible product of the succession by the particular individual living being via electronic analysis of refuse left by the particular individual living being is carried out by electronically receiving the feedback information regarding ingestion of at least one instance of the ingestible product of the succession by the particular individual living being via electronic analysis of refuse left by the particular individual living being (e.g. electronic analysis of the weight of refuse left by the particular individual being after consumption of each serving in the succession is used to determine user satisfaction with modification to each serving in accordance with the allocation plan, etc.).

In one or more implementations, operation o11 includes an operation o1177 for electronically receiving the feedback information regarding ingestion of at least one instance of the ingestible product of the succession by the particular individual living being via electronic input by the particular individual living being. A non-transitory signal bearing medium includes one or more receiving information input instructions i1177 that when executed will direct performance of the operation o1177. In an implementation, the one or more receiving information input instructions i1177 when executed direct electronically receiving the feedback information regarding ingestion of at least one instance of the ingestible product of the succession by the particular individual living being via electronic input by the particular individual living being (e.g. electronic analysis of textual comments inputted by the particular individual being after consumption of each serving in the succession is used to determine user satisfaction with modification to each serving in accordance with the allocation plan, etc.). Furthermore, the receiving information input electrical circuitry arrangement e1177 when activated will perform the operation o1177. In an implementation, the receiving information input electrical circuitry arrangement e1177, when activated performs electronically receiving the feedback information regarding ingestion of at least one instance of the ingestible product of the succession by the particular individual living being via electronic input by the particular individual living being (e.g. electronic analysis of textual comments inputted by the particular individual being after consumption of each serving in the succession is used to determine user satisfaction with modification to each serving in accordance with the allocation plan, etc.). In an implementation, the electronically receiving the feedback information regarding ingestion of at least one instance of the ingestible product of the succession by the particular individual living being via electronic input by the particular individual living being is carried out by electronically receiving the feedback information regarding ingestion of at least one instance of the ingestible product of the succession by the particular individual living being via electronic input by the particular individual living being (e.g. electronic analysis of textual comments inputted by the particular individual being after consumption of each serving in the succession is used to determine user satisfaction with modification to each serving in accordance with the allocation plan, etc.)

In one or more implementations, operation o11 includes an operation o1178 for electronically receiving the feedback information regarding ingestion of at least one instance of the ingestible product of the succession by the particular individual living being via electronic analysis of frequency of ingestion of the instances of the ingestible product by the particular individual living being. A non-transitory signal bearing medium includes one or more receiving information frequency instructions i1178 that when executed will direct performance of the operation o1178. In an implementation, the one or more receiving information frequency instructions i1178 when executed direct electronically receiving the feedback information regarding ingestion of at least one instance of the ingestible product of the succession by the particular individual living being via electronic analysis of frequency of ingestion of the instances of the ingestible product by the particular individual living being (e.g. electronic analysis when each serving in the succession is ordered by the particular individual is used to determine user satisfaction with modification to each serving in accordance with the allocation plan, etc.). Furthermore, the receiving information frequency electrical circuitry arrangement e1178 when activated will perform the operation o1178. In an implementation, the receiving information frequency electrical circuitry arrangement e1178, when activated performs electronically receiving the feedback information regarding ingestion of at least one instance of the ingestible product of the succession by the particular individual living being via electronic analysis of frequency of ingestion of the instances of the ingestible product by the particular individual living being (e.g. electronic analysis when each serving in the succession is ordered by the particular individual is used to determine user satisfaction with modification to each serving in accordance with the allocation plan, etc.). In an implementation, the electronically receiving the feedback information regarding ingestion of at least one instance of the ingestible product of the succession by the particular individual living being via electronic analysis of frequency of ingestion of the instances of the ingestible product by the particular individual living being is carried out by electronically receiving the feedback information regarding ingestion of at least one instance of the ingestible product of the succession by the particular individual living being via electronic analysis of frequency of ingestion of the instances of the ingestible product by the particular individual living being (e.g. electronic analysis when each serving in the succession is ordered by the particular individual is used to determine user satisfaction with modification to each serving in accordance with the allocation plan, etc.).

As shown in FIG. 38, the operational flow o10 proceeds to operation o12 for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan. An exemplary version of a non-transitory signal bearing medium of information storage subsystem s200 is depicted as bearing one or more controlling preparation instructions i12 that when executed will direct performance of the operation o12. In an implementation, the one or more controlling preparation instructions i12 when executed direct electronically using the electronically received operation information with the updated allocation plan to electronically direct control (e.g. the CPU component s104 uses the operation information and updated allocation plan to send electronic instructions via the electronic communication subsystem s500 to direct control, etc.) of the at least partial preparation (e.g. the blending component s714 is controlled in at least partial preparation of a smoothie, etc.) of at least one of the instances of the ingestible product of the succession designated to be ingested by the particular individual living being, the at least one of the instances of the ingestible product containing the quantity of the at least one substance according to the updated allocation plan (e.g. successive servings of the smoothie are modified according to the allocation plan so that blending is performed in accordance with variation of at least one substance contained in the smoothie such as the amount of ice and sugar used, etc.). Furthermore, the controlling preparation electrical circuitry arrangement e12 when activated will perform the operation o12. In an implementation, the controlling preparation electrical circuitry arrangement e12, when activated performs electronically using the electronically received operation information with the updated allocation plan to electronically direct control (e.g. the CPU component s104 uses the operation information and updated allocation plan to send electronic instructions via the electronic communication subsystem s500 to direct control, etc.) of the at least partial preparation (e.g. the blending component s714 is controlled in at least partial preparation of a smoothie, etc.) of at least one of the instances of the ingestible product of the succession designated to be ingested by the particular individual living being, the at least one of the instances of the ingestible product containing the quantity of the at least one substance according to the updated allocation plan (e.g. successive servings of the smoothie are modified according to the allocation plan so that blending is performed in accordance with variation of at least one substance contained in the smoothie such as the amount of ice and sugar used, etc.). In an implementation, the electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan is carried out by electronically using the electronically received operation information with the updated allocation plan to electronically direct control (e.g. the CPU component s104 uses the operation information and updated allocation plan to send electronic instructions via the electronic communication subsystem s500 to direct control, etc.) of the at least partial preparation (e.g. the blending component s714 is controlled in at least partial preparation of a smoothie, etc.) of at least one of the instances of the ingestible product of the succession designated to be ingested by the particular individual living being, the at least one of the instances of the ingestible product containing the quantity of the at least one substance according to the updated allocation plan (e.g. successive servings of the smoothie are modified according to the allocation plan so that blending is performed in accordance with variation of at least one substance contained in the smoothie such as the amount of ice and sugar used, etc.).

Figure 65:
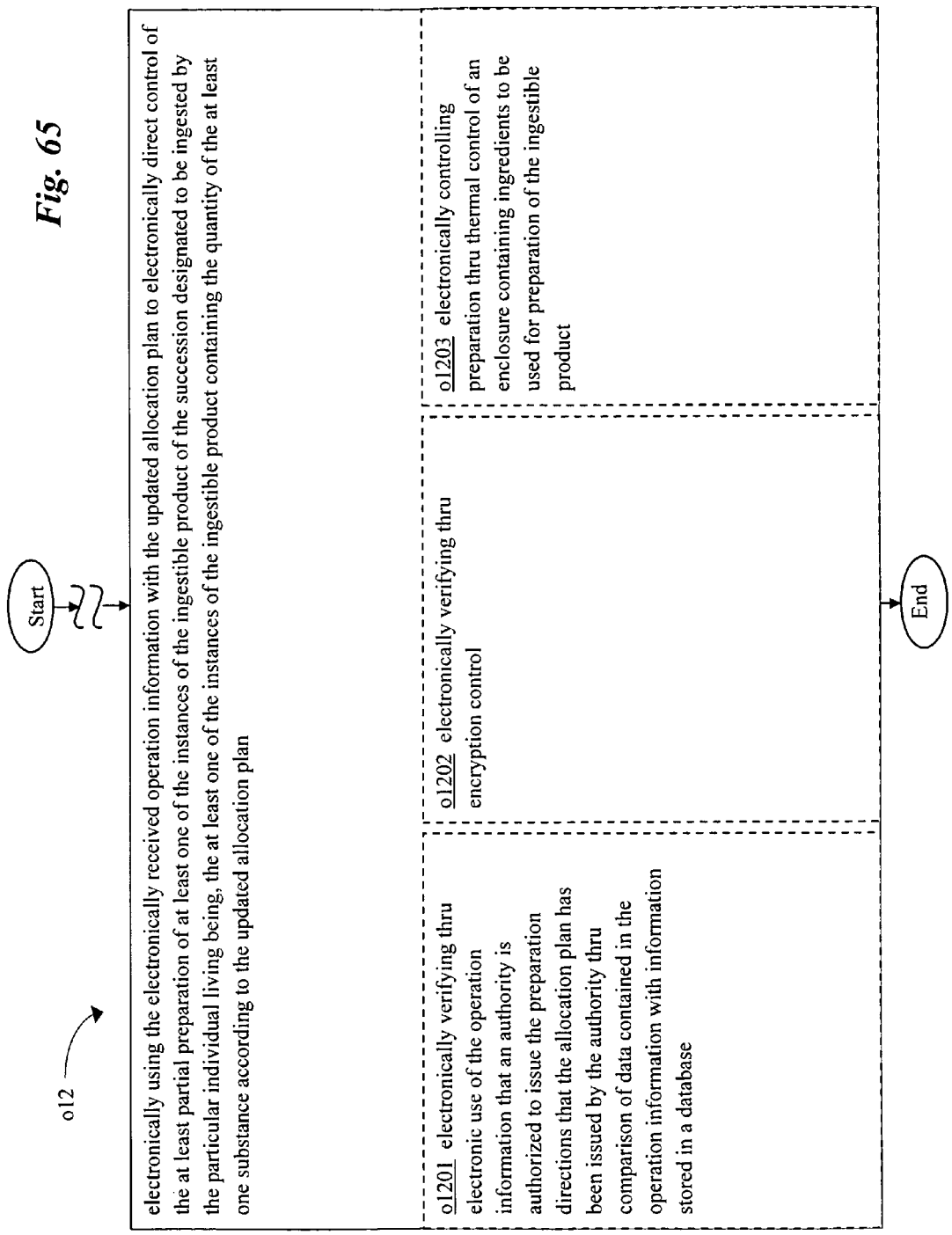
FIG. 65 is a high-level flowchart including exemplary implementations of operation O12 of FIG. 38.

In one or more implementations, as shown in FIG. 65, operation o12 includes an operation o1201 for electronically verifying thru electronic use of the operation information that an authority is authorized to issue the preparation directions that the allocation plan has been issued by the authority thru comparison of data contained in the operation information with information stored in a database. An exemplary version of a non-transitory signal bearing medium of information storage subsystem s200 is depicted as bearing one or more verifying thru comparison instructions i1201 that when executed will direct performance of the operation o1201. In an implementation, the one or more verifying thru comparison instructions i1201 when executed direct electronically verifying thru electronic use of the operation information that an authority is authorized to issue the preparation directions that the allocation plan has been issued by the authority thru comparison of data contained in the operation information with information stored in a database (e.g. an implementation of the processor component s102 is configured to electronically compare data contained in the operation information and received by the receiver component s528 with information stored in the hard drive component s222 to verify that a physician at a local health clinic has issued the preparation directions involving the allocation plan, etc.). Furthermore, the verifying thru comparison electrical circuitry arrangement e1201 when activated will perform the operation o1201. In an implementation, the verifying thru comparison electrical circuitry arrangement e1201, when activated performs electronically verifying thru electronic use of the operation information that an authority is authorized to issue the preparation directions that the allocation plan has been issued by the authority thru comparison of data contained in the operation information with information stored in a database (e.g. an implementation of the processor component s102 is configured to electronically compare data contained in the operation information and received by the receiver component s528 with information stored in the hard drive component s222 to verify that a physician at a local health clinic has issued the preparation directions involving the allocation plan, etc.). In an implementation, the electronically verifying thru electronic use of the operation information that an authority is authorized to issue the preparation directions that the allocation plan has been issued by the authority thru comparison of data contained in the operation information with information stored in a database is carried out by electronically verifying thru electronic use of the operation information that an authority is authorized to issue the preparation directions that the allocation plan has been issued by the authority thru comparison of data contained in the operation information with information stored in a database (e.g. an implementation of the processor component s102 is configured to electronically compare data contained in the operation information and received by the receiver component s528 with information stored in the hard drive component s222 to verify that a physician at a local health clinic has issued the preparation directions involving the allocation plan, etc.).

In one or more implementations, operation o12 includes an operation o1202 for electronically verifying thru encryption control. An exemplary version of a non-transitory signal bearing medium of information storage subsystem s200 is depicted as bearing one or more verifying thru encryption instructions i1202 that when executed will direct performance of the operation o1202. In an implementation, the one or more verifying thru encryption instructions i1202 when executed direct electronically verifying thru encryption control (e.g. an implementation of the processor component s102 is configured to electronically implement an encryption key control that a physician was authorized to issue the substance information pertaining to a pharmaceutical medication, etc.). Furthermore, the verifying thru encryption electrical circuitry arrangement e1202 when activated will perform the operation o1202. In an implementation, the verifying thru encryption electrical circuitry arrangement e1202, when activated performs electronically verifying thru encryption control (e.g. an implementation of the processor component s102 is configured to electronically implement an encryption key control that a physician was authorized to issue the substance information pertaining to a pharmaceutical medication, etc.). In an implementation, the electronically verifying thru encryption control is carried out by electronically verifying thru encryption control (e.g. an implementation of the processor component s102 is configured to electronically implement an encryption key control that a physician was authorized to issue the substance information pertaining to a pharmaceutical medication, etc.).

In one or more implementations, operation o12 includes an operation o1203 for electronically controlling preparation thru thermal control of an enclosure containing ingredients to be used for preparation of the ingestible product. An exemplary version of a non-transitory signal bearing medium of information storage subsystem s200 is depicted as bearing one or more control prep thermal instructions i1203 that when executed will direct performance of the operation o1203. In an implementation, the one or more control prep thermal instructions i1203 when executed direct electronically controlling preparation thru thermal control of an enclosure containing ingredients to be used for preparation of the ingestible product (e.g. an implementation of the processor component s102 is configured to electronically control the laser component s708 according to a temperature profile included in the operation information, etc.). Furthermore, the control prep thermal electrical circuitry arrangement e1203 when activated will perform the operation o1203. In an implementation, the control prep thermal electrical circuitry arrangement e1203, when activated performs electronically controlling preparation thru thermal control of an enclosure containing ingredients to be used for preparation of the ingestible product (e.g. an implementation of the processor component s102 is configured to electronically control the laser component s708 according to a temperature profile included in the operation information, etc.). In an implementation, the electronically controlling preparation thru thermal control of an enclosure containing ingredients to be used for preparation of the ingestible product is carried out by electronically controlling preparation thru thermal control of an enclosure containing ingredients to be used for preparation of the ingestible product (e.g. an implementation of the processor component s102 is configured to electronically control the laser component s708 according to a temperature profile included in the operation information, etc.).

Figure 66:
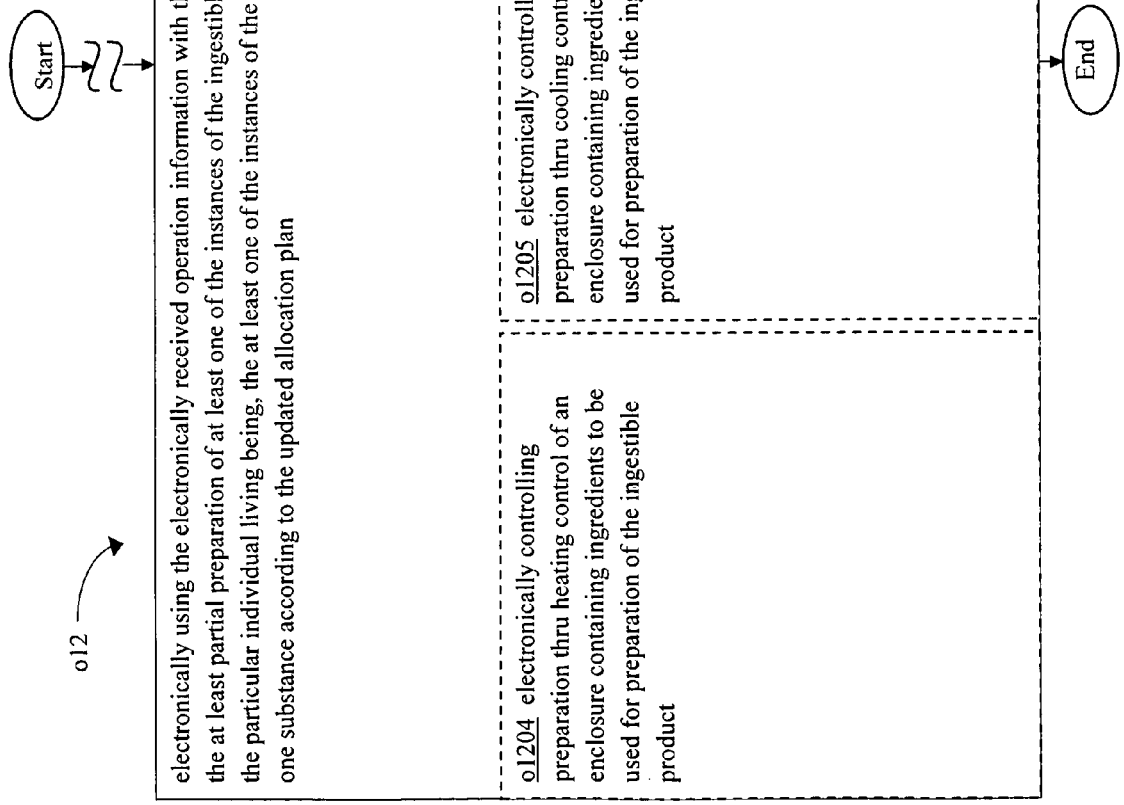
FIG. 66 is a high-level flowchart including exemplary implementations of operation O12 of FIG. 38.

In one or more implementations, as shown in FIG. 66, operation o12 includes an operation o1204 for electronically controlling preparation thru heating control of an enclosure containing ingredients to be used for preparation of the ingestible product. An exemplary version of a non-transitory signal bearing medium of information storage subsystem s200 is depicted as bearing one or more control prep heating instructions i1204 that when executed will direct performance of the operation o1204. In an implementation, the one or more control prep heating instructions i1204 when executed direct electronically controlling preparation thru heating control of an enclosure containing ingredients to be used for preparation of the ingestible product (e.g. an implementation of the processor component s102 is configured to electronically control the heating component s702 according to a temperature profile included in the operation information, etc.). Furthermore, the verifying thru comparison electrical circuitry arrangement e1204 when activated will perform the operation o1204. In an implementation, the control prep heating electrical circuitry arrangement e1204, when activated performs electronically controlling preparation thru heating control of an enclosure containing ingredients to be used for preparation of the ingestible product (e.g. an implementation of the processor component s102 is configured to electronically control the heating component s702 according to a temperature profile included in the operation information, etc.). In an implementation, the electronically controlling preparation thru heating control of an enclosure containing ingredients to be used for preparation of the ingestible product is carried out by electronically controlling preparation thru heating control of an enclosure containing ingredients to be used for preparation of the ingestible product (e.g. an implementation of the processor component s102 is configured to electronically control the heating component s702 according to a temperature profile included in the operation information, etc.).

In one or more implementations, operation o12 includes an operation o1205 for electronically controlling preparation thru cooling control of an enclosure containing ingredients to be used for preparation of the ingestible product. An exemplary version of a non-transitory signal bearing medium of information storage subsystem s200 is depicted as bearing one or more control prep cooling instructions i1205 that when executed will direct performance of the operation o1205. In an implementation, the one or more control prep cooling instructions i1205 when executed direct electronically controlling preparation thru cooling control of an enclosure containing ingredients to be used for preparation of the ingestible product (e.g. an implementation of the processor component s102 is configured to electronically control the cooling component s704 according to a temperature profile included in the operation information, etc.). Furthermore, the control prep cooling electrical circuitry arrangement e1205 when activated will perform the operation o1205. In an implementation, the control prep cooling electrical circuitry arrangement e1205, when activated performs electronically controlling preparation thru cooling control of an enclosure containing ingredients to be used for preparation of the ingestible product (e.g. an implementation of the processor component s102 is configured to electronically control the cooling component s704 according to a temperature profile included in the operation information, etc.). In an implementation, the electronically controlling preparation thru cooling control of an enclosure containing ingredients to be used for preparation of the ingestible product is carried out by electronically controlling preparation thru cooling control of an enclosure containing ingredients to be used for preparation of the ingestible product (e.g. an implementation of the processor component s102 is configured to electronically control the cooling component s704 according to a temperature profile included in the operation information, etc.).

In one or more implementations, operation o12 includes an operation o1206 for electronically controlling preparation thru portion size control of an amount of the substance to be used in preparation of the ingestible product. An exemplary version of a non-transitory signal bearing medium of information storage subsystem s200 is depicted as bearing one or more control prep portion size instructions i1206 that when executed will direct performance of the operation o1206. In an implementation, the one or more control prep portion size instructions i1206 when executed direct electronically controlling preparation thru portion size control of an amount of the substance to be used in preparation of the ingestible product (e.g. an implementation of the processor component s102 is configured to electronically control the sorting component s728 according to a ingredient size distribution profile included in the operation information, etc.). Furthermore, the control prep portion size electrical circuitry arrangement e1206 when activated will perform the operation o1205. In an implementation, the control prep portion size electrical circuitry arrangement e1206, when activated performs electronically controlling preparation thru portion size control of an amount of the substance to be used in preparation of the ingestible product (e.g. an implementation of the processor component s102 is configured to electronically control the sorting component s728 according to a ingredient size distribution profile included in the operation information, etc.). In an implementation, the electronically controlling preparation thru portion size control of an amount of the substance to be used in preparation of the ingestible product is carried out by electronically controlling preparation thru portion size control of an amount of the substance to be used in preparation of the ingestible product (e.g. an implementation of the processor component s102 is configured to electronically control the sorting component s728 according to a ingredient size distribution profile included in the operation information, etc.).

Figure 67:
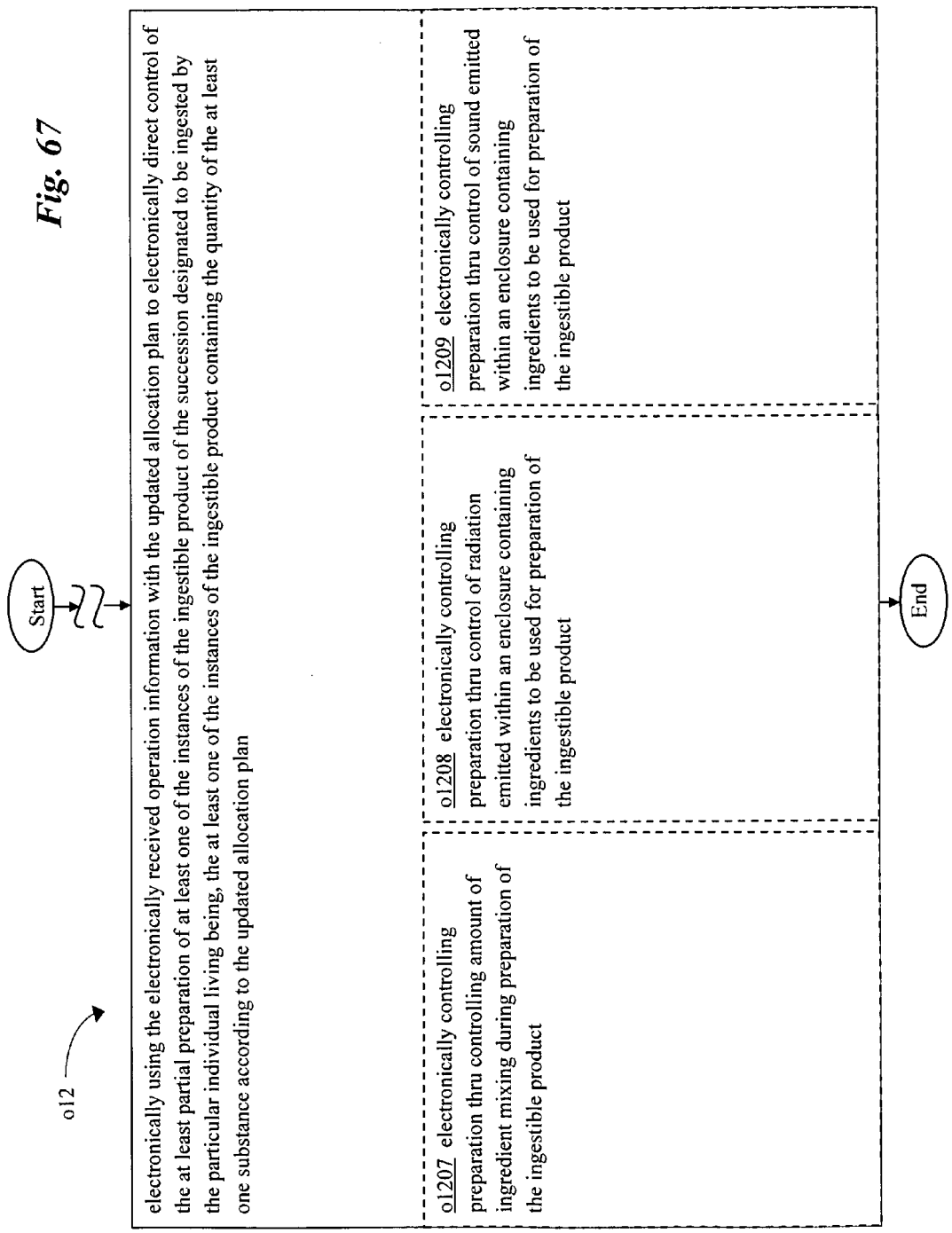
FIG. 67 is a high-level flowchart including exemplary implementations of operation O12 of FIG. 38.

In one or more implementations, as shown in FIG. 67, operation o12 includes an operation o1207 for electronically controlling preparation thru controlling amount of ingredient mixing during preparation of the ingestible product. An exemplary version of a non-transitory signal bearing medium of information storage subsystem s200 is depicted as bearing one or more control prep mixing instructions i1207 that when executed will direct performance of the operation o1207. In an implementation, the one or more control prep mixing instructions i1207 when executed direct electronically controlling preparation thru controlling amount of ingredient mixing during preparation of the ingestible product (e.g. an implementation of the processor component s102 is configured to electronically control the mixer component s716 according to a mixing profile included in the operation information, etc.). Furthermore, the control prep mixing electrical circuitry arrangement e1207 when activated will perform the operation o1207. In an implementation, the control prep mixing electrical circuitry arrangement e1207, when activated performs electronically controlling preparation thru controlling amount of ingredient mixing during preparation of the ingestible product (e.g. an implementation of the processor component s102 is configured to electronically control the mixer component s716 according to a mixing profile included in the operation information, etc.). In an implementation, the electronically controlling preparation thru controlling amount of ingredient mixing during preparation of the ingestible product is carried out by electronically controlling preparation thru controlling amount of ingredient mixing during preparation of the ingestible product (e.g. an implementation of the processor component s102 is configured to electronically control the mixer component s716 according to a mixing profile included in the operation information, etc.).

In one or more implementations, operation o12 includes an operation o1208 for electronically controlling preparation thru control of radiation emitted within an enclosure containing ingredients to be used for preparation of the ingestible product. An exemplary version of a non-transitory signal bearing medium of information storage subsystem s200 is depicted as bearing one or more control prep radiation instructions i1208 that when executed will direct performance of the operation o1208. In an implementation, the one or more control prep radiation instructions i1208 when executed direct electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the operation information, etc.). Furthermore, the control prep radiation electrical circuitry arrangement e1208 when activated will perform the operation o1208. In an implementation, the control prep radiation electrical circuitry arrangement e1208, when activated performs electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the operation information, etc.). In an implementation, the electronically controlling preparation thru control of radiation emitted within an enclosure containing ingredients to be used for preparation of the ingestible product is carried out by electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the operation information, etc.).

In one or more implementations, operation o12 includes an operation o1209 for electronically controlling preparation thru control of sound emitted within an enclosure containing ingredients to be used for preparation of the ingestible product. An exemplary version of a non-transitory signal bearing medium of information storage subsystem s200 is depicted as bearing one or more control prep sound instructions i1209 that when executed will direct performance of the operation o1209. In an implementation, the one or more control prep sound instructions i1209 when executed direct electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the operation information, etc.). Furthermore, the control prep sound electrical circuitry arrangement e1209 when activated will perform the operation o1209. In an implementation, the control prep sound electrical circuitry arrangement e1209, when activated performs electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the operation information, etc.). In an implementation, the electronically controlling preparation thru control of sound emitted within an enclosure containing ingredients to be used for preparation of the ingestible product is carried out by electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the operation information, etc.).

Figure 68:
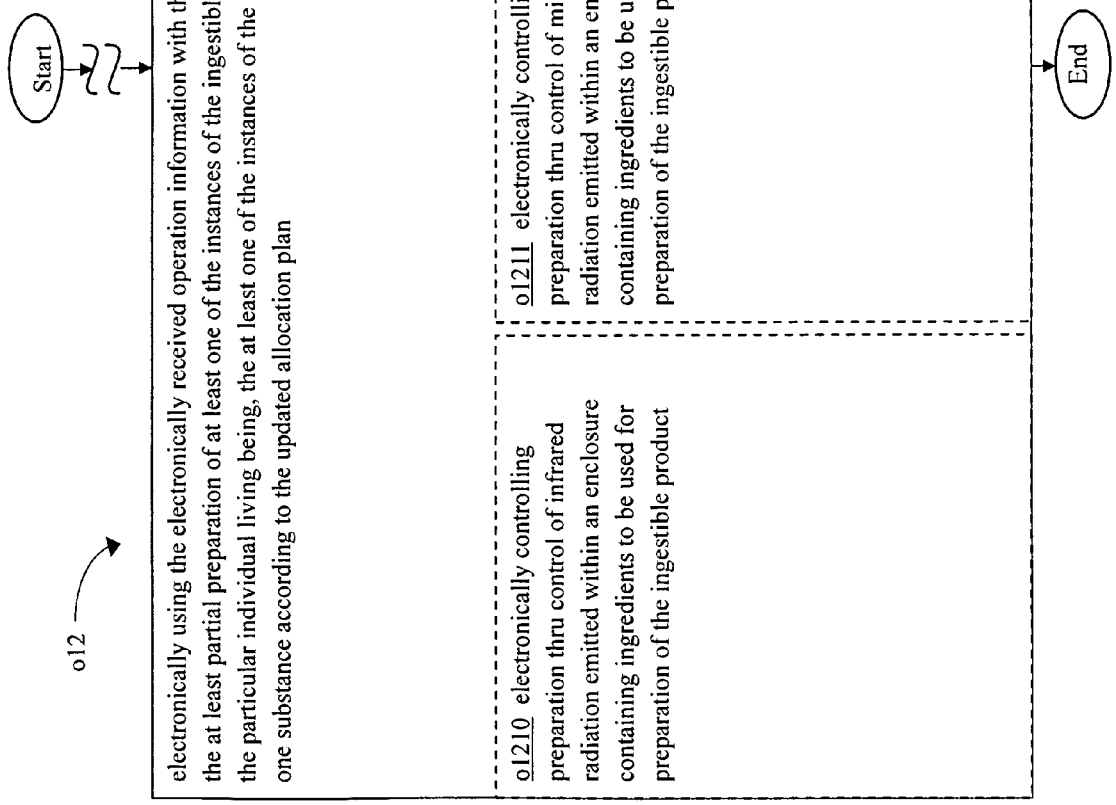
FIG. 68 is a high-level flowchart including exemplary implementations of operation O12 of FIG. 38.

In one or more implementations, as shown in FIG. 68, operation o12 includes an operation o1210 for electronically controlling preparation thru control of infrared radiation emitted within an enclosure containing ingredients to be used for preparation of the ingestible product. An exemplary version of a non-transitory signal bearing medium of information storage subsystem s200 is depicted as bearing one or more control prep infrared instructions i1210 that when executed will direct performance of the operation o1210. In an implementation, the one or more control prep infrared instructions i1210 when executed direct electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the operation information, etc.). Furthermore, the control prep infrared electrical circuitry arrangement e1210 when activated will perform the operation o1210. In an implementation, the control prep infrared electrical circuitry arrangement e1210, when activated performs electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the operation information, etc.). In an implementation, the electronically controlling preparation thru control of infrared radiation emitted within an enclosure containing ingredients to be used for preparation of the ingestible product is carried out by electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the operation information, etc.).

In one or more implementations, operation o12 includes an operation o1211 for electronically controlling preparation thru control of microwave radiation emitted within an enclosure containing ingredients to be used for preparation of the ingestible product. An exemplary version of a non-transitory signal bearing medium of information storage subsystem s200 is depicted as bearing one or more control prep microwave instructions i1211 that when executed will direct performance of the operation o1211. In an implementation, the one or more control prep microwave instructions i1211 when executed direct electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the operation information, etc.). Furthermore, the control prep microwave electrical circuitry arrangement e1211 when activated will perform the operation o1211. In an implementation, the control prep microwave electrical circuitry arrangement e1211, when activated performs electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the operation information, etc.). In an implementation, the electronically controlling preparation thru control of microwave radiation emitted within an enclosure containing ingredients to be used for preparation of the ingestible product is carried out by electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the operation information, etc.).

In one or more implementations, operation o12 includes an operation o1212 for electronically controlling preparation thru control of an outlet of an ingredient container holding an ingredient used for preparation of the ingestible product. An exemplary version of a non-transitory signal bearing medium of information storage subsystem s200 is depicted as bearing one or more control prep container instructions i1212 that when executed will direct performance of the operation o1212. In an implementation, the one or more control prep container instructions i1212 when executed direct electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the operation information, etc.). Furthermore, the control prep container electrical circuitry arrangement e1212 when activated will perform the operation o1212. In an implementation, the control prep container electrical circuitry arrangement e1212, when activated performs electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the operation information, etc.). In an implementation, the electronically controlling preparation thru control of an outlet of an ingredient container holding an ingredient used for preparation of the ingestible product is carried out by electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the operation information, etc.).

Figure 69:
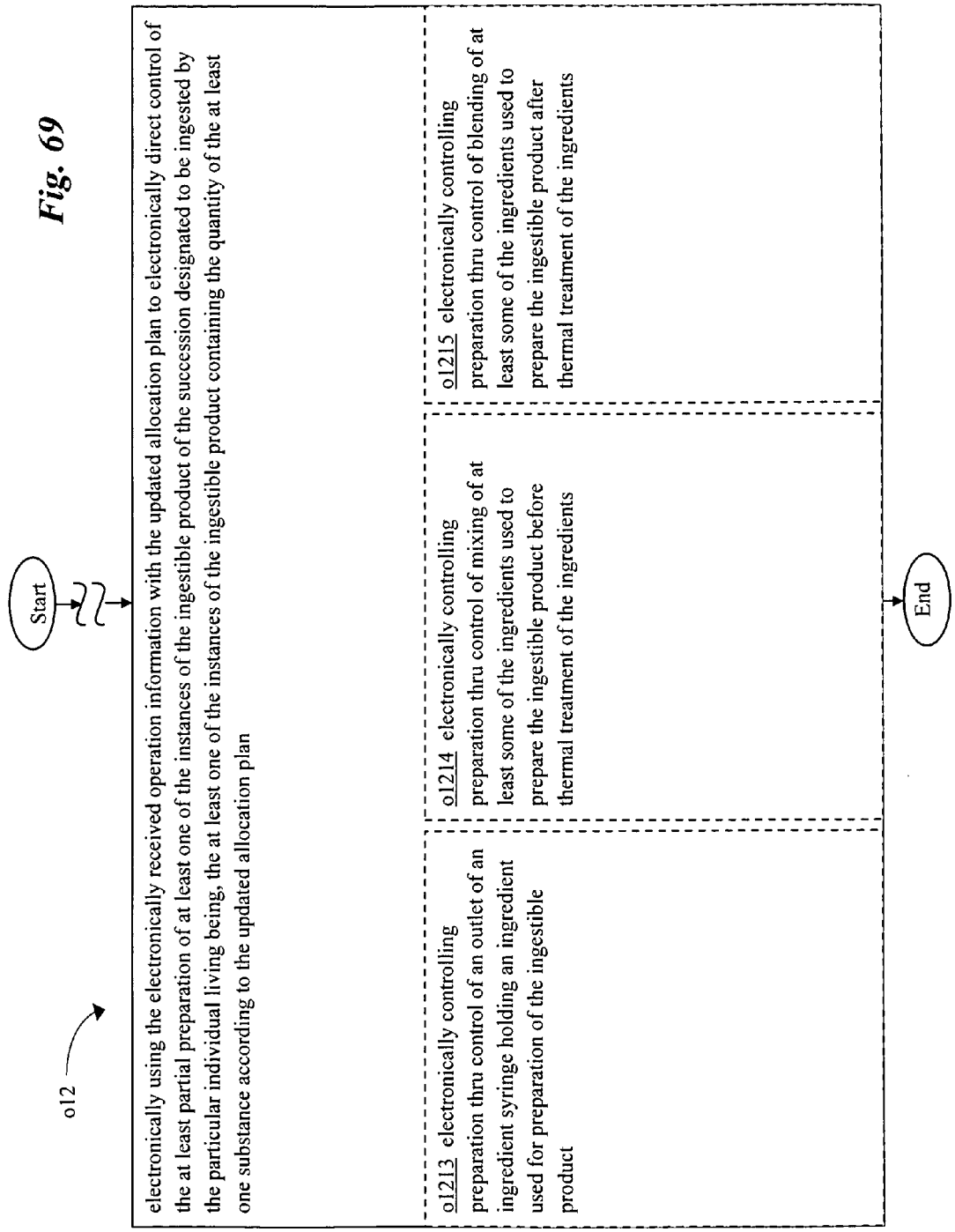
FIG. 69 is a high-level flowchart including exemplary implementations of operation O12 of FIG. 38.

In one or more implementations, as shown in FIG. 69, operation o12 includes an operation o1213 for electronically controlling preparation thru control of an outlet of an ingredient syringe holding an ingredient used for preparation of the ingestible product. An exemplary version of a non-transitory signal bearing medium of information storage subsystem s200 is depicted as bearing one or more control prep syringe instructions i1213 that when executed will direct performance of the operation o1213. In an implementation, the one or more control prep syringe instructions i1213 when executed direct electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the operation information, etc.). Furthermore, the control prep syringe electrical circuitry arrangement e1213 when activated will perform the operation o1213. In an implementation, the control prep syringe electrical circuitry arrangement e1213, when activated performs electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the operation information, etc.). In an implementation, the electronically controlling preparation thru control of an outlet of an ingredient syringe holding an ingredient used for preparation of the ingestible product is carried out by electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the operation information, etc.).

In one or more implementations, operation o12 includes an operation o1214 for electronically controlling preparation thru control of mixing of at least some of the ingredients used to prepare the ingestible product before thermal treatment of the ingredients. An exemplary version of a non-transitory signal bearing medium of information storage subsystem s200 is depicted as bearing one or more control prep mix before thermal instructions i1214 that when executed will direct performance of the operation o1214. In an implementation, the one or more control prep mix before thermal instructions i1214 when executed direct electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the operation information, etc.). Furthermore, the control prep mix before thermal electrical circuitry arrangement e1214 when activated will perform the operation o1214. In an implementation, the control prep mix before thermal electrical circuitry arrangement e1214, when activated performs electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the operation information, etc.). In an implementation, the electronically controlling preparation thru control of mixing of at least some of the ingredients used to prepare the ingestible product before thermal treatment of the ingredients is carried out by electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the operation information, etc.).

In one or more implementations, operation o12 includes an operation o1215 for electronically controlling preparation thru control of blending of at least some of the ingredients used to prepare the ingestible product after thermal treatment of the ingredients. An exemplary version of a non-transitory signal bearing medium of information storage subsystem s200 is depicted as bearing one or more control prep re mix after thermal instructions i1215 that when executed will direct performance of the operation o1215. In an implementation, the one or more control prep re mix after thermal instructions i1215 when executed direct electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the operation information, etc.). Furthermore, the control prep re mix after thermal electrical circuitry arrangement e1215 when activated will perform the operation o1215. In an implementation, the control prep re mix after thermal electrical circuitry arrangement e1215, when activated performs electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the operation information, etc.). In an implementation, the electronically controlling preparation thru control of blending of at least some of the ingredients used to prepare the ingestible product after thermal treatment of the ingredients is carried out by electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the operation information, etc.).

Figure 70:
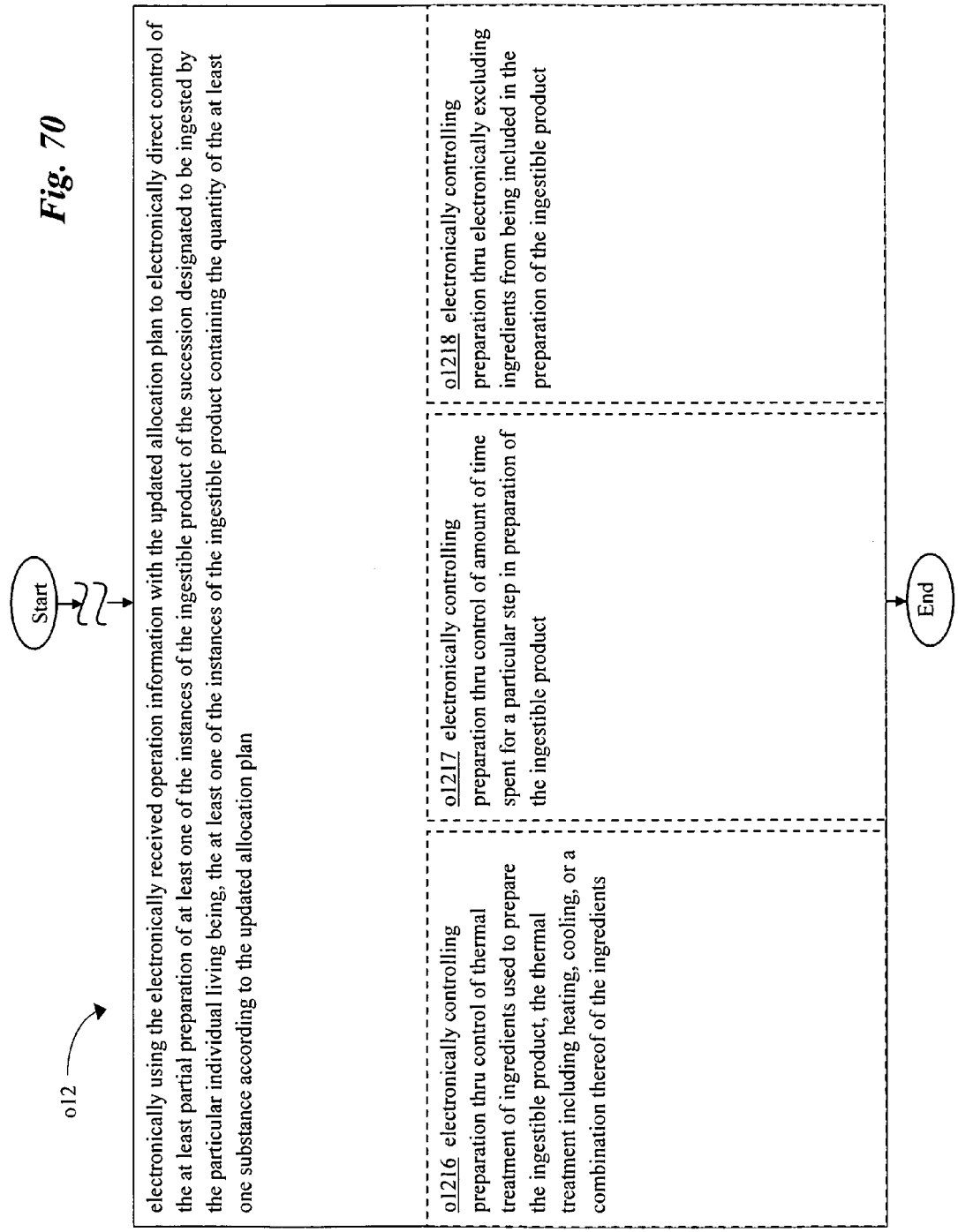
FIG. 70 is a high-level flowchart including exemplary implementations of operation O12 of FIG. 38.

In one or more implementations, as shown in FIG. 70, operation o12 includes an operation o1216 for electronically controlling preparation thru control of thermal treatment of ingredients used to prepare the ingestible product, the thermal treatment including heating, cooling, or a combination thereof of the ingredients. An exemplary version of a non-transitory signal bearing medium of information storage subsystem s200 is depicted as bearing one or more control prep heating cooling instructions i1216 that when executed will direct performance of the operation o1216. In an implementation, the one or more control prep heating cooling instructions i1216 when executed direct electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the operation information, etc.). Furthermore, the control prep heating cooling electrical circuitry arrangement e1216 when activated will perform the operation o1216. In an implementation, the control prep heating cooling electrical circuitry arrangement e1216, when activated performs electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the operation information, etc.). In an implementation, the electronically controlling preparation thru control of thermal treatment of ingredients used to prepare the ingestible product, the thermal treatment including heating, cooling, or a combination thereof of the ingredients is carried out by electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the operation information, etc.).

In one or more implementations, operation o12 includes an operation o1217 for electronically controlling preparation thru control of amount of time spent for a particular step in preparation of the ingestible product. An exemplary version of a non-transitory signal bearing medium of information storage subsystem s200 is depicted as bearing one or more control prep time control instructions i1217 that when executed will direct performance of the operation o1217. In an implementation, the one or more control prep time control instructions i1217 when executed direct electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the operation information, etc.). Furthermore, the control prep time control electrical circuitry arrangement e1217 when activated will perform the operation o1217. In an implementation, the control prep time control electrical circuitry arrangement e1217, when activated performs electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the operation information, etc.). In an implementation, the electronically controlling preparation thru control of amount of time spent for a particular step in preparation of the ingestible product is carried out by electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the operation information, etc.).

In one or more implementations, operation o12 includes an operation o1218 for electronically controlling preparation thru electronically excluding ingredients from being included in the preparation of the ingestible product. An exemplary version of a non-transitory signal bearing medium of information storage subsystem s200 is depicted as bearing one or more control prep ingredient exclusion instructions i1218 that when executed will direct performance of the operation o1218. In an implementation, the one or more control prep ingredient exclusion instructions i1218 when executed direct electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the operation information, etc.). Furthermore, the control prep ingredient exclusion electrical circuitry arrangement e1218 when activated will perform the operation o1218. In an implementation, the control prep ingredient exclusion electrical circuitry arrangement e1218, when activated performs electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the operation information, etc.). In an implementation, the electronically controlling preparation thru electronically excluding ingredients from being included in the preparation of the ingestible product is carried out by electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the operation information, etc.).

In one or more implementations, as shown in FIG. 71, operation o12 includes an operation o1219 for electronically controlling preparation thru electronically including ingredients in the preparation of the ingestible product. An exemplary version of a non-transitory signal bearing medium of information storage subsystem s200 is depicted as bearing one or more control prep ingredient inclusion instructions i1219 that when executed will direct performance of the operation o1219. In an implementation, the one or more control prep ingredient inclusion instructions i1219 when executed direct electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the operation information, etc.). Furthermore, the control prep ingredient inclusion electrical circuitry arrangement e1219 when activated will perform the operation o1219. In an implementation, the control prep ingredient inclusion electrical circuitry arrangement e1219, when activated performs electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the operation information, etc.). In an implementation, the electronically controlling preparation thru electronically including ingredients in the preparation of the ingestible product is carried out by electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the operation information, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture (limited to patentable subject matter under 35 USC 101). Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure (limited to patentable subject matter under 35 USC 101). In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (limited to patentable subject matter under 35 U.S.C. 101) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more") the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system comprising:
a receiving information electrical circuitry arrangement operable for electronically receiving operation information including at least:
living being identification information associated with a particular individual living being;
one or more preparation directions designated to be associated with the particular individual living being for at least:
electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession,
electronically imaging the particular living being at least one of during or near in time to at least one instance of ingestion of the ingestible product to generate image recognition information, and
electronically receiving feedback information regarding at least one instance of ingestion of the ingestible product of the succession by the particular individual living being to generate an updated allocation plan based at least in part on the feedback information, the feedback information being at least partially based on the image recognition information; and
a controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan.

2. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information credit card electrical circuitry arrangement operable for electronically receiving the operation information via a credit card swipe.

3. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information bar code electrical circuitry arrangement operable for electronically receiving the operation information via bar code communication.

4. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information Internet electrical circuitry arrangement operable for electronically receiving the operation information via Internet communication.

5. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information network electrical circuitry arrangement operable for electronically receiving the operation information via an electronic network.

6. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving encrypted information electrical circuitry arrangement operable for electronically receiving the operation information as encrypted data.

7. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
   a receiving information wirelessly electrical circuitry arrangement operable for electronically receiving the operation information wirelessly.

8. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
   a receiving information reeds history electrical circuitry arrangement operable for electronically receiving the operation information including at least the allocation plan associated with the at least one substance as associated with a medication history.

9. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
   a receiving information prescription number electrical circuitry arrangement operable for electronically receiving the operation information including at least the allocation plan associated with a prescription serial number.

10. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
   a receiving information handwritten electrical circuitry arrangement operable for electronically receiving the operation information including at least the allocation plan associated with a data image of handwritten text.

11. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
   a receiving information audio file electrical circuitry arrangement operable for electronically receiving the operation information including at least the allocation plan associated with a computer audio file.

12. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information RFID electrical circuitry arrangement operable for electronically receiving the operation information including at least the allocation plan associated with an RFID tag.

13. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information holographic electrical circuitry arrangement operable for electronically receiving the operation information including at least the allocation plan associated with a holographic image.

14. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information over the counter drug electrical circuitry arrangement operable for electronically receiving the operation information including at least the allocation plan associated with a food component.

15. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information herbal electrical circuitry arrangement operable for electronically receiving the operation information including at least the allocation plan associated with an herbal substance.

16. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information homeopathic electrical circuitry arrangement operable for electronically receiving the operation information including at least the allocation plan associated with a homeopathic substance.

17. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information nutritional electrical circuitry arrangement operable for electronically receiving the operation information including at least the allocation plan associated with a nutritional substance.

18. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information third medications electrical circuitry arrangement operable for electronically receiving the operation information including at least the allocation plan associated with an antipyretic, an antiviral, an anti-ulcer agent, an antidyspeptic, an antacid, a beta-blocker, a bronchodilator, a cold treatment, or a corticosteroid.

19. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving fifth medications electrical circuitry arrangement operable for electronically receiving the operation information including at least the allocation plan associated with a hormone, a hypoglycemic, an immunosuppressive, a laxative, a muscle relaxant, a sedative, a tranquilizer, an appetite modulator, a vitamin, or a combination thereof.

20. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information ID card electrical circuitry arrangement operable for electronically receiving the operation information including at least living being identification associated with an electronic identification card.

21. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information voice electrical circuitry arrangement operable for electronically receiving the operation information including at least living being identification associated with an electronic voice print.

22. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information dental electrical circuitry arrangement operable for electronically receiving the operation information including at least living being identification associated with electronic dental records.

23. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information password electrical circuitry arrangement operable for electronically receiving the operation information including at least living being identification associated with a password.

24. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information breathalyzer electrical circuitry arrangement operable for electronically receiving the operation information including at least living being identification associated with a breathalyzer test.

25. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information swallow electrical circuitry arrangement operable for electronically receiving the preparation directions including at least one or more directions for the at least partial preparation of the succession of instances of the ingestible product to be swallowed.

26. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information inhaled electrical circuitry arrangement operable for electronically receiving the preparation directions including at least one or more directions for the at least partial preparation of the succession of instances of the ingestible product to be inhaled.

27. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information transdermal electrical circuitry arrangement operable for electronically receiving the preparation directions including at least one or more directions for the at least partial preparation of the succession of instances of the ingestible product to be ingested transdermally.

28. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information sandwich electrical circuitry arrangement operable for electronically receiving the preparation directions including at least one or more directions for the at least partial preparation of the succession of instances of the ingestible product to be used in sandwich form.

29. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information smoothie electrical circuitry arrangement operable for electronically receiving the preparation directions including at least one or more directions for the at least partial preparation of the succession of each of the instances of the ingestible product to be used as a smoothie.

30. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information baked electrical circuitry arrangement operable for electronically receiving the preparation directions including at least one or more directions for the at least partial preparation of the succession of each of the instances of the ingestible product to be used as a baked good.

31. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
- a receiving information assembled electrical circuitry arrangement operable for electronically receiving the preparation directions including at least one or more directions for the at least partial preparation of the succession of each of the instances of the ingestible product to be used as an assembled concoction.

32. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
- a receiving information periods electrical circuitry arrangement operable for electronically receiving the preparation directions including at least one or more directions for the at least partial preparation of the succession of each of the instances of the ingestible product to be used periodically.

33. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
- a receiving information care giver electrical circuitry arrangement operable for electronically receiving the operation information including at least verification information to electronically verify issuance of the operation information by an authority including at least indication as to the operation information being issued by a medical physician, naturopathic physician, chiropractic physician, physician, nurse practitioner, nurse, dentist, or a combination thereof.

34. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
- a receiving information preventive electrical circuitry arrangement operable for electronically receiving the operation information including at least verification information to electronically verify issuance of the operation information by an authority including at least indication as to the operation information being issued by a provider of preventive medicine, a provider of therapeutic medicine, a provider of maintenance care, a provider of palliative care, a provider of folk medicine, or a combination thereof.

35. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
    a receiving information individual electrical circuitry arrangement operable for electronically receiving the operation information including at least verification information to electronically verify issuance of the operation information by an authority including at least indication as to the operation information being issued by a self designated individual expert, a sales agent, a dispenser or a combination thereof.

36. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
    an electrical circuitry arrangement operable for electronically receiving the operation information including at least the allocation plan specifying a quantity of substance for each of the instances of the ingestible product in the succession wherein for the amount of substance in one instance of the digestible product in the succession is smaller than the amount in another prior instance of the digestible product in the succession.

37. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
    an electrical circuitry arrangement operable for electronically receiving the operation information including at least the allocation plan specifying a quantity of substance for each of the instances of the ingestible product in the succession wherein each instance of the digestible product is a hamburger.

38. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
    an electrical circuitry arrangement operable for electronically receiving the operation information including at least the allocation plan specifying a quantity of substance for each of the instances of the ingestible product in a unit of volumetric measure including at least one of fluid ounces or milliliters.

39. The system of claim 1, wherein receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:
    an electrical circuitry arrangement operable for electronically receiving the feedback information regarding ingestion of at least one instance of the ingestible product of the succession by the particular individual living being including at least that the particular individual living being did not mind a change of quantity of the substance between the two most recent instances of the ingestible product so that the updated allocation plan remains unchanged from the allocation plan immediately preceding the updated allocation plan.

40. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via electronic imaging of the particular individual living being.

41. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via electronic audio recording of the particular individual living being.

42. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via electronic analysis of refuse left by the particular individual living being.

43. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via electronic analysis of frequency of ingestion of the instances of the ingestible product by the particular individual living being.

44. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a verifying thru comparison electrical circuitry arrangement operable for electronically verifying thru electronic use of the operation information that an authority is authorized to issue the preparation directions that the allocation plan has been issued by the authority thru comparison of data contained in the operation information with information stored in a database.

45. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a verifying thru encryption electrical circuitry arrangement operable for electronically verifying thru encryption control.

46. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep thermal electrical circuitry arrangement operable for electronically controlling preparation thru thermal control of an enclosure containing ingredients to be used for preparation of the ingestible product.

47. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep portion size electrical circuitry arrangement operable for electronically controlling preparation thru portion size control of an amount of the substance to be used in preparation of the ingestible product.

48. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep mixing electrical circuitry arrangement operable for electronically controlling preparation thru controlling amount of ingredient mixing during preparation of the ingestible product.

49. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep container electrical circuitry arrangement operable for electronically controlling preparation thru control of an outlet of an ingredient container holding an ingredient used for preparation of the ingestible product.

50. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep syringe electrical circuitry arrangement operable for electronically controlling preparation thru control of an outlet of an ingredient syringe holding an ingredient used for preparation of the ingestible product.

51. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep mix before thermal electrical circuitry arrangement operable for electronically controlling preparation thru control of mixing of at least some of the ingredients used to prepare the ingestible product before thermal treatment of the ingredients.

52. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep re mix after thermal electrical circuitry arrangement operable for electronically controlling preparation thru control of blending of at least some of the ingredients used to prepare the ingestible product after thermal treatment of the ingredients.

53. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep heating cooling electrical circuitry arrangement operable for electronically controlling preparation thru control of thermal treatment of ingredients used to prepare the ingestible product, the thermal treatment including heating, cooling, or a combination thereof of the ingredients.

54. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep time control electrical circuitry arrangement operable for electronically controlling preparation thru control of amount of time spent for a particular step in preparation of the ingestible product.

55. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep ingredient exclusion electrical circuitry arrangement operable for electronically controlling preparation thru electronically excluding ingredients from being included in the preparation of the ingestible product.

56. The system of claim 1, wherein the controlling preparation upon verify electrical circuitry arrangement operable for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan comprises: a control prep ingredient inclusion electrical circuitry arrangement operable for electronically controlling preparation thru electronically including ingredients in the preparation of the ingestible product.

57. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information electrical circuitry arrangement operable for electronically receiving feedback information regarding ingestion of at least one instance of the ingestible product of the succession by the particular individual living being to generate an updated allocation plan, the feedback information including at least data concerning refuse analysis of a weight of a quantity of wrappers.

58. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information electrical circuitry arrangement operable for electronically receiving feedback information regarding ingestion of at least one instance of the ingestible product of the succession by the particular individual living being to generate an updated allocation plan, the feedback information including at least data concerning a weight of one or more leftovers.

59. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

a receiving information electrical circuitry arrangement operable for electronically receiving feedback information regarding ingestion of at least one instance of the ingestible product of the succession by the particular individual living being to generate an updated allocation plan, the feedback information including at least data concerning audio analysis of one or more unsolicited comments from the particular individual living being.

60. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least electromagnetic sensing of the particular individual living being.

61. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least weight sensing.

62. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least temperature sensing.

63. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least chemical sensing.

64. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least solid sensing.

65. The system of claim 1, wherein the receiving information electrical circuitry arrangement operable for electronically receiving operation information including at least: living being identification information associated with a particular individual living being; one or more preparation directions designated to be associated with the particular individual living being for at least: electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession, electronically imaging the particular living being at least one of during or near in time to at least one instance of ingestion of the ingestible product to generate image recognition information, and electronically receiving feedback information regarding at least one instance of ingestion of the ingestible product of the succession by the particular individual living being to generate an updated allocation plan based at least in part on the feedback information, the feedback information being at least partially based on the image recognition information, comprises:

an electrical circuitry arrangement operable for electronically receiving the feedback information regarding ingestion of at least one instance of the ingestible product of the succession by the particular individual living being via at least liquid sensing.

66. An article of manufacture comprising:
one or more non-transitory signal bearing storage media bearing at least:
one or more receiving information instructions for electronically receiving operation information including at least:
living being identification information associated with a particular individual living being;
one or more preparation directions designated to be associated with the particular individual living being for at least:
electronically directing at least partial preparation of a succession of instances of an ingestible product designated to be ingested by the particular individual living being according at least in part to an allocation plan specifying a quantity for each instance of the succession of at least one substance to be included in preparation of each instance of the ingestible product in the succession,
electronically imaging the particular living being at least one of during or near in time to at least one instance of ingestion of the ingestible product to generate image recognition information, and
electronically receiving feedback information regarding at least one instance of ingestion of the ingestible product of the succession by the particular individual living being to generate an updated allocation plan based at least in part on the feedback information, the feedback information being at least partially based on the image recognition information; and
one or more controlling preparation upon verify instructions for electronically using the electronically received operation information with the updated allocation plan to electronically direct control of the at least partial preparation of at least one of the instances of the ingestible product of the succession designated to be ingested by the particular individual living being, the at least one of the instances of the ingestible product containing the quantity of the at least one substance according to the updated allocation plan.

* * * * *